US010295547B2

(12) United States Patent
Ranum et al.

(10) Patent No.: US 10,295,547 B2
(45) Date of Patent: May 21, 2019

(54) USE AND TREATMENT OF DI-AMINO ACID REPEAT-CONTAINING PROTEINS ASSOCIATED WITH ALS

(71) Applicant: University of Florida Research Foundation, Incorporated, Gainesville, FL (US)

(72) Inventors: Laura Ranum, Gainesville, FL (US); Tao Zu, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 14/775,278

(22) PCT Filed: Mar. 10, 2014

(86) PCT No.: PCT/US2014/022670
§ 371 (c)(1),
(2) Date: Sep. 11, 2015

(87) PCT Pub. No.: WO2014/159247
PCT Pub. Date: Oct. 2, 2014

(65) Prior Publication Data
US 2016/0025747 A1    Jan. 28, 2016

Related U.S. Application Data

(60) Provisional application No. 61/883,219, filed on Sep. 27, 2013, provisional application No. 61/786,258, filed on Mar. 14, 2013.

(51) Int. Cl.
| | |
|---|---|
| *A61K 35/28* | (2015.01) |
| *C07K 16/18* | (2006.01) |
| *G01N 33/68* | (2006.01) |
| *B01D 21/26* | (2006.01) |
| *C12Q 1/6883* | (2018.01) |

(52) U.S. Cl.
CPC ...... *G01N 33/6896* (2013.01); *A61K 35/28* (2013.01); *B01D 21/262* (2013.01); *C07K 16/18* (2013.01); *C12Q 1/6883* (2013.01); *C07K 2317/34* (2013.01); *C12Q 2600/158* (2013.01); *G01N 2800/285* (2013.01); *G01N 2800/2835* (2013.01)

(58) Field of Classification Search
None
See application file for complete search history.

(56) References Cited

U.S. PATENT DOCUMENTS

| | | | | |
|---|---|---|---|---|
| 5,011,912 | A * | 4/1991 | Hopp | C07K 7/06 |
| | | | | 435/331 |
| 6,204,008 | B1 * | 3/2001 | Borneman | C07K 5/06 |
| | | | | 435/219 |
| 6,342,581 | B1 | 1/2002 | Rosen et al. | |
| 7,481,997 | B1 | 1/2009 | Hardy | |
| 9,448,232 | B2 * | 9/2016 | Petrucelli | G01N 33/5308 |
| 2003/0233675 | A1 | 12/2003 | Cao et al. | |
| 2007/0093426 | A1 | 4/2007 | Wormser | |
| 2008/0227699 | A1 | 9/2008 | Chiba et al. | |
| 2012/0076785 | A1 | 3/2012 | Nikolaev et al. | |
| 2012/0220534 | A1 | 8/2012 | Levin et al. | |
| 2014/0206102 | A1 | 7/2014 | Petrucelli et al. | |
| 2014/0336133 | A1 | 11/2014 | Miller et al. | |
| 2015/0361166 | A1 * | 12/2015 | Edbauer | G01N 33/6893 |
| | | | | 424/139.1 |

FOREIGN PATENT DOCUMENTS

| | | |
|---|---|---|
| EP | 2 948 471 A1 | 12/2015 |
| WO | WO 2001/75067 A2 | 10/2001 |
| WO | WO 2006/083800 A2 | 8/2006 |
| WO | WO 2010/115033 A2 | 10/2010 |
| WO | WO 2013/030588 A1 | 3/2013 |
| WO | WO 2014/114303 A1 | 7/2014 |
| WO | WO 2014/114660 A1 | 7/2014 |
| WO | WO 2014/116865 A1 | 7/2014 |

OTHER PUBLICATIONS

Yanagisawa et al., Protein Binding of a DRPLA Family Through Arginine-Glutamic Acid Dipeptide repeats is Enhanced by Extended polyglutamine, 2000, Human Molecular Genetics 9(9):1433-1442.*
Extended European Search Report for Application No. EP 14776090.4 dated Sep. 30, 2016.
International Search Report and Written Opinion for Application No. PCT/US2014/022670.
International Preliminary Report on Patentability for Application No. PCT/US2014/022670.
Ash et al., Unconventional translation of C9ORF72 GGGGCC expansion generates insoluble polypeptides specific to c9FTD/ALS. Neuron. Feb. 20, 2013;77(4):639-46. doi:10.1016/j.neuron.2013.02. 004. Epub Feb. 12, 2013.
Ashizawa et al., GGCCTG repeats put a hex on Purkinje cells and motor neurons in SCA36. Neurology. Jul. 24, 2012;79(4):302-3. doi: 10.1212/WNL.0b013e31826043d9. Epub Jun. 27, 2012.
Baboonian et al., Cross reaction of antibodies to a glycine/alanine repeat sequence of Epstein-Barr virus nuclear antigen-1 with collagen, cytokeratin, and actin. Ann Rheum Dis. Nov. 1991;50(11):772-5.
Gómez-Tortosa et al., C9ORF72 hexanucleotide expansions of 20-22 repeats are associated with frontotemporal deterioration. Neurology. Jan. 22, 2013;80(4):366-70. doi: 10.1212/WNL. 0b013e31827f08ea. Epub Jan. 2, 2013.

(Continued)

*Primary Examiner* — John D Ulm
(74) *Attorney, Agent, or Firm* — Wolf, Greenfield & Sacks, P.C.

(57) ABSTRACT

Disclosed herein are methods and compositions for identifying and/or treating subjects having or likely to have amyotrophic lateral sclerosis (ALS) or frontotemporal dementia (FTD). Antibodies specific for one or more di-amino acid repeat-containing proteins are also provided herein.

3 Claims, 35 Drawing Sheets

Specification includes a Sequence Listing.

(56) References Cited

OTHER PUBLICATIONS

Mori et al., The C9orf72 GGGGCC repeat is translated into aggregating dipeptide-repeat proteins in FTLD/ALS. Science. Mar. 15, 2013;339(6125):1335-8. doi: 10.1126/science.1232927. Epub Feb. 7, 2013. Supplementary information included.
Sha et al., Treatment implications of C9ORF72. Alzheimer's Res Ther. Nov. 27, 2012;4(6):46. doi: 10.1186/alzrt149. eCollection 2012.
Shoesmith et al., Amyotrophic lateral sclerosis: update for family physicians. Can Fam Physician. Dec. 2006;52(12):1563-9.
International Search Report and Written Opinion for Application No. PCT/US2016/034738 dated Sep. 21, 2016.
International Preliminary Report on Patentability for Application No. PCT/US2016/034738 dated Dec. 14, 2017.
Chen et al., Functional genomics in *Drosophila* models of human disease. Briefings in Functional Genomics. Aug. 22, 2012;11(5):405-415.
[No Author Listed] EGNA1—Epstein-Barr nuclear antigen 1—Epstein-Barr virus (strain GD1) (HHV-4)—EBNA1 gene & protein, Jan. 2018 2018. Retrieved from the internet under https:://www.uniprot.org/uniprot/Q3KSS4 on Sep. 12, 2018. 6 pages.
Duellman et al., Antigen-binding properties of monoclonal antibodies reactive with EBNA1 and use in immunoaffinity chromatography. PLoS One. 2009;4(2):e4614. doi: 10.1371/journal.pone.0004614. Epub Feb. 26, 2009, 8 pages.
Satoh et al., Dystrophic neurites express C9orf72 in Alzheimer's disease brains. Alzheimers Res Ther. Aug. 16, 2012;4(4):33. doi: 10.1186/alzrt136. 13 pages.

\* cited by examiner

| | Case Information | | | | | RAN Inclusions | | | | |
|---|---|---|---|---|---|---|---|---|---|---|
| | Case | C9 EXP | Age | Sex/Race | PMD | DX | GP | PA | PR | GR | GA |
| Hippocampus | 1 | + | 59 | F/W | 4 | ALS | +++ | + | + | ++ | ++ |
| | 2 | + | 42 | M/W | 10 | A/F | +++ | + | NA | NA | NA |
| | 3 | + | 74 | F/W | 16 | FTD | +++ | +++* | +++* | ++ | + |
| | 4 | + | 45 | M/W | 3 | ALS | +++ | | + | ++ | + |
| | 5 | + | 82 | F/W | 17 | FTD | +++ | + | + | ++ | + |
| | 6 | + | 86 | F/W | 10 | A/F | ++ | | + | ++ | |
| | 7 | – | 76 | M/W | 7 | ALS | | | | | |
| | 8 | – | 55 | M/W | 7.5 | ALS | – | | NA | NA | NA |
| | 9 | – | 60 | M/W | 16 | CON | | | NA | NA | NA |
| | 10 | – | 81 | M/W | 6 | FTD | | NA | NA | | |
| | 11 | – | 83 | M/W | 17 | FTD– | | | | | |
| | 12 | – | 77 | M/W | 16 | CON | | | | | |
| Motor Cortex | 1 | + | 59 | F/W | 4 | ALS | +++ | | | ++ | ++ |
| | 2 | + | 42 | M/W | 10 | A/F | +++ | + | | + | + |
| | 7 | – | 76 | M/W | 7 | ALS | | | | | |
| | 8 | – | 55 | M/W | 7.5 | ALS | – | | | | |
| | 9 | – | 60 | M/W | 16 | CON | | | | | |
| Spinal Cord | 2 | + | 42 | M/W | 6 | A/F | + | | | | |
| | 13 | + | 53 | M/W | 10 | ALS | + | | | | |
| | 14 | + | 55 | F/W | 7 | A/F | + | | | | |
| | 7 | – | 76 | M/W | 7 | ALS | | | | | |
| | 8 | – | 55 | M/W | 7.5 | ALS | – | | | | |
| | 9 | – | 60 | M/W | 16 | CON | | | | | |
| | 15 | – | 64 | F/W | 0 | ALS | – | | | | |
| | 16 | – | 79 | M/W | 33 | ALS | – | | | | |
| | 17 | – | 79 | M/W | 10 | ALS | | | | | |

(–) no inclusions, (+) occasional, (++) moderate, (+++) numerous inclusions. (.) Variable staining from section to section. DX =diagnosis. FTD=frontrotemporal dementia, ALS=amyotrophic lateral sclerosis. F=female, M=Male. PMD=post-mortem interval. NA = not available. HIPPO=hippocampus, M Cortex = motor cortex. The apparent differences in the frequencies of the various inclusions may reflect differences in protein conformation and epitope availability or differences in the affinities of these antibodies.

FIG. 18

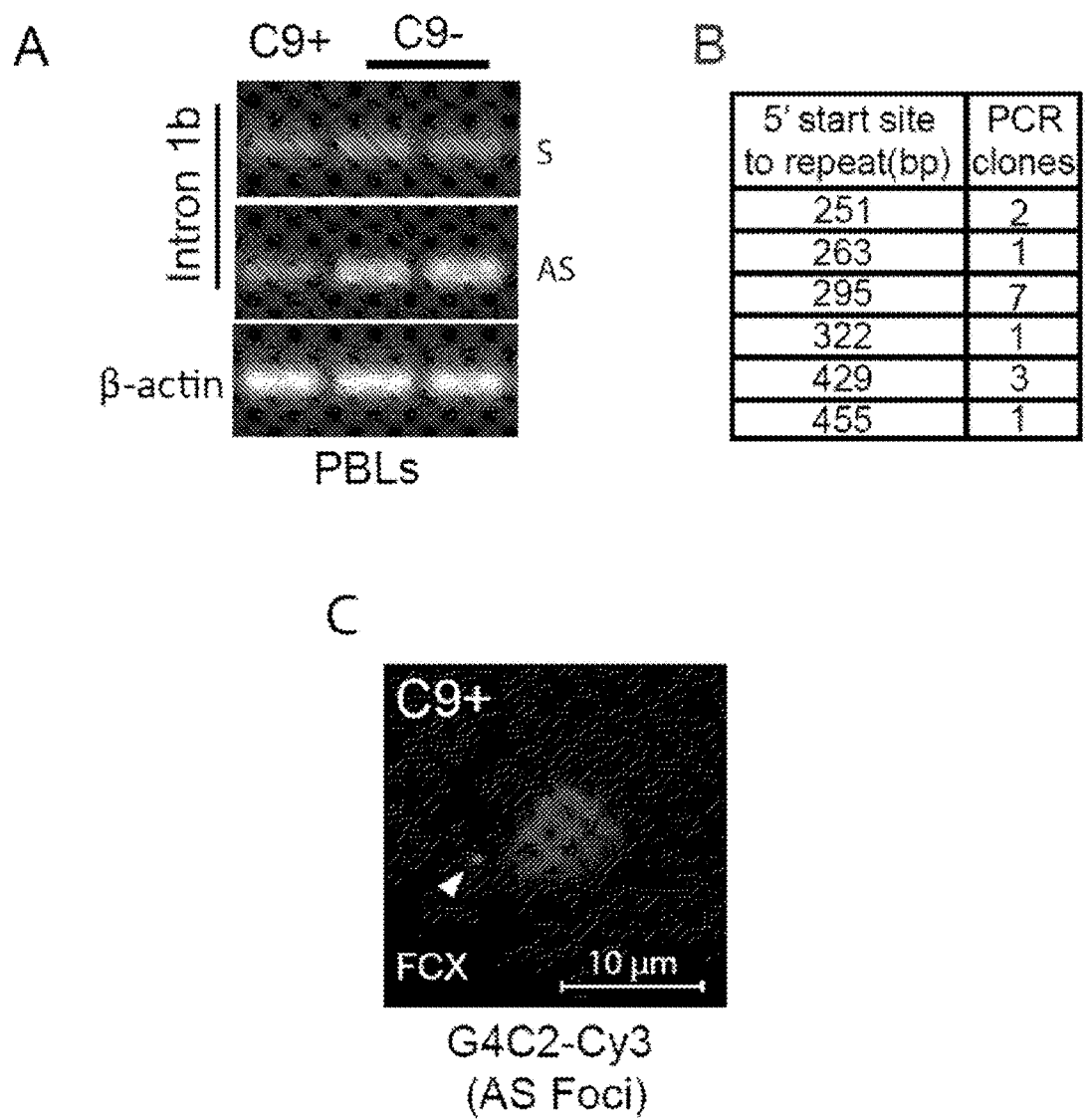
FIG. 19A-C

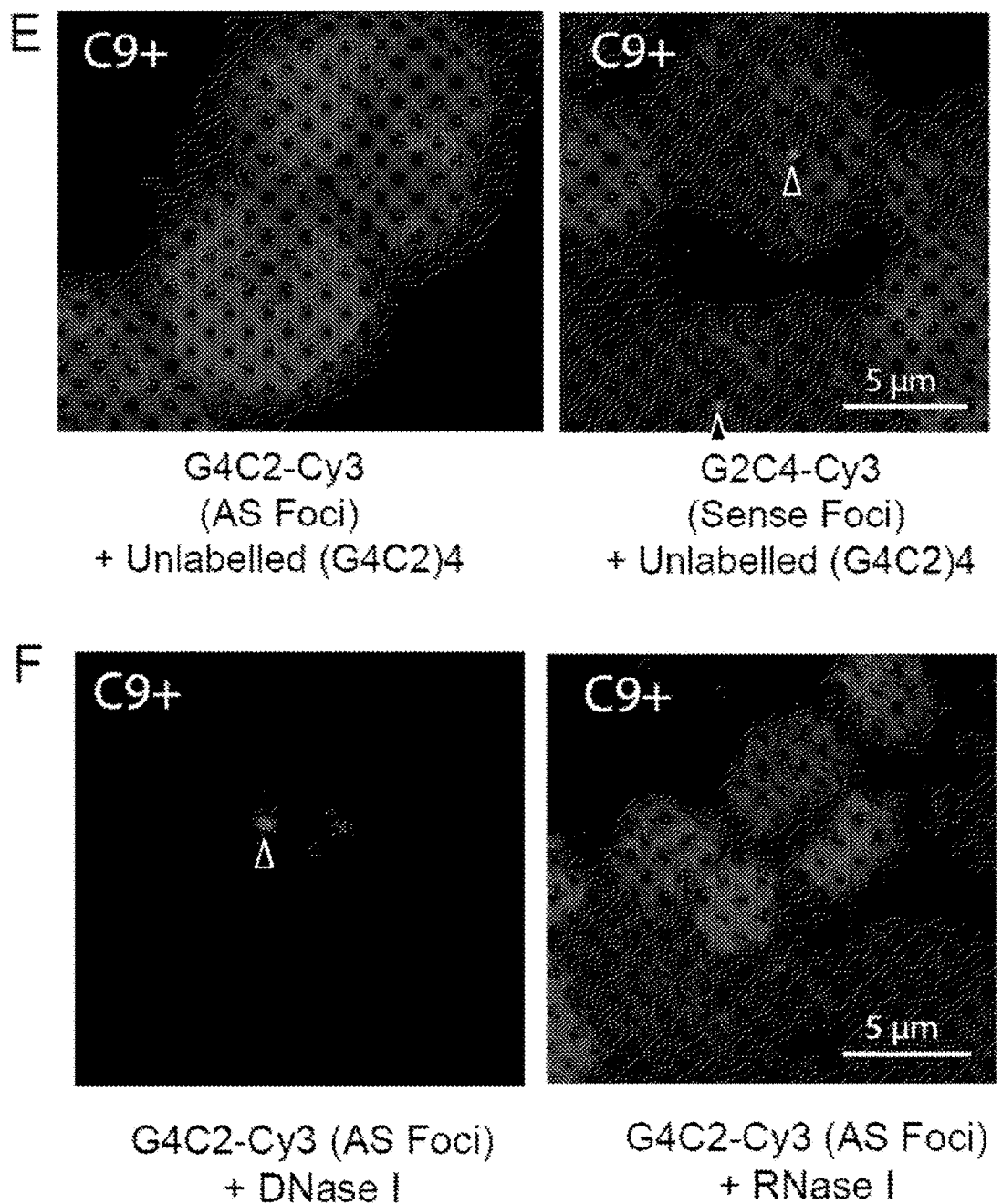
FIG. 19E-F

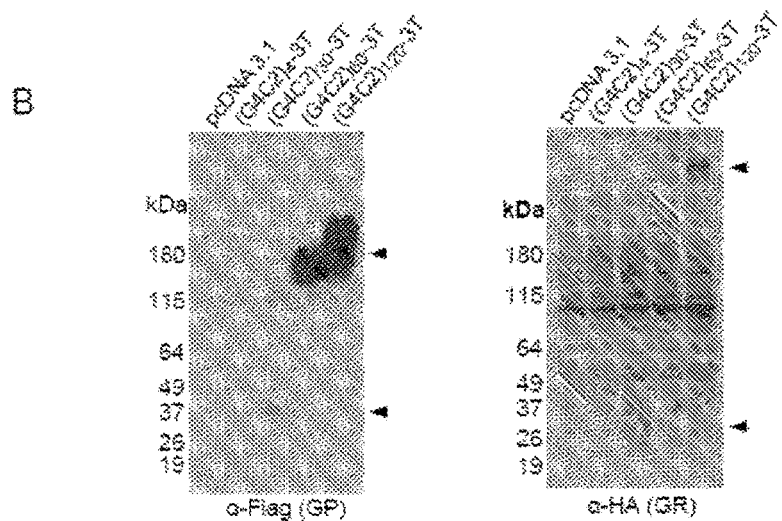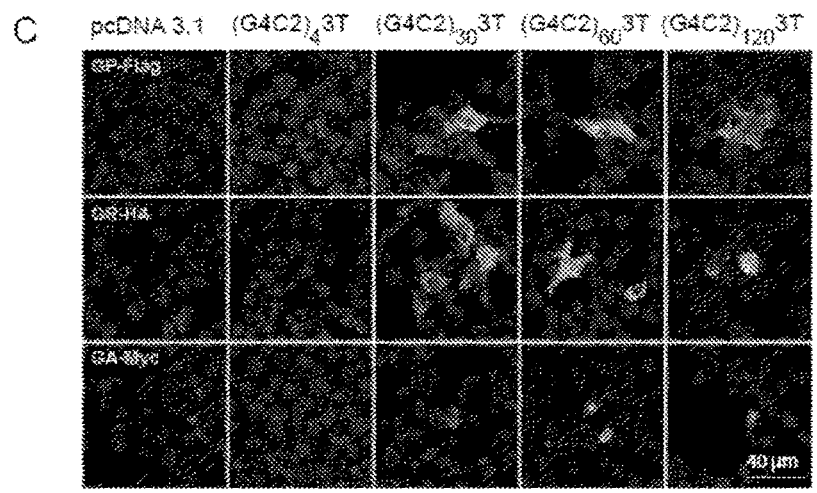
FIG. 20

G₂C₄ strand

Frame 1
*GEPPLLPAPLPGSKTPNSHPPGCRLLTHPLATACASAAAGAGTATAAPPRARPRARPDHAPAPA
PAPAPAPAPAPAPA(PA)₁₋₄₀PAPAPSARLLSSRACYRLRLEPSLFSSG*

Frame 2
MQAIPPVARGESPTPSFGQRNERESKNASSSEESPRFYPRLFPAAEPQTATRQDAASSLTHSPPP
APPPPRAQAPQPQPRPGPAPGPAPTTPRPRPRPRPRPRPRPRPR(PR)₁₋₄₀PHERPLARDS*

Frame 3
MRGKVKMRRALRRAPASTRASSRQPNPKQPPARMPPPHSPTRHRLRLRRRGRRHRNRSPAPGPPP
GPPRPRPGPGPGPGPGPGPGPGP(GP)₁₋₄₀GPGP*

G₄C₂ strand

Frame 1
*GPGPGPGPGPGPGPGP(GP)₁₋₄₀GPGPGRGRGGPGGGPGAGLRLRCLRPRRRRRRNRVGE*

Frame 2
*RLTRRKQGGKQPQPVASSGTQESRARGRGRGRGRGRGRGRGR(GR)₁₋₄₀GRGRGVVGAGPGAG
PGRGCGCGACARGGGGAGGGEWVSEEAASWRVAVWGSAAGKRRG*

Frame 3
*QALELRSRALGAGAGAGAGAGAGAGAGA(GA)₁₋₄₀GAGAWSGRARGRARGGAAVAVPAPAAAE
AQAVASG*

*FIG. 21*

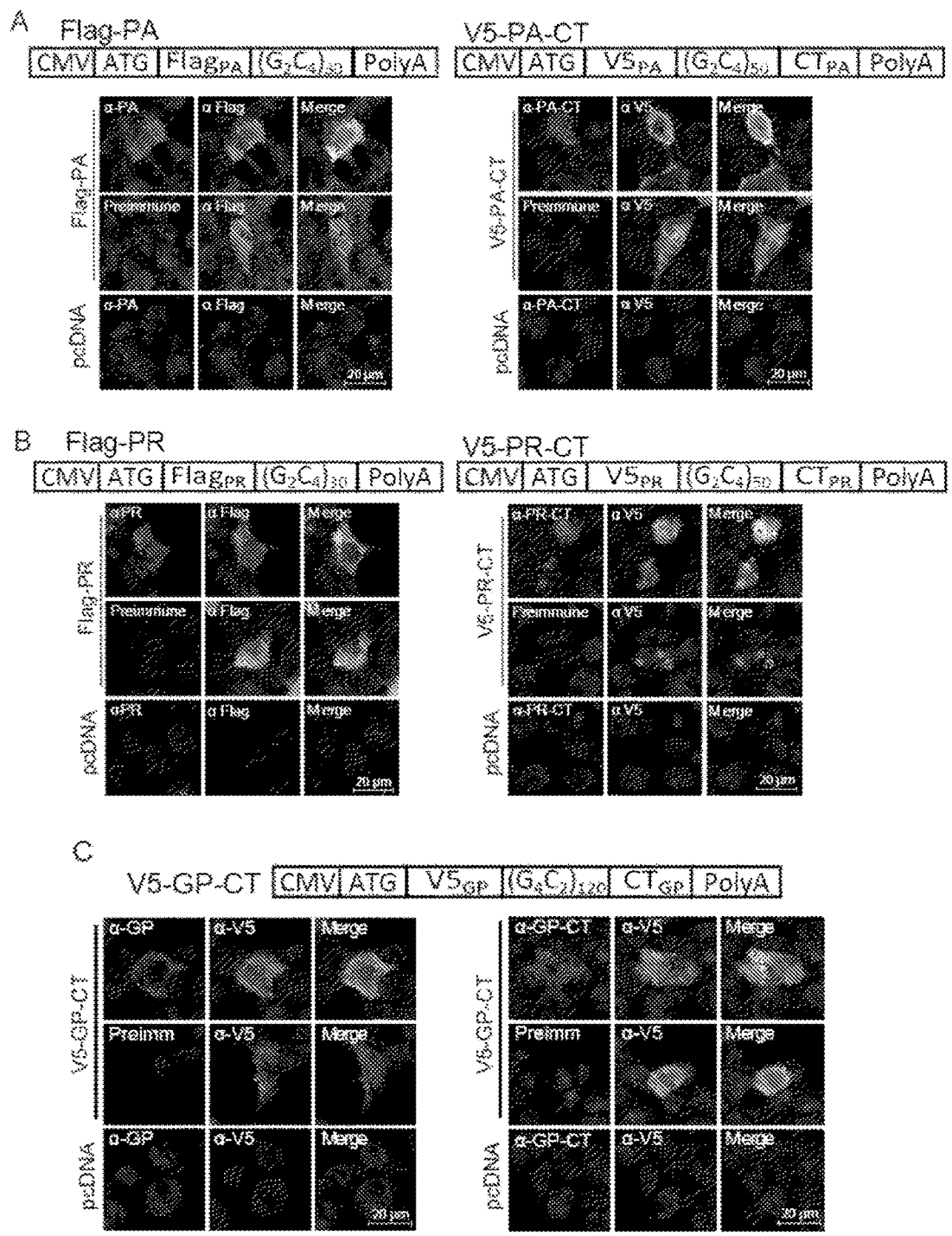
FIG. 22A-C

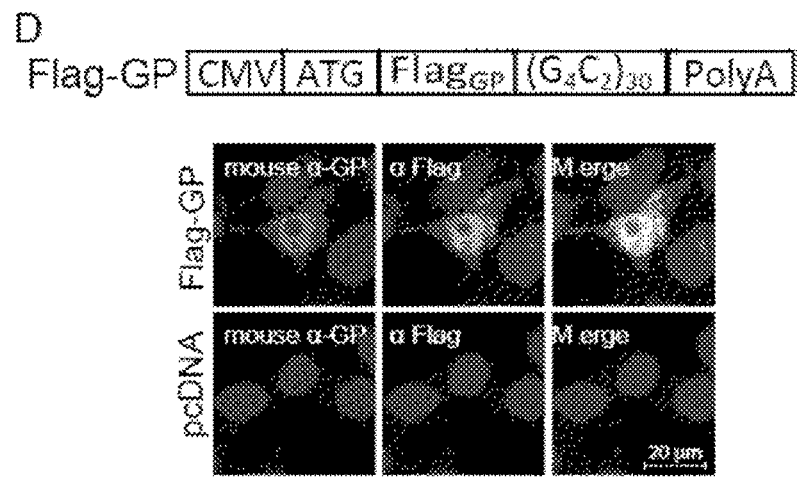
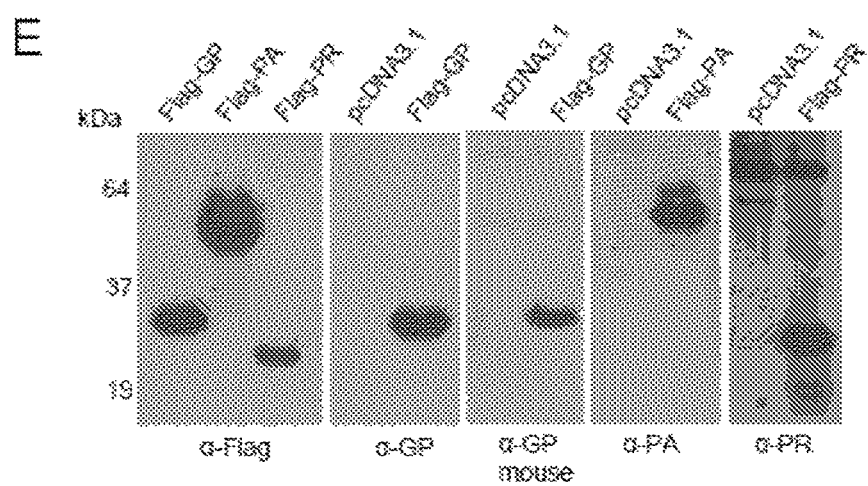
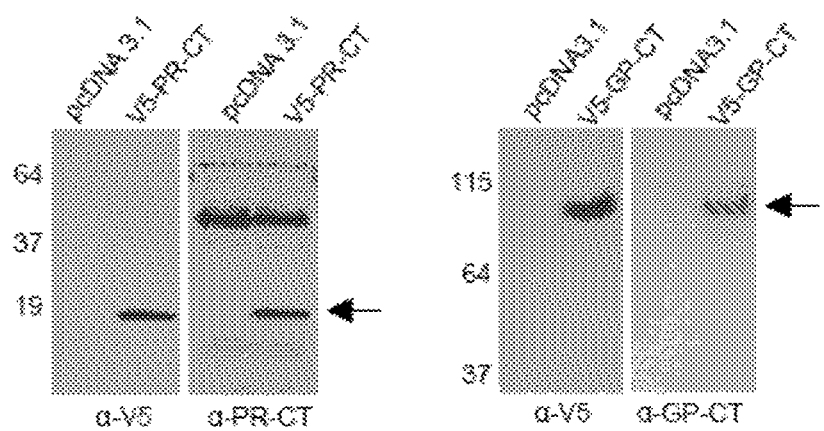
*FIG. 22D-E*

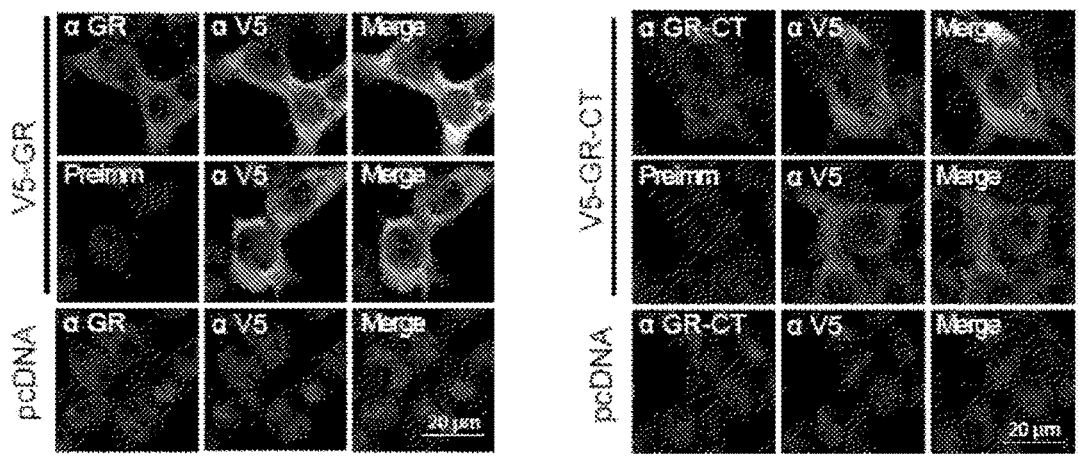
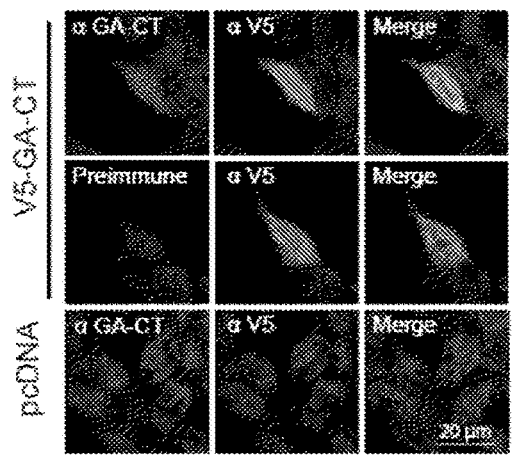
*FIG. 23A-B*

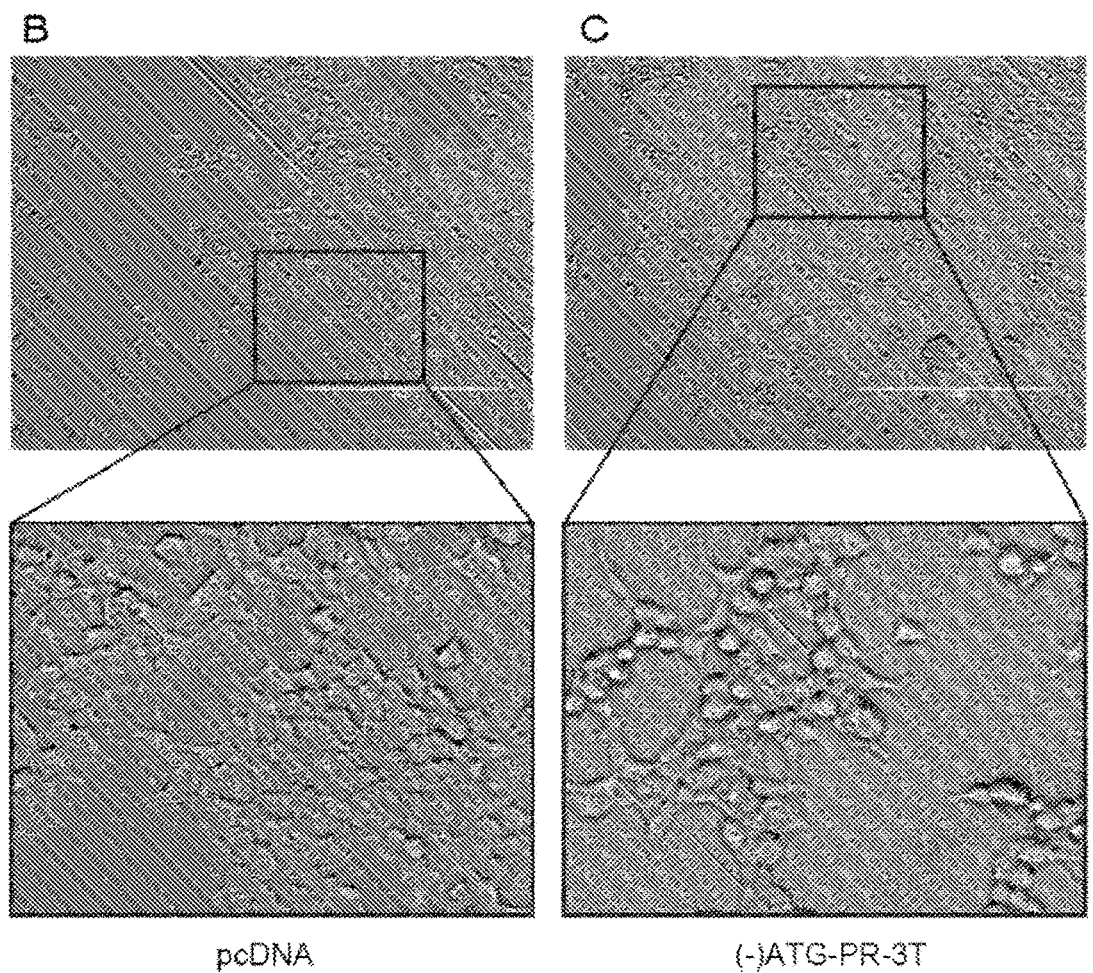
FIG. 26B-C

| Primer Name | Primer Sequence (5' to 3') |
|---|---|
| ASORF-F | AGTCGCTAGAGGCGAAAGC |
| ASORF-R | CGAGTGGGTGAGTGAGGAG |
| LK-ASORF-R | CGACTGGAGCACGAGGACACTGACGAGTGGGTGAGTGAGGAG |
| LK-ASORF-F | CGACTGGAGCACGAGGACACTGAAGTCGCTAGAGGCGAAAGC |
| 1a-F | GCCCACGTAAAAGATGACGC |
| 1a-R | CCTCCTAAACCCACACCTGC |
| LK-1a-R | CGACTGGAGCACGAGGACACTGACCTCCTAAACCCACACCTGC |
| LK-1a-F | CGACTGGAGCACGAGGACACTGAGCCCACGTAAAAGATGACGC |
| LK | CGACTGGAGCACGAGGACACTGA |
| 5'GSP1 | GCTTTCGCCTCTAGCGACT |
| 5'GSP2 | TCTAGCGACTGGTGGAATTGCCT |
| 3'GSP1 | CTGCGGTTGTTTCCCTCCTT |
| 3'GSP2 | TTTCTTGTTCACCCTCAGCGA |
| ACTB3 | CTGGAACGGTGAAGGTGACA |
| ACTB4 | GGGAGAGGACTGGGCCATT |
| 3xTag-Fw | ACGACATCGATTACAAGGACG |
| 3xTag-RV | ATCAGCTTCTGCTCGCTATG |

*FIG. 27*

| Strand | Antigen | ID # | Sequence | Species | IB | IHC | IF |
|---|---|---|---|---|---|---|---|
| AS-G₂C₁ | poly(PA) | H3152 | H2N-APAPAPAPAPAPAPAPACKKKK-amide | Rabbit | Y | Y | Y |
| | PA C-term | H3159 | Ac-CYRLRLFPSLFSSG-OH | Rabbit | Y | Y | Y |
| | poly(PR) | H3150 | Ac-RPRPRPRPRPRPRPRPRC-amide | Rabbit | Y | Y | Y |
| | PR C-term | H3192 | Ac-CRPRPLARDS-OH | Rabbit | Y | Y | Y |
| Both Strands | poly(GP) | H3154 | H2N-GPGPGPGPGPGPGPGPGCKK-amide | Rabbit | Y | Y | Y |
| | poly(GP) | F3M1 | H2N-GPGPGPGPGPGPGPGPGCKK-amide | Mouse | Y | Y | Y |
| S-G₃C₂ | GP C-term | H3157 | Ac-CRRRRWRVGE-OH | Rabbit | Y | Y | Y |
| | poly(GR) | H3148 | Ac-RGRGRGRGRGRGRGRGRC-amide | Rabbit | Y | Y | Y |
| | GR C-term | H3160 | Ac-CRVAVWGSAAGKRRG-OH | Rabbit | Y | Y | Y |
| | GA C-term | H3184 | Ac-CSGRARGRARGGA-amide | Rabbit | Y | Y | Y |

Summary of sense and antisense antibodies including antigen recognized, identification number (ID#), and peptide sequence used for injections in rabbits or mice. Detection of recombinant proteins by various methods is summarized on right. IB=immunoblot, IHC=immunohistochemistry, IF=immunofluorescence, Y=yes, N=no, AS=Antisense, S=Sense.

*FIG. 28*

```
SEQUENCE LISTING

<160> NUMBER OF SEQ ID NOS: 65

<210> SEQ ID NO 1
<211> LENGTH: 31
<212> TYPE: PRT
<213> ORGANISM: Artificial sequence
<220> FEATURE:
<223> OTHER INFORMATION: Synthetic polypeptide

<400> SEQUENCE: 1

Trp Ser Gly Arg Ala Arg Gly Arg Ala Arg Gly Gly Ala Ala Val Ala
1               5                   10                  15

Val Pro Ala Pro Ala Ala Ala Glu Ala Gln Ala Val Ala Ser Gly
            20                  25                  30

<210> SEQ ID NO 2
<211> LENGTH: 34
<212> TYPE: PRT
<213> ORGANISM: Artificial sequence
<220> FEATURE:
<223> OTHER INFORMATION: Synthetic polypeptide

<400> SEQUENCE: 2

Gly Arg Gly Arg Gly Gly Pro Gly Gly Pro Gly Ala Gly Leu Arg
1               5                   10                  15

Leu Arg Cys Leu Arg Pro Arg Arg Arg Arg Arg Trp Arg Val
            20                  25                  30

Gly Glu
```

<210> SEQ ID NO 3
<211> LENGTH: 54
<212> TYPE: PRT
<213> ORGANISM: Artificial sequence
<220> FEATURE:
<223> OTHER INFORMATION: Synthetic polypeptide

<400> SEQUENCE: 3

```
Gly Val Val Gly Ala Gly Pro Gly Ala Gly Pro Gly Arg Gly Cys Gly
1               5                   10                  15

Cys Gly Ala Cys Ala Arg Gly Gly Gly Ala Gly Gly Glu Trp
            20                  25                  30

Val Ser Glu Glu Ala Ala Ser Trp Arg Val Ala Val Trp Gly Ser Ala
        35                  40                  45

Ala Gly Lys Arg Gly
    50
```

<210> SEQ ID NO 4
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 4

```
Pro Ser Ala Arg Leu Leu Ser Ser Arg Ala Cys Tyr Arg Leu Arg Leu
1               5                   10                  15

Phe Pro Ser Leu Phe Ser Ser Gly
            20
```

<210> SEQ ID NO 5
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 5

```
Pro Leu Ala Arg Asp Ser
1               5
```

<210> SEQ ID NO 6
<211> LENGTH: 780
<212> TYPE: DNA
<213> ORGANISM: H. sapiens

<400> SEQUENCE: 6

```
ccccatttcg ctagcctcgt gagaaaacgt catcgcacat agaaaacaga cagacgtaac      60
ctacggtgtc ccgctaggaa agagaggtgc gtcaaacagc acaagttcc gcccacgtaa      120 aagatgacgc ttggtgtgtc agccgtccct gctgcccggt tgcttctctt ttggggcgg      180 ggtctagcaa gagcaggtgt gggtttagga ggtgtgtgtt tttgtttttc ccaccctctc    240
tccccactac ttgctctcac agtactcgct gagggtgaac aagaaaagac ctgataaaga    300
ttaaccagaa gaaaacaagg agggaaacaa ccgcagcctg tagcaagctc tggaactcag    360
gagtcgcgcg ctaggggccg gggccggggc cggggcgtgg tcgggcggg cccgggggcg     420 ggcccggggc ggggctgcgg ttgcggtgcc tgcgcccgcg gcggcggagg cgcaggcggt    480
ggcgagtggg tgagtgagga ggcggcatcc tggcgggtgg ctgtttgggg ttcggctgcc    540
gggaagaggc gcgggtagaa gcgggggctc tcctcagagc tcgacgcatt tttactttcc    600
```

| | |
|---|---|
| ctctcatttc tctgaccgaa gctgggtgtc gggctttcgc tctagcgac tggtggaatt | 660 |
| gcctgcatcc gggccccggg cttcccggcg gcggcggcgg cggcggcggc gcagggacaa | 720 |
| gggatgggga tctggcctct tccttgcttt cccgccctca gtacccgagc tgtctccttc | 780 |

<210> SEQ ID NO 7
<211> LENGTH: 780
<212> TYPE: DNA
<213> ORGANISM: H. sapiens

<400> SEQUENCE: 7

| | |
|---|---|
| gaaggagaca gctcgggtac tgagggcggg aaagcaagga agaggccaga tccccatccc | 60 |
| ttgtccctgc gccgccgccg ccgccgccgc cgccgggaag cccggggccc ggatgcaggc | 120 |
| aattccacca gtcgctagag gcgaaagccc gacacccagc ttcggtcaga gaatgagag | 180 |
| ggaaagtaaa aatgcgtcga gctctgagga gagccccgc ttctaccgc gcctcttccc | 240 |
| ggcagccgaa cccaaacag ccaccgcca ggatgccgcc tcctcactca cccactcgcc | 300 |
| accgcctgcg cctccgccgc cgcgggcgca ggcaccgcaa ccgcagcccc gccccgggcc | 360 |
| cgccccggg cccgccccga ccacgccccg gccccggccc cggccccag cgcgcgactc | 420 |
| ctgagttcca gagcttgcta caggctgcgg ttgtttccct ccttgttttc ttctggttaa | 480 |
| tctttatcag gtcttttctt gttcaccctc agcgagtact gtgagagcaa gtagtgggga | 540 |
| gagagggtgg gaaaaacaaa aacacacacc tcctaaaccc acacctgctc ttgctagacc | 600 |
| ccgcccccaa aagagaagca accgggcagc agggacggct gacacaccaa gcgtcatctt | 660 |
| ttacgtgggc ggaacttgtc gctgtttgac gcacctctct ttcctagcgg gacaccgtag | 720 |
| gttacgtctg tctgttttct atgtgcgatg acgttttctc acgaggctag cgaaatgggg | 780 |

<210> SEQ ID NO 8
<211> LENGTH: 33
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: GA repeats

<400> SEQUENCE: 8

Gly Ala Trp Ser Gly Arg Ala Arg Gly Arg Ala Arg Gly Gly Ala Ala
1               5                   10                  15

Val Ala Val Pro Ala Pro Ala Ala Glu Ala Gln Ala Val Ala Ser
            20                  25                  30

Gly

<210> SEQ ID NO 9
<211> LENGTH: 34
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: AG repeats

<400> SEQUENCE: 9

Ala Gly Ala Trp Ser Gly Arg Ala Arg Gly Arg Ala Arg Gly Gly Ala
1               5                   10                  15

Ala Val Ala Val Pro Ala Pro Ala Ala Glu Ala Gln Ala Val Ala
            20                  25                  30

Ser Gly

<210> SEQ ID NO 10
<211> LENGTH: 36
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: GP repeats

<400> SEQUENCE: 10

Gly Pro Gly Arg Gly Arg Gly Gly Pro Gly Gly Gly Pro Gly Ala Gly
1               5                   10                  15

Leu Arg Leu Arg Cys Leu Arg Pro Arg Arg Arg Arg Arg Arg Arg Trp
            20                  25                  30

Arg Val Gly Glu
        35

<210> SEQ ID NO 11
<211> LENGTH: 37
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: PG repeats

<400> SEQUENCE: 11

Pro Gly Pro Gly Arg Gly Arg Gly Gly Pro Gly Gly Gly Pro Gly Ala
1               5                   10                  15

Gly Leu Arg Leu Arg Cys Leu Arg Pro Arg Arg Arg Arg Arg Arg Arg
            20                  25                  30

Trp Arg Val Gly Glu
        35

<210> SEQ ID NO 12
<211> LENGTH: 56
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: GR repeats

<400> SEQUENCE: 12

Gly Arg Gly Val Val Gly Ala Gly Pro Gly Ala Gly Pro Gly Arg Gly
1               5                   10                  15

Cys Gly Cys Gly Ala Cys Ala Arg Gly Gly Gly Ala Gly Gly Gly
            20                  25                  30

Glu Trp Val Ser Glu Glu Ala Ala Ser Trp Arg Val Ala Val Trp Gly
            35                  40                  45

Ser Ala Ala Gly Lys Arg Arg Gly
    50                  55

<210> SEQ ID NO 13

```
<211> LENGTH: 57
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: RG repeats

<400> SEQUENCE: 13

Arg Gly Arg Gly Val Val Gly Ala Gly Pro Gly Ala Gly Pro Gly Arg
1               5                   10                  15

Gly Cys Gly Cys Gly Ala Cys Ala Arg Gly Gly Gly Ala Gly Gly
            20                  25                  30

Gly Glu Trp Val Ser Glu Glu Ala Ala Ser Trp Arg Val Ala Val Trp
        35                  40                  45

Gly Ser Ala Ala Gly Lys Arg Arg Gly
    50                  55

<210> SEQ ID NO 14
<211> LENGTH: 27
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: AP repeats

<400> SEQUENCE: 14

Ala Pro Ala Pro Ser Ala Arg Leu Leu Ser Ser Arg Ala Cys Tyr Arg
1               5                   10                  15

Leu Arg Leu Phe Pro Ser Leu Phe Ser Ser Gly
            20                  25

<210> SEQ ID NO 15
<211> LENGTH: 26
<212> TYPE: PRT
<213> ORGANISM: Artificial sequence
<220> FEATURE:
<223> OTHER INFORMATION: Synthetic polypeptide

<400> SEQUENCE: 15

Pro Ala Pro Ser Ala Arg Leu Leu Ser Ser Arg Ala Cys Tyr Arg Leu
1               5                   10                  15

Arg Leu Phe Pro Ser Leu Phe Ser Ser Gly
            20                  25

<210> SEQ ID NO 16
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: PR repeats

<400> SEQUENCE: 16

Pro Arg Pro Leu Ala Arg Asp Ser
1               5

<210> SEQ ID NO 17
```

```
<211> LENGTH: 9
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: RP repeats

<400> SEQUENCE: 17

Arg Pro Arg Pro Leu Ala Arg Asp Ser
1               5

<210> SEQ ID NO 18
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 18

Arg Gly Arg Gly Arg Gly Arg Gly Arg Gly Arg Gly Arg Gly Arg Gly
1               5                   10                  15

Arg Cys

<210> SEQ ID NO 19
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 19

Arg Pro Arg Pro Arg Pro Arg Pro Arg Pro Arg Pro Arg Pro Arg Pro
1               5                   10                  15

Arg Cys

<210> SEQ ID NO 20
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 20

Ala Pro Ala Pro Ala Pro Ala Pro Ala Pro Ala Pro Ala Pro Ala Cys
1               5                   10                  15

Lys Lys Lys Lys
            20

<210> SEQ ID NO 21
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 21

Gly Pro Gly Pro Gly Pro Gly Pro Gly Pro Gly Pro Gly Pro Gly Pro
1               5                   10                  15

Gly Cys Lys Lys
            20

<210> SEQ ID NO 22
```

```
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 22

Cys Arg Arg Arg Arg Trp Arg Val Gly Glu
1               5                   10

<210> SEQ ID NO 23
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 23

Cys Tyr Arg Leu Arg Leu Phe Pro Ser Leu Phe Ser Ser Gly
1               5                   10

<210> SEQ ID NO 24
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 24

Cys Arg Val Ala Val Trp Gly Ser Ala Ala Gly Lys Arg Arg Gly
1               5                   10                  15

<210> SEQ ID NO 25
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 25

Cys Arg Pro Arg Pro Leu Ala Arg Asp Ser
1               5                   10

<210> SEQ ID NO 26
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 26

Cys Ser Gly Arg Ala Arg Gly Arg Ala Arg Gly Gly Ala
1               5                   10

<210> SEQ ID NO 27
<211> LENGTH: 32
<212> TYPE: PRT
<213> ORGANISM: Artificial sequence
<220> FEATURE:
<223> OTHER INFORMATION: Synthetic polypeptide

<400> SEQUENCE: 27

Ala Trp Ser Gly Arg Ala Arg Gly Arg Ala Arg Gly Gly Ala Ala Val
1               5                   10                  15

Ala Val Pro Ala Pro Ala Ala Ala Glu Ala Gln Ala Val Ala Ser Gly
            20                  25                  30
```

<210> SEQ ID NO 28
<211> LENGTH: 35
<212> TYPE: PRT
<213> ORGANISM: Artificial sequence
<220> FEATURE:
<223> OTHER INFORMATION: Synthetic polypeptide

<400> SEQUENCE: 28

```
Pro Gly Arg Gly Arg Gly Gly Pro Gly Gly Pro Gly Ala Gly Leu
1               5                   10                  15

Arg Leu Arg Cys Leu Arg Pro Arg Arg Arg Arg Arg Trp Arg
            20                  25                  30

Val Gly Glu
        35
```

<210> SEQ ID NO 29
<211> LENGTH: 55
<212> TYPE: PRT
<213> ORGANISM: Artificial sequence
<220> FEATURE:
<223> OTHER INFORMATION: Synthetic polypeptide

<400> SEQUENCE: 29

```
Arg Gly Val Val Gly Ala Gly Pro Gly Ala Gly Pro Gly Arg Gly Cys
1               5                   10                  15

Gly Cys Gly Ala Cys Ala Arg Gly Gly Gly Ala Gly Gly Gly Glu
            20                  25                  30

Trp Val Ser Glu Glu Ala Ala Ser Trp Arg Val Ala Val Trp Gly Ser
        35                  40                  45

Ala Ala Gly Lys Arg Arg Gly
    50                  55
```

<210> SEQ ID NO 30
<211> LENGTH: 25
<212> TYPE: PRT
<213> ORGANISM: Artificial sequence
<220> FEATURE:
<223> OTHER INFORMATION: Synthetic polypeptide

<400> SEQUENCE: 30

```
Ala Pro Ser Ala Arg Leu Leu Ser Ser Arg Ala Cys Tyr Arg Leu Arg
1               5                   10                  15

Leu Phe Pro Ser Leu Phe Ser Ser Gly
            20                  25
```

<210> SEQ ID NO 31
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 31

```
Arg Pro Leu Ala Arg Asp Ser
1               5
```

<210> SEQ ID NO 32
<211> LENGTH: 99
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (92)..(93)
<223> OTHER INFORMATION: PR repeats

<400> SEQUENCE: 32

Met Gln Ala Ile Pro Pro Val Ala Arg Gly Glu Ser Pro Thr Pro Ser
1               5                   10                  15

Phe Gly Gln Arg Asn Glu Arg Glu Ser Lys Asn Ala Ser Ser Ser Glu
            20                  25                  30

Glu Ser Pro Arg Phe Tyr Pro Arg Leu Phe Pro Ala Ala Glu Pro Gln
        35                  40                  45

Thr Ala Thr Arg Gln Asp Ala Ala Ser Ser Leu Thr His Ser Pro Pro
    50                  55                  60

Pro Ala Pro Pro Pro Arg Ala Gln Ala Pro Gln Pro Gln Pro Arg
65                  70                  75                  80

Pro Gly Pro Ala Pro Gly Pro Ala Pro Thr Thr Pro Arg Pro Leu Ala
                85                  90                  95

Arg Asp Ser

<210> SEQ ID NO 33
<211> LENGTH: 74
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (73)..(74)
<223> OTHER INFORMATION: GP repeats

<400> SEQUENCE: 33

Met Arg Gly Lys Val Lys Met Arg Arg Ala Leu Arg Arg Ala Pro Ala
1               5                   10                  15

Ser Thr Arg Ala Ser Ser Arg Gln Pro Asn Pro Lys Gln Pro Pro Ala
            20                  25                  30

Arg Met Pro Pro Pro His Ser Pro Thr Arg His Arg Leu Arg Leu Arg
        35                  40                  45

Arg Arg Gly Arg Arg His Arg Asn Arg Ser Pro Ala Pro Gly Pro Pro
    50                  55                  60

Pro Gly Pro Pro Arg Pro Arg Pro Gly Pro
65                  70

<210> SEQ ID NO 34
<211> LENGTH: 68
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (67)..(68)
<223> OTHER INFORMATION: GP repeats

<400> SEQUENCE: 34

Met Arg Arg Ala Leu Arg Arg Ala Pro Ala Ser Thr Arg Ala Ser Ser
1               5                   10                  15

Arg Gln Pro Asn Pro Lys Gln Pro Pro Ala Arg Met Pro Pro Pro His
            20                  25                  30

Ser Pro Thr Arg His Arg Leu Arg Leu Arg Arg Arg Gly Arg Arg His
        35                  40                  45

Arg Asn Arg Ser Pro Ala Pro Gly Pro Pro Pro Gly Pro Pro Arg Pro
    50                  55                  60

Arg Pro Gly Pro
65

<210> SEQ ID NO 35
<211> LENGTH: 41
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (40)..(41)
<223> OTHER INFORMATION: GP repeats

<400> SEQUENCE: 35

Met Pro Pro Pro His Ser Pro Thr Arg His Arg Leu Arg Leu Arg Arg
1               5                   10                  15

Arg Gly Arg Arg His Arg Asn Arg Ser Pro Ala Pro Gly Pro Pro Pro
            20                  25                  30

Gly Pro Pro Arg Pro Arg Pro Gly Pro
        35                  40

<210> SEQ ID NO 36
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 36
agtcgctaga ggcgaaagc                                                19

<210> SEQ ID NO 37
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 37
cgagtgggtg agtgaggag                                                19

<210> SEQ ID NO 38
<211> LENGTH: 42
<212> TYPE: DNA
<213> ORGANISM: Artificial sequence
<220> FEATURE:
<223> OTHER INFORMATION: Synthetic polynucleotide

<400> SEQUENCE: 38
cgactggagc acgaggacac tgaagtcgct agaggcgaaa gc                       42

<210> SEQ ID NO 39
<211> LENGTH: 42
<212> TYPE: DNA
<213> ORGANISM: Artificial sequence
<220> FEATURE:
<223> OTHER INFORMATION: Synthetic polynucleotide

<400> SEQUENCE: 39
cgactggagc acgaggacac tgacgagtgg gtgagtgagg ag                       42

<210> SEQ ID NO 40
<211> LENGTH: 23
<212> TYPE: DNA

<213> ORGANISM: Artificial sequence
<220> FEATURE:
<223> OTHER INFORMATION: Synthetic polynucleotide

<400> SEQUENCE: 40
cgactggagc acgaggacac tga                                              23

<210> SEQ ID NO 41
<211> LENGTH: 91
<212> TYPE: PRT
<213> ORGANISM: Artificial sequence
<220> FEATURE:
<223> OTHER INFORMATION: Synthetic polypeptide

<400> SEQUENCE: 41

Met Gln Ala Ile Pro Pro Val Ala Arg Gly Glu Ser Pro Thr Pro Ser
1               5                   10                  15

Phe Gly Gln Arg Asn Glu Arg Glu Ser Lys Asn Ala Ser Ser Ser Glu
            20                  25                  30

Glu Ser Pro Arg Phe Tyr Pro Arg Leu Phe Pro Ala Ala Glu Pro Gln
        35                  40                  45

Thr Ala Thr Arg Gln Asp Ala Ala Ser Ser Leu Thr His Ser Pro Pro
    50                  55                  60

Pro Ala Pro Pro Pro Arg Ala Gln Ala Pro Gln Pro Gln Pro Arg
65                  70                  75                  80

Pro Gly Pro Ala Pro Gly Pro Ala Pro Thr Thr
                85                  90

<210> SEQ ID NO 42
<211> LENGTH: 72
<212> TYPE: PRT
<213> ORGANISM: Artificial sequence
<220> FEATURE:
<223> OTHER INFORMATION: Synthetic polypeptide

<400> SEQUENCE: 42

Met Arg Gly Lys Val Lys Met Arg Arg Ala Leu Arg Ala Pro Ala
1               5                   10                  15

Ser Thr Arg Ala Ser Ser Arg Gln Pro Asn Pro Lys Gln Pro Pro Ala
            20                  25                  30

Arg Met Pro Pro Pro His Ser Pro Thr Arg His Arg Leu Arg Leu Arg
        35                  40                  45

Arg Arg Gly Arg Arg His Arg Asn Arg Ser Pro Ala Pro Gly Pro Pro
    50                  55                  60

Pro Gly Pro Pro Arg Pro Arg Pro
65                  70

<210> SEQ ID NO 43
<211> LENGTH: 66
<212> TYPE: PRT
<213> ORGANISM: Artificial sequence
<220> FEATURE:
<223> OTHER INFORMATION: Synthetic polypeptide

<400> SEQUENCE: 43

Met Arg Arg Ala Leu Arg Arg Ala Pro Ala Ser Thr Arg Ala Ser Ser
1               5                   10                  15

Arg Gln Pro Asn Pro Lys Gln Pro Pro Ala Arg Met Pro Pro Pro His
            20                  25                  30

Ser Pro Thr Arg His Arg Leu Arg Leu Arg Arg Arg Gly Arg Arg His
        35                  40                  45

Arg Asn Arg Ser Pro Ala Pro Gly Pro Pro Pro Gly Pro Pro Arg Pro
        50                  55                  60

Arg Pro
65

<210> SEQ ID NO 44
<211> LENGTH: 39
<212> TYPE: PRT
<213> ORGANISM: Artificial sequence
<220> FEATURE:
<223> OTHER INFORMATION: Synthetic polypeptide

<400> SEQUENCE: 44

Met Pro Pro Pro His Ser Pro Thr Arg His Arg Leu Arg Leu Arg Arg
1               5                   10                  15

Arg Gly Arg Arg His Arg Asn Arg Ser Pro Ala Pro Gly Pro Pro Pro
            20                  25                  30

Gly Pro Pro Arg Pro Arg Pro
        35

<210> SEQ ID NO 45
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 45
gcccacgtaa aagatgacgc                                                   20

<210> SEQ ID NO 46
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 46
cctcctaaac ccacacctgc                                                   20

<210> SEQ ID NO 47
<211> LENGTH: 43
<212> TYPE: DNA
<213> ORGANISM: Artificial sequence
<220> FEATURE:
<223> OTHER INFORMATION: Synthetic polynucleotide

<400> SEQUENCE: 47
cgactggagc acgaggacac tgacctccta aacccacacc tgc                         43

<210> SEQ ID NO 48
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 48
cgactggagc acgaggacac tga                                               23

<210> SEQ ID NO 49
<211> LENGTH: 19
<212> TYPE: DNA
<213> ORGANISM: Artificial sequence

```
<220> FEATURE:
<223> OTHER INFORMATION: Synthetic polynucleotide

<400> SEQUENCE: 49
gctttcgcct ctagcgact                                                 19

<210> SEQ ID NO 50
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 50
tctagcgact ggtggaattg cct                                            23

<210> SEQ ID NO 51
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 51
ctgcggttgt ttccctcctt                                                20

<210> SEQ ID NO 52
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 52
tttcttgttc accctcagcg a                                              21

<210> SEQ ID NO 53
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 53
ctgggaacgg tgaaggtgac a                                              21

<210> SEQ ID NO 54
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 54
gggagaggac tgggccatt                                                 19

<210> SEQ ID NO 55
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 55
acgacatcga ttacaaggac g                                              21
```

<210> SEQ ID NO 56
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 56
atcagcttct gctcgctatg                                               20

<210> SEQ ID NO 57
<211> LENGTH: 106
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (78)..(79)
<223> OTHER INFORMATION: AP repeats

<400> SEQUENCE: 57

Gly Glu Pro Pro Leu Leu Pro Leu Pro Leu Pro Gly Ser Arg Thr Pro
1               5                   10                  15

Asn Ser His Pro Pro Gly Cys Arg Leu Leu Thr His Pro Leu Ala Thr
            20                  25                  30

Ala Cys Ala Ser Ala Ala Ala Gly Ala Gly Thr Ala Thr Ala Ala Pro
        35                  40                  45

Pro Arg Ala Arg Pro Arg Ala Arg Pro Asp His Ala Pro Ala Pro Ala
    50                  55                  60

Pro Ala Pro Ala Pro Ala Pro Ala Pro Ala Pro Ala Pro Ala Pro Pro
65                  70                  75                  80

Ala Pro Ala Ser Ala Arg Leu Leu Ser Ser Arg Ala Cys Tyr Arg Leu
                85                  90                  95

Arg Leu Phe Pro Ser Leu Phe Ser Ser Gly
            100                 105

<210> SEQ ID NO 58
<211> LENGTH: 119
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (108)..(109)
<223> OTHER INFORMATION: PR repeats

<400> SEQUENCE: 58

Met Gln Ala Ile Pro Pro Val Ala Arg Gly Glu Ser Pro Thr Pro Ser
1               5                   10                  15

Phe Gly Gln Arg Asn Glu Arg Glu Ser Lys Asn Ala Ser Ser Ser Glu
            20                  25                  30

Glu Ser Pro Arg Phe Tyr Pro Arg Leu Phe Pro Ala Ala Glu Pro Gln
        35                  40                  45

Thr Ala Thr Arg Gln Asp Ala Ala Ser Ser Leu Thr His Ser Pro Pro
    50                  55                  60

Pro Ala Pro Pro Pro Arg Ala Gln Ala Pro Gln Pro Gln Pro Arg
65                  70                  75                  80

Pro Gly Pro Ala Pro Gly Pro Ala Pro Thr Thr Pro Arg Pro Arg Pro
                85                  90                  95

```
Arg Pro Arg Pro Arg Pro Arg Pro Arg Pro Arg Pro Arg Pro
            100                 105                 110

Arg Pro Leu Ala Arg Asp Ser
        115

<210> SEQ ID NO 59
<211> LENGTH: 94
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (89)..(90)
<223> OTHER INFORMATION: GP repeats

<400> SEQUENCE: 59

Met Arg Gly Lys Val Lys Met Arg Arg Ala Leu Arg Arg Ala Pro Ala
1               5                   10                  15

Ser Thr Arg Ala Ser Ser Arg Gln Pro Asn Pro Lys Gln Pro Pro Ala
            20                  25                  30

Arg Met Pro Pro Pro His Ser Pro Thr Arg His Arg Leu Arg Leu Arg
        35                  40                  45

Arg Arg Gly Arg Arg His Arg Asn Arg Ser Pro Ala Pro Gly Pro Pro
    50                  55                  60

Pro Gly Pro Pro Arg Pro Arg Pro Gly Pro Gly Pro Gly Pro Gly Pro
65                  70                  75                  80

Gly Pro Gly Pro Gly Pro Gly Pro Gly Pro Gly Pro
                85                  90

<210> SEQ ID NO 60
<211> LENGTH: 56
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (17)..(18)
<223> OTHER INFORMATION: GP repeats

<400> SEQUENCE: 60

Gly Pro Gly Pro Gly Pro Gly Pro Gly Pro Gly Pro Gly Pro Gly Pro
1               5                   10                  15

Gly Pro Gly Pro Gly Pro Gly Arg Gly Arg Gly Gly Pro Gly Gly
            20                  25                  30

Pro Gly Ala Gly Leu Arg Leu Arg Cys Leu Arg Pro Arg Arg Arg
        35                  40                  45

Arg Arg Arg Trp Arg Val Gly Glu
    50                  55

<210> SEQ ID NO 61
<211> LENGTH: 98
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (39)..(40)
<223> OTHER INFORMATION: GR repeats

<400> SEQUENCE: 61

Arg Leu Thr Arg Arg Lys Gln Gly Gly Lys Gln Pro Gln Pro Val Ala
```

```
                1               5                  10                 15
            Ser Ser Gly Thr Gln Glu Ser Arg Ala Arg Gly Arg Gly Arg Gly Arg
                                20                  25                 30

Gly Arg Gly Arg Gly Arg Gly Arg Gly Arg Gly Arg Gly Val Val Gly
                        35                  40                 45

Ala Gly Pro Gly Ala Gly Pro Gly Arg Gly Cys Gly Cys Gly Ala Cys
             50                  55                  60

Ala Arg Gly Gly Gly Ala Gly Gly Gly Glu Trp Val Ser Glu Glu
             65                  70                  75                 80

Ala Ala Ser Trp Arg Val Ala Val Trp Gly Ser Ala Ala Gly Lys Arg
                            85                  90                 95

Arg Gly

<210> SEQ ID NO 62
<211> LENGTH: 65
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (29)..(30)
<223> OTHER INFORMATION: GA repeats

<400> SEQUENCE: 62

Gln Ala Leu Glu Leu Arg Ser Arg Ala Leu Gly Ala Gly Ala Gly Ala
             1               5                  10                 15

Gly Ala Gly Ala Gly Ala Gly Ala Gly Ala Gly Ala Gly Ala Gly Ala
                        20                  25                 30

Gly Ala Trp Ser Gly Arg Ala Arg Gly Arg Ala Arg Gly Gly Ala Ala
                    35                  40                  45

Val Ala Val Pro Ala Pro Ala Ala Glu Ala Gln Ala Val Ala Ser
             50                  55                  60

Gly
             65

<210> SEQ ID NO 63
<211> LENGTH: 98334
<212> TYPE: DNA
<213> ORGANISM: H. sapiens
<220> FEATURE:
<221> NAME/KEY: repeat_region
<222> LOCATION: (51933)..(51938)
<223> OTHER INFORMATION: GGGGCC repeats

<400> SEQUENCE: 63
aagcttgata atattatcaa atattagata aatgtaatat tagaagaaaa cttttttgaa      60
aagatatata aaataaattt cattcaaaat ttttatattt aatttaaatt tttaatgaaa    120
atatatctaa gttttgtacg ctttaaatgt aattatgttt gataatttaa tcatttacta    180
ttcgttctct attgctgccc taacaaatta ccatagttca gtggcttaca aaacacaaat    240
ttattatctt accattctgt gagtcaaaat tccaaaatag gtgtcactag gctaaaatga    300
aggactgcat ttcttcctgc aggctccagg agagatctat gtcttactct tttcggcttc    360
taaaggctgc ccacattcct cgactagtgg cgtccctcct tcgtctctaa acccagcaac    420
aacaggttga gtcctcatgt cacatctttc ttacctttct gtcatctcat ctcgctgact    480
gctgctggga aaaattctcc acttttaagg gctatcatga ttagactatg cccactagat    540
aatacaagat ctcagatcct taacttccat cacatctgca aagtcgcttt tgcctcataa    600
```

-continued

```
aagagtctga ggtttagacg ggagatctta aggggctat taatatgcct accataatca      660
ctgagaataa gtacaagtta agattataat agcaatagaa tatacaaacg tgaagctcca      720
aaagaacaac aacaacaaaa aaggtgaaca ggaaaaagaa actgaaaatc tttaaaaagg      780
cagtctgttt aaatctataa aaactggaaa aaatgagag tggacaaata tctggtaagc       840
atgatggact taaaatttgt gactagggca ttacatttt tatattaata taatgaagat       900
tgaattactg atcaaaacaa ttaaaaagca agagaactat tctcatcaaa tctgcaacac      960
gaaaagttca gacaaaattc caacaacttc acattctgaa ctaaatgagg actaattacc     1020
agttcgagca atgagaatat atgaggtcct ccgtttgcac tttgccaggg atctgaaaac     1080
gttgggagta ggtcggcttc accctgaagc cagaccatcg acagccagtt ttccctccct     1140
tctccaccca caggtcttag gccctcatcc ttcccagcct cagaactagt ctccaaagaa     1200
gaggaaagtt agaggagaga gtaaatcgtt gaataggatg aaggagatgt gggaaaaaga     1260
aaaagagagg ctgcaagaga gagggtccca gggataactc tgctcttgga agggtggcca     1320
cagtcatgtg gtcccaagag gcaacaacaa gcttaggaag ccagagaaac cagttacaat     1380
cactgctact cttttcgatt ctgtgttgtt taagaaatat cacccgccag gagttctcca     1440
gaaacatttt ccctgattcc atgtaagtgc tcaaccagtg aatggtaatc ccattttggt     1500
ttagtctgta ccatcccta ttccaaaata aagggaaaaa tggtgggttt atatcttaaa      1560 tttctactt tactaaactc aagggaaata gccaagcaaa aacgaaagct gagactcttg      1620
ctaattatcc tttccataga atgtttgcta aaattccttg tcaaggaagg ataacaaag      1680 ctagtccacg ctctgtatag ggtgtttcca attagttata ctttaaagta taagtattta     1740
acaaaatcta taaattttgt taattatta cttgtagtga aaaatgagcc attctcaagc      1800
aaatcacttt ttattacaca ttccagagaa taaccataaa aggacattta ttatagcaaa     1860
aataaccaca tctggatgga acttcaatca ccagtattta ctaaataaat gcccagaaaa     1920
aaaatagttc atctttaatt tcagtcatca ttaataaag ctgaagtacc tcttcagatc      1980 tttgatcat tttctgttgg attgtttct ttttactgag ttgcaaatgc tctttatata      2040
ttttggatac aaagctttat cacataggca ttttgcaagt atttttcca agttttttta      2100 tcttttcatt tatttaataa tatcttcaa agaacgggaa ttttataatt tttatgaagt      2160
ccatttataa ttttttcttt tatgggttgg tggggttgg gggttgtgtt gtcctaagaa      2220
atcttggctc aacacaaaaa gattagtttc tatattttct tctagaagtt ttatagtacg     2280
atctcagatc catttcagat gatgaataag cacataaaaa aaggatactc atcgttagtc     2340
attagagaaa tgcatattaa aaccataagg aaatactact atatacatat attagatagg     2400
atgaagagca actggaatct catacagtgc tgattgaaat gcaaaatggc aaaacaactt     2460
tagaaaccaa tttggaagca gctgtactga catggaattt tgagctggaa gaatcttaga     2520
aaaagaatac tttaccacct cccccattct cttcaccctg ggaactgtt aaatgaggaa      2580 attgtggttc aaggaggaac ttgtctatat gctttctcag ctttcccgtg gtaattacca     2640
tcttgataat ataacgtaat gtatgtatat gttatcaaat aatataatat cttcatcata     2700
tatttatcat cttcataatg ttagctgtct agtggtaact ttttttgct ctttattgcc      2760 tccctctttt ttccctcttt gttgttttt gtcatacaat tatgatatat gtgtatatat      2820
tctcactgta aagatgtaaa caacacaaag attattgaac aaatcacgaa agtaaccctt     2880
ccttcattct taccctatcc aaccctcatc tcctcagaag aatacaccat tttagttgta     2940
```

```
aatgttttc  tagctctttt  tcaatgtttc  tacctatatg  catgtatgta  taatgtatat   3000
acatacatat  atacatacat  attgatatat  acatatatag  aggtatggtt  ttttaactta   3060
aatggaattg  cattgtggat  attgtcctat  gacttgcttt  caaccaaatt  atatgtcttg   3120
gaaatacata  catatattta  aaaaatatgt  tatgtatatg  taacatacta  tatgtgcata   3180
atatatatta  catagatata  ataaggccta  ggaagaaatt  gtgtgcaacc  tctagtacat   3240
cttcctctat  atctactgta  catacataca  acccattctt  tttttaattt  ttttattttt   3300
ttagacagaa  tcttgctctg  tcgcccaggc  tggagtgcag  tggcacaatc  tcggctcact   3360
gcaagctcca  cctcctgggt  tcacgccatt  ctcctgcctc  agcctcccaa  gtagctggga   3420
atacaggcac  ctgccatcag  gcccagctaa  ttttttttg  tatttttagt  acagatgggg    3480
tttcaccgtg  ttagccagga  tggtctccat  ctcctgacct  cgtgatccgc  ccacctcatc   3540
ctcccaaagt  gctgggattt  acaggcgtga  gccaccgcgc  ccagccacaa  ctcattgcag   3600
agtagtccaa  aatatggatg  gactgtagct  taattactta  ttctcccatt  gatagacact   3660
taggactttt  ctaattttta  taatttaaaa  atatgctgca  attaacaaac  attcttgtgt   3720 atcttttgc  tgtatgtatg  catatttctt  tagtatgggt  tttggaagag  gaatcacaaa    3780
ggaggcatag  aatataaata  ttttattttt  gaaaaataca  gttgtaattt  aataacccac   3840
caaaagactc  taacagttta  gattcacatc  aacagtgtaa  gaacatgtct  gttttactgc   3900
atccttaccc  ccactggtta  taatactttt  aattaacaat  cttatggatg  aagaatacta   3960
tcgcaatgtt  gttttaatgc  attttttccaa  ttactagtga  gattgaacat  taattctttt  4020
attttatgga  tcactggctt  ttctccttct  gtgaactacc  tgttcacatc  ctctgctttt   4080
cagctcttga  gctgttatct  ttttcttatt  gatttatatg  agctctttat  atattcaaga   4140
tgttaatcat  ttgtatttta  tgtatatggc  aatgattttc  ttccaaacca  atgcttgtct   4200
tttatttatt  tatttattta  tttatttatt  tgagaccgag  tctcgctctg  tcgcccaggc   4260
tggagtgcag  tggcgcgatc  tcggctcact  gcaagctccg  cctcccgggt  tcacgccatt   4320
ctcctgcctc  agcctcctga  gtaggtggga  ctacaggcgc  ccgctgccac  acccggctaa   4380 tttttttgtat  ttttagtaga  gacagggttt  caccgtgtta  gccaggatgc  tctctatctc   4440
ctgacctcgt  gatccgcccg  cctcggcctt  ccaaagtggt  cggattacag  gcatgagcca   4500
ccacgcctgg  ccaatgcttg  tcttttatc  tctgtttatg  gcatcttca  tactatggac      4560 atttttattt  ttatttttta  tgttgattta  ttcttgaatt  gtatacatgt  taattatacc   4620
taagttattg  taatacccttt  aaagccaagt  tctacacata  tatttaattt  gctttcccaa  4680
taggtctctg  agggaacaca  tttttcaaa  tcactttgtt  tcatctttt  taggtgttga     4740 tcaattatta  aggagtttga  aataatcatt  taaacggaat  tcttcagatg  aaaacataaa   4800
gacatttatc  gggtcagagc  attggtcggt  tcacatactc  aggatcagtg  gcctgggtgg   4860
gcaggcactg  ggtgaatgga  gagctgcagg  tattggaaga  gagcccagtt  ggatatgtag   4920
tttccaaaga  tcatcaaggc  agacaaccaa  agggaaaccg  tgggaaacac  ctgctttggg   4980
ccatctaaga  tgagatgata  aagtaaggaa  agagttgagc  ccaacacagt  gatagccaat   5040
ctgaaagcgg  gcagaactga  caagaccaaa  caagtaggtg  aactggctgc  aggcagccag   5100
ccaccacagg  gacagcgtgt  actccaggga  caagctcaag  gctataggta  gttagttcaa   5160
ggctactagg  gtgagaagag  caggaactga  gttctatacc  agtgcttctc  aaaactaatg   5220
tgcatcctaa  tcacctggaa  atcttgtaaa  aatgtagatt  ctgattcagt  gagtctgaag   5280
cagagcttaa  gatactacat  gcttaacaag  agcctagttg  atgctgacac  tgctggtccc   5340
```

```
tggagctctc tttgagtagc aggcttctgg aaggcttgtg tcactaagca cagagaagcc    5400
tcacttatca aatctgcacc aaaacaggaa aactaatgtg aagaataatg tgatgcacac    5460
gtcagagcat gaggcagttg ctttgtccct gaggttgcgc tccagatggc ttcctaagat    5520
gcgacaggct gatcttgtgc gtggggtcc cggaggcttg ggccacggga gagacaggac    5580
ctcagaggct gggagacagg cagagacaga agagtgacat cctgctgctt ttgaatttgc    5640
acattctgta gaataataac agcagtaaac tgttacacaa tatctattct cagcatcttg    5700 aagcccttc acatattgtt acttccatta atggggccct ttgctgctat ttctactttt    5760
ctcttcagct atcaacaata tggctttcca cacctccatc agacagtagc cagatgaaat    5820
aaaatgtgcc agaatgaaaa cttgttcatt tgtctacttt ttgccaagac tagacaggca    5880
ggaaattgaa tgtattttta cagaaaaggt tttcaaaact ttttcccctc tgtggctcat    5940
ttaggtaaac taaaaggcat aagacccacc taaaacatgg gttcccgctt tttattggag    6000
aaagaacata gtactttaaa aaatacata aaataataaa aaggaaagac aaagataatg    6060
aaggttgtac atggtaccaa attttgtat cccataataa cacatgagta gatcactact    6120
aagtaggttt tagtgacata taggaaacat taaaatctac agaaatttgc attattttct    6180
gtcaaaaagg atcatttcac agcctttcag ggggaaccca ttgcccacag gaactcatgc    6240
attccatgct ttgaggatca ctagatctaa gaagccttcc ttggaggttc tagcctccaa    6300
cccttatttt agtaaaagaa gctccagttt tatctgtttc taagtcagac taccacacaa    6360
cattgggctt aaagaaaggt ttccagggct aaagcagact ttgaggatta ctaattccga    6420
gttaaatttc tgtgtattat ctctggattt gacttattca cactggacta tcactcataa    6480
atatacataa tacagagtta actatttaaa tttataaaga gagtattttc ctttttatg    6540 agcaaaacat gctgccaact acttggacca catactgatc cataaatact gacagctttg    6600
taattggaaa taataaatac acactaatga agcatctcaa aagggaagag ccacaggtaa    6660
tctgagtgat taggcattca tgttaggtta ggctttgatc attgttttta atcgcaattt    6720
cattgcagtg catctataaa tccatgtcca gaagtatgaa gtggttctat agtaagaata    6780
agatgctaca gataatgcga ctaaataaga cactataggt aatgacacag attcaagtct    6840
tattgttgat gggaagaggt caataatgga tgatataata tactacagca atgagaatta    6900
ttgaatgttt tccagactca cttgtataat tggccataac agcaaacaaa aaacaggttc    6960
tgatagcaaa atgatataca gtactaacaa aggtgaatct tgaggtgaac cttctcttta    7020
taagtttaaa tagtttaccc ccgacctttt cccatagtag aacagcctaa aaagtatctt    7080
tcagtagaat gctagtgctt atgaggtttt cttaagatat cattttcaa ttaaaattta    7140 tttcacaaaa gactcacatc cttgccagcc ttcagggtga gtgttgattc aggctgtgtc    7200
caacggcaac gatgagtgaa cttctcaccc tcagaatcac atgagcattc ctgagatgtt    7260
ttatcagagt gataccaact tcattattag aatattgagt ccctatttcc tatattcaat    7320
gtcctttcaa gccctaactt tgtccgggtt gaaggcaaag atccaaataa tcacatttgt    7380
ctttgataac tgaaactggg agaactggga ctgtctcaag agttctacgt gactgtaggt    7440
tgcaagtact gtggttgcat ctccaaatat taaccaatcc cagtgacaat tcaatggggt    7500
ctcctgaacc atgatcctca tgtctccagt gaaggaaatg ggcaagggg attcaaaaat    7560 ccctttttgga ggaataggaa acttctgctt tccttcattt cataacattt gcgatggaac    7620
aaaggctttt ttagaatgga gcaaccagat cctttttttgg gggaatcagc ttaaatgtcc    7680
```

```
cttcttctca tactacttttt atctatgtga tcctattctt ttctgttgtg gattgaatca   7740
tgtccctcaa aaagattgaa tttagagtgt gctctaaatt caatgtggag aaatttggac   7800
acagaggcag acacacaggg agaaccccgt gtgacaatgg aggaagagga tgcatttatg   7860
ctgccacaag ccaaggaaca ccaaagattg tcagcagcca ccagaagcta ggataaaggc   7920
atggcacatc actccctctg agcccccaaa aggagccaag actgctaata ctctgatctc   7980
ggacttctgg cctgaaacag tgagagaata aggttctgtt gtttcaagct acccagcttg   8040
cggtattttg tcacagaagc acaaggaatc aagtacattt tctttctcag cacttgtgat   8100
aatttgattt tttctttact cagtggttgt ttcacaccta tgtccccatc agactgtaag   8160
cttaaagaga cctggatctg gtctgtcttc accactgttg attcattacc agcacagtgc   8220
ctggcccatg gtcactgaat aaacgtttgt tgagagaatg aatgtgctta accagaagta   8280
ctattgacct attaggccaa gttcaaggtg cctaacagct cagctgtgaa ggatacctct   8340
cctttcagtc ctctgttaca tatgtccctg atagatgtgt tatttgtatc tcctcctggc   8400
cctcaagttt gtttgagggc aggacccttt tttgtatatc tgtagagctt cgtagtacct   8460
aaatactact ttgcatatat aataaagttt cgataaatat tcattaaata aagaaataaa   8520
tgaaatgact aagtttctta agatgttaca actagattga agatatttag ctcattattt   8580
aacaagaaaa ctatggttaa ttatggtgtc ctgtgtgaaa atggttatag tttgttttt    8640
aattaatata agcatgtatg tgcattatca gtatacacaa tttgtggtat gagtgttttg   8700
tgtccctgca cacagaccac ggaaatcctg agaaacaaac tgccaccccca gagcaggtgc  8760
ctaacacaga gactttttaat ccttaaagtt tttctataac taagcaatgt tttttcaaat  8820
gcaataacac tgatatgcag acatattgat tgtccactca caaagccatt cctcaatatc   8880
attacaacat gcctctttga atgtcattaa aaatagatgt ctcattttc taggacaagt    8940
tggctgaagt tctgcttgaa aactggtaat agaaaataca atttctcaac ccgctttggc   9000
cttttaattc tgttctacaa ccttgccagt tcactttcaa agtcaaggga tgcatcttgc   9060
aaaaccatga catctttga gtaactcctt ctgttcttaa cacatattcc caggagctta    9120
ataaatattg tttttgcaac ttgtttagtg gcaaaataat gagtccttgg tgtatgctta   9180
tcctctgctt tgctattaga aagatatat tcagactgtt ttaaacaaat taattcaagg    9240
gcagggaaca gtcctaaaac ctgttaaaat tcaaatactt ggtcactgta tgtgcagcat   9300
gtgtgttcta gaaagtccta ttattttaaa atataaattg aatcttgttg agaaattaat   9360
gtcatatgaa tatattaata actgaaatgc tgccaagttt acaaaaagcc ctcaatgaaa   9420
ctgtgacctt gtatagacaa gggcctgtgg agggacattt ttaaaccatc tctttttta    9480
tttcctcatg agatctacaa tgtaagtgca ttaaagttga tgaatgaatt gcagtgcaac   9540
ttttcctgcc tcttttgcct ttcatttgtc tatatttcaa gcttcactga agtgatagat   9600
tttgggcttt gccacattgt cctctgattg cttccctctg ctcctccttt tcctagtgaa   9660
tctttgtttt actggtggaa aaatctacat cttttgtatct tggcatttta ctttcacatt   9720
atctcataga ttttatttca agttgctata aagttatcaa cttttatttt taactaatat   9780
tatttttaac aattagaaaa ttgttgacca ggtaattcca gcactttggg aagctgaagc   9840
gggaggatca cgtgagccca ggagctcgag accagcctgg gcaatgcaag gagactgtct   9900
ctacaaaata taaaaataca ttagccaggt ttggcggtgc atgcctgggg tccagctatt   9960
caggaagctg aggtgggagg atcacttgag ctggagaggt tgaggctgca gtgagcagtg   10020
atcgcaccac tgcactccag tctgggtgac agagggagac cctatctcga aaaaaggaa    10080
```

```
aagaagagga ttttgctggc aagatggctg aataggaata gctccgttct gcagctccca    10140
gtgagatcaa tgcagaaggc aggtgatttc tgcatttcca acagaggtac ctggttcatc    10200
tcactgggac tggttggacg gtgggtgcag cccatggagg gtgagcagaa gtagggtggg    10260
gcgttgcctc actcaggaag tgcaaggggt ccctcttcta gccaagtgaa gccgtcaggg    10320
actgtgccat aagaacagtg cactctggtc caggcttttc ccacagtctt tgcaacccac    10380
agaccaggag ataacaagcg gtgcctatgc caccagggcc cggggtttca agcacaaaac    10440
tgggtggcca tttgggcaga catcaagcta gctgcaggag ttttattttt catacccag     10500 tggtgcctgg aacgccagtg agacagaacc gttcactccc ctggataagg ggcagaatcc    10560
agggagccaa gtggtctggc ttggcgggtc ccacacccac ggcgcccagc aagctaagat    10620
ccactggctt gaaactctcg cttccagcac agcagtctga ggtccacctg agacgcccgg    10680
gcttggtgtg gggaggggca tccaccattg ctgaggcttg agtaggcggt tttaccctca    10740
cggtgtaaac aaagctgcct ggaaggtcca gctgggcaca gcccaccaca gctcaccaag    10800
gccgctgtgg ccagagtgcc cctctggatt cctcctctct gggcaaggca tctctgaaaa    10860
aaaggcagca gcgccagtca gagacttata gataaaaccc ccatcaccct gggacagagc    10920
acctcaggga aggagtggct gtgggtgcag tttcagcaga tttaaacgtt cctgcctgac    10980
agctctgaga gagcaacaga tctcccagca cagcgttcaa gctctgttaa agatcagact    11040
gcctcctcaa gtgggtccct gactcccatg tctcctgatt gagagacacc tcccagtagg    11100
ggctgacaaa cacctcataa aggagagctc cagctggcat ctggcaggtg cccctctggg    11160
acgaagcttc cagaggaagg aacaggcagc aatctttgct gttctgcagt ctcagctgat    11220
gatacccagt caaacaggtc ctggagtgga cctccagcaa actccagcag acctgcagca    11280
gaggggcctg accgttagaa ggaaaattaa caaatagaaa ggaatagtat caacatcaac    11340
aaaaaggacg tccactcaga gaccccatcc aaaagtcacc aacatcaaag accaaaggta    11400
gataaatcca caaagatggg gagaaaccag tgcaaaaaag tctgaaaatt ccaaaaacca    11460
gaacgcctct tctcctccaa agaatcacca ctcctcacta gcaaggtaac aaaactggac    11520
agagaatgag tttgacaaat tcacagaatt agtgttcaga aggtgggcaa taacaaactc    11580
ctccaagcta acggagcatg caaggaagct aagaaccttg aaaaaagtta gagcaattgc    11640
taactagaat aaccagttta gagaagaaca taaatgacct gatggagctg aaaaacacag    11700
cacgagaact ttgtgaagca tacacaagta tcaatagcca aatcgatcac gtggaagaaa    11760
ggatatcaga gattaaagat caacttaatg aaataaattg agaagacaag attagagaaa    11820
aaagaatgaa aaggaatgaa caaagcctcc aagcaatata ggactatgtg aaaagaccaa    11880
atctatgttt gactggtgta ccagaaagtg acggggagca tggaaccaag ctggaaaaca    11940
ctcttcagga tattatccag gagaacgtcc ccaacctagc aaaacaggcc aacatttaaa    12000
ttcaagaaat acagacaaca ccacaaagat actcctcgag aagaccaacc caagacaca     12060 taatcgtcag attcaccaag gttgaaatga agaaaaaaat gttaagggca gccagagaga    12120
aaggtcaggt tacccacaaa ggaagcccat cagactaaca gcagatctct ctgcagaaac    12180
cctacaagcc agaagagagt gggggccaat attcaacatt tttaaagaaa agaattttca    12240
acccagaatt tcatgtccag ccaaactaag cttcataagt gaaggagaaa taaaatcctt    12300
tacagacaac caaatgctga gagattttgt caacagcaag cgtgccttac aagagctcct    12360
gaaggaagca ctaaacgtgg aaaggaacaa tcggtaccag ccactgcaaa agcacaccaa    12420
```

```
attttaaagt ccattgacac tatgaaaaaa ctgcatcaac taacaggcaa ataaccagc   12480 tagcatcata atgacaggat caaattaacc ttaattaagt tagccttaaa tgtaaacggg   12540
ctaaatgccc cagttaaaag acacagactg gccacctgta taaagagtaa agacccatca   12600
gtgtgctata ttcaggagac ccatctcaca tgaaaagaca cacataggct caaaataaag   12660
ggatggagga atatttacta agcaaatggg aagcaaagaa aacaaaaagc aggggttgca   12720
atcctagtct ctgataaaac agactttaaa ccaacaaaga tcaaaataga caaacaaggg   12780
cattacataa tggtaaaggg atcaatgcaa caagaacagc taactatcct aaatatatat   12840
gcacccaata caggagcacc cagattcata aagcaagttc ttagagacct acaaagagac   12900
ttagactccc acacaataat aatgggagac tttaacactc cactgtcaat attagacaga   12960
tcaatgagat aggaaattaa caaggatact caggacttga actcagttct ggatcaagtg   13020
gtcctaatag atacctacag aactctccac cccaaatcaa cagaatttac attcttctca   13080
gcaccacatc gcacttattc taaaattcac cacatagttg gaagtaaaac actcctcagc   13140
aaatgcaaaa gaacggaaat cataacagtc tcttagacca cagtgcagtc aaattagaac   13200
tcaggattaa gaaactcact caaaaccgca caactacatg gaaactgaac ctgttcctga   13260
atgactactg ggtaaataat gaaatgaagg gcaaaataaa gaagttcttt gaaaccaatg   13320
acaacaaaca cacaatgtac cagaatctct gggacacatt taaagcagtg ttaagaggga   13380
aatttatagc actagatgcc caaaaagaa agcagaaaag atctaaaatc gacaccctag   13440
catcacaatt aaaagaacta gagaagcaag agcaaacaaa ttcaaaagct agcagaagac   13500
aataaataag atcagagcag aactgaagag gagagagaca tgaaaaaccc ttcaaaaaaa   13560
tcaatgaatc caggagctgg tttttttgaag agattgacaa aacagataga ccactagcca   13620
gacaataaag aaggagagaa gaatcaaata gatgcaataa aaaatgataa aggggggtatc   13680 accactgatc ccacagaaat acaaactacc atcagagaga atactataaa caactacaca   13740
aataaactag aaaatctaga agaaatggat aaattcctgg acacatacac cctcccaagt   13800
ctaaaccagg aagaagttga atccctgaat agaccaataa caagttctga aattcaggta   13860
gtaattaata gcctaccaac caaaaaaagt ccaggaccag acagattcac agccgaattc   13920
tatcagaggt acaaacagga gctggtacca ttccttctga aactattcca atagaaaaag   13980
agggaatcct ccctaactga ttgtatgaag ccagcatcat cgtgatacca aaacctggca   14040
gagacacaac aaaaaaaga aattttcagg ccaatatccc tgatgaacat tgatgcgaaa   14100
atcctcaata aaatactggc aagcggaatc cagcagcgca tcaaaaagct tatccgccag   14160
gatcaagtcg gcttcatctc tgggatgcaa ggctggttca acatacgcaa atcaataaac   14220
catcattctc agcaaattat cacaagaaca gaaaaccaaa caccgcatgt tctcactcat   14280
aagagggagt tgaacaatga gaacacgtgg acccaaggag gggaacatca catactgcgg   14340
cctgtcgagg gatttggggt tgagggagtg atagcattag gagaaatacc taatgtaggt   14400
aacaggttga tgggtgcagc aaaccacaat gcgatgtgta tacctaccta acaaacctgc   14460
acgttctgca catgcactcc agaacttaaa gtataataat aaaaggcgct gcctcaggat   14520
gtaaagtgta acaaggggc tggggtgggc agcgtgggcc tctgagacct ttggttgccc   14580
gtgtccgcag ctcgccccgc agccggctcc acaatggtcc gctccgtttg ccacgtgcgg   14640
attcgggttc cagactgaag gctgcgtgtt ctctgccgcc cacagcccaa gtttattgtg   14700
gcaaccgccg gagcagcctt ccccgctgtg gaggagcctg gggctacccc tcagcggtat   14760
ttggggctgg tcctggggga gctaagcagg gttgtggcag cactgcctga aagtgtgaga   14820
```

```
ccagactcta atccttatgg ttttccatgg gagttggtga tatgtgcagc tgtacatgga   14880
ttttttgctg ttctcttttt ttgtgtggag aagttttaga tcggttggga gtcggcttta   14940
tgtgggaaga gaaaaaaagc ttgctgtaat gctttctgga ctaattgaag aaaagcataa   15000
actacttgaa aaatttagcc atgttcaaaa agagtatgaa ggctatgaag tagagtcatc   15060
tttaaagaat gccagctttg agaaggaggc aacctgtgaa aagctaaaca ggtccaattc   15120
tgaacttgag gatgaaatac tctgtctaga aaaagagtta aaataagaga aatctaaaca   15180
ttctgaacaa ggtgaattga tggtggatat ttgcaaaagg atacagtctc tagaagatga   15240
gtcaaaatcc ctcaaatgac aagtagctga agccaaaatg aacttgacga tatttcaaat   15300
gaatgaagaa cgactgaaga tagcaataaa agatgctttg aatgaaaatt ctcaactcca   15360
ggaaaacgag agacagcttt tgcaagaagc tgaggtatgg aaagaacaag tgagtgaact   15420
taataaacag aaaataacat ttgaagactc caaagtacat gcagaacaag ttctaaatga   15480
taaagaaaat cacatcaaga ctctgaacgc ttgctaaaaa tgaaagatca ggctgctatg   15540
cttggagaag acataacgga tgatggtaac ttggaattag aaatgaacag tgaatcggaa   15600
aatggtgctt acttagataa tcctccgaaa ggagctctga agaaactgat ttatgctgct   15660
aagttaaatg cttctttaaa aaccttacaa ggagaaagaa accaaattta tagtcagtta   15720
tctgaagttg ataaaggaag agcttacaga gcatattaaa aatcttcaga ctgaacaagc   15780
atctttgcag tcagaaaaca cacattttga aagtgagaat cagaagcttc aacaaaaact   15840
taaagtaatg attgaatttt atcaagaaaa tgaaatgaaa ctccagagga aattaacagt   15900
agatgaaatt accggttaga aaggaagaa aaactttcta aagtacacga aagatcagc   15960 cgtgccactg aagagttgga gacctataga aagtgagcca aagatcttga agaagagttg   16020
gcgagaacta ttcattctta tcaaggatgg attatttccc acgagaaaaa agcacataat   16080
aattggttgg cagcttggac tgctgaaaga aacctcaatg gtttaaggaa agaaagtgct   16140
cacaacagac aaaaattaac tgaagcagag tttaaatttg aacttttaga aaaagatcct   16200
tatgcacttc atgttccaaa tacagcattt ggcagagagc attccccata tggtccctca   16260
ccactgggtc ggccttcatc ctaaacaaga gcttttctct gagggcccac tgagactctc   16320
atctttgcta acaggaggag gaggaagagg ctcaagaggt ccagggaatc ctctggacca   16380
tcagattacc aatgaaagag gagaatcaag atgtgacagg ttaaccaatc ctcacagggc   16440
ttctctgaca ctgggtccct gtcacctcca tgggaacagg accgtaggat gatgtttctt   16500
ccaccaggac aatcatatcc tgattcagct cttcctccac aaaggcaaga cagatttat   16560 tctaattctg gcacactgtc tggaccagca gaactcagaa ggtttaatat gacttctttg   16620
gataaagtgg atgggtcaat gctttcagaa atggaatcca gcagaaatga taccaaagat   16680
gaccttggta atttaaatgt gcctgattca tctctccctg ctgaaaatga agcaactggc   16740
ccttactttt ctcctccacc tcttgctcca atcagaggtc cattgttttcc ggggataca   16800 aggagcctgt tcatgagaag aggacctcct ttcccccac ctcctccagg aaccatgttt   16860
ggagcttctc aagattattt tccaccaagg gatttcccag atccaccaca tgctccattt   16920
gcaatgaaaa atgtctatcc agcgaggcgt ttcctcctta ccttccccca aaacctggat   16980
ttttccccat aaaccccaca ttctgaaggt agaagtgagt tccctgcagg gctgattctg   17040
ccttcaaatg agcctgctac tgaacatcca gaaccacagc aagaaacctg acaatatttt   17100
tgctctcttc aaaagtaatt ttgactgatc tcattttcag tttaagtaac tgctgttact   17160
```

```
taagtgatta cacttttgct cccactgaag cttaatggaa ttataattct caggatagtg   17220
ttttctaaat aaagatgatt taaatatgaa tcttatgagt aaattattc cattttatgt    17280 tattctggat agtataacta ttttaatttg ataaactaat ccacgattat ataaacaata   17340
atgggagttt tatatatgta atcttgcagg tagggaggct ttaaattata aaggttgtgt   17400
ctttatgcca agaactgtat taactgtggt tgtagacaaa tgtgaaagta attttatgct   17460
tcattaaata aattttagtt gatttttttt taaaaaaaga aaatggttaa tctatcattt   17520
aggtgcatca tcagttgttt aaccattctc tcttactgaa cattgggttg tttaaaaagt   17580
gttgttattt ttgaatcatg gttcagtgaa caattttgga cacataactt tttatctgat   17640
gagttatttc ctaaggatcc agctcagaaa ctcagcacat aaacctaata agaaaaaaac   17700
aatttgaagt ggctaacctc ttatcccaat aaaaatgttg tatttatgtt tggatttaga   17760
tgcctttcag tggtcatacc ttcacctaac ttttatggat tctacttta acatgtagag    17820 tgactgttta aatcacctaa actcactgag ttttaagttc cttttattc aacaagactg    17880 gattgtatgt tccagctcct caaacttagt taccaaccac catcctagag aagtgaattc   17940
acatgaggcc tgtccagaag aacaatctcc ctttcagtgt cctcatgcat gcagtgacca   18000
gagaccaacc ttgataaatt atggaaaaag tacagcacat tctggaagag ccatgaaaga   18060
tccagatcat ctggtgctgg ataagaatat taatggacag gctgggcgcg gtggctcacg   18120
cctgtaatcc tagcactttg ggaggccgag gcgggcggaa catgaggtca ggagatcgag   18180
accatcctgg ctaacacggt gaaacccgt ctctactgaa aatacaaaa attagccggg     18240 catggtggcg ggcgcctgta gtcccagcta cacgagaggc tgaggcagga gaatggcgtg   18300
aacccgggag gcagagcttg tagtgagccc agatggcgcc attgcacttc agcctgggcg   18360
acagagtgag actccgtttc aaaaaaaaaa aaaaagaat attaatggac aaaaagatta    18420
atgaaagaac atattgaagc atccaattac ctggtgtctg ctcaaatgag gaatcggtga   18480
gataggtcag ttagcagtca agatttataa aagagacgat ggccttggga ggggctgccc   18540
tactcgactt tttaatggct agaagctatt aagggctaag ccagaaccct tcagtatggt   18600
tcagtgagga tcccaatttg gggtccaaaa gtaaatgaca actcccagga accattaaga   18660
ataaaaatca tggagcatta ctgagaattt atgttatcta agtctgagga aaattaatgt   18720
taaggaagct ttcaaaagtc taatatttac accgaattcc agggcaccat gctctaagac   18780
aaagcactct ggtcctgccc ctctcctttc ctcatgtttt ttggttcttg ggatccttaa   18840
gggtcaatgt tattcttaaa atacagagca tcctggaaac taaaaaagtg gaagatattc   18900
aaattctaat gaatgtactg gcagtattgt agatcatgga gtataacata aagacaagaa   18960
tccctagcct cttccaccat actttgtaat ggtaaggaga aaggatagaa ttttgagaag   19020
tctgggaaga caatgtatga taacatctgg agaagctctg cataagttac ttttgttcag   19080
gcttaagaaa aattctagct tgcccctgca ctgtcatcag gtatcatgaa agtaaataaa   19140 accttttaaag attcttcaag ccagcagact tctatcttct ctatactatc ctgtgatcct   19200
aaactcttaa cagttactac gtataatttc cctacatttg ctactagtat tttatcatac   19260
acaatattac actcaatatt tcaaaagtgg atgattcatc tcccgaagag actgcaaaat   19320
tcatgagtta agatttgaga atactatttt agacaagatt tagtcagatt ttagagagtt   19380
agaaacctgt aacaattctc taacaatact gcttctcctt ttgtgtatta aggaattttt   19440
gtctatcaaa gatagtacga ggtagaccag aagataactt gccttcaaaa tgtctggaat   19500
gtaaaatggc aacagtagta tttggggact tcgtagggga tggccaatat acacccattc   19560
```

```
ttagaggtac tgatgatata atgtataaga caaaatcaag tggtctccat caccatataa    19620
tgtttaaaat ggcaaagagg gagcagaaca aacacccttt gcaaatctct tcatagaatc    19680
taccgtaata aacttgtact tgcttaaagt gtgtctcttc agtggtctta ttaccactac    19740
tttgggaaa atgaggctgc ttaaaagatt aacagacatt acattttaca tatctgtggc     19800
agagaaaaca ctatgtattc accaaaccac ttcttttcct tcccagtcac tcgggaagag    19860
gtcatttctt tgtccccttt catctaattg aggtgccgtg actacttcta gacaggcaat    19920
gtgagcagaa ggtatgcacg ccacgtatag gcctggtctt caaaaatccc tcagatatga    19980
tcttcttctc tcgtctcttt catggacaaa ctacaggcca tgtaataagg atggtggggt    20040
tccaaactga aagagcctgg atttctgatt tactgttttg agaagagttc accagggaaa    20100
cagcctggaa atacgcacag gaaaatatgc acaggaccct gtgtgagcaa gatataaaga    20160
tctattacat ggtgccatta aggtgagagt attgtgctta tagtatccag cattaattat    20220
cctcactact acaacttctt tgtatccatc atgtggaaaa gtagagtatt taataaatga    20280
ttattgagtt tattacccttt tttatattcc aatcattgct aattgtacgt tacctcattt    20340
caaggtaaag gtgaccaagg gctaaagcag tgctatccaa accaagccag acatcaaaat    20400
cacacaaaac cttttgaaaa tacaactttg aagatgccat tcacatagat atttattcag    20460
tgggttttca aatggaaccc tggaatctac agtctttaac aaggcttccc aagttattct    20520
gatatacagc aggcaaatct gagaaccact ggacaagaag aaaataaagg ctatatcttt    20580
cgacaacaaa gacaatgcct taaacataga atgtattcaa ttaaagcttg tagaaagata    20640
ggtttgtgaa caggcacagg gactagcctc gagcaaatta ataagggcag caatgttttt    20700
cactgaaacc attattcccc ctatttt att tcttctgggg ctctgtgttt cctttctcct    20760
atcaaaatcc attctaaggt tggaggttgg gggtatctct tgcctactcc atacagcaag    20820
gaataaaatt agtatttctc gaactatctg tgacagcaga cccattgtag gccagtactt    20880
ttgtaaaatg caataaaaat taacttctag agaatgaaat tttaaaatca cagacattca    20940
aaatacaaat tccaattttt ttattattaa ctgtaagaaa tttaaaatta aatctcaata    21000
aataaaatta aagcaaacat aagatagaaa aaaataagca ttatggattg gcccagtctg    21060
caaactgtat acactttgcc aaacatgggc ataaattact aagaagcaaa atcttccatc    21120
tgtaaacatt tccatttcca ttgacaatat gtgtgaggga aaggagggat gcttctgttt    21180
tagaatgcca ggcgtcagct aacaagtgac aaatacgtat tgagactgag atctccccag    21240
cctctcagta gtcagcaaga acatgttgag gcctctgttt ttgactaaaa aattggccag    21300
tgcatgggca acatgcatag gtcctgaatg aaaaaaatag cagcagcaga aatttaaaag    21360
aattttcaca gctaggccac agtaaattct caagcccttc atcagaagcc actgtggggc    21420
ctcatttatg cctttgtttt tattaaattg gatgtgatct taagattctt ctgtcaaaat    21480
tccactagca tgtgaaggca ccaaaagttt aaaatgtaaa attaacccaa gttaagctat    21540
tccattatta agcaatagca gatatatttg ttattatatg agaagaaagt taacagggag    21600
ctaagattga tgttactgat aagaaacaga aacaagactt taaaattaaa taaatgaatt    21660
atttatttaa taagaaccaa ttgacagatt ctcgataaag actgtaagat gtcttaaaac    21720
attaggtgta tggagataac atttgtaact ttgacaattt atatgatgag aaaaatcaag    21780
gaatgttatt gtttattggc agagttctag aattacaatt ccatcattct gttttgggga    21840
agtttccctt gaagtaaatg ataacagggc ttgaaatagt acacctcagc attttgttta    21900
```

```
taaaactgtg gaataggtaa ggtttgtatt gtaactgaac ccaggttcag ctgcttgctg   21960
ctctaaagct agacataaga gaggaaggtt ggtgggagga aaagcgattt taatcggaga   22020
agcagcaaac caagaagatg gtgaacaata gtcacagaac catcttaaat tttaaaattt   22080
accatagagt gttcaaagga aaacttggta tgggaggcat gcaggagggg tgcaggggc    22140 ggggtctgtg tgtcttgttc caatggctat ctcagatagt cacccatctg gaggtctagt   22200
tggtattatt ttgaattcag cccagtggtg gtggactgtc agtgactcct cgctaagcag   22260
gaggattctg cactcagggc tccatgcatg gtttgtttca agattggcct ctggaatttc   22320
tcaagcaaga acataattaa ataagcaggc attgccagag gggagtgtct ggaaaggaaa   22380
ggaatgaaga gatgaaagga aagtgggtgg ttaaactata tttttaaaac tgaggttccc   22440
agttatagta tgtttcgcac gctcccccca ttttagcacc cctgacagaa tttagtaatc   22500
tcctcatctt gtcctctact tcaggtcccc tatctgtcct tgtactctcc agggtttcct   22560
tttcttcttc acgaccttcc ttccctgcaa ttttataagc tattcctatc ccagtgattt   22620
agtttcagct tataaaactg tgtctttgcc attgtaatca aattgaaggg cctctgcttc   22680
atggttggat tctgtgacca ggagactctt acgaggagtt ggccaggtct ctgttaggaa   22740
agcaaaaaag aacaatggag gcaattatcc cattgatttc agctataaat cctattttgc   22800
ctgaattgtc tgaacgatga gtattctgtg aaaatgctgc tctctagtgc aatagaactg   22860
caaataatgc acatctattt cttataatct catccaacat acccacagag attcagatct   22920
aacaaaacag aggtgatttg gttattgaat cataatataa atatggggaa gaggagggaa   22980
atttcaagcc tgaggaaact gtagtaggag taagtatgct gtgtttaaga ggtcacagat   23040
aaaattaata ttaccaatcc atcaataggc aattactaat agcttactac acacacagga   23100
ataaaatgtg aagacagagg aagtgtaaaa tggagccgcc aactctacgg agttgtttgc   23160
aatttggtct ggtagaaagc tatgaaataa ggaagtacat gattgagagc tagagaatgt   23220
ggcacaggct ctgaacccgg accgttcaat gtagtaagct ctagccacac tggacacttg   23280
caatgtggct tgtccaaact gacatgtgct ttaagtataa aatataatcc agatttctaa   23340
gacttcaaaa aaaatggaaa tatctcatta ataatcttaa gtttattaca ggtagaaatg   23400
atagattaaa taaactatat tgtcaaaatt catttgatct gtttctacag tataacaaac   23460
ttacttgtgt ggtttgcatt ttatttctac tggataacat ggctttaaaa atggtatttt   23520
agaggaagga aagcttggta gagaatggac taatccggat ccctggaaga aatggacctt   23580
gaatgggtct tgatgacttg gagaggcaga gagagaaaaa gaaaagtcaa acataggggaa  23640 ttggttgata aaatgaaggt gaggggagaa ggaacagagg gaggagaaga tccagtttga   23700
gggatattac agcgagcagc ctgagaaaga aggataagaa aggagagaaa aaatgcaagg   23760
gaagtaaccc ttcaaagcca gtcagaagtt tctgggttcc tcagcagcca gaaaagaagc   23820
cgttgaaaag atctgagtaa cggagattct ggacgaaaac tgaagttatg gaagggaagt   23880
ttagacatgg gttattaaac gctttagcgc attagaagtt tcttatgtaa tcactaaatt   23940
cagatcctga aataatgcca caagaactat acagctcagc cacccaattc aataagaagt   24000
tacagcacag tctcacacat atccaattaa ccttggcctt tagtcaacat ctgggttctt   24060
tttgtcattt tcaaatacta tcacccagag gtgctatgat ttatattggg gaggggatta   24120
aaagaaaata agtaagttgg tgataagaaa aagcttcag atgattccat ctgaattaac    24180
agccctcttt agttgtctag gaagaggat gcttttctt gaaagtgctt tgaaatgatg      24240
atgtgcttgt tagtaaacat caattatttt caaatcgtaa tgtttgcaag tttgtcttcc   24300
```

```
tgtagctcac cctttatgta ggtccagaat atgattgtca caaatatctg ggtgagcaag  24360
actatgaaat gtggtcataa agtaagtgat tatttctaaa ctcatctttg tcactcgtag  24420
tgcttcacaa agcacctttt cctggactac aattcatttt aattgatccc atcagcacta  24480
tatctgtatc ctgagtgact tcacaatacc ctctatttca agagaaacca atcaggttat  24540
gggtttgtta gtaataaaaa ttaccaagga gcagtttgtg gatggtaaaa gcaatgcaaa  24600
ttctaaagag aagtcataag agcaataata agcatcctcc tcacttcttg gaagtgaaca  24660
attccaagct ccctgaagca acacttaacc tatcatatta aacagtaatg gacaaatatt  24720
agaaatgttg atgtcagctt tcagaatctg tgggcatcaa aacatcactt aagttctccg  24780
aagtattctc tgtcaagttt ccttctacag tattcttttc ctactaggac agagccttaa  24840
gccctagaag aataattttg cttgtgtgtt aattatttgt ttactggttc attccagagt  24900
gtgagctgga aaaaggggga agtgtcataa atagttttttt atggcccatg gttttcaac  24960 tacgtcacta ttggtagcag tttccactgc aggatctatt tgcaaagcct aggaaattag  25020
cattaagcaa gctgctagga agacttcaac agtaactagg ccacaggcct cacacatttt  25080
tcctccaccc cagcctcctc tggagagtac ttgctaaacc tctgtgacac ataatgaagc  25140
aaagaaagtg atagaacaac agaattacac gggcagatcc ttgtttcttc ttctctctct  25200
aaagaattcc ttggactgaa aagcagttta ttttggagga gtgagaaagt ggtgacagaa  25260
ttagaagggc ctgggagggc ttcattttag gagacagttt taggctgaaa agagatttca  25320
tgagtgtgat ttacctgagg tgacttttgg gggctcttat aaaaaggaag ttcatgctga  25380
atgggaggtg gcttctgaga tgcagattct ggtgagctaa gagggctcgg taaagaggag  25440
gcaggagtta agtagcgtga actatgcagt agcagccttc ttccccccctt gcttggggca  25500 ggtcatcaca acccttctca ataaaggggt ccaggaacca ctaggaataa atgggcattt  25560
gcacttcagg tgaaacccat ttgtcataac tgcttggact ttaagcttac aaataaaaag  25620
aaccacatat ttcccttttgc agcttgattt agttaatgtc atttttgagaa agaaagaaga  25680 cattgttatc ccgtcccttt ttttttttttt tttttttttt tatgaagaga ctgggactca  25740
gagaagtcaa gtgatttttcc cagaaccaga aaacacagaa gtagcagagc tgagatgact  25800
actccggtct tctgattcca aattccaaat tcattcttct aagcgatttc ccaaaacggg  25860
aaatgggttt atcttctatt tatgggaagt gatagtggta ttctatttag agaacttata  25920
taaaatctta cttttaaaata aataatattt caaaaagtaa gcttaattta aagaaaataa  25980
tcaagaaagt ctggtatatt tttacaaata taccaaatga ccttgctcta aaatacatct  26040
actttccagc aagccaaagt gaaacaattt gaaataagtg gcatttactg accactccct  26100
aaagttcaca caaagagagt agtactctaa cttaaatata caaggtgaag aaatagctta  26160
ctcagcctgt tgggcttcct cttctacact cttgggaaat gccctccgtg ttaaccaaga  26220
attctcaggc cttggaggga gttttccatt ctcagtaaac tgagattgca gttgcgaaa  26280 ttaagaggta tctgtccagc acttcattcc cttaaggtca ggatctgtgc ttttaataat  26340
gacaattagc taacatatac aattaagcca tgcaaatgaa gtaagagaaa gctagaggag  26400
aaattcagga gccagttgcc tttttccagac atccttgtaca aatagtgttc aaaggactaa  26460
ttcaaaagat gggattcttc gcttgaaccc aggaggtgga gtttgcagtg agcggagatc  26520
gctccactgc actccagcct gggtgacaaa gtgagacccc atccaaaaaa aaaaaaaaa  26580 aaaaaaaaaa aagatgggat tcttttttaa aaaataaatt ttactgcgta tttttaaggt  26640
```

```
atacaacgtg atgttataag atggatatag atagtgaaaa ggtaactgta gtgaagcaaa    26700
ttaacatatt catcatctca catagttatc ttttatttgt tttgttttga tgggattttt    26760
aagatagtag aaaggaatgg tagacaataa acatttgagg gaaagtgggg ctttgtagaa    26820
ctcctaaaat gacagcacgc acaaatgtcc ccattatgtc taaagggtaa ctcgttccta    26880
cttctaggga cagctgaggg acatcaatgt aaatttctaa atgacttcct gaactttta     26940 tttttatttt ttgtattttt agaggaaatt ataataacat caagccacct ctggaccata    27000
tcgctgctga tatcatcagc aaatggcact attcctaaat cctaagatgc acttttccct    27060
tcacatttca acatttgtga aactcgattg tacctacacc tgattttata tacaatgcag    27120
cctttccttt tcttttgtca ttgcatctta cgcctgattt ctccttggaa ttgagtaaat    27180
ataatgctta catgtgttaa taagaattga ggtcactcat aattttgaa atatgccacc     27240 aaatataagc ctttctacat attgttgact ttgaagtcat ttcttttttt aactactaaa    27300
caataacact ttttgttgag aaaaattgca tatgaacaag agaccaagca ggtagagaga    27360
aaaaaacttt taataatcaa gagaatgtta ctgtgtccca aaggctaaag tcaccttact    27420
atcaagagag aaggacagga acagagagaa ccaggtaaat tacgaattga aaattccatg    27480
gttcatttat cttattttt aataattcca tttgtgtgat tgtgttgacc acaaggtcat     27540
aatgttactc ttcatactga cttctcatgt aaattataaa taagttttta tgctaatgat    27600
ttatggagta agctattcat cttccgaca gagagttacc tacaaagaaa taattattct     27660
acctctgaga tgaaatatca tgaaaggagt ggtttccaga tattttgact tttaaaagct    27720
taaagaatat atgtagtata aaattctaaa gcaggcaaaa ttaatccttt tagcaatcaa    27780
gatagcggct acttttggtg agaaggacaa ggtagtgata gagaagggc tcagggtct     27840 ttcctgaaga cagtgaggtg ggcaatggta ttttccttga cctggatggt gattaaacag    27900
atgtgtttac tttgtgataa ttgactaggc tgtgcaccta tgaactgcat acttttccat    27960
atatgtactg tattcttata cttaaaaaga agttaaaaa taaatgcaac agatatagga    28020
cttcctatat tactcgttga ccaaaaaaat ggattcattt ttctttcagg taaaacgtac    28080
tagtggtttt aatattatat tgaccaggga gtaaatgttt accttaggaa ccttaatctt    28140
gatgttctcc aaagtcatta tctgttcttt ctgattatca gaatagagta tatctctata    28200
taaatgaaaa tttctggtca ttctcaaaaa ataacactaa gcatgaaaat cagaaatatt    28260
gatcttgttt tgtaatgatg tttctattga tgtgaagtag tttctagtag agttgctgtc    28320
ctaacacaca aatgaaattg cactgttttgg aagacacaac tgtgaatgac ttgcttcagt   28380
aaggaatttc caacatgatg gtttagggat agaggtgctc gattcctctg tctccggtta    28440
cccaggttat tgaggacagg gaggtcaata agtaatgccc tcctcccacc catagcacaa    28500
aacagagcgg ggttcagaga ataggtaagg ctttggccag ggtgttgagg agacttacat    28560
ccctgggaac cagtcagaat gggggcgctg aaaacaatgt tttaaattct agcacccagc    28620
aacatatgtg tgaagattaa atgtactcgt gctaaattca cttgctccat tactgaattt    28680
gggtggtgtc tgttaaagat gggaacaaag gcattcaggt cctggtatct tctaccactc    28740
ccagcatgaa cagactcatg tcagtgggta agggatggta tttcccgaga aggctttgaa    28800
ctcttgtagt gggtcaaata atggccccc acttaaaaat gttcatgtcc aaatccctgg     28860
aagctgtgaa aagggggtttt tgcacatgta attaagtcaa agatattgaa attagatcat    28920
cctggattac ataggtgggc cctacatta atgacaagta tcctcataac agaagaggag    28980
aaggtgatgt gagatttgga gcagcagaga ttggagtgat gtggccacca atcaaggaaa   29040
```

```
ccaaggactt ccagcagcca ccagaagctg gaagaggcaa ggaaggactc ttccctaaag  29100
cctttaaagg agcacagccc tactaacacc ttgcttttgg gctctggccc gcaaaactgt  29160
gaaaggatac attgctgtta tttgaagcca cagttcgtag taaatttatt acagcagccc  29220
tagaaactga tacaactcct aaatacaccc ttagcaacac tgctcaacaa gaagtaggca  29280
atttcctcct gactgaaaaa tactgatact gttatgggat ccttgggggt gttgcttttc  29340
tgtccagaaa cctctgtggc ggtggcacct ttgcatgagt tttgctcggg tccactgggc  29400
ccactcatcc tggcaggctg cgctcagctg acactactgg cgtggatccc atgcctccaa  29460
agagactgga gcgaagcggt gagggatgtg tgaggaagtg agcgtggggt ctggcacaca  29520
gtcaggctca atggctgcta cagcgggatg ggcagcttca ggtgctggca cgggtgctgg  29580
ctcactgcaa ggctgtggct gcaccaagca gcgcagcaac ggaacgcatt ggtgcctgga  29640
aacttggaga ctccaggaac ctcagggctc caaaaggcaa atcacagccc tagcttcggg  29700
agctcccagg tctgggctgc caaagggctg cagctcttct ctcctctctc tctcttcgct  29760
cctctccctt tctctcttca ctcctccctc tttctctctt cactcctcct gtcgcctatg  29820
aacagcgaat tcaaccttcc agttttcaga ctaggaatgc tggagttgtc cttgattact  29880
ctgaattgtt cactccgcat atgggcactg aggatacgtt gatgaactac acagacaaaa  29940
aggatagaaa ttcctgtcaa gactacattc aatagggatg aagcaggcaa taatgaataa  30000
acatactaag ttgaatatga ctatttaaat atatataaca catgactt gtataatgtt  30060 aaatatttta agttttttaa attcttccct tcatagattt tacattatag tagaagaggc  30120 attttgttg ttgttctttt tgttttggat tcagagggta aatgtgcggg gttgttacat  30180
gggtatattg cataatgctg atgatggtcc catcacccag gtggtaaaca tagtacgtaa  30240
taggtgaatt tttagcccgt gcttccctct cccatctagt cgtcctgagt gtttatcgtt  30300
gctacgttta tgtcaatgtg tattcaatat ttagctccca cttataattg agaatatgca  30360
gtatttcgtt ttttgttctc gtgttaattt gtttaggata atggcctaca aagaacatga  30420
tttcattatt tttatggaca tgtagtattt catggtgtat atgtaccacg gtttctttat  30480
acaatcccac tgttgatggg cacctaggtt gattctattg ctgttgtgaa tagggctgca  30540
atgaacatac aagtgcatgt atcttttttgg taacaaaaat tttatatttg gattacccag  30600
tagaattgct gggttgaata atagttttgg tttaagttct ctgagaaatc tccaaactgc  30660
tttccacagt agctgaacta atttacattt ccactagcag tgtataagcg ttctcttttc  30720
tccacaatct tttcaccagc atctgttatg ttttggcttt ttaatagcct tttgatgact  30780
gtgaaatggt atctcactgt ggtttggatt tccatttctc taatgattag tgaatgttga  30840 gcatttttt catatgttta ttggccgttt gtatgtcttc ttttgataag cgtctgttca  30900
tgtcctttac acattttcaa ttaaaatatt tgttttttgc ttgctgattt aagttctttg  30960
tatattctgg aaattagatc tttgtcagat gcatagtttg caaatatttt ctcccattct  31020
gtagcctgtt tactctgttg gtaatttctt ttgctgtaca gaaactcttt aattaggtcc  31080
cacttgccta tttttagttt tgttgcaatt attctctgga acttagccat aaattgtttg  31140
ccaaagccaa cgtggagaag gatatttttct aggttttctt ctaggatttt atagtttaag  31200
ttttacattt aaatctttaa tccatcttga gttaattttt gtatatgttg agaagcagga  31260
gtctaatttc attcttctgc atagggctag ccattatctt ggcaccattt attgaataga  31320
gagtcctttc cttattgctt atttctgtca attttgttga atatcagatc gtcgtaggtg  31380
```

```
tatgggtcca tttctgggtt ttctattctg ttctatttgt ctctgtgtct gttttttgtac   31440 cagaaccatg ctgcttggtt actgtagcct tttagtatag tttgaagttg ggtaatgtga   31500
tgtctctggc ttcgttcttt ttgcttagga ttgctttggc tattcaggct ccttttttggt  31560 tccatatgaa ttttagaata tttttctgat tctgtgaaaa atgacttgat attttgctag   31620
ggatagcatt ggagtggtaa cttgctttgg acagtgtggc cattttaatg atattgatta   31680
ttccaatcca tgagcatgga gtattttttat atttattcag tcatcttgat ttctttcagc  31740
agtgttttgt agttcaccct gtagaacatt tcacttccat ggttagatgt attcctatttt 31800 tgtggctatt gtaaatggca ttgtattttt tttatttgg ccctaaacta gaatgttatt    31860
ggtgtataga attgctactg attttttgtac attgattttg tatccttaaa ctttactgaa  31920
gttatttatc agttctagga gacttttgga gaagtctttta gggttttcta tgtatgaaat  31980
catatcatca gcaaagagag acagtttgac ttcttcttct ttttggatgc catttatttc   32040
tttctcttgc ctagttgctc tgactaggac ttccagggca atgctgaata ggagtggtga   32100
gagtgggcat ccttgtcttg ttccagtact caagagaaat gcttccagca tttacctgtt   32160
tagtatgatg ttggctgtgg tttgtcatag gtggatctta ttattctaag gtatattcct   32220
ttgatgccta gcctgtcgag ggttttttaat catgaatgga tattgaattt tattgaaggt  32280
tttttctgaa actattgaga tgatcatatg gttttttgttt tttcattctg tttatgtggt  32340
gaatcacact tattgatttg ttatgttgaa ccagccttgc atcccaggaa taaagcctac   32400
ttgattgttg tgaattaact ttttgatgtg cttcttgatt tagtttgctc atattttgtt   32460
gaggattttc gtgtttatgt taatcagaga tattgtcctg aagttttctt ttttcattgt   32520
gtctctggca gattttgata tcaggatgat gctggcattg tagaatgagt tagggaggag   32580
cccctctcct taatattatg gaatagtttc agtaagatta ctatcagttc ttctttgtat   32640
gcttggtaga attcagttgt gaatccatct ggtccagggc taaatttggt tggtaggttt   32700
tttattactg attcaattttt ggaacttgtt ataggtctgt tcaagttttc acttccgtcc   32760
tggttcaatc ttgggaggtt gtatgttttcc aggaatttat ccatttcctc tagatttcct   32820
actttgtgtg catagaggtg ttcataacgg tctctgaaaa tctttggcat ttctgtggga   32880
ttggtcgtaa tgtcattttt gtcatttctt gtgcttttttg gaacttctgt ctgttttttcc 32940 tcgttttttct agctagcagt ctattagtct tgtttattct tatgaaaaac caactctttg   33000
tttcactaac attttatgga cttttgcatc tcaattttat ttagtcatta tctgattttta  33060 gttatgtctt ttcctctgct agctgtgaga ttgaattgtg ctctttttttt ctagttcctc   33120 tagtgttatg ttagattgtt tagttgagat cttttctaacc tcttgatgaa ggcattttag   33180
cactataaac tttcctctta acactgctttt tgctacatcc caaagatttt ggaaagttgt   33240 gtctctatttt tcattaattt caaataattt ttttgatttct gccttaattt cattgttcac   33300
ccaacagtta ttcgggagca tgtggcttaa tttccatgct tttgtgtagt tttgagagat  33360
cttcttggta ttgatttcta ttgttatttc actatgattt gagagtggcc tttgtatgat   33420
tttaattttt tttaattat tgagacttgc tttatgactg agcatgtggg gcaatcttag    33480
aatacgttcc atgtgcatat gagaagaatg tgtgttctgt cattgttggc ttgagtatcc   33540
tagagaggtc tattaggtcc aactggtcaa gtgtcaagtt taattccaga attccttcgt    33600
cagttttctg cctcagtgat ctgtctaatg ctatcagtgg agtgataaag cccccactaa   33660
tattgtgctg ccatctacgt tttattgtag gccaataatt tgtttttatga atctgagtgc   33720 tccagtgttg ggtgcatata tgtttagaat agttaagtct ttttgttcaa ttgaaccttt    33780
```

```
tatcatttta taatgcccctt ctttgtcctt cctgattgtt gttggtttaa agtatgtttt    33840
aatctgattt aagggtagca actcctgctc ttttttgttt ttcatttgca tggtagatct    33900
ttcttcattc tttcactttg agcctgtgag tgtcattcat gtaggatgca tcttctgaaa    33960
acagcagaca gttgtgtctt gtctttttat ccagcttacc actttatgca ttttaaaggg    34020
agagtgtaga ctgtttacat ttagggttag cattgacatg tgagattttg ctcctgtcat    34080
tgtgttgttt agctggttgt tttgtagact tcattgtgta ataagtgtat ttttattggt    34140
agcaggtttc gtctttcatt tccatgttta gcaatcactt acggatttcc tgtaagaatc    34200
atctggtggt aatgaatctc cttggtgctt gcttgtctga gaaggattgt atttctcctt    34260
cacttatgaa actcagtttg gtgggatatg agttcttggt tgaaatttat tttctttaat    34320
aatgctgaaa atataggccc ccccatatct tctggcttgt aaggtttctg ctgacagaac    34380
tgttgctggc ctgatgaggt tctttttgta ggtgacctga cctttctcac tagctgcctt    34440
aacaattttt tcttttgcat tgaccttggt gaatctgatg actatgtgac ttggcaatgg    34500
ttgtcttgta tagtgtctca caggagttct ctgtatttct tgaatttgta tgcccacctc    34560
tctggtgaga taggggaaat tttcatggac tgcatcctca gatgtatgtt ctaagttgct    34620
tactctcttt ctcaggaatg actgtgagtc atagacttgg tctctttaca taacctcata    34680
aatcttgaag gttttgttca tgtttaaat tcttttttct ttattttgt ccaaccaagt    34740
tgattcaaat aactggtctt caaactctga gattctttcc tcagcttggt ctgttctgct    34800
gttaatgcct ctgactatat tatgaaattt ttgaagttga tccctcaatt tctgaagttc    34860
agttttgttc tttcttaaaa tagctatttc atctttaagc tctttgatca tttttctgga    34920
ttccttgagt tccttgtatt gggtttcaat gatctcctgg atcttgatgt acttccttgc    34980
catccagatt ctgaattcta tgtatgtcat ttgagtcatt ttaatctggt taaaatcctt    35040
tgctggagga cttgtgtgtt tgtctggagg taaggagaca ccagcttttt tgaattgcta    35100
gagttcttga gatgactctt taacatatga gggctggtgt tccattaaca atagtgtaca    35160
ttgagtatag tcagttggct tcattctgag tgctttcaaa gggccaaagc tctgtacagc    35220
atctttattt gtggctagat ttttgctta ggtttcacag gtgctgtata ttggaaaaat    35280
gttttggtg ttgtcatttg gggtgcaatc cagtaggtga tgcttaagag tggtagctgg    35340
cagataggct cttactcagt ccacagctct tttgtatttt ggtgcagtcc tcagtagtgc    35400
tctgtggtgg tagggagaga tgaccccctc accagataca ttcctgggcc ttgggggagc    35460
cctctcttat tactggcact gcacctgcat ttcatttatt aggtgtcctg ggctgcaggg    35520
tgccctcagg cagaggctgc ggctggaaaa tagaccatac ccttccctgg ctggccctgc    35580
acaaggaggc acaccctgtt cctgagccag tccatgaacc cagctgtctc accctctca    35640
gtgttctgag agtaggggat cccccactgc ttgagcacca tgagcccctc ctggctacag    35700
gcagtggggg taggtatagt ctctcaaccc actgtccaac tgatttccag ggtaacagag    35760
agctgtgcct gcccacagag ttcaggcaga ggccaggcca ttgtgctgga agctgatgct    35820
aagccttgtc tgatgatggg gagtgaagca atgtaacggc tccctaactg tggcttctct    35880
cagggctatg gcagctggca tgagactgct ccaggtccaa ggcctgtggg acttcctgtg    35940
gacttgagtt ttgcctctgc aaacactcca gcaactctct atgtcagtct agaggcccag    36000
ggacacggat caggtattgg gatgaagggg ttctccagtt cccaggattt cacaggtccc    36060
tgtggaaagt gaggatcccc caggggctct cactcactca cccttctct atgttgggga    36120
```

```
gcttcccctg gctccatgcc catcttgggt ggccagctgc ccagcttcac tcttccctgt    36180
tctctgtgtc ccctcactcc cttaattgtc ctgatatcgt tccttaggtg atctacttgc    36240
agaggcagtg tttactcgcc acttgttttc tctctgtgag agtagcacac actagctgct    36300
actcatctag catcttgaat tcttcccatc tgaaaaagtt tcaactgcaa tcacagttaa    36360
agaaatacaa aaacaatagc actctaagtt acaacttctc acctatagaa ttcaaaaaca    36420
tccaaatgat taactaaaca tttgtttggt agatctgtgg gaaaacatga attccttgtg    36480
aattactgga gaaaatgaaa atgatgcaac acttatggaa gaaaatttgg ggattttttgg   36540 ggggagggg aacaatatat ttaaaactat aaatgcattt atcctagcaa ttctatgaat    36600
ggggatttat cttagggtac acctgcacac ttaggaaata atgtatgcag tcattcatta   36660
cagaattgtt tgtaatagca acaacctgaa aagcaactca tatatccatc catcacacag   36720
ggactggttt catgactacg gttcatgaat actctgcagc ccttagaaag aatgaggaag   36780
tggccgggca cggtggctca tgcctgtaat cccagcactt tgggaggccg aggcgggtgg   36840
atcacgaggt caggagatca agaccatcct ggctaacacg gtgaaacccc gtctctacta   36900
aaaacaatac aaaaaaatta gccaggcagg cgcctatagt cccagctatt cgggaggctg   36960
aggccggaga atggcatgaa cccgggaggc agagcttgca gtgagccgag ataacgccac   37020
tgcactccat ccagcctggg cgacagagcg agactccgtc aaaaaaaaaa aaaaagagga   37080
agttctctat gcgctgacat ggaaggaaga cagatggttg aatgaaaaaa gtacataatt   37140
agccataaag tgtaagactt tttgtctaaa aagaagggt gatataattg catatttata   37200
ttttcttcca tttatattaa gagataataa aggtacacaa attggctaga ataaagtggg   37260
ttcctataaa gggtaagagt aattgagtgg atgaagacta gggttaggga tagatttctc   37320
agtgtattca ttttaatata tgtattcatt ttatatatgt actaattttt atatatgtat   37380
ttattttata ttttgatttt cttaacataa atatattatt ccttcataaa attaaacttg   37440 atacatttt gattactaga tatgtagaaa gcattatgtt cagtaccaca gtaatacttt    37500
caaaccagct acaattagta tttatgagca tctatgtgcc agacattgtg ttctgctttg   37560
gttggtgggg gtagaggagg aaaggaaacc atggcttaca taggagtgga agtcttgtct   37620
ttcactttgc acctctctcc ttcagaccta gcataaatat gaccttaggg gaggcagaac   37680
acatatgata aagagataac tagcaagaga cataatagta gctaaataaa tactgaagga   37740
aaaattcagg aagaggtagg aaggatatgc ctcatcactt ccacctgtta agaaaaactt   37800
tagacattct tgccaatatt ccttattgcc tgtcttttga acaaatgcca ttatcactag   37860
agtgaaatga tatttcattg tagttttgat ttgcatttct ctcatgatcg gtgatgttga   37920 gcacctttt atatacctgt ttgccatttg tatgtcttct cttgaaaaat gtctattcag   37980
atctttgccc atttttaaat ggcgtaatac atttttttcct attgagttgt ttgagttctt   38040
tatatattct ggttattaat cccttgtcag atgaataatt tgcaaatatt ttctcccatt   38100
ctgaggatta ccagaggctc agaggggtaa tggtggtggg ggagaataaa aatggttaat   38160
gagtacaaaa atatagatag gagtaataag atctagtatc tgatagcaca acagggtaat   38220
tacagccaac aaaaatttat tgtgcatttc aaaataacta agagtataat tggaatgtct   38280
gtaacacaaa gaagcaataa atgcttgagg tgatgtgagg ggatggatat ctaatttacc   38340
ttgatgtgat tattacatat tgtatgcctg catcaaaata gctcatgtat cttataagta   38400
tatacaccta ttatgtaccc attaaatttt ttaagaactt taaacaaatc aaatttaaca   38460
gagtttaatt gggcaaagaa tgatttgagg atcaggcaac ccccagaaac agaagaggtt   38520
```

```
caaagcaact cagtgctgtc acatggttgg agaggattta tgggcagaaa agggaaagag   38580
agatacagaa aatggaagtg aggtacacaa acagctggat tggttacagc ttgccatttg   38640
cgttatttga acataatctg aacagttggc tgtctttgct tgaccaaaac ttggtgtttg   38700
gtacaagagc agattacagt ctatttacac atccagttag tttacagttc actatacacg   38760
aagaagaaac ctttaagcag aacttaaaat atgcaaagag gaagctttaa gttaaactta   38820
atttaacaca cccaattatc aaaaaatgag tagctctgca aaagtggatt ttcctggtca   38880
tctttggtac ttccttaaaa aagagaaaag tagtactcac gataaaaaaa aaaagtcct   38940 caagtcttta ttttattcct ttccaattta aaatgttaca tcatctgagg aaggtttttc   39000
cctttgaccg ctttcataga catttcttct gcatgggttg ccagaatca  aagagtaat   39060 tgtaactttc tgttcttgtc ctacagttac aaagcggttt cactttgtaa atgctctttg   39120
gatggcagga accaagcagc catgaaaaga ggagttacac ctttaaagga gtcattccat   39180
catgactctc aggactggaa catggaatac ctgaatggcc tctttggcac agataggcca   39240
cccttgaaag gtgttccaag ctaggaactc actaccactg ttacatcgat gcaactctgt   39300
gagaagtttt tatctggtga tggaaaatct catctcttca acacactgac tactaccagt   39360
ctcagaaccc tgtaaacaag attcattcat ctcaaattgg gttaaagcag tcaccctgcc   39420
ttacattagt ttggaataag gatgtgggga tggtggtaga ggaggggagt ggatgatgat   39480 tttttattg  ttatttgatt ctaaagaaac ttctatacat tttgcattta aataattat   39540 gtttttaaca atgtttggat taattcaaaa taggatatta tatcctatta tattaaatat   39600
actatttaat catcttgttg accaaatgca acttaaacat gtaaaatggt aaatagcata   39660
ataattgtct tctaagcctg cactataaag tatttcagtg gcctcattat taaaggacca   39720
aggtgcccaa agaaacaaaa tttagtaatc ataaacaaga gacaaaccta cttctttttcc   39780 cccagagttc tggccacatt gaaataaggt gtttgaatgc ttaataagaa ttattttggc   39840
ccacacagtg gctcatgcct gtaatctcag cactttggga tgccaaggtg agcagatcac   39900
ttgaggccag gagttcaaga ccagcgtggc caacgtggtg aaaccccatc tctactaaaa   39960
atacaaaaat tagcccggtg tggtggtaca cgcctatagt cccagctact cgggagactg   40020
aggtgggaga atcacttgaa cccgggaggc caaggctgca atatcgagat cacaccactg   40080
cactctagcc tgggcaacag agtgagagtg agactctttc tcggaaaaaa aaaaaagaa    40140 ttatttgaa caaagtgctg tcacctaagt tagcaaaact ccaagcaagg ttttggctc    40200 tgtaaggaaa gaattagcct actcatttgg aaatttagtg gtgtttgtaa tgcagaaagt   40260
gacagtgaga ctggaaaggg attggctttg gggcttgttc tgctttataa ataataatga   40320
atcttctcca acatgaagta atgtgaatta aaaaaaaaaa atctgtcctt agagtacaaa   40380
attacttcat aacccaatct gcatttctcc actccaagca tatttctgg  gagttctact   40440 tagagagtga aagctgctgt gtgtgtgata attaatttta acaaacactt ggcaaactga   40500
gctggactat gtataagcta ccctagacta agcatgaatt tgaactgcac ttttttatggt   40560 gttttttcca caatgacatt atttaggcat ttaaagttat ctgaactgca attttttgtt   40620
cttttttttt taatttgact ttttaaaaaa aattattcct gaataaagag gcagtttgta   40680
aaaactcgag aactgtgaga gataattgga tctttgtgta gcaaaactag aagggtgttg   40740
ggtatctgct ctttatcaaa tggaccactt acttttcttt tcttttttgc cctgtgttca   40800
gaaaacaaat gtgcgtgtct cctgatttat aatgtatagt tcattaatgg agaaagtgct   40860
```

```
tgagaattag atcctaatgt catttcccat gcagcatctt cattcttttc taaagcacta   40920
tttggtaaaa acaactgata gtcgtcagag gtgatcagca atgtttgagc actatttcct   40980
ttttatatcc tgcacatgga atatggacag gcaaacaaat catttccaag taagaaaata   41040
aattttgagg gagttaatac tataatttga aagtaataac ctcctattta tccatctagt   41100
ttgttgttct gtactaaatt atttgtgcat gtctctgtgt ctataattta tgtgaaactt   41160
tgcacaatct taaataggac aaaatagaca ttctgtaatt tcccaggcaa gctatttaag   41220
gtgactatct ctctacatat ttgagatgaa aaacaataac atgacaatcc atcccttctt   41280 aggttttttgt aagcagactt actacctgtg actcagtttt gttctcacag ggtactaatt   41340
aatccttcac gataataact tgtcaaattc cattacttct gtaaaggcaa tactttatat   41400
ttgtttgtat tcaaatttta aactgatgtt aaatgccgtg ggtgcaactg caggttaaaa   41460
atatgtgttt gaatctctta ttcttttttgc ttggcaatgt atgaaataac tgctctttct   41520
agaaatcttg atgatgaagt ggcctgttgt tttgtcacct aaaaatgcaa taatgttcaa   41580
attaagcttt tctttattaa catcacttga ttgtgtgcca tatttagagc ttagtgaaat   41640
tttaatctac acattgatta aatacatttt atttattctt gtttctaatg ggaacttttct   41700 ttgtttctaa tgggaacttt cttaaaattaa attacatcca acatttatta aagacctaaa   41760
acataggcaa ttactgtgct tagaggaaaa gcgcagacga aagtgaatca gacaagttcc   41820
ctgccctccg gaagctttca gtctagtgat gagaaagacg tatacacacc ttatgttgat   41880
ttaaaaaaaa aaaagctct tacctggttg ctggcatatg aaagtgttag ttacagatct   41940
gccccaaact aaaggtgtca cctcgagtaa atctctttcc ctttcccttt caatctcttc   42000
atctataaac taggggttgg gaatacattt attaacaaac acaaattgag cgtctaccat   42060 gtgataaatag tagctaaact tactgagcaa ttaccatggg gcaggtatca agataaaccc   42120
tttatgatgg taacctcatt taatcctcaa agcaattcca ttttcaagag gaggaaattg   42180
aggctcaaaa atgttaagta actcccccaa ggatgcaaag tgattgagcc agaattcaag   42240
actaggttgg tttgactcca aaactcatgc cattaaaccc tattgtgtca ctgcaaacaa   42300
ctctaatagt ttcaaattat tagttctatt aatattatat taccattatt tgcccccaaa   42360
atgtaaaatg taaatacaaa gagtttggtt tttgtattac tagtggaggt taaaggtgca   42420
caatggaatt attcaaactg ggaaaatcca ggaagacttc atggaggagg cagcatatgg   42480
ctgcagttaa taaggtttgc tcacacaaaa tggagaggtg aggacatttc aggcagagag   42540
aattatatga gaggttacag agcagtaaac agtcatgcgt ctgcaagatc aaagggaaag   42600
ggcggtaaga gagaagcttg aaagtcaagt ggagccagat tgtggaaaaa ctagagagtc   42660
atgccaagga ccttgacata tagaaaatgg gaagccctg aaaggtgaag aacatgagag   42720
tgaaatgatt agtaactttt tggtttagga cttgtttctt ttgtgttttg gttgctttct   42780
tgttttgttt tgtttgtggt ttttaaattt acaaccaata agaatattta gtaaggtttc   42840
caaatacatc atgaatatat aaaactagcc tgactcaagg ataataattc tgggtagttg   42900
gagtgaagtt tcaatcagct acgtggcatt tgctaatcat ctgatatgag ctaacaataa   42960
aggagttaac aaataaactg tcagcctaca gtccagggtc tcaaatagca tgtgacatag   43020
ttgagaagca gttttccata tcatacatga aataactaaa gaaactactt acaaagcact   43080
ataccagtaa ctacaataaa atacaactat acatgcaaaa taatgctgaa agctgcaagt   43140
agaggggtaa agctaggcca gttgctcagg gaaccattct gaagtggatt tgggaagtat   43200
gtctagaagg ggagccattg ctgtgagagt gctgaggctc atctgctact agtcccccac   43260
```

```
tactcaggca tatggtaggt cagtaacaaa accatcattg tgcactgttc tttccatcta   43320
aattccatca aattatgacc aacctatcaa ggtactagtt caaattctct cttcctctat   43380
aagctagtgg tcttctctaa aatttaagaa gatcgtgctc atcttcctac ttcttgttct   43440
ctttcttctg tgttttctga ggctgcaatg aactaggaac ttcctctccc cagaactctg   43500
tattccaggc cttagatcac tcaaaactgt tgcttataaa gtgcagagaa tcaacagaga   43560
aggaatagag gttaatgtct ggtcaaagat gtgattctct tgttgaaaag ttcattagct   43620
tattatttat agaatcataa gtcccaggaa aaaccaaaag gaaatatata ttggatccta   43680
atgatattct cttttttct tttttctttt cccccactcc attgcccagg ctggagtgca    43740
gtggcataat ctcagctcac tgcaacctcc acctcccggg ttcaagggac tctcctgcct   43800
cagccttcca gtagatggga attacaggca tgtgccacca catctggcta atttttttt    43860 gtattttag tagagatggg gtttcaccat gttagtcagg ctggtgttga actcctgacc    43920
tcaaatgatc caccagcctc ggcctcccag tgtgctggga ttgcaggcgt gagccaccac   43980
acccggcctg atattctctt gcaagggcat tgtttacatt gtctatcatc agaactgtag   44040
agtgttggct ccaggcacag aaccctaga gttttgtaaa ccatttatat cacactggca    44100
accagaagta actttatata ctcaagaatc aagatttcac ctagaagtac ctcaggtagg   44160
tgttggttca ttcacattcc aaccaaaaga taatgtacca taaagtgcat accgcctagt   44220
ccgtaatgat taaggcaacc acataaaatc tcattattta aaagaaatta agtccaggca   44280
cggtggctca cacctgtaat ctcagcactt cgggaggcca aggagggcag atcacctgag   44340
gttgggagtt tgagaccagc ctgatcaaca tggagaaatc ccatctctac taaaaataca   44400
aaattagcgg ggcatggtgg tgcatgccta taatcccagc tactcaggag gctgaggcag   44460
gagaatcact tgaacccagg aggtggaggt tgagatcgtg ccattgcact ccagcctgga   44520
caacaagagt gaaactctgt ctcaaaaaag aaaaaaagaa aaagaaatta aatgcactat   44580
ggtttatgga gcggtattcc tcctccatgt cctacataag atctttcaca tgccagtcac   44640
agttaaatct aatttgctgt aatctggata aatgggagct aatcaacaag ctctcagctc   44700
tagctctgaa tcagcagcag atattgcatt tttgaaatac actaatagca agaatgcctt   44760
cctgacaaca actggcattt ttgacacagc aggaagttta tctggattct gatataatag   44820
ttattggaat catacatagg tacatagttt aaaaggctaa taagtcattt gttattgctt   44880
ttattatctc tgcatagtta gtaaaattga gattagaacc acttctcgaa tgtactgttc   44940
taaatcctta gcttgcttga tcacacatga ccctcacaat gatcctagga gaaattattc   45000
tgcatgccat tttgtagctg gggaaactga ggcacagaga aatacagtac tgcccaaaat   45060
gtcataacta atcaaaggca aagacaatac tcacaccagc tctgattcca gagcccactc   45120
tcttaaccat atgcttttct gcttccctag ttgtagagtc tttttgtatg actgcattaa   45180
ttatatgtga agagttcaaa aatttctata aaggtctttt aagggtgtc attctggttg    45240 aaaatggagg actaggcttc tcacttgaag acatatttct gtagaaaaac ctattttcat   45300
ttagatgcta cagttacttg atgtggttaa taaaccagtt aacagagtat gaaaaggata   45360
agggttaaag ccctcccaag ccatctttca tgctgctaat atgaatcaca ttactagata   45420
cttaaatatc attttctctt tggttcccag aagactgcat atatgctaga atatttgtcc   45480 tcctcttta cccttcagg caataaagta ttttggacca ctgtactatg ttataattat     45540
tgtttctctc ctgatttttt tgctccaatc taatgaaaga catacaagct actatactgc   45600
```

```
tacacaatga ctaaatacct gttggattag gtgggggaa gatacacagt cactggctag    45660
aaagcatcat gcatacagag ccatttttcac catatatttt atttctcatg atcatgtaga   45720
atttaggctt tggtgttgat tatttctctc ttaggaaaca tagttgtttc agggttgata    45780
tcacaaaaaa acagaaaaac ctattcgaga aaaggaaaat tatttgtctg taggccaaat    45840
tttgaagtag gaaaacctgc ttttggagtt gtattcccct cccaggcact taatccaagt    45900
tccagtctta ttctaaactg gggatgctag tattaaccac cataggagtt atctgagatg    45960
agttatcatc aacttggtac caggttgttg tcctctggac tcagtgagct ctagaattgc    46020
atgaaactgg cctaatttat caaagtatgt agccttgggt aaataattca agctctcaga    46080
ggtccagtta tctcctctgt aaaacatatc tacatcctag ggatgacaat atctacatcc    46140
tagagatgtc aggaggatta agtgtaattt tttttaattg tatgtattta aaatgggcaa    46200
cataatgttt tgatatacac gtgtatagtg attactacag tcaagcaaat taacatatcc    46260
atcatttcat agctaccttt tatgtatgtg ataagattat ctaaaatcta ttctcttacc    46320
aaatttccag tatacaatat tgatatggtt tgatccatat ccccatccaa atctcatgtt    46380
cagttgcaat ccccaacgtt ggagatggag cctggttgga ggtgattgga tcacaggggt    46440
ggcttctaat ggttcagcac catcctttct tggtactgta tagtgagtaa gttctcacga    46500
gatctggttg tttaaaagtg tgtaacacct cccccacttt ccctctctct gttcctcctg    46560
ctcccgctat gtgaagtgcc agctccctct ttgccttccg ccatgattgt aagttctctg    46620
aggcatcccc agaagctgat gctgccatgc ttcctataca gcctgcagaa ccatgagtca    46680
attaaacctc ttttctttgt aaattaccca gtctcaagta tttctttata gcaatgcaag    46740
aatggactaa tacagaaaat tgttactgag aagaagggca ttgctataaa gatacctgaa    46800
aatgtagaag tgactttgga accggctaac aggcagaagt tgaaacattt tagagggctc    46860
agaagaagac agaaagatga gagaaagttt ggaactcgct aggaacttgt tgagtggttg    46920
taaccaaaat actgatagtg atatagacag tgaagtccag gctgaggagg tctcagatgg    46980
aaatgagaaa tttattggga atgagtaaag gtcaggtttg ctatgcttta gcaaagagct    47040
tagctgcatt gttcctctgt tctagggatc tgtgaaatct tagacttaag aatgatgatt    47100
tagggtatct ggcagaagaa atttctaagc agcagagtgt tcaagaagta acctagctgc    47160
ttctaatagc ctatgctcat aggcatgagc acagaaatga cctgaaattg gaacttacac    47220
ttaaaaggga agcagagcat aaaagtttgt aaattttgca gcctggccat gtggtagtaa    47280
agaaaagctc gttctcagga gaggaagtca agcaggctgc ataaatttgc ataactaaaa    47340
ggaaggcaag ggctgataac caaaacaatg gggagaaaga ctcataggac taacaggcat    47400
tttattttat tttattttta ttttattatt attatacttt aagttttagg gtacatgtgc    47460
acaatgtgca ggttagttgc atatgtatac atgtgccatg ctggtgtgct gcacccatta    47520
actcgtcatt tagcattagg tatatctcct aatgctatcc ctcccccctc cccaccccca    47580
caacagtccc cagagtgtga tgttcccctt cctgtgtcca tgtgttctca ttgttcaatt    47640
cccacctatg agtgagaaca tgtggtgttt ggttttttga ccttgcaata gtttactgag    47700
aatgacgatt tccaatttca tccatgtccc tacaaaggac atgaactcat cattttttat    47760
ggctgcatag tattccatgg tgtatatgtg ccacattttc ttaatccagt ctatcactgt    47820
tggacatttg ggttggttcc aagtctttgc tattgtgaat agtgccacaa taaacatagt    47880
gtgcatgtgt ctttatagca gcaggattta tagtcctttg ggtatatacc cagtgatggg    47940
atggctgggt caaatggtat ttctagttct agatccctga ggaatcgcca cactgacttc    48000
```

```
cacaatggtt gaactagttt acagtcccac caacagtgta aaagtgttcc taataggcat    48060
tttaggcttt catggtggtc cctctcatca caggccccga ggcctaggag gactgaatca    48120
tttcctgggc caggcctagg gccctgctc cctcttacag ccttgggact ctgctccctg     48180
aatcccagct gctcaaaggg gcccaggtac tgttacagta ggtagctaat caggcatgag    48240
tggggtaaga gagaagtccc caccacccac caggaatgtc aggcaaccat cagatgatgg    48300
tcaggcagtt gtcatactgc ctctctaaaa tagtaattgg ttgcagccag caccaggag    48360 aggcaacttc tcaatagata gaaacacctg aaattggtaa ctgggcgctt ccaataagat    48420
ctcaggaact gagagagtgg gcttaacatg cacattaaga ggcaaaatgg tgaagtatga    48480
cctttggggg cattccaccg gaaaagggaa gaaagcctca ggtaagcatg tatacaactc    48540
cagtaaacac actgcacacg ctcaccttcc aagtgcaagc agggcaccat gcatgcggca    48600
agctcaccct tagggaagga ccaagggaaa ggggcacaag atgtcagaag taggccagtg    48660
tataagatcc taggttcaag gtcaaacagg gcacttgacc tccaaggtgc ccacttgggc    48720
ctcttccaaa tgtactttcc tttcattcct gttctaaagc tttttaataa acttttactc    48780
ctgctctgaa acttgtcgca gtctcttttt ctgccttatg cctcttggtc aaattctttc    48840
ttctgaggag gcaagaattg aggttgctgc agacccacat ggatttgcag ctggtaactc    48900
agataacttt caccagtaag aatacagttc aggctgctgc ttcacagggt gccaggcata    48960
agccttggtg gcttccataa gctgtgaagc cggcgggcgc acataatgca agagttgagg    49020
cttaagaagc tctgcctaga ttttagagga tgtatgaaaa agcctggatg tccagacaga    49080
agcctgttac tggggtggaa tcctcatgga gaacatctac tagggaagca aggagaagaa    49140
atgtggggtt gcagccccca cagagagtcc cctgggcac tgcctagcag agctatgaca     49200
agacagccac cgtcctccag accccagaat ggtagatcca ccaacaactt gcaccctgca    49260
gcctggaaaa gctgcaagca ctcaatgcta gcccatgaga gcagctgtgg gagatgaacc    49320
ctggaaaacc acagggtgg ttctgcccaa ggttttggga gcccactcat tgcatcagtg      49380
ttccctgggt gtgagtcaaa ggagattatt tcagagcttt aacatttaat gactgcccgg    49440
ctggctttca gacttgcaat ggggccctat agcctctttc ttttggcaga tttctccctt    49500
tcggaatggc agtatctgcc caatgcctat acccccattg tatctttgaa gcaattacct    49560 tgttttgat tttacaggtt cataggtaga agggactagc ttcgtctcag gtgagacttg     49620
ggactttgga ctttgaatg aatgctggat cgagttaaga ctttggggaa ctgttggtaa     49680
ggcacgacag tattttgcaa tatgagaagg acattagatt tgggaggggc cagagttgga    49740
ataacatggt ttggatctct gtccccaccc aaatctcatg ttcaactgta atccccagtg    49800
ttggaggttg ggcctggtgg gaggtgagtg gattatgggg tggcttctaa tggttttgta    49860
cagtcccctc ttggtactat atagtgagtt ctgacaagat ctagttgttt aaacgtatgt    49920
agcacctccc atttctctct tccccagtt cctgccatgt gaagtctggg gtctccctat      49980
gccttccatc atgattttaa gttccctatg gcctgcccag aagctgatcc agccatgctt    50040
cttgtacagc ctgcagaact gtgagccatt aaacttttct ttataaatta cccagtttca    50100
gttatttctt tatagcagtg taagaatgga ctaacacaat tattaacgct agtcctcatg    50160
ttgtacatta aatctctaga tgtattagac gtaactgcaa cttgtaccc taccctacaa      50220 ttttctttcc cccaagccc cccaaccaag ggtctactct gtttctataa attcagttgt      50280
tttttaattc cacgtataag tgaagtacaa ctcagtgtag aaacttggta aatgctagct    50340
```

```
acttgttata agctgtcagt caaaataaaa atacagagat gaatctctaa attaagtgat    50400
ttatttggga agaaagaatt gcaattaggg catacatgta gatcagatgg tcttcggtat    50460
atccacacaa caaagaaaag ggggaggttt tgttaaaaaa gagaaatgtt acatagtgct    50520
ctttgagaaa attcattggc actattaagg atctgaggag ctggtgagtt tcaactggtg    50580
agtgatggtg gtagataaaa ttagagctgc agcaggtcat tttagcaact attagataaa    50640
actggtctca ggtcacaacg ggcagttgca gcagctggac ttggagagaa ttacactgtg    50700
ggagcagtgt catttgtcct aagtgctttt ctacccccta cccccactat tttagttggg    50760
tataaaaaga atgacccaat ttgtatgatc aactttcaca aagcatagaa cagtaggaaa    50820
agggtctgtt tctgcagaag gtgtagacgt tgagagccat tttgtgtatt tattcctccc    50880
tttcttcctc ggtgaatgat taaaacgttc tgtgtgattt ttagtgatga aaagattaa     50940
atgctactca ctgtagtaag tgccatctca cacttgcaga tcaaaaggca cacagtttaa    51000
aaaacctttg ttttttttaca catctgagtg gtgtaaatgc tactcatctg tagtaagtgg   51060
aatctataca cctgcagacc aaaagacgca aggtttcaaa aatctttgtg ttttttacac    51120
atcaaacaga atggtacgtt tttcaaaagt taaaaaaaaa caactcatcc acatattgca    51180
actagcaaaa atgacattcc ccagtgtgaa aatcatgctt gagagaattc ttacatgtaa    51240
aggcaaaatt gcgatgactt tgcaggggac cgtgggattc ccgcccgcag tgccggagct    51300
gtcccctacc agggttgtca gtggagtttt gaatgcactt aacagtgtct tacggtaaaa    51360
acaaaatttc atccaccaat tatgtgttga gcgcccactg cctaccaagc acaaacaaaa    51420
ccattcaaaa ccacgaaatc gtcttcactt tctccagatc cagcagcctc ccctattaag    51480
gttcgcacac gctattgcgc caacgctcct ccagagcggg tcttaagata aagaacagg     51540
acaagttgcc ccgcccatt tcgctagcct cgtgagaaaa cgtcatcgca catagaaaac     51600
agacagacgt aacctacggt gtcccgctag aaagagagg tgcgtcaaac agcgacaagt     51660
tccgcccacg taaagatga cgcttggtgt gtcagccgtc cctgctgccc ggttgcttct      51720
cttttggggg cggggtctag caagagcagg tgtgggttta ggaggtgtgt gttttttgttt   51780
ttcccaccct ctctccccac tacttgctct cacagtactc gctgagggtg aacaagaaaa    51840
gacctgataa agattaacca gaagaaaaca aggagggaaa caaccgcagc ctgtagcaag    51900
ctctggaact caggagtcgc gcgctagggg ccggggccgg ggccggggcg tggtcggggc    51960
gggcccgggg gcgggccggg ggcggggctg cggttgcggt gcctgcgccc gcggcggcgg    52020
aggcgcaggc ggtggcgagt gggtgagtga ggaggcggca tcctggcggg tggctgttttg   52080
gggttcggct gccgggaaga ggcgcgggta gaagcggggg ctctcctcag agctcgacgc    52140
attttttactt tccctctcat ttctctgacc gaagctgggt gtcgggcttt cgcctctagc   52200
gactggtgga attgcctgca tccgggcccc gggcttcccg gcggcggcgg cggcggcggc    52260
ggcgcaggga caagggatgg ggatctggcc tcttccttgc tttcccgccc tcagtacccg    52320
agctgtctcc ttcccgggga cccgctggga gcgctgccgc tgcgggctcg agaaaaggga    52380
gcctcgggta ctgagaggcc tcgcctgggg gaaggccgga gggtgggcgg cgcgcggctt    52440
ctgcggacca agtcggggtt cgctaggaac ccgagacggt ccctgccggc gaggagatca    52500
tgcgggatga gatgggggtg tggagacgcc tgcacaattt cagcccaagc ttctagagag    52560
tggtgatgac ttgcatatga gggcagcaat gcaagtcggt gtgctcccca ttctgtggga    52620
catgacctgt ttgcttcaca gctccagatt gacacagact tgcttaaagg aagtgactat    52680
tgtgacttgg gcatcacttg actgatggta atcagttgtc taaagaagtg cacagattac    52740
```

```
atgtccgtgt gctcattggg tctatctggc cgcgttgaac accaccaggc tttgtattca   52800
gaaacaggag ggaggtcctg cactttccca ggaggggtgg ccctttcaga tgcaatcgag   52860
attgttaggc tctgggagag tagttgcctg gttgtggcag ttggtaaatt tctattcaaa   52920
cagttgccat gcaccagttg ttcacaacaa gggtacgtaa tctgtctggc attacttcta   52980
cttttgtaca aaggatcaaa aaaaaaaaag atactgttaa gatatgattt ttctcagact   53040
ttgggaaact tttaacataa tctgtgaata tcacagaaac aagactatca tatagggat   53100 attaataacc tggagtcaga atacttgaaa tacggtgtca tttgacacgg gcattgttgt   53160
caccacctct gccaaggcct gccactttag gaaaaccctg aatcagttgg aaactgctac   53220
atgctgatag tacatctgaa acaagaacga gagtaattac cacattccag attgttcact   53280
aagccagcat ttacctgctc caggaaaaaa ttacaagcac cttatgaagt tgataaaata   53340
ttttgtttgg ctatgttggc actccacaat ttgctttcag agaaacaaag taaaccaagg   53400
aggacttctg tttttcaagt ctgccctcgg gttctattct acgttaatta gatagttccc   53460
aggaggacta ggttagccta cctattgtct gagaaacttg gaactgtgag aaatggccag   53520
atagtgatat gaacttcacc ttccagtctt ccctgatgtt gaagattgag aaagtgttgt   53580
gaactttctg gtactgtaaa cagttcactg tccttgaagt ggtcctgggc agctcctgtt   53640
gtggaaagtg gacggtttag gatcctgctt ctctttgggc tgggagaaaa taaacagcat   53700
ggttacaagt attgagagcc aggttggaga aggtggctta cacctgtaat gccagagctt   53760
tgggaggcgg aggcaagagg atcacttgaa gccaggagtt caagctcaac ctgggcaacg   53820
tagaccctgt ctctacaaaa aattaaaaac ttagccgggc gtggtgatgt gcacctgtag   53880
tcctagctac ttgggaggct gaggcaggag ggtcatttga gcccaagagt ttgaagttac   53940
cgagagctat gatcctgcca gtgcattcca gcctggatga caaaacgaga ccctgtctct   54000
aaaaaacaag aagtgagggc tttatgattg tagaattttc actacaatag cagtggacca   54060
accacctttc taaataccaa tcagggaaga gatggttgat tttttaacag acgtttaaag   54120
aaaaagcaaa acctcaaact tagcactcta ctaacagttt tagcagatgt taattaatgt   54180
aatcatgtct gcatgtatgg gattatttcc agaaagtgta ttgggaaacc tctcatgaac   54240
cctgtgagca agccaccgtc tcactcaatt tgaatcttgg cttccctcaa aagactggct   54300
aatgtttggt aactctctgg agtagacagc actacatgta cgtaagatag gtacataaac   54360
aactattggt tttgagctga tttttttcag ctgcatttgc atgtatggat ttttctcacc   54420
aaagacgatg acttcaagta ttagtaaaat aattgtacag ctctcctgat tatacttctc   54480
tgtgacattt catttcccag gctatttctt ttggtaggat ttaaaactaa gcaattcagt   54540
atgatctttg tccttcattt tctttcttat tctttttgtt tgtttgtttg tttgttttt   54600 tcttgaggca gagtctctct ctgtcgccca ggctggagtg cagtggcgcc atctcagctc   54660
attgcaacct ctgccacctc cgggttcaag agattctcct gcctcagcct cccgagtagc   54720
tgggattaca ggtgtccacc accacacccg gctaattttt tgtatttta gtagaggtgg   54780 ggtttcacca tgttggccag gctggtcttg agctcctgac ctcaggtgat ccacctgcct   54840
cggcctacca aagagctggg ataacaggtg tgacccacca tgcccggccc attttttttt   54900
tcttattctg ttaggagtga gagtgtaact agcagtataa tagttcaatt ttcacaacgt   54960
ggtaaaagtt tccctataat tcaatcagat tttgctccag ggtcagttc tgttttagga   55020 aatactttta ttttcagttt aatgatgaaa tattagagtt gtaatattgc ctttatgatt   55080
```

| | | | | | |
|---|---|---|---|---|---|
| atccacctttt | ttaacctaaa | agaatgaaag | aaaaatatgt | ttgcaatata | atttatggt  55140 |
| tgtatgttaa | cttaattcat | tatgttggcc | tccagtttgc | tgttgttagt | tatgacagca 55200 |
| gtagtgtcat | taccatttca | attcagatta | cattcctata | tttgatcatt | gtaaactgac 55260 |
| tgcttacatt | gtattaaaaa | cagtggatat | tttaaagaag | ctgtacggct | tatatctagt 55320 |
| gctgtctctt | aagactatta | aattgataca | acatatttaa | aagtaaatat | tacctaaatg 55380 |
| aatttttgaa | attacaaata | cacgtgttaa | aactgtcgtt | gtgttcaacc | atttctgtac 55440 |
| atacttagag | ttaactgttt | tgccaggctc | tgtatgccta | ctcataatat | gataaaagca 55500 |
| ctcatctaat | gctctgtaaa | tagaagtcag | tgctttccat | cagactgaac | tctcttgaca 55560 |
| agatgtggat | gaaattcttt | aagtaaaatt | gtttactttg | tcatacattt | acagatcaaa 55620 |
| tgttagctcc | caaagcaatc | atatggcaaa | gataggtata | tcatagtttg | cctattagct 55680 |
| gctttgtatt | gctattatta | taaatagact | tcacagtttt | agacttgctt | aggtgaaatt 55740 |
| gcaattcttt | ttactttcag | tcttagataa | caagtcttca | attatagtac | aatcacacat 55800 |
| tgcttaggaa | tgcatcatta | ggcgattttg | tcattatgca | aacatcatag | agtgtactta 55860 |
| cacaaaccta | gatagtatag | cctttatgta | cctaggccgt | atggtatagt | ctgttgctcc 55920 |
| taggccacaa | acctgtacaa | ctgttactgt | actgaatact | atagacagtt | gtaacacagt 55980 |
| ggtaaatatt | tatctaaata | tatgcaaaca | gagaaaggt  | acagtaaaag | tatggtataa 56040 |
| aagataatgg | tatacctgtg | taggccactt | accacgaatg | gagcttgcag | gactagaagt 56100 |
| tgctctgggt | gagtcagtga | gtgagtggtg | aattaatgtg | aaggcctaga | acactgtaca 56160 |
| ccactgtaga | ctataaacac | agtacgctga | agctacacca | aatttatctt | aacagttttt 56220 |
| cttcaataaa | aaattataac | tttttaactt | tgtaaactt  | ttaattttt  | aacttttaaa 56280 |
| atacttagct | tgaaacacaa | atacattgta | tagctataca | aaaatatttt | ttctttgtat 56340 |
| ccttattcta | gaagcttttt | tctattttct | atttttaaatt | tttttttta | cttgttagtc 56400 |
| gttttttgtta | aaaactaaaa | cacacacact | ttcacctagg | catagacagg | attaggatca 56460 |
| tcagtatcac | tcccttccac | ctcactgcct | tccacctcca | catcttgtcc | cactggaagg 56520 |
| ttttttagggg | caataacaca | catgtagctg | tcacctatga | taacagtgct | ttctgttgaa 56580 |
| tacctcctga | aggacttgcc | tgaggctgtt | ttacatttaa | cttaaaaaaa | aaaaagtag  56640 |
| aaggagtgca | ctctaaaata | acaataaaag | gcatagtata | gtgaatacat | aaaccagcaa 56700 |
| tgtagtagtt | tattatcaag | tgttgtacac | tgtaataatt | gtatgtgcta | tactttaaat 56760 |
| aacttgcaaa | atagtactaa | gaccttatga | tggttacagt | gtcactaagg | caatagcata 56820 |
| ttttcaggtc | cattgtaatc | taatgggact | accatcatat | atgcagtcta | ccattgactg 56880 |
| aaacgttaca | tggcacataa | ctgtatttgc | aagaatgatt | tgttttacat | taatatcaca 56940 |
| taggatgtac | cttttttagag | tggtatgttt | atgtggatta | agatgtacaa | gttgagcaag 57000 |
| gggaccaaga | gccctggggtt | ctgtcttgga | tgtgagcgtt | tatgttcttc | tcctcatgtc 57060 |
| tgttttctca | ttaaattcaa | aggcttgaac | gggccctatt | tagcccttct | gttttctacg 57120 |
| tgttctaaat | aactaaagct | tttaaattct | agccatttag | tgtagaactc | tctttgcagt 57180 |
| gatgaaatgc | tgtattggtt | tcttggctag | catattaaat | atttttatct | ttgtcttgat 57240 |
| acttcaatgt | cgttttaaac | atcaggatcg | ggcttcagta | ttctcataac | cagagagttc 57300 |
| actgaggata | caggactgtt | tgcccatttt | ttgttatggc | tccagacttg | tggtatttcc 57360 |
| atgtcttttt | tttttttttt | tttttgacc  | tttagcggc  | tttaaagtat | ttctgttgtt 57420 |
| aggtgttgta | ttacttttct | aagattactt | aacaaagcac | cacaaactga | gtggctttaa 57480 |

```
acaacagcaa tttattctct cacaattcta gaagctagaa gtccgaaatc aaagtgttga    57540 cagggggcatg atcttcaaga gagaagactc tttccttgcc tcttcctggc ttctggtggt    57600
taccagcaat cctgagtgtt cctttcttgc cttgtagttt caacaatcca gtatctgcct    57660
tttgtcttca catggctgtc taccatttgt ctctgtgtct ccaaatctct ctccttataa    57720
acacagcagt tattggatta ggccccactc taatccagta tgaccccatt ttaacatgat    57780
tacacttatt tctagataag gtcacattca cgtacaccaa gggttaggaa ttgaacatat    57840
ctttttgggg gacacaattc aacccacaag tgtcagtctc tagctgagcc tttcccttcc    57900 tgttttctc cttttagtt gctatgggtt aggggccaaa tctccagtca tactagaatt    57960
gcacatggac tggatatttg ggaatactgc gggtctattc tatgagcttt agtatgtaac    58020
atttaatatc agtgtaaaga agccttttt taagttattt ctttgaattt ctaaatgtat    58080
gccctgaata taagtaacaa gttaccatgt cttgtaaaat gatcatatca acaaacattt    58140
aatgtgcacc tactgtgcta gttgaatgtc tttatcctga taggagataa caggattcca    58200
catctttgac ttaagaggac aaaccaaata tgtctaaatc atttggggtt ttgatggata    58260
tctttaaatt gctgaaccta atcattggtt tcatatgtca ttgtttagat atctccggag    58320
catttggata atgtgacagt tggaatgcag tgatgtcgac tctttgccca ccgccatctc    58380
cagctgttgc caagacagag attgctttaa gtggcaaatc acctttatta gcagctactt    58440
ttgcttactg ggacaatatt cttggtccta gagtaaggca catttgggct ccaaagacag    58500
aacaggtact tctcagtgat ggagaaataa cttttcttgc caaccacact ctaaatggag    58560
aaatccttcg aaatgcagag agtggtgcta tagatgtaaa gttttttgtc ttgtctgaaa    58620
agggagtgat tattgtttca ttaatctttg atggaaactg gaatggggat cgcagcacat    58680
atggactatc aattatactt ccacagacag aactagtttt ctacctccca cttcatagag    58740
tgtgtgttga tagattaaca catataatcc ggaaaggaag aatatggatg cataaggtaa    58800
gtgatttttc agcttattaa tcatgttaac ctatctgttg aaagcttatt ttctggtaca    58860
tataaatctt attttttttaa ttatatgcag tgaacatcaa acaataaatg ttatttattt    58920
tgcatttacc ctattagata caaatacatc tggtctgata cctgtcatct tcatattaac    58980
tgtggaaggt acgaaatggt agctccacat tatagatgaa aagctaaagc ttagacaaat    59040
aaagaaactt ttagaccctg gattcttctt gggagccttt gactctaata ccttttgttt    59100 cccttttcatt gcacaattct gtcttttgct tactactatg tgtaagtata acagttcaaa    59160
gtaatagttt cataagctgt tggtcatgta gcctttggtc tctttaacct ctttgccaag    59220
ttcccaggtt cataaaatga ggaggttgaa tggaatggtt cccaagagaa ttccttttaa    59280
tcttacagaa attattgttt tcctaaatcc tgtagttgaa tatataatgc tatttacatt    59340
tcagtatagt tttgatgtat ctaaagaaca cattgaattc tccttcctgt gttccagttt    59400
gatactaacc tgaaagtcca ttaagcatta ccagttttaa aaggcttttg cccaatagta    59460
aggaaaaata atatctttta aaagaataat tttttactat gtttgcaggc ttacttcctt    59520
ttttctcaca ttatgaaact cttaaaatca ggagaatctt ttaaacaaca tcataatgtt    59580
taatttgaaa agtgcaagtc attctttttcc tttttgaaac tatgcagatg ttacattgac    59640
tgttttctgt gaagttatct ttttttcact gcagaataaa ggttgttttg attttatttt    59700
gtattgttta tgagaacatg catttgttgg gttaatttcc tacccctgcc cccatttttt    59760
ccctaaagta gaaagtattt ttcttgtgaa ctaaattact acacaagaac atgtctattg    59820
```

```
aaaaataagc aagtatcaaa atgttgtggg ttgttttttt aaataaattt tctcttgctc   59880
aggaaagaca agaaaatgtc cagaagatta tcttagaagg cacagagaga atggaagatc   59940
aggtatatgc aaattgcata ctgtcaaatg tttttctcac agcatgtatc tgtataaggt   60000
tgatggctac atttgtcaag gccttggaga catacgaata agcctttaat ggagctttta   60060
tggaggtgta cagaataaac tggaggaaga tttccatatc ttaaacccaa agagttaaat   60120
cagtaaacaa aggaaaatag taattgcatc tacaaattaa tatttgctcc cttttttttt   60180
ctgtttgccc agaataaatt ttggataact tgttcatagt aaaaataaaa aaaattgtct   60240 ctgtatatgtt cttaaggta ctacttctcg aacctttccc tagaagtagc tgtaacagaa   60300
ggagagcata tgtacccctg aggtatctgt ctggggtgta ggcccaggtc cacacaatat   60360
ttcttctaag tcttatgttg tatcgttaag actcatgcaa tttacatttt attccataac   60420
tattttagta ttaaaatttg tcagtgatat ttcttaccct ctcctctagg aaaatgtgcc   60480
atgtttatcc cttggctttg aatgcccctc aggaacagac actaagagtt tgagaagcat   60540
ggttacaagg gtgtggcttc ccctgcggaa actaagtaca gactatttca ctgtaaagca   60600
gagaagttct tttgaaggag aatctccagt gaagaaagag ttcttcactt ttacttccat   60660
ttcctcttgt gggtgaccct caatgctcct tgtaaaactc caatatttta aacatggctg   60720
ttttgccttt ctttgcttct ttttagcatg aatgagacag atgatacttt aaaaaagtaa   60780
ttaaaaaaaa aaacttgtga aaatacatgg ccataataca gaacccaata caatgatctc   60840
ctttaccaaa ttgttatgtt tgtactttg tagatagctt tccaattcag agacagttat   60900
tctgtgtaaa ggtctgactt aacaagaaaa gatttcccctt tacccaaaga atcccagtcc   60960
ttatttgctg gtcaataagc agggtcccca ggaatggggt aactttcagc accctctaac   61020
ccactagtta ttagtagact aattaagtaa acttatcgca agttgaggaa acttagaacc   61080
aactaaaatt ctgcttttac tgggattttg ttttttcaaa ccagaaacct ttacttaagt   61140
tgactactat taatgaattt tggtctctct tttaagtgct cttcttaaaa atgttatctt   61200
actgctgaga agttcaagtt tgggaagtac aaggaggaat agaaacttaa gagattttct   61260
tttagagcct cttctgtatt tagccctgta ggatttttt tttttttttt tttttggtg   61320 ttgttgagct tcagtgaggc tattcattca cttatactga taatgtctga gatactgtga   61380
atgaaatact atgtatgctt aaacctaaga ggaaatattt tcccaaaatt attcttcccg   61440
aaaaggagga gttgccttttt gattgagttc ttgcaaatct cacaacgact ttattttgaa   61500
caatactgtt tggggatgat gcattagttt gaaacaactt cagttgtagc tgtcatctga   61560
taaaattgct tcacagggaa ggaaatttaa cacggatcta gtcattattc ttgttagatt   61620
gaatgtgtga attgtaattg taaacaggca tgataattat tactttaaaa actaaaaaca   61680
gtgaatagtt agttgtggag gttactaaag gatggttttt ttttaaataa aacttttcagc  61740 attatgcaaa tggcatatg gcttaggata aaacttccag aagtagcatc acatttaaat   61800
tctcaagcaa cttaataata tggggctctg aaaaactggt taaggttact ccaaaaatgg   61860
ccctgggtct gacaaagatt ctaacttaaa gatgcttatg aagactttga gtaaaatcat   61920
ttcataaaat aagtgaggaa aaacaactag tattaaattc atcttaaata atgtatgatt   61980
taaaaaatat gtttagctaa aaatgcatag tcatttgaca atttcattta tatctcaaaa   62040
aatttactta accaagttgg tcacaaaact gatgagactg gtggtggtag tgaataaatg   62100
agggaccatc catatttgag acactttaca tttgtgatgt gttatactga attttcagtt   62160
tgattctata gactacaaat ttcaaaatta caatttcaag atgtaataag tagtaatatc   62220
```

```
ttgaaatagc tctaaaggga attttttctgt tttattgatt cttaaaatat atgtgctgat    62280
tttgatttgc atttgggtag attatacttt tatgagtatg gaggttaggt attgattcaa    62340
gttttcctta cctatttggt aaggatttca aagtctttt gtgcttggtt ttcctcattt    62400
ttaaatatga aatatattga tgacctttaa caaattttt ttatctcaaa ttttaaagga    62460
gatcttttct aaaagaggca tgatgactta atcattgcat gtaacagtaa acgataaacc    62520
aatgattcca tactctctaa agaataaaag tgagctttag ggccgggcat ggtcagaaat    62580
ttgacaccaa cctggccaac atggcgaaac cccgtctcta ctaaaaatac aaaaatcagc    62640
cgggcatggt ggcggcacct atagtcccag ctacttggga ggatgagaca ggagagtcac    62700
ttgaacctgg gaggagaggt tgcagtgagc tgagatcacg ccattgcact ccagcctgag    62760
caatgaaagc aaaactccat ctcaaaaaaa aaaaagaaa agaaagaata aaagtgagct    62820
ttggattgca tataaatcct ttagacatgt agtagacttg ttttgatactg tgtttgaaca    62880 aattacgaag tattttcatc aaagaatgtt attgttgat gttattttta ttttttattg    62940
cccagcttct ctcatattac gtgattttct tcacttcatg tcactttatt gtgcagggtc    63000
agagtattat tccaatgctt actgagaag tgattcctgt aatggaactg ctttcatcta    63060
tgaaatcaca cagtgttcct gaagaaatag atgtaagttt aaatgagagc aattatacac    63120
tttatgagtt ttttgggtt atagtattat tatgtatatt attaatattc taattttaat    63180
agtaaggact ttgtcataca tactattcac atacagtatt agccacttta gcaaataagc    63240
acacacaaaa tcctggattt tatggcaaaa cagaggcatt tttgatcagt gatgacaaaa    63300
ttaaattcat tttgtttatt tcattacttt tataattcct aaaagtggga ggatcccagc    63360
tcttatagga gcaattaata tttaatgtag tgtcttttga aacaaaactg tgtgccaaag    63420
tagtaaccat taatggaagt ttacttgtag tcacaaattt agtttcctta atcatttgtt    63480
gaggacgttt tgaatcacac actatgagtg ttaagagata cctttaggaa actattcttg    63540
ttgttttctg attttgtcat ttaggttagt ctcctgattc tgacagctca gaagaggaag    63600
ttgttcttgt aaaaattgtt taacctgctt gaccagcttt cacatttgtt cttctgaagt    63660
ttatggtagt gcacagagat tgttttttgg ggagtcttga ttctcggaaa tgaaggcagt    63720
gtgttatatt gaatccagac ttccgaaaac ttgtatatta aaagtgttat ttcaacacta    63780
tgttacagcc agactaattt ttttattttt tgatgcattt tagatagctg atacagtact    63840
caatgatgat gatattggtg acagctgtca tgaaggcttt cttctcaagt aagaattttt    63900
cttttcataa aagctggatg aagcagatac catcttatgc tcacctatga caagatttgg    63960
aagaaagaaa ataacagact gtctacttag attgttctag ggacattacg tatttgaact    64020
gttgcttaaa tttgtgttat ttttcactca ttatatttct atatatattt ggtgttattc    64080
catttgctat ttaaagaaac cgagtttcca tcccagacaa gaaatcatgg ccccttgctt    64140
gattctggtt tcttgtttta cttctcatta aagctaacag aatcctttca tattaagttg    64200
tactgtagat gaacttaagt tatttaggcg tagaacaaaa ttattcatat ttatactgat    64260
ctttttccat ccagcagtgg agtttagtac ttaagagttt gtgcccttaa accagactcc    64320
ctggattaat gctgtgtacc cgtgggcaag gtgcctgaat tctctataca cctatttcct    64380
catctgtaaa atgcaataa tagtaatagt acctaatgtg tagggttgtt ataagcattg    64440
agtaagataa ataatataaa gcacttagaa cagtgcctgg aacataaaaa cacttaataa    64500
tagctcatag ctaacatttc ctatttacat ttcttctaga aatagccagt atttgttgag    64560
```

```
tgcctacatg ttagttcctt tactagttgc tttacatgta ttatcttata ttctgtttta    64620
aagtttcttc acagttacag attttcatga aatttttactt ttaataaaag agaagtaaaa    64680
gtataaagta ttcactttta tgttcacagt cttttccttt aggctcatga tggagtatca    64740
gaggcatgag tgtgtttaac ctaagagcct aatggcttg aatcagaagc actttagtcc      64800
tgtatctgtt cagtgtcagc ctttcataca tcattttaaa tcccatttga ctttaagtaa    64860
gtcacttaat ctctctacat gtcaatttct tcagctataa aatgatggta tttcaataaa    64920
taaatacatt aattaaatga tattatactg actaattggg ctgttttaag gctcaataag    64980
aaaatttctg tgaaaggtct ctagaaaatg taggttccta tacaaataaa agataacatt    65040
gtgcttatag cttcggtgtt tatcatataa agctattctg agttatttga agagctcacc    65100
tacttttttt tgtttttagt ttgttaaatt gtttttatagg caatgttttt aatctgtttt    65160
ctttaactta cagtgccatc agctcacact tgcaaacctg tggctgttcc gttgtagtag    65220
gtagcagtgc agagaaagta aataaggtag tttatttat aatctagcaa atgatttgac     65280
tctttaagac tgatgatata tcatggattg tcatttaaat ggtaggttgc aattaaaatg    65340
atctagtagt ataaggaggc aatgtaatct catcaaattg ctaagacacc ttgtggcaac    65400
agtgagtttg aaataaactg agtaagaatc atttatcagt ttattttgat agctcggaaa    65460
taccagtgtc agtagtgtat aaatggtttt gagaatatat taaaatcaga tatataaaaa    65520
aaattactct tctatttccc aatgttatct ttaacaaatc tgaagatagt catgtacttt    65580
tggtagtagt tccaaagaaa tgttatttgt ttattcatct tgatttcatt gtcttcgctt    65640
tccttctaaa tctgtcccctt ctagggagct attgggatta gtggtcatt gattattata    65700 ctttattcag taatgtttct gacccttttcc ttcagtgcta cttgagttaa ttaaggatta    65760
atgaacagtt acatttccaa gcattagcta ataaactaaa ggattttgca cttttcttca    65820
ctgaccatta gttagaaaga gttcagagat aagtatgtgt atctttcaat ttcagcaaac    65880
ctaatttttt aaaaaaagtt ttacatagga aatatgttgg aaatgatact ttacaaagat    65940
attcataatt tttttttgta atcagctact ttgtatattt acatgagcct taatttatat    66000
ttctcatata accatttatg agagcttagt atacctgtgt cattatattg catctacgaa    66060
ctagtgacct tattccttct gttacctcaa acaggtggct ttccatctgt gatctccaaa    66120
gccttaggtt gcacagagtg actgccgagc tgctttatga agggagaaag gctccatagt    66180
tggagtgttt tttttttttt ttttaaacat tttttcccatc ctccatcctc ttgagggaga    66240
atagcttacc ttttatcttg ttttaatttg agaaagaagt tgccaccact ctaggttgaa    66300
aaccactcct ttaacataat aactgtggat atggtttgaa tttcaagata gttacatgcc    66360 ttttttatttt tcctaataga gctgtaggtc aaatattatt agaatcagat ttctaaatcc    66420
cacccaatga cctgcttatt ttaaatcaaa ttcaataatt aattctcttc tttttggagg    66480
atctggacat tctttgatat ttcttacaac gaatttcatg tgtagaccca ctaaacagaa    66540
gctataaaag ttgcatggtc aaataagtct gagaaagtct gcagatgata taattcacct    66600
gaagagtcac agtatgtagc caaatgttaa aggttttgag atgccataca gtaaatttac    66660
caagcatttt ctaaatttat ttgaccacag aatccctatt ttaagcaaca actgttacat    66720
cccatggatt ccaggtgact aaagaatact tatttcttag gatatgtttt attgataata    66780
acaattaaaa tttcagatat cttctcataag caaatcagtg gtctttttac ttcatgtttt    66840
aatgctaaaa tattttcttt tatagatagt cagaacatta tgccttttttc tgactccagc    66900 agagagaaaa tgctccaggt tatgtgaagc agaatcatca tttaaatatg agtcagggct    66960
```

```
ctttgtacaa ggcctgctaa aggtatagtt tctagttatc acaagtgaaa ccacttttct   67020
aaaatcattt ttgagactct ttatagacaa atcttaaata ttagcattta atgtatctca   67080
tattgacatg cccagagact gacttccttt acacagttct gcacatagac tatatgtctt   67140
atggatttat agttagtatc atcagtgaaa caccatagaa tacccttttgt gttccaggtg   67200 ggtccctgtt cctacatgtc tagcctcagg acttttttttt ttttaacaca tgcttaaatc   67260
aggttgcaca tcaaaaataa gatcatttct ttttaactaa atagatttga atttttattga   67320 aaaaaatttt taaacatctt taagaagctt ataggattta agcaattcct atgtatgtgt   67380
actaaaatat atatatttct atatataata tatattagaa aaaaattgta tttttctttt   67440
atttgagtct actgtcaagg agcaaaacag agaaatgtaa attagcaatt atttataata   67500
cttaaaggga agaaagttgt tcaccttgtt gaatctatta ttgttatttc aattatagtc   67560
ccaagacgtg aagaaatagc tttcctaatg gttatgtgat tgtctcatag tgactacttt   67620
cttgaggatg tagccacggc aaaatgaaat aaaaaaattt aaaaattgtt gcaaatacaa   67680
gttatattag gcttttgtgc atttttcaata atgtgctgct atgaactcag aatgatagta   67740
tttaaatata gaaactagtt aaaggaaacg tagtttctat ttgagttata catatctgta   67800
aattagaact tctcctgtta aaggcataat aaagtgctta atacttttgt ttcctcagca   67860
ccctctcatt taattatata atttttagttc tgaaagggac ctataccaga tgcctagagg   67920
aaatttcaaa actatgatct aatgaaaaaa tatttaatag ttctccatgc aaatacaaat   67980
catatagttt tccagaaaat accttttgaca ttatacaaag atgattatca cagcattata   68040
atagtaaaaa aatggaaata gcctcttttct tctgttctgt tcatagcaca gtgcctcata   68100
cgcagtaggt tattattaca tggtaactgg ctaccccaac tgattaggaa agaagtaaat   68160
ttgttttata aaaatacata ctcattgagg tgcatagaat aattaagaaa ttaaaagaca   68220 cttgtaatttt tgaatccagt gaatacccac tgttaatatt tggtatatct ctttctagtc   68280 ttttttttccc ttttgcatgt attttctttta agactcccac ccccactgga tcatctctgc   68340
atgttctaat ctgctttttt cacagcagat tctaagcctc tttgaatatc aacacaaact   68400
tcaacaactt catctataga tgccaaataa taaattcatt tttatttact taaccacttc   68460
ctttggatgc ttaggtcatt ctgatgtttt gctattgaaa ccaatgctat actgaacact   68520
tctgtcacta aaactttgca cacactcatg aatagcttct taggataaat ttttagagat   68580
ggatttgcta aatcagagac cattttttaa aattaaaaaa caattattca tatcgtttgg   68640
catgtaagac agtaaatttt cctttttattt tgacaggatt caactggaag ctttgtgctg   68700
cctttccggc aagtcatgta tgctccatat cccaccacac acatagatgt ggatgtcaat   68760
actgtgaagc agatgccacc ctgtcatgaa catatttata atcagcgtag atacatgaga   68820
tccgagctga cagccttctg gagagccact tcagaagaag acatggctca ggatacgatc   68880
atctacactg acgaaagctt tactcctgat ttgtacgtaa tgctctgcct gctggtactg   68940
tagtcaagca atatgaaatt gtgtctttta cgaataaaaa caaaacagaa gttgcattta   69000 aaagaaaga aatattacca gcagaattat gcttgaagaa acatttaatc aagcattttt   69060
ttcttaaatg ttcttctttt tccatacaat tgtgtttacc ctaaaatagg taagattaac   69120
ccttaaagta aatatttaac tatttgttta ataaatatat attgagctcc taggcactgt   69180
tctaggtacc gggcttaata gtggccaacc agacagcccc agcccagcc cctacattgt   69240 gtatagtcta ttatgtaaca gttattgaat ggacttatta acaaaaccaa agaagtaatt   69300
```

```
ctaagtctttt tttttcttga catatgaata taaaatacag caaaactgtt aaaatatatt    69360
aatggaacat tttttttactt tgcattttat attgttattc acttcttatt tttttttaaa    69420
aaaaaaagcc tgaacagtaa attcaaaagg aaaagtaatg ataattaatt gttgagcatg    69480
gacccaactt gaaaaaaaaa atgatgatga taaatctata atcctaaaac cctaagtaaa    69540
cacttaaaag atgttctgaa atcaggaaaa gaattatagt atacttttgt gtttctcttt    69600
tatcagttga aaaaaggcac agtagctcat gcctgtaaga acagagcttt gggagtgcaa    69660
ggcaggcgga tcacttgagg ccaggagttc agaccagcc tgggcaacat agtgaaaccc     69720
catctctaca aaaaataaaa aagaattatt ggaatgtgtt tctgtgtgcc tgtaatccta    69780
gctattccga aagctgaggc aggaggatct tttgagccca ggagtttgag gttacaggga    69840
gttatgatgt gccagtgtac tccagcctgg ggaacaccga gactctgtct tatttaaaaa    69900
aaaaaaaaaa aaaatgcttg caataatgcc tggcacatag aaggtaacag taagtgttaa    69960
ctgtaataac ccaggtctaa gtgtgtaagg caatagaaaa attggggcaa ataagcctga    70020
cctatgtatc tacagaatca gtttgagctt aggtaacaga cctgtggagc accagtaatt    70080
acacagtaag tgttaaccaa aagcatagaa taggaatatc ttgttcaagg gacccccagc    70140
cttatacatc tcaaggtgca gaaagatgac ttaatatagg acccattttt tcctagttct    70200
ccagagtttt tattggttct tgagaaagta gtaggggaat gttttagaaa atgaattggt    70260
ccaactgaaa ttcatgtca gtaagttttt atatattggt aaattttagt agacatgtag      70320
aagtttctca attaatctgt gccttgaaac attttctttt ttcctaaagt gcttagtatt    70380
ttttccgttt tttgattggt tacttgggag ctttttttgag gaaatttagt gaactgcaga    70440
atgggtttgc aaccatttgg tatttttgtt ttgttttta gaggatgtat gtgtattta      70500 acatttctta atcattttta gccagctatg tttgttttgc tgatttgaca aactacagtt    70560
agacagctat tctcattttg ctgatcatga caaaataata tcctgaattt ttaaattttg    70620
catccagctc taaattttct aaacataaaa ttgtccaaaa aatagtattt tcagccacta    70680
gattgtgtgt taagtctatt gtcacagagt cattttactt ttaagtatat gttttttacat   70740 gttaattatg tttgttattt ttaattttaa cttttttaaaa taattccagt cactgccaat    70800
acatgaaaaa ttggtcactg gaatttttt tttgacttt attttaggtt catgtgtaca      70860
tgtgcaggtg tgttatacag gtaaattgcg tgtcatgagg gttggtgta caggtgattt      70920 cattacccag gtaataagca tagtacccaa taggtagttt tttgatcctc accttctcc     70980 caccctcaag taggccctgg tgttgctgtt tccttctttg tgtccatgta tactcagtgt    71040
ttagctccca cttagaagtg agaacatgcg gtagttggtt ttctgttcct ggattagttc    71100
acttaggata atgacctcta gctccatctg gttttatgg ctgcatagta ttccatggtg      71160
tatatgtatc acattttctt tatccagtct accattgata ggcatttagg ttgattccct    71220
gtctttgtta tcatgaatag tgctgtgatg aacatacaca tgcatgtgtc tttatggtag    71280
aaaaatttgt attcctttag gtacatatag aataatgggg ttgctagggt gaatggtagt    71340
tctattttca gttatttgag aaatcttcaa actgctttc ataatagcta aactaattta     71400
cagtcccgcc agcagtgtat aagtgttccc ttttctccac aaccttgcca acatctgtga    71460
ttttttgact ttttaataat agccattcct agagaattga tttgcaattc tctattagtg    71520
atattaagca ttttttcata tgcttttag ctgtctgtat atattcttct gaaaatttt       71580 catgtccttt gcccagtttg tagtggggtg ggttgttttt tgcttgttaa ttagttttaa    71640
gttccttcca gattctgcat atcccttttgt tggatacatg gtttgcagat attttttctcc  71700
```

```
cattgtgtag gttgtctttt actctgttga tagtttcttt tgccatgcag gagctcgtta   71760
ggtcccattt gtgtttgttt ttgttgcagt tgcttttggc gtcttcatca taaaatctgt   71820
gccagggcct atgtccagaa tggtatttcc taggttgtct tccagggttt ttacaatttt   71880
agattttacg tttatgtctt taatccatct tgagttgatt tttgtatatg cacaaggaa    71940 ggggtccagt ttcactccaa ttcctatggc tagcaattat cccagcacca tttattgaat   72000
acggagtcct ttccccattg cttgtttttt gtcaactttg ttgaagatca gatggttgta   72060
agtgtgtggc tttatttctt ggctctctat tctccattgg tctatgtgtc tgtttttata   72120 acagtacccct gctgttcagg ttcctatagc cttttagtat aaaatcggct aatgtgatgc  72180
ctccagcttt gttcttttttg cttaggattg ctttggctat ttgggctcct ttttgggtcc  72240
atattaattt taaaacagtt ttttctggtt ttgtgaagga tatcattggt agtttatagg   72300
aatagcattg aatctgtaga ttgctttggg cagtatggcc attttaacaa tattaattct   72360
tcctatctat gaatatggaa tgttttttcca tgtgtttgtg tcatctcttt atacctgatg  72420
tataaagaaa agctggtatt attcctactc aatctgttcc aaaaaattga ggaggaggaa   72480
ctcttcccta atgaggccag catcattctg ataccaaaac ctggcagaga cacaacagaa   72540 aaagaaaac ttcaggccaa tatccttgat gaatatagat gcaaaatcc tcaacaaaat     72600 actagcaaac caaatccagc agcacatcaa aaagctgatc tactttgatc aagtaggctt   72660
tatccctggg atgcaaggtt ggttcaacat acacaaatca ataagtgtga ttcatcacat   72720
aaacagagct aaaaacaaaa accacaagat tatctcaata ggtagagaaa aggttgtcaa   72780
taaaatttaa catcctccat gttaaaaacc ttcagtaggt caggtgtagt gactcacacc   72840
tgtaatccca gcactttggg aggccaaggc gggcatatct cttaagccca ggagttcaag   72900
acgagcctag gcagcatggt gaaacccat ctctacaaaa aaaaaaaaaa aaaaaaatta    72960
gcttggtatg gtgacatgca cctatagtcc cagctattca ggaggttgag gtgggaggat   73020
tgtttgagcc cgggaggcag aggttggcag cgagctgaga tcatgccacc gcactccagc   73080
ctgggcaacg gagtgagacc ctgtctcaaa aagaaaaat cacaaacaat cctaaacaaa    73140
ctaggcattg aaggaacatg cctcaaaaaa ataagaacca tctatgacag acccatagcc   73200
aatatcttac caaatgggca aaagctggaa gtattctcct tgagaaccgt aacaagacaa   73260
ggatgtccac tctcaccact cctttcagc atagttctgg aagtcctagc cagagcaatc    73320
aggaaagaga aagaaagaaa gacattcaga taggaagaga agaagtcaaa ctatttctgt   73380
ttgcaggcag tataattctg tacctagaaa atctcatagt ctctgcccag aaactcctaa   73440
atctgttaaa aatttcagca aagttttggc attctctata ctccaacacc ttccaaagtg   73500
agagcaaaat caagaacaca gtcccattca caatagccgc aaaacgaata aaatacctag   73560
gaatccagct aaccagggag gtgaaagatc tctatgagaa ttacaaaaca ctgctgaaag   73620
aaatcagaga tgacacaaac aaatggaaat gttctttttt aacaccttgc tttatctaat   73680
tcacttatga tgaagatact cattcagtgg aacaggtata ataagtccac tcgattaaat   73740
ataagcctta ttctctttcc agagcccaag aagggggcact atcagtgccc agtcaataat   73800
gacgaaatgc taatattttt cccctttacg gtttctttct tctgtagtgt ggtacactcg   73860
tttcttaaga taaggaaact tgaactacct tcctgtttgc ttctacacat acccattctc   73920
tttttttgcc actctggtca ggtataggat gatccctacc actttcagtt aaaaactcct    73980
cctcttacta aatgttctct taccctctgg cctgagtaga acctagggaa aatggaagag   74040
```

```
aaaaagatga aagggaggtg gggcctggga agggaataag tagtcctgtt tgtttgtgtg   74100
tttgctttag cacctgctat atcctaggtg ctgtgttagg cacacattat tttaagtggc   74160
cattatatta ctactactca ctctggtcgt tgccaaggta ggtagtactt tcttggatag   74220
ttggttcatg ttacttacag atggtgggct tgttgaggca aacccagtgg ataatcatcg   74280
gagtgtgttc tctaatctca ctcaaatttt tcttcacatt ttttggtttg ttttggtttt   74340
tgatggtagt ggcttatttt tgttgctggt tgttttttg tttttttttg agatggcaag   74400
aattggtagt tttatttatt aattgcctaa gggtctctac ttttttaaa agatgagagt   74460 agtaaaatag attgatagat acatacatac ccttactggg gactgcttat attctttaga   74520
gaaaaaatta catattagcc tgacaaacac cagtaaaatg taaatatatc cttgagtaaa   74580
taaatgaatg tatattttgt gtctccaaat atatatatct atattcttac aaatgtgttt   74640
atatgtaata tcaatttata agaacttaaa atgttggctc aagtgaggga ttgtggaagg   74700
tagcattata tggccatttc aacatttgaa ctttttttctt ttcttcattt tcttcttttc   74760
ttcaggaata ttttttcaaga tgtcttacac agagacactc tagtgaaagc cttcctggat   74820
caggtaaatg ttgaacttga gattgtcaga gtgaatgata tgacatgttt tctttttta   74880 tatatcctac aatgcctgtt ctatatattt atattcccct ggatcatgcc ccagagttct   74940
gctcagcaat tgcagttaag ttagttacac tacagttctc agaagagtct gtgagggcat   75000
gtcaagtgca tcattacatt ggttgcctct tgtcctagat ttatgcttcg ggaattcaga   75060
cctttgttta caatataata aatatattg ctatctttta aagatataat aataagatat   75120
aaagttgacc acaactactg ttttttgaaa catagaattc ctggtttaca tgtatcaaag   75180
tgaaatctga cttagctttt acagatataa tatatacata tatatatcct gcaatgcttg   75240
tactatatat gtagtacaag tatatatata tgtttgtgtg tgtatatata tatagtacga   75300
gcatatatac atattaccag cattgtagga tatatatatg tttatatatt aaaaaaaagt   75360
tataaactta aaaccctatt atgttatgta gagtatatgt tatatatgat atgtaaaata   75420
tataacatat actctatgat agagtgtaat atattttta tatatattttt aacatttata   75480 aaatgataga attaagaatt gagtcctaat ctgttttatt aggtgctttt tgtagtgtct   75540
ggtctttcta aagtgtctaa atgatttttc cttttgactt attaatgggg aagagcctgt   75600
atattaacaa ttaagagtgc agcattccat acgtcaaaca acaaacattt taattcaagc   75660
attaacctat aacaagtaag ttttttttttt tttttgaga agggaggtt gtttatttgc   75720 ctgaaatgac tcaaaatat ttttgaaaca tagtgtactt atttaaataa catctttatt   75780
gtttcattct tttaaaaaat atctacttaa ttacacagtt gaaggaaatc gtagattata   75840
tggaacttat ttcttaatat attacagttt gttataataa cattctgggg atcaggccag   75900
gaaactgtgt catagataaa gctttgaaat aatgagatcc ttatgtttac tagaaatttt   75960
ggattgagat ctatgaggtc tgtgacatat tgcgaagttc aaggaaaatt cgtaggcctg   76020
gaatttcatg cttctcaagc tgacataaaa tccctcccac tctccacctc atcatatgca   76080
cacattctac tcctacccac ccactccacc ccctgcaaaa gtacaggtat atgaatgtct   76140
caaaaccata ggctcatctt ctaggagctt caatgttatt tgaagatttg ggcagaaaaa   76200
attaagtaat acgaaataac ttatgtatga gttttaaaag tgaagtaaac atggatgtat   76260
tctgaagtag aatgcaaaat ttgaatgcat ttttaaagat aaattagaaa acttctaaaa   76320
actgtcagat tgtctgggcc tggtggctta tgcctgtaat cccagcactt tgggagtccg   76380
aggtgggtgg atcacaaggt caggagatcg agaccatcct gccaacatgg tgaaaccccg   76440
```

```
tctctactaa gtatacaaaa attagctggg cgtggcagcg tgtgcctgta atcccagcta   76500
cctgggaggc tgaggcagga gaatcgcttg aacccaggag gtgtaggttg cagtgagtca   76560
agatcgcgcc actgcacttt agcctggtga cagagctaga ctccgtctca aaaaaaaaaa   76620
aaaatatcag attgttccta cacctagtgc ttctatacca cactcctgtt aggggggcatc  76680 agtggaaatg gttaaggaga tgtttagtgt gtattgtctg ccaagcactg tcaacactgt   76740
catagaaact tctgtacgag tagaatgtga gcaaattatg tgttgaaatg gttcctctcc   76800
ctgcaggtct ttcagctgaa acctggctta tctctcagaa gtactttcct tgcacagttt   76860
ctacttgtcc ttcacagaaa agccttgaca ctaataaaat atatagaaga cgatacgtga   76920
gtaaaactcc tacacggaag aaaaaccttt gtacattgtt tttttgtttt gtttcctttg   76980
tacattttct atatcataat ttttgcgctt cttttttttt ttttttttt ttttttccca    77040 ttatttttag gcagaaggga aaaagcccct ttaaatctct tcggaacctg aagatagacc   77100
ttgatttaac agcagagggc gatcttaaca taataatggc tctggctgag aaaattaaac   77160
caggcctaca ctcttttatc tttggaagac cttttctacac tagtgtgcaa gaacgagatg  77220
ttctaatgac ttttttaaatg tgtaacttaa taagcctatt ccatcacaat catgatcgct  77280
ggtaaagtag ctcagtggtg tggggaaacg ttcccctgga tcatactcca gaattctgct   77340
ctcagcaatt gcagttaagt aagttacact acagttctca caagagcctg tgaggggatg   77400
tcaggtgcat cattacattg ggtgtctctt ttcctagatt tatgcttttg ggatacagac   77460
ctatgtttac aatataataa atattattgc tatctttaa agatataata ataggatgta    77520
aacttgacca caactactgt tttttgaaa tacatgattc atggtttaca tgtgtcaagg    77580
tgaaatctga gttggctttt acagatagtt gactttctat cttttggcat tctttggtgt   77640
gtagaattac tgtaatactt ctgcaatcaa ctgaaaacta gagcctttaa atgatttcaa   77700
ttccacagaa agaaagtgag cttgaacata ggatgagctt tagaaagaaa attgatcaag   77760
cagatgttta attggaattg attattagat cctactttgt ggatttagtc cctgggattc   77820
agtctgtaga aatgtctaat agttctctat agtccttgtt cctggtgaac cacagttagg   77880
gtgttttgtt tattttattg ttccttgctat tgttgatatt ctatgtagtt gagctctgta  77940
aaaggaaatt gtattttatg ttttagtaat tgttgccaac tttttaaatt aattttcatt   78000 attttttgagc caaattgaaa tgtgcacctc ctgtgccttt tttctcctta gaaaatctaa  78060
ttacttggaa caagttcaga tttcactggt cagtcatttt catcttgttt tcttcttgct   78120
aagtcttacc atgtacctgc tttggcaatc attgcaactc tgagattata aaatgcctta   78180
gagaatatac taactaataa gatcttttt tcagaaacag aaaatagttc cttgagtact    78240
tccttcttgc atttctgcct atgttttga agttgttgct gtttgcctgc aataggctat    78300
aaggaatagc aggagaaatt ttactgaagt gctgttttcc taggtgctac tttggcagag   78360
ctaagttatc ttttgttttc ttaatgcgtt tggaccattt tgctggctat aaaataactg   78420
attaatataa ttctaacaca atgttgacat tgtagttaca caaacacaaa taaatatttt   78480
atttaaaatt ctggaagtaa tataaaaggg aaaatatatt tataagaaag ggataaaggt   78540
aatagagccc ttctgccccc cacccaccaa atttacacaa caaatgaca tgttcgaatg    78600 tgaaaggtca taatagcttt cccatcatga atcagaaaga tgtggacagc ttgatgtttt   78660
agacaaccac tgaactagat gactgttgta ctgtagctca gtcatttaaa aaatatataa   78720
atactacctt gtagtgtccc atactgtgtt ttttacatgg tagattctta tttaagtgct   78780
```

```
aactggttat tttctttggc tggtttattg tactgttata cagaatgtaa gttgtacagt    78840
gaaataagtt attaaagcat gtgtaaacat tgttatatat cttttctcct aaatggagaa    78900
ttttgaataa aatatatttg aaattttgcc tctttcagtt gttcattcag aaaaaaatac    78960
tatgatattt gaagactgat cagcttctgt tcagctgaca gtcatgctgg atctaaactt    79020
tttttaaaat taattttgtc ttttcaaaga aaaatatttt aaagaagctt tataatataa    79080
tcttatgtta aaaaaacttt ctgcttaact ctctggatttt cattttgatt tttcaaatta    79140
tatattaata tttcaaatgt aaaatactat ttagataaat tgttttttaaa cattcttatt   79200 attataatat taatataacc taaactgaag ttattcatcc caggtatcta atacatgtat    79260
ccaaagtaaa aatccaagga atctgaacac tttcatctgc aaagctagga ataggtttga    79320
cattttcact ccaagaaaaa gttttttttt gaaatagaa tagttgggat gagaggtttc     79380 tttaaagaa gactaactga tcacattact atgattctca aagaagaaac caaaacttca     79440
tataatacta taaagtaaat ataaaatagt tccttctata gtatatttct ataatgctac    79500
agtttaaaca gatcactctt atataatact attttgattt tgatgtagaa ttgcacaaat    79560
tgatatttct cctatgatct gcagggtata gcttaaagta acaaaaacag tcaaccacct    79620
ccatttaaca cacagtaaca ctatgggact agttttatta cttccatttt acaaatgagg    79680
aaactaaagc ttaaagatgt gtaatacacc gcccaaggtc acacagctgg taaaggtgga    79740
tttcatccca gacagttaca gtcattgcca tgggcacagc tcctaactta gtaactccat    79800
gtaactggta ctcagtgtag ctgaattgaa aggagagtaa ggaagcaggt tttacaggtc    79860
tacttgcact attcagagcc cgagtgtgaa tccctgctgt gctgcttgga gaagttactt    79920
aacctatgca aggttcattt tgtaaatatt ggaaatggag tgataatacg tacttcacca    79980
gaggatttaa tgagaccta tacgatcctt agttcagtac ctgactagtg cttcataaat     80040 gcttttcat ccaatctgac aatctccagc ttgtaattgg ggcatttaga acatttaata    80100
tgattattgg catggtaggt taaagctgtc atcttgctgt tttctatttg ttcttttgt     80160 tttctcctta cttttggatt ttttattct actatgtctt ttctattgtc ttattaacta     80220
tactctttga tttattttag tggttgtttt agggttatac ctctttctaa tttaccagtt    80280
tataaccagt ttatatacta cttgacatat agcttaagaa acttactgtt gttgtcttt     80340 tgctgttatg gtcttaacgt ttttatttct acaaacatta taaactccac actttattgt    80400
tttttaattt tacttataca gtcaattatc ttttaaagat atttaaatat aaacattcaa    80460
aacaccccaa ttaaaagtca gagattgtta ataccacatg atctcactta cacacagaat    80520
tgaaaaactt ggaactcata gaagcagaga gtaaaaacat ggttaccagg tgctggggag    80580
aggcggtggg ctggggagat gttggtcaaa gttagacagg aggaataagt tcaagagatc    80640
tattgtacaa cttattcagt tagataggag gaataagcta aagatcaaga gatctattgt    80700
acaatgtgac tataaccaac aacatatatt gtacacttga aaattgctaa cagtatcttt    80760
taagtgttct ctctacaaat aaatatgtga ggtaatgtat atattaatta actgtagtca    80820
tttcacaatg tatacttatt tcaaaacatc atattgtatg ctataaatat atacaacttt    80880 tattttcaa ttttagaaat gtccttaaaa aatcagattt tcagatcaga taaaaaagca     80940
agacccaact atatgctgcc aacaggaaac acaccttaaa aataaaggac gaacaaacag    81000
attaaaagta aaaggatgga gaaaagatac atcatattgg taattagaag aaaactggag    81060
tgacaatatg aaacaaaata gatttcgagag caaagaatat taccagggggt aaaaatgatc   81120 attttataat gataaaagag tcagttcagc aaaaggatat aacagtccta aatgttttt    81180
```

```
cacctcatag ctgtgtcaaa atagatgaag caaaaactga tagaactgta agaagtagac   81240
aagtccacaa ttatgtttgg agattttttt tttttttttt tttgtcgccc aggctggagt   81300
gcagtggcag gatctcagct cactgcaagc tccgcctccc aggttcacgc cattctcctg   81360
cttcagcctc cccagtagct gggactacag gcggccacca ccacgcctgg ctaattttt   81420 tgtatttta gtagagacgg ggtttcaccg tgttagccag gatggtctcg atctcctgac   81480
ctcgtgatct gcctgcctcg gcctcccaaa gtgctgggat tacaggcatg agccactgca   81540
cgcagcctgg agattttaat atcctttcaa tgtttagtag aacaagaata cacaaaatca   81600
gtaaggatat agaagattag aacaagacta tcaaacaatt tgacttaaat gacatttgta   81660
gagcacagca gtccccaaca acaataaatc acacattctt tccaagagta catgaaacat   81720
gtaccaagat agaccgtatt ttgagccatg aaacaaatct tgataaattt aaaggattc    81780 aagtcataga aaatatgttc tctgaccaca atggaattaa attattaacc aataacaaat   81840
atctgggaaa acctcaaaaa cttggacacc agcgcttta aaagactaaa taatttctaa    81900
attatctgtg ttgggggaa aagagaaatg gattagagag caaaagggt atcagagtgc     81960 tgtggtacga ttttatgaa gagtggaaca gaatctgcct ttggcgtttc cccactacag    82020
cccattcttc acattgataa cagcatgatc cttctaaaat taaatctaac gatcacttct    82080
gcttaatggc tctccaacac ttacagaatt aggtccaaaa ttctagcaca gtttctgttc   82140
atctttctaa cctttcttcc cacaggtcta gctagtacgt atttctttta ttgcatttat   82200
tacactattc ctttgcttat ctatctcccc acctaggcta aagaacaaga ttcttgtctt   82260 tttcatttt gtgtctcagt gcctagcatg gtgccaggca cacagcatgc ttccagtaaa    82320
tgttagctgg atggatgtaa tgagtatatt aaatattaat ttatttgttt ttccccaaaa   82380
agaattattt cctgcaaatc aaggaaattg cttttcttta taatcaaaa acttattttc    82440 ccagaagatt cttcattaaa aattaagcct atgcacaacc tagctctaaa gtttcaaaga   82500
ttttaggcag caattttttca atcttttga agtaatacat ttgaatcttt tcaaatttct   82560
gtttctgcat ttgtgccaca ccatctcatc tcttgctgaa atgtttttgt taaattaatt   82620
gcttgataaa ttgctaagta cttttcatca gaccaattag gacaatagta agtatccatc   82680
tgtggagcgc ggacattcaa gaaatctgat ccagtattta gaaagtcatt cctgagctga   82740
gttggctcaa actggcacct tctggcattt gcttgtgggt ggggaatgtg gaatgctttg   82800
aaagctgaat gagtttgtca agttttaaaa ttcccttatg gctaaggaa aacaacattc    82860 attgtttaaa aacaccattg tttgttttt ctgctttttt gttctttgga gcctgaatct    82920
gcaaaaacac tcacacccag cattttgctt catgtaccac tcctaagatg ttttagaga    82980 cttgaatagt gtctccgcac tacttttat tgtgattgtt cagaatgttc ataacaaatg    83040
gtaaaaagtc agttttagtg ctcaaattga gttttatgga gaaagaccat aatttatgtt   83100
tgtcattgta aattgatagg agaattttg gaagtttgcg tcctagaacc agatttccaa    83160
ggctcagatc cttatttct cacttcctag ctgtgtgacc ttagacaagg tattaaacct    83220
gtctgtgctg cctcagtgtc ctcatctatt ctttaagagt aagaatagaa cctacccgat   83280
agagtcactt gaagattaag tgggttagta aattcagaat gcttggaaca gtaactagca   83340
cagaataagt gtccaataaa attgggttgc agctattatc agtattattc ctgtcataat   83400
catcatcacc attaagcaat taatgtaga gttccaaaat ttgattatga aactacagtt    83460
atacagccat gattcccggt gataccacgt cagtaacaag attatttcct tagcttgagc   83520
```

```
cagtcactac ctcattgcat gtggcagagt gtgttgccgt aggcaaatgt cattgtaggg    83580
aatgaaaaaa aaattgcctg tgagctgctc tccagaggcc tcatcccatt ttcccatcgt    83640
ccactttact ccatctccac tgccactatt aggacttat  catttcttgt ctagattaat    83700
tcaacagctt ccttccttct agtctccatg atttcaccca ctagccatcc cctcccttt     83760 gcccaatttt ctccatttat ggtagagtga tctttctaat aggaaactcc tgacttgcct    83820
taaaaagccc tcattgaggc cggacgtggt ggctcatgcc tgtaatccca gcactttggg    83880
aggccgaggc aggtggatca cgaggtcaag agattgagac catcgtgact aacacagtga    83940
aaccccatct gtactaaaaa tacaagaaat tagccaggcg tggtggcggg tgcctgtagt    84000
cgcagctact tgggaggctg aggcaggaga atggcgtgaa cccgggaggc agagcttgca    84060
gtgagccgag attgcgccac tgcactccag cctgggcgac agagtgagac tccgtctcaa    84120
aaaaaaaaag ccctcattga caaccttcaa cccacaatcc atggtgaagc acaggagcct    84180
tggggatctg cccccagcac acctctccac ccttgtctct cactgctcct gccttcatgg    84240
agagccctga tgaactattt gtagtttccc ctgactcacc ttgctgttac tgggcctgtg    84300
tgcgtgttgc tcccactacc tgcaatacgc ttacccactt cacctgggtg aactttactt    84360
aggattcacc ttaggtgggc atcatgttct tccaggcccc tcctctaact tttagttgag    84420
agtattccag acttaaggct ccatgggata gggatcttgt ctatgcacca gcttattccc    84480
aactgcctgg cacgtaatgc atttattaaa tatatattga attgattacc ctacttgggg    84540
ctcttgtttg cttctacact tacagttcta gcatagcact taactcatta tcatgcatca    84600
ttattatggg tttgttttgt ctcccattag actgtgagct ccacaaggct gtgtccttgt    84660
cttatacatc attgtatttc cagcttccaa catagtgctt gccatgacac aggaagtcag    84720
taagctctga atgaatgaat agtatctaca taccattaat ctgaggttta aagtttcccc    84780
aaattctgaa gcaaggggat ttacggactt ccctgacaat ttttggatgt catcccaatg    84840
ataccactaa cattttaagg gacagcttgc atatatacat ttttctggat ggcagttttt    84900
tttcccacag gcttcatcag atatttctcc atagccttcc tcagattctc aaagggtct    84960 ctgattcccc caaagataa  gaaactgtca taaaaaatta tttctaaata tcaattgtta    85020
aataaaatgt ttgcaaagca gcctgatgaa tcatttcagg ccacttgacc ccgatgagtt    85080
agagagtttg tgctctgcaa tctgactgct tccagcagtc tcactgctgc tggactgtgg    85140
cacttccaat tggcagcagg gcaagtttct tctggatgaa tattctgtca tagggg tccc   85200 ccttccacac atacctgtag gagcagtttg aaactcatat gcatggtctt cctggttcta    85260
ggcacatgag tcatttaagc tgctggagcc aggaccagct agtatgctag cccggcattc    85320
agaaagttaa aatttggggt caaaactgag aaccttcttt gatccacctt ggccagacat    85380
tttctctggc ttccattaat agcctcaaca ttttttttt  ttctggccta gacccacaca    85440
ggcaagagac cagagcttct ctaaggagct aagggaaagc acattttaaa aataacttga    85500
gcaaatgaat tcatctggca aaagcaaccc cactacgtaa aataaaacctt tttagtttcg    85560 caatagcagt tcctgaaaat gtaaacaacc tcagggtcta catgcactga atcatttgct    85620
gaacagaaag tccctggtcc aaattctgca agaataaaca ccttacaaaa ctagggtca    85680 atgaccttca tatgggaaca aggagggtgt gggggcagc  aacccaccct gaggacaatg    85740
agaaagtctt gagacttgat attcaaaatg ctggctttct aaaccaaaaa ctggcatgag    85800
tggagggaga aggggagggt gggcacagtc tatgcctcag gctcttgctc agaccctacc    85860
aggcccctgc cttccctagg gaaagcgaga gtctactcac tgtcatgaag ccagaggaag    85920
```

```
gccctgcagg tttcactgtg tgttctgttg acaagatgat ggttccattg aaactgtaat   85980
aacatacttg gccaactaag cccatacgat cgtagtaact ttgtacccag tcctagcttt   86040
tcaaacataa tgataatatg ttctttctaa tgtggcccat actgttctaa tgaacttatg   86100
ctgagttttt ctgagtacta gaataatatt cgccataaat aatagatata attattctca   86160
tttaatattt gcgtagctct tctttaaagc agaaagtatt ttctcattcc ttactagaac   86220
cttcctgtgt gaggagcact gagctagaac ccatatctta gaatggtcag aatttggaga   86280
aattcaggga aaaggcactg gactcatttt taaagactag aaaatgcaac ctccagaaaa   86340
agattcaaga gttttttact cccagagatg taggaaagat tggagtaaat cttaatatta   86400
tatttcaggt aaacaaagga tcactgtcaa aatagcagca tttattgagt aatggctgtg   86460
tgccaggtac tttacagttt cacatttaac cctcataata accttgtaaa gtggatatcc   86520
cctcagtaca tgatgagaac actgaagctt aggttaaatg attgtccaaa tcggacaatc   86580
attttcaaaa tctcccccct tttttctcct ttcttatctg caaggcagat tgccctttcc   86640
ctttcagtga aacttgtgca tgaccacatg actctctttg gccaatgaaa catgaacaag   86700
cagcgtttat cactttcaga tggaaggctt tgcatgagct ttgcctcctt ttcactctgc   86760
cacagtggcc actaacattc cagatagtgg cgctctgcag gctaggtcct atagtgggag   86820
ctatgggcag agccccctt cccaccccca tcaagatgtg catgctgcat aagccatgca   86880
ttaatctttg cagttttaag ccactaagtt ttggagttat attaatcatt aatcatggtt   86940
ctcaagagaa acagagtggg ggagtggtat tcattatggg aattggctta catgattatg   87000
gaagctgagt agtcccccag tctgctgttt ttgagctgga gaactagagg agccagtggt   87060
ataattcagc ccaagcctga aggcctgaga aatgggatgg gggaattggg agggtgggtg   87120
tgctagggta ggataagtcc tgaagttcaa aggccagcca gaaggtggat gtttcagcac   87180
cagaagagag agcaaattcg cttttcttct gcctttttgt cctctctggg ccctcaatgg   87240
attggatgat gccctcccac attggtaagg gtggatcttc tatactcagt ctgctaatttt  87300
cttccagaaa catcttcaca gacacatcca gaaataatgt tttaccagct atctcggtat   87360
cccttagcct agtccatatt taaaaattaa tgatcacaag cagttgtttg tttccacagc   87420
aaaacctggg tgacagacca agtgacccag atgactagaa tttgaccttc ttttgttgcc   87480
cacaccatac tctgaactaa catgctgtgc tgccttccaa gtggagaatg atggctaagt   87540
atcttctacc taatttgagt cacagaaaaa aaaaaaaaag gttattaact gcagtgacaa   87600
gaattgtgat tccccagggg gcagatcaag actgatagat aagagaagtg aggaacatct   87660
ggggaatgtc cattgaaaat ttactcagaa gagaagaata attaatataa taatatgata   87720
tattgaatta taataaataa tattttgatg tatttccttc caggcatgtt taagttatag   87780
actttgagta tattttctca aagggggttc tatgtaagag actatttctt aatatagttc   87840
ctagcttgga attgctcttg ctggtttaag ctgagcttat tttattacag acttcacaac   87900
aataacgttt tccttcacta gtcagtacac aagatggtct tcatttccag tttggaatcc   87960
cacactatca gagcctgaga caaggactag tatgcagtta gtttgtttgg gaggtgattc   88020
caggaagtgg gaatgagaga tcagtcagcc tgcaacacga aggaggaaaa gtcaatataa   88080
ggatgaattt ggcaattggc cgtttcatgc aactggggct aaattttgct tggctctcta   88140
agaaatgtaa agaatgcctc ccgtaattgc tcacctcaag tatttattca ttggctctca   88200
tgctccattg gttgtccatg agaactttag ccctccctcg ctgcagcaca gacactgtgc   88260
```

| | |
|---|---|
| tttctcctag gctgagcaag ctcctgcatc tgtggaaacc gtcccggggc agatagtgaa | 88320 |
| ataatgactg ctgcgtgctt gagatctggg aaagaggcca catcataagt gcactgaaat | 88380 |
| cagagatgtg tcaagagatg tgacacaggg catctgaggt gtctactgca ccagctataa | 88440 |
| ctccctaaac gctaatctca gttcttacag aggggatgga tgcaagggaa cagtcatgat | 88500 |
| tgagagcacc gaagaagctc tgtatgaacc ttaggcaagt ttcctaatct ccaaaatgaa | 88560 |
| ggtaataata cccaccatcc aagatcttcg ggaggaatag atgaactaat gtatgtgaaa | 88620 |
| atgtccagca caggtcctaa cccatagtag gtgctcacca aatgttagtt ccctgccctc | 88680 |
| cacgttgtgt gtatccggag ctgcactaga tgctgaggca aatggtctca aatgtacttt | 88740 |
| aacacttaat gactgagatt ttttctgagc tgcctacagg ttattgacta tattcattat | 88800 |
| taataataat atatatggcc acttcaggca actggggcta aattttgctt ggctctctaa | 88860 |
| gaaatgtaaa gaatgcctcc tgtaattgct cacctcaagt atttattcat ggctctcgt | 88920 |
| gctttattgg ttgtccctga ggactttagc cctctctcac tgcagcacag acactgtgct | 88980 |
| ttctcctagt ttctgtggca agtgacagga gcccacctca aactaaagca aaagggactt | 89040 |
| cattggctct tgtagctagg aattccaggg ttggcactgg ctttgggcac tactggatgc | 89100 |
| aggaattcaa acaatgtctt caactctttc ttttggtgtt tctctcagct gtgcttctct | 89160 |
| tgtcgtttct ttttcccatt ttacagataa gttcatccgt aactgagaga ggtgaaaagg | 89220 |
| ggatggctgc agagaactct ggcttatatc atccttgctt gctgacctca aggtccatgt | 89280 |
| ataaattctc agagaagaag ccctctggtt ggtgatgctt ggaacatgcc ctggagggtg | 89340 |
| ggccccttga agtggagctt gctggaacca catgggctgg agcaaggcgc tagggccaga | 89400 |
| agagagaggt aggcagggct gctggccagg cactcttcac caagacaagg caagaggagg | 89460 |
| ggcatgattg aggcagtgat acagaaagca gacagtagag gtcgtggcaa gtgtgccgtt | 89520 |
| acttgctacc tgtggttgat gggagagtca caccacattt aggaggagag aatccatttg | 89580 |
| ccacttctga caatgccaca agaatcacat atttcatcca gaggttgaat ttggcccatg | 89640 |
| ctgagcttta aaatacagag ctgtcttgga acaatggctc agtacattca tttggtgtcc | 89700 |
| aacaaagcct gcctctgttg ccttccctct ctctgtgtgc ccttcaagat cttcattgtg | 89760 |
| ctttggggag agaaagagaa aatgtcatat cagggtagct caccccatgt gtcctggact | 89820 |
| caggaaaaga gtatcttatc accttactct tttgttatta taaaaaataa agttgaacgt | 89880 |
| cttcaaataa aataagaag tatagaaaaa attttaaatt aacctgttat gattctacct | 89940 |
| agagaaccat tgtcaacatc ttggtatatg tacttccaga tactttccta tgaatatata | 90000 |
| cattgtagat ttttaatat taaaaggcta tcatgctgct ttgtatacag gctttctta | 90060 |
| ctgatatgta atataataca cagacaaata tacaaatcct aagccatcaa ctcattgaat | 90120 |
| ttttattcat tgttttaat acctgcattg tgttccattg ttaggctatg tcacaacata | 90180 |
| tttaattaag cccctattga tgaatattaa tttactctat ttgccagttc attccagtcc | 90240 |
| aacatttatt gagtgtctac ttacgggcca ggcactcttg tattcatcaa gatcaccaca | 90300 |
| ttatctgtat cagttattta ttgccacaat aaaactgcat aacaaatcac tccaaaatgt | 90360 |
| agcaccttaa aactacaact acttattatt tctcaagagt caatgggtca gctgagcagt | 90420 |
| tctgccgata ggggtcaagg tcaacacatt tcaactagac tacttgtaaa aaagaatgag | 90480 |
| tgtctgggta ggtgtgttct tctaaaaata aaacaaggaa tgaggaaatt gcaggtagga | 90540 |
| taagaggggt ggttggcaac caaaccccac aaaaggcaga caaattttaa ggaaacataa | 90600 |
| tgccagactc ctatgtcatc atccaagtag atgcagtgaa gtataacctg gggcgtagta | 90660 |

```
gggtaggagt ggggagagca gaggagaagg aagggagatt gcttttcatc acttttggat   90720
tccctaataa cagacatgac tgccagtatt aaaatttaac aaaggatatc tgatcattaa   90780
ttttcctgta taagtcactg gtgatcttca acatctctcc ctcccttcct cccttccttc   90840
ctcccaccct cccttccttc cttctttcct cttttgcttt caacttcctt ttctcgtttc   90900
cttttgcttt cttctctctc tcccttttt ctgtcactct gggcgtatgt agtagtgtaa   90960
aaaggttgac agagaaatca aatataacag gagcagggcc ctgagaaaag cacctggcat   91020
cctgtaggca aaccattgtt tctaaaagaa gggactgaga gattgaggag ctcaggacat   91080
tgccaaatga acaaggcaag cacatttatt cagtaccaaa caaacggaaa acggcctttc   91140
caaataactg acctataaaa cagccttttc acaagagtac cgtaattact ggccaacagc   91200
aacaatgaaa aacaactccc aaacaaagaa atatttctgg attaaaagcc atgagatctg   91260
gattctaaca agctgtgctc ctcaaactac aagtacaaaa tctggctcta aactaacaag   91320
ctatgagcct caaactgatg actggcatgt ttgggtctcc atctccttct tgggggttgg   91380
ggtcttagag acccttttcc acgccctgat tctcttacta gtgtgtatgc tttccttttg   91440
acttctcatg ctgaccgtct gagcaggagt gagaagcaat ttcaaaggaa aacatcgttt   91500
atcatctgct gaaagaaacc aaaaagaaca caggaaaaca aaaagacaag gaaagggaat   91560
gaaaatgtaa ttcattttat taaaaagaag aattattctt ctgggacact ggatagaaac   91620
cttaatgagt tacctagcta tcataaatcc tctaacagag aagagaagag aaagaaacaa   91680
agacggaaga gggcaggata aaagaaagaa aaaaggaagg gaaaaatgaa ggaaggaagt   91740
tatctattca tttctacaga gactctgctg agcagtagac aagaagactt gggaaaaatt   91800
taactgaaac ttttccaaaa atcttttcag agggatttt tccctctgaa aagcatcatt   91860
agaggctgtt caatacccaa ggcaagcctc tttcatatta cttactgtac atgaaacact   91920
catgcaattg aggctagcca gaggccattt agaaattcaa taattattca acccaagggg   91980
ctttccaaat ggtgaagtag cttcttaaga ggaaattaat attgagcagt atagcaaacc   92040
taattggaat cttgagaaaa tagttctgtg tcgttagaac agctagaggc taaagaagat   92100
caggttggat gataccttca tttttgtctc tttccttaat tatgatgtaa agggaaaaat   92160
cttgtttatt ttctatgcca ggagggtaga gggtgatttg gagaggttcc aagtttatca   92220
aaatctacct tcagtctggc agtagaaaag tttacttcct tcatttcttt cctatagaca   92280
ttcaaagaga gctaaggaga tccaaaaacc tttttttcta tatttgcaat gcaaggcagt   92340
tgggaattaa tgactgattt gttggtgagg gcagtgggca ttgatcacaa aagcagtaaa   92400
gctgtgtttc tcaaagagag aaagtctctt tgagatcttc attatttac tatttagaag   92460 agaaaggggc gttatatcac gttggaagca tccatgagtc actagtctct tctctatctt   92520
tctatgcctt tctgtattaa ttactttgaa agcacaacat tccaaaccca ttgagcacac   92580
agtggtctga tttctccact tgtgaaaggt gctaaagtct cactgtagga ttaatttggg   92640
```

-continued

```
ggtccaggct atgggcttgt agatatgact accttagact ttggttctcc tggcaactaa   92700 cccttttttgg atcgtatcta agttgacctg tttcacagtg agagaactcc tctccattac   92760
tcagaatact gaggcagatc acaagtgtac cacacctggc taatgttaag ccagacagaa   92820
acatcaggct catctcttga aagaagggt cgcttattaa ggatacaaac tattttttt    92880 tttttttttt gagacagggt ctcattgccc aggttagagt gcagtggtgc aatcatagct   92940
cactgcagcc tcaaccacat gggtatttt aaataagaaa aaataccat ctgatagata    93000 tgaaggagca ttgggtcact ataaacaaaa cagattctaa gagcaggaag aaagagtaca   93060
gtctcttttc aataattttt ttttaaactt gggaagaac actcactcta ttcctataga    93120
ccagaaagca gataattgtc cattatgatt ccacatgaca ctatcttgtt cagctgtcac   93180
tgaaacaact ttgaacactg tcatatgttc ttcccagctc ctgaactctg acctttttat   93240
gccttagttc cactttcaca aaagggatt gatgtaatgt gcatttcaga ggaaacgact    93300
atagacattt agtgtcatta taaatgttga gaagtatgct ggcagaaatt atgccttaag   93360
atcatatatg gattcttgta tggtttgaaa ttgcttaaaa gatatatatg atctctaaaa   93420
tgtgtgtgta tatatatatg atgtcttctt atatatctat atgtgatata tttatatata   93480
tataaatctg tgtatatcac atatataaat ttgctgttat ttgaattgcc attacctcag   93540
tgcttagggg aagccatgca cgtttgtttc ttttcagtac ccagagttaa ttaacataag   93600
ttatcacaga agctcccata agcattgaga caatttctct atacctgtga ctatttaagg   93660
ttttgaaaac aaaacagaag caggtaagga ggaagtacgc tttactattg aagatttatt   93720
aggtacacat ttagatttgt gaactcacat tgcttaggat gaaagggact cttgaggatg   93780
tctgctgttt gttagtgaac tgcctgtaac aattacaatt agcacacaca tgagcacaat   93840
gaactgggta gtcagactca gccaaaatga atagaaatag cctcttacca aatttacttt   93900
gagtagccct tggactctga gcactgctgc ccagagcaat atgactgtag gtccaagttt   93960
gtcaatgact atgcaaatgt gctttcttcg cttttactct attgtcatct gtctattaca   94020
atgttgctat ggtgacacct ttccaatatc cctgtgcttc tttggtatcc tctaagggga   94080
agctgtaatg aagtggcttg gcaaaagaat cctcttggaa ttttttttt ttcatatgct    94140 actgaaaacc agcatgattt tcctcttatg ggaaatgtat aaagtatgag ttggaaatga   94200
tggaaattaa tctgtactga cttgggcaag gaatgtgaat gttattcatt ctgttccaaa   94260
ctacctgaaa atattctctt tctgttccta ctttccagga gataacatct aagggacac    94320 tgaagcttgt gcgtgtgtga gtagaacacg tgctgggggc tcttgagctc atgagggagg   94380
ggctacatgt cggtggggtg ataactgtat gctggaaaca atgataggtg gtgaccctgg   94440
agcacttacc atgtgacagg tgttatgcta agcatgttgt atgcattcct tcattgaatg   94500
acagctacct atattatcct cattttataa gatgaggtaa cagagcttca gaaaggttag   94560
actcagctgc tatgggtctg tctgactctg gtgttcttcc tcttaaaaac tggggcactt   94620
tggaaatgag attcctcggt gatgaacaga atattgctt agcggctgta tttttgtatc    94680
```

```
tggcagtttt cccatatttg agtcttatat tcacaatcgg tatctttaca ttacacaaaa   94740
gtgacacaga attagagtca tttaatccag ggttgatatc attaagtcat gactatttat   94800
taaatgtttc ttacaatatc tgagatgata ttgcaaaaga tgtaagtgat tttagaagtt   94860
ctcacttcgt agttagttgc agaaacctct tttggaggag ggatgttttc tctatatatc   94920
ctaatttcta cttaatatat ttccacacct ctttgaagtg tgtagtaaga atggtaaaat   94980
gcagtacttc gtcatttggt acagttcaat caatatgcat taagatgtga tcatatgggt   95040
aatagaaaaa tgtgaaagat ccaattcttt ttctccagaa ggcaggaagc tcatatttga   95100
tttctgttac tataaactat aaaaacgttt caaatgtagt ttacccgtaa ccatcaccct   95160
gcaagggtga tattgctccc cgccaattta cggaggagaa tactgaggct ttaaggttgt   95220
agatagacca agaccacaca agtagagagt ggcgggctgt gggttgagct ttaaaatcca   95280
ggttcatcca tgactcccag tgtgttctag taaatccact agaatctgag tattttccaa   95340
tgatttatgc tccgctctgt gtcaggcagt tcatggtatt tttcaacaat cagaaaatcc   95400
tggggaaggc aaactgtttc cccctctcta ggtgccttgg aagtggccgt tgtggaccca   95460
gagatcatcc tttctgatct gacaccttct tcactgccct ggcccagtgt cttttctgca   95520
aggctggaag cccccttaga ctggtcatgt cccatctctt tccggaggga agatgatccc   95580
aaagacgact tttctctcca cggtgctgcc ataccgcagg cggccgccag gggtccccgc   95640
tcggcgtccc cgcgagacag tcgagcccg gccggctgcg cggcgcgctg ggtgcatgag   95700
ggggctgctc cggagcgacg gcggctgcag ctggagccag gcgctcgccc gtccgccggt   95760
tggctcgccg ggacctcgcg caccggcggc agagtccctt gcgtggattg gcaagcgacg   95820
ccccaccctgc cccgagctca ccattttctt tcgcgctggc tgcagctgac ccggcgaagg   95880
gagccgaccg ggccctgggc tggaggtaaa accccacggt gagtaagaac ccgctccaag   95940
ctagggagg cggcgcagcc cggtggctgc tcgctcccga tctcgcccgg gcgggcggcg   96000
aggtttgggg cgcacctggg cgcgggtgca agaaggtgcg ggaggcggcg gaccggtctt   96060
ctgcccgccg gccacgggct tccggggctg gagtcctctt cagaccccctg ccggcgcctg   96120
ggtttctggc cggctcctcg tgtgcacttc ccggcaggaa caagggtcgc ccactttcca   96180
ccccgggatc ttgatttgtc cttgatttga aaagatataa atcaataaga tcgtccttct   96240
ttcggggtgc aagactccga gcccatcccc agccgcggac gcctgcaggg tgcgtgttgg   96300
gctgtgggtg gcgggaagac aaactttac aaaagtgcgc ctgggctggg ggacaacgct   96360
tgggcgtcct gatcctgagg gaggagtctc ggcttgggc agcgtagggg aagtccgcac   96420
cgtcagccag gtcgcccccg gggctgacga tgcctcacgg aggtggggag cgtgtaaagg   96480
ccgtacaaat cgcgcttaac tttggggcca acaactgtca aacatctgga atcccagccc   96540
ctcccttttcc ctgaactggg gaagaaggtg aaaacccttc aagttttctt tgattgcccc   96600
ttcccacctt cagaccccctg ctgggagggt aaagcgccga cccctggtgc ctggcaagta   96660
ccagagactc taaatctctc gggatccccc ccctcgcgct ctttcctgac cctctcccct   96720
aaccctcccc acagagatct ctctacgcag ccgactgaga tcgtggcgaa tggccttttg   96780
tttctccgcg tttcccctat tgtttgcctt tccaacatct ggcggggctt ggggagagaa   96840
ggaagcccct ctggtccccc tccccgccc ccacgccagc tccggcaggg gatcccagct   96900
gggaaagtgg aggagcccga ccccagcgag gccgccccac cccgcccttg tggttagagg   96960
gcggagggaa agttgttcct tccccgcctc cgctgctgcc tgtggcccag ggcgcatttc   97020
```

| | |
|---|---|
| tcagatctca gcccaggcgc gccgcaaagg ctcaaatccg agaaggtgct gctttcgaga | 97080 |
| cagtggaagc gcgttccgcc ccaatccaga gcgtccagtg gttggttcca gaggatttca | 97140 |
| atctctagcc aaaggcgttg gggctgggcc gctgctaggg cagtgggagg ggatcggggc | 97200 |
| acctttggta ggcggaaagc tgagattctg gggtccacaa gtttccaagg gcgggagggc | 97260 |
| aggctagtcg ccaaaaagag aacgaagatg caaataacga ggaagcctta tgacgttgcc | 97320 |
| tggaaatagt agtgtggtgg ttcactccgg aatgaacgtg gagttctggc tttgagtacc | 97380 |
| gctccaagtt taaatcccaa gtcccctttc ttcattgtag aaaaagagga ctcagacgac | 97440 |
| gcaacacaga tacggctaga gcacagttcc tgcttccacg tcccagagaa caagtggctt | 97500 |
| aggatggtcc cgagttcccc tgtgggtgcg cttgttgggt tgcaggcggc cctgtttccc | 97560 |
| tgcacaagtc agatgcttac acattgtgtt cattcttagt gtggattatt gattaaagaa | 97620 |
| ctggggcaaa agcaaagtag ctactctgag aagtcagggt ccccagatgg tgcccagcga | 97680 |
| gttgtcttgc ctctgagggg aggctgactg agactgtgca cctgttagaa cctatgctac | 97740 |
| cccatagcct tgcagttgac ttgctgttgc cagcttttcc tgtgggatcc ccaatgagtc | 97800 |
| cctcttccaa ggaagctcaa ttacactttt gattcctcct caacccaggg gaagaaagag | 97860 |
| gcttctgtag gaacattatg atctatgtac ccactcagac attgtcagtg gataccagaa | 97920 |
| gcttggctct gcacagctct gagagttttc cctttgcgaa ctcaacagaa cttttgagtt | 97980 |
| tccatttaac ataaaagaag tgagactgct aagccaggaa tgcgacacat agagcacttt | 98040 |
| ctctagtgat ttctgggtat tatatctctt taccttccca acggtggaac caggaaaaga | 98100 |
| aaaaaagca acatctttga agtactgcaa ggcactttac aaacatttca ttatgaaaat | 98160 |
| gatccccaag gaaggattcc tttgaaattt agcagcagca acccagaagc aacaaaaag | 98220 |
| accaaagtta ctcaagaagt acccaaaggc atcattaaca aaataaaaga gcatttcttg | 98280 |
| tcttggccta ccccgctaag gaaaacaggg taattatagt ggaagttaag cttg | 98334 |

<210> SEQ ID NO 64
<211> LENGTH: 28
<212> TYPE: DNA
<213> ORGANISM: Artificial sequence
<220> FEATURE:
<223> OTHER INFORMATION: Synthetic polynucleotide

<400> SEQUENCE: 64

| | |
|---|---|
| cccggggccg gggccggggc cggggccc | 28 |

<210> SEQ ID NO 65
<211> LENGTH: 212
<212> TYPE: DNA
<213> ORGANISM: Artificial sequence
<220> FEATURE:
<223> OTHER INFORMATION: Synthetic polynucleotide

<400> SEQUENCE: 65

| | |
|---|---|
| cccggggccg gggccggggg cccggggccc ggggcccggg gccggggccg cggggcccgg | 60 |
| ggcccggggc ccggggcccg gggcccgggg cccggggccc ggggcccggg gccggggcc | 120 |
| cggggcccgg ggcccggggc cccggggccg gggcccgggg cccggggccc ggggcccggg | 180 |
| gcccggggcc cggggcccgg ggcccggggc cc | 212 |

USE AND TREATMENT OF DI-AMINO ACID REPEAT-CONTAINING PROTEINS ASSOCIATED WITH ALS

CROSS-REFERENCE TO RELATED APPLICATIONS

This application is a national stage filing under 35 U.S.C. § 371 of International PCT application PCT/US2014/022670, filed Mar. 10, 2014 which claims the benefit of the filing date of U.S. Provisional Application No. 61/786,258, filed Mar. 14, 2013, and the benefit of the filing date of U.S. Provisional Application No. 61/883,219, filed Sep. 27, 2013. The entire contents of each of these referenced applications are incorporated by reference herein.

FEDERALLY SPONSORED RESEARCH OR DEVELOPMENT

This invention was made with government support under PO1NS058901 and RO1NS040389 awarded by the National Institutes of Health. The Government has certain rights in the invention.

BACKGROUND OF THE INVENTION

Expansion of a GGGGCC hexanucleotide sequence within the intron of the human C9ORF72 gene is associated with both amyotrophic lateral sclerosis and frontotemporal dementia in humans. Amyotrophic lateral sclerosis (ALS) is a debilitating disease with varied etiology characterized by rapidly progressing weakness, muscle atrophy, muscle spasticity, difficulty speaking (dysarthria), difficulty swallowing (dysphagia), and difficulty breathing (dyspnea). Although the order and rate of symptoms varies from person to person, eventually most subjects are not able to walk, get out of bed on their own, or use their hands and arms. Most subjects with ALS will eventually die from respiratory failure, usually within three to five years from the onset of symptoms. Riluzole (Rilutek) is the only currently available treatment for ALS and only slows progression and increases survival to a modest extent. Frontotemporal dementia (FTD) is also a devestating group of disorders resulting from atrophy or shrinkage of the frontal and temporal lobes of the brain. This shrinkage or atrophy results in severe behavioral changes. There is currently no cure for FTD and limited medications for managing the symptoms of FTD. New methods for diagnosing and treating ALS and/or FTD would greatly benefit ALS and FTD subjects.

SUMMARY OF THE INVENTION

Expansion of a GGGGCC hexanucleotide sequence within the intron of the human C9ORF72 gene is associated with both amyotrophic lateral sclerosis and frontotemporal dementia in humans. As described herein, an expanded GGGGCC hexanucleotide repeat sequence within the intron of the C9ORF72 gene was found to be transcribed such that RNA transcripts containing the hexanucleotide repeat in both the sense and anti-sense direction were produced. These sense and anti-sense transcripts were found to be translated to produce di-amino acid repeat-containing proteins. The sense transcript (containing 5'-GGGGCC-3' hexanucleotide repeats) was found to be translated through repeat-associated non-ATG (RAN) translation such that poly-(Gly-Ala), poly-(Gly-Pro), and poly-(Gly-Arg) proteins were produced. The anti-sense transcript (containing 5'-GGCCCC-3' hexanucleotide repeats) was found to be translated through repeat-associated non-ATG (RAN) translation such that poly-(Pro-Ala), poly-(Pro-Arg), poly-(Gly-Pro) proteins were produced. Additionally, the anti-sense transcript was found to be translated through ATG-initiated translation to produce Met . . . poly-(Pro-Arg) and Met . . . poly-(Gly-Pro) proteins.

These di-amino acid repeat-containing proteins were found to be present in ALS subject blood samples. Accordingly, aspects of the disclosure relate to a method of detection of di-amino acid-repeat containing protein levels in sample (e.g., blood) obtained from a subject, the method comprising measuring di-amino acid-repeat-containing protein levels in the sample of the subject. In some aspects, detection of di-amino acid-repeat containing protein levels may identify (or diagnose) or aid in identification (or aid in diagnosis) of a subject having ALS or FTD or likely to develop ALS or FTD. Alternatively or additionally, detection of di-amino acid-repeat containing protein levels, e.g., in a blood sample of the subject, may identify (or diagnose) or aid in identification (or aid in diagnosis) of a subject as having a risk factor of ALS or FTD, such as an elevated level of a di-amino acid-repeat containing protein or proteins in the cerebrospinal fluid of the subject. Aspects of the disclosure also relate to treatment of a subject having ALS or FTD by decreasing or stabilizing di-amino acid-repeat-containing protein levels in the blood of the subject.

Additionally, expression of the anti-sense transcript (containing 5'-GGCCCC-3' hexanucleotide repeats) was found to be highly elevated in subjects having the expanded GGGGCC hexanucleotide repeat compared to controls. Foci of sense and anti-sense transcripts were also detectable using fluorescent in situ hybridization (FISH) in brain and blood cells of patients having the expanded GGGGCC hexanucleotide repeat sequence within the intron of the C9ORF72 gene. Thus, other aspects of the disclosure relate to a method of detection of a hexanucleotide repeat-containing transcript, the method comprising measuring a level a hexanucleotide repeat-containing transcript and/or measuring the presence or absence of a hexanucleotide repeat-containing transcript focus. In some aspects, detection of a hexanucleotide repeat-containing transcript may identify (or diagnose) or aid in identification (or aid in diagnosis) of a subject as having ALS or FTD or likely to develop ALS or FTD. Alternatively or additionally, detection of a hexanucleotide repeat-containing transcript, e.g., in a blood sample of the subject, may identify (or diagnose) or aid in identification (or aid in diagnosis) of a subject as having a risk factor of ALS or FTD, such as an elevated level of a di-amino acid-repeat containing protein or proteins in the cerebrospinal fluid of the subject.

In some aspects, the disclosure relates to a method for identifying a subject as having ALS or FTD or likely to develop ALS or FTD, the method comprising determining, in a blood sample obtained from a subject, a level of one or more di-amino acid repeat-containing proteins selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein, wherein a level of the one or more di-amino acid repeat-containing proteins that is elevated compared to a control level indicates that the subject has ALS or FTD or is likely to develop ALS or FTD. In some embodiments, the level of the one or more di-amino acid repeat-containing proteins is determined by performing an assay. In some embodiments, the assay comprises an immuno-based assay. In some embodiments, the immuno-based assay comprises an isolated antibody specific for an antigen comprising a sequence as set for in Tables 1, 2, or 3. In some embodiments, the immuno-based assay comprises an isolated antibody specific for the C-terminus of the one or more di-amino acid repeat-containing protein.

In some embodiments, the method further comprises identifying the subject as having ALS or FTD or likely to develop ALS or FTD if the level of the di-amino acid repeat-containing protein is elevated compared to a control level. In some embodiments, the method further comprises treating the subject having ALS or FTD or likely to develop ALS or FTD. In some embodiments, treating comprises administering to the subject an effective amount of one or more of riluzole, baclofen, diazepam, phenytoin, trihexyphenidyl or amitriptyline. In some embodiments, treating comprises performing a procedure selected from plasmapheresis or a bone marrow transplant.

In some embodiments, the one or more di-amino acid repeat-containing proteins is selected from the poly-(Pro-Ala), poly-(Pro-Arg), Met . . . poly-(Pro-Arg) or Met . . . poly-(Gly-Pro) protein. In some embodiments, the one or more di-amino acid repeat-containing proteins is two or more di-amino acid repeat-containing proteins.

Other aspects of the disclosure relate to a method for treating a subject with ALS or FTD, the method comprising decreasing or preventing an increase in a level of one or more di-amino acid repeat-containing proteins selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein in the blood of the subject. In some embodiments, decreasing or preventing an increase of the level of one or more di-amino acid repeat-containing proteins comprises removing the one or more di-amino acid repeat-containing proteins from the blood of the subject. In some embodiments, the one or more di-amino acid repeat-containing proteins from the blood of the subject is removed using a procedure selected from plasmapheresis or a bone marrow transplantation. In some embodiments, the bone marrow transplantation is an allogeneic bone marrow transplantation.

In yet another aspect, the disclosure relates to an isolated antibody specific for one or more di-amino acid repeat proteins selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein. In some embodiments, the di-amino acid repeat protein is selected from a poly-(Pro-Ala), poly-(Pro-Arg), Met . . . poly-(Pro-Arg) or Met . . . poly-(Gly-Pro) protein. In some embodiments, the isolated antibody is specific for an antigen comprising a sequence or fragment of a sequence as set for in Tables 1, 2, or 3.

Other aspects of the disclosure relate to a method for identifying a subject as having ALS or FTD or likely to develop ALS or FTD, the method comprising determining, in a sample obtained from a subject, a level of a 5'-GGGGCC-3' hexanucleotide repeat-containing RNA and/or a 5'-GGCCCC-3' hexanucleotide repeat-containing RNA, wherein a level of the 5'-GGGGCC-3' hexanucleotide repeat-containing RNA and/or a 5'-GGCCCC-3' hexanucleotide repeat-containing RNA that is elevated compared to a control level indicates that the subject has ALS or FTD or is likely to develop ALS or FTD. In some embodiments, the level is determined by performing an assay. In some embodiments, the assay comprises a nucleic acid-based assay, such as in-situ hybridization (e.g., FISH) or RT-PCR (e.g., quantitative RT-PCR or strand specific quantitative RT-PCR). In some embodiments, the method further comprises identifying the subject as having ALS or FTD or likely to develop ALS or FTD if the level of a 5'-GGGGCC-3' hexanucleotide repeat-containing RNA and/or a 5'-GGCCCC-3' hexanucleotide repeat-containing RNA is elevated compared to a control level. In some embodiments, the method further comprises treating the subject having ALS or FTD or likely to develop ALS or FTD. In some embodiments, treating comprises administering to the subject an effective amount of one or more of riluzole, baclofen, diazepam, phenytoin, trihexyphenidyl or amitriptyline. In some embodiments, treating comprises performing a procedure selected from plasmapheresis or a bone marrow transplant. In some embodiments, the level of a 5'-GGGGCC-3' hexanucleotide repeat-containing RNA and/or a 5'-GGCCCC-3' hexanucleotide repeat-containing RNA is a level of a 5'-GGCCCC-3' hexanucleotide repeat-containing RNA.

Yet other aspects of the disclosure relate to a method for identifying a subject as having ALS or FTD or likely to develop ALS or FTD, the method comprising determining, in a sample obtained from a subject, the presence or absence of foci containing 5'-GGGGCC-3' hexanucleotide repeat-expansion-containing RNA and/or a 5'-GGCCCC-3' hexanucleotide repeat-expansion-containing RNA, wherein the presence of the foci of the 5'-GGGGCC-3' hexanucleotide repeat-expansion-containing RNA and/or a 5'-GGCCCC-3' hexanucleotide repeat-expansion-containing RNA indicates that the subject has ALS or FTD or is likely to develop ALS or FTD. In some embodiments, presence or absence of foci or elevated C9ORF72 sense or antisense RNA levels is determined by performing an assay. In some embodiments, the assay comprises a nucleic acid-based assay, such as strand specific RT-PCR or in-situ hybridization (e.g., FISH).

Yet other aspects of the disclosure relate to transgenic mice. In some embodiments, the transgenic mouse comprises a human C9ORF72 gene and optionally human flanking sequences. In some embodiments, the transgenic mouse comprises SEQ ID NO: 63.

These and other aspects are described in more detail herein and illustrated by the non-limiting figures and examples.

BRIEF DESCRIPTION OF THE DRAWINGS

The drawings are first described.

FIG. 18 is a table summarizing histopathological findings in C9ORF72 positive ALS/FTD cases and controls.

FIGS. 19A-19F are a series of images and datasets. (A) shows strand-specific RT-PCR detection of sense (S) and antisense (AS) transcripts (across intron 1) of PBLs of C9(+) patient and normal controls. (B) is a summary of 5' RACE products. (C) shows FISH staining of frontal cortex from a C9(+) case showing an example of cytoplasmic RNA foci. (D) shows FISH staining of peripheral blood leukocytes showing the accumulation of antisense (AS) $G_2C_4$ and sense (S) $G_4C_2$ RNA foci in C9(+) but not C9(−) cells. (E) shows antisense foci specificity assay showing excess unlabeled $(G_4C_2)_4$ oligo blocks labeling of G4C2-Cy3 antisense (AS)

but not G₂C₄-Cy3 labeled sense foci. (F) shows additional controls for antisense RNA foci showing expected DNase I resistance and RNase I sensitivity.

FIG. 20 is a series of images of in vitro evidence for RAN translation of the sense GGGGCC repeat expansion. (A) shows constructs containing varying GGGGCC repeat lengths with upstream 6×Stop cassette and 3' tags in each reading frame. Immunoblots (B) and/or immunofluorescence staining (C) showing RAN translation occurs in all three frames (GP, GR, GA) in cells transfected with constructs containing 30, 60 and 120 repeats.

FIG. 21 is a schematic of putative protein products in sense and antisense directions for all reading frames SEQ ID NOs: 57-62, from top to bottom. Underlined sequences were used to generate polyclonal antibodies. *=Stop codon.

FIGS. 22A-22E are a series of images showing validation of dual antibodies to detect putative polyPA, polyPR, polyGP proteins by immunofluorescence and protein blot (A-D Top): Schematic diagrams of constructs expressing ATG-initiated N-terminal epitope-tagged (V5 or Flag) repeat proteins with or without endogenous C-terminal sequences. (A-D Bottom panels), co-localization of α-Flag or α-V5 staining in transfected HEK293T cells with staining using the following newly developed antibodies: (A) α-PA or α-PA-CT (antisense); (B) α-PR or α-PR-CT (C) rabbit α-GP or α-GP-CT (sense); (D) mouse α-GP. Similar staining was not seen in preimmune or pcDNA3.1 empty vector controls; (E) Corresponding immunoblots showing six of the seven antibodies tested also detect recombinant proteins by Western.

Figure 23C:
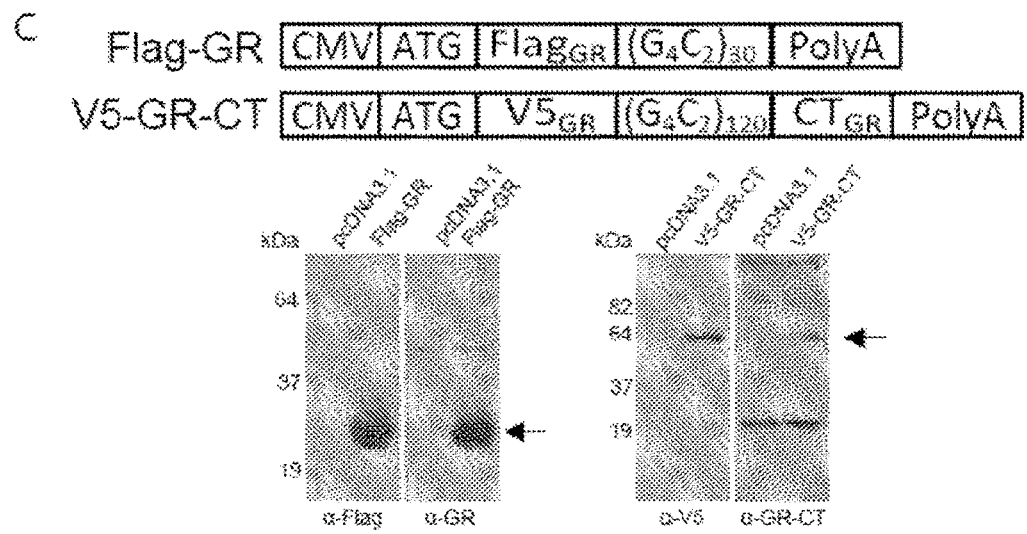

FIGS. 23A-23C are a series of images showing validation of additional sense repeat and C-terminal polyclonal antibodies. (A, B Top): Schematic diagrams of constructs expressing ATG-initiated N-terminal V5-epitope tagged GR or GA repeat proteins with endogenous C-terminal sequences. (A-B Bottom panels), co-localization of α-V5 staining in transfected HEK293T cells with α-GR, α-GR-CT and α-GP-CT respectively. Similar staining was not seen in preimmune or pcDNA3.1 empty vector controls. (C) α-GR detection of recombinant protein in Flag-GR transfected cells by protein blot.

Figure 24:
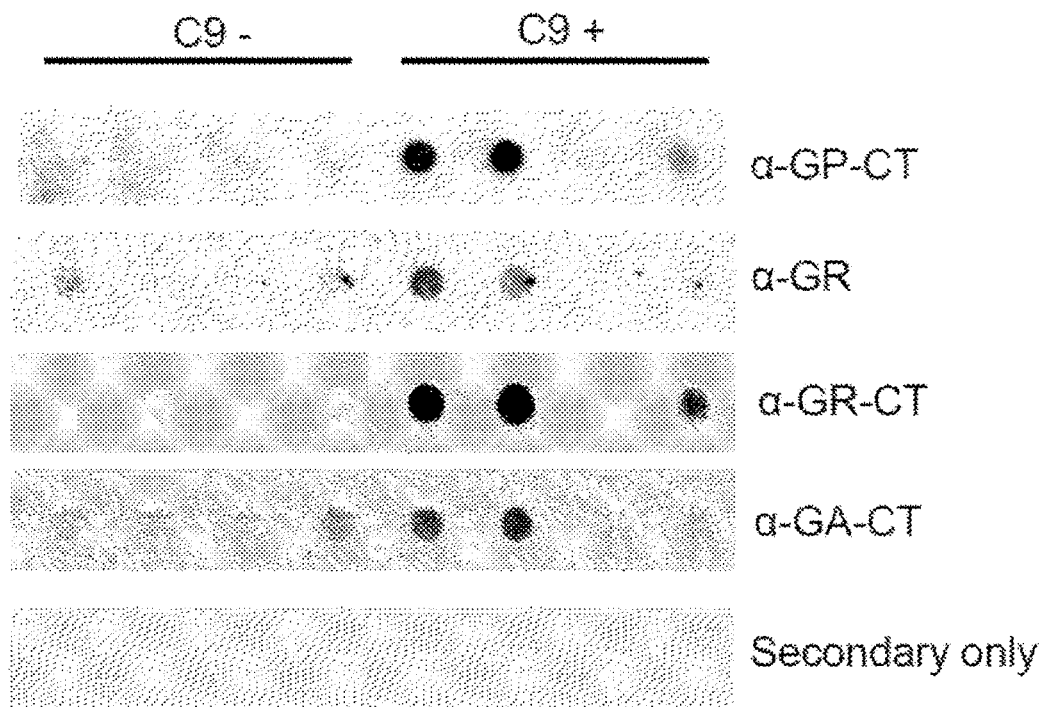

FIG. 24 is a series of images of immunoblots of 2% soluble lysates from C9(+) and C9(−) ALS frontal cortices with α-GP-CT, α-GR, α-GR-CT and α-GA antibodies.

Figure 25:
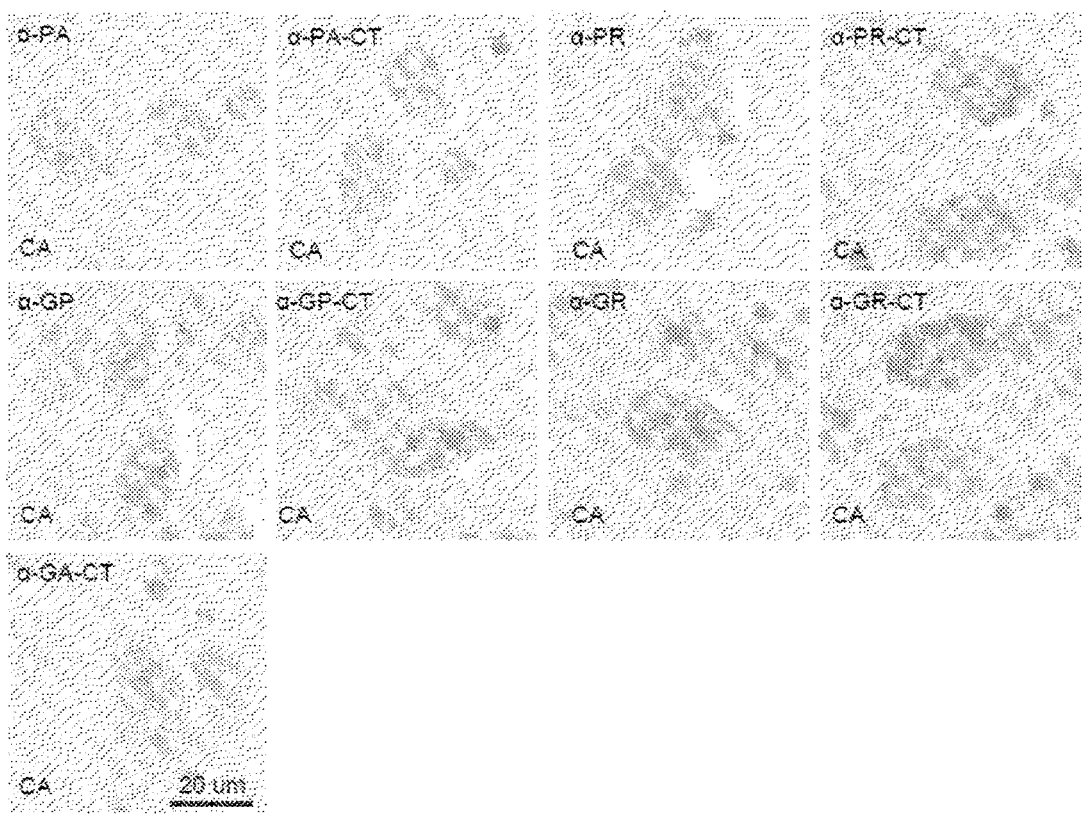

FIG. 25 is a series of images showing negative IHC staining of C9(−) ALS/FTD hippocampal sections with antibodies against sense and antisense proteins.

FIGS. 26A-26D are a graph and a series showing images RAN translation and PR protein expression affect cell viability. (A) qRT-PCR shows expression of expansion transcripts are similar in HEK293T cells transfected with (−)ATG-PR-3T and (+)ATG-PR-3T constructs. (B-D) Bright-field microscopy images showing changes in cell morphology in cells expressing RNA and RAN proteins from (−)ATG-PR-3T constructs compared to empty vector control (pcDNA3.1) and worsening effects in (+)ATG-PR-3T cells expressing increased levels of PR protein.

FIG. 27 is a table describing primers used for RT-PCR and RACE (SEQ ID NOs: 17 of them (in order. SEQ ID NOs: 36, 37, 39, 38, 45-47, 40, 48-56).

FIG. 28 is a table describing novel sense and antisense antibodies. (in order SEQ ID NOs: 20, 23, 19, 25, 21, 21, 22, 18).

Figure 29:
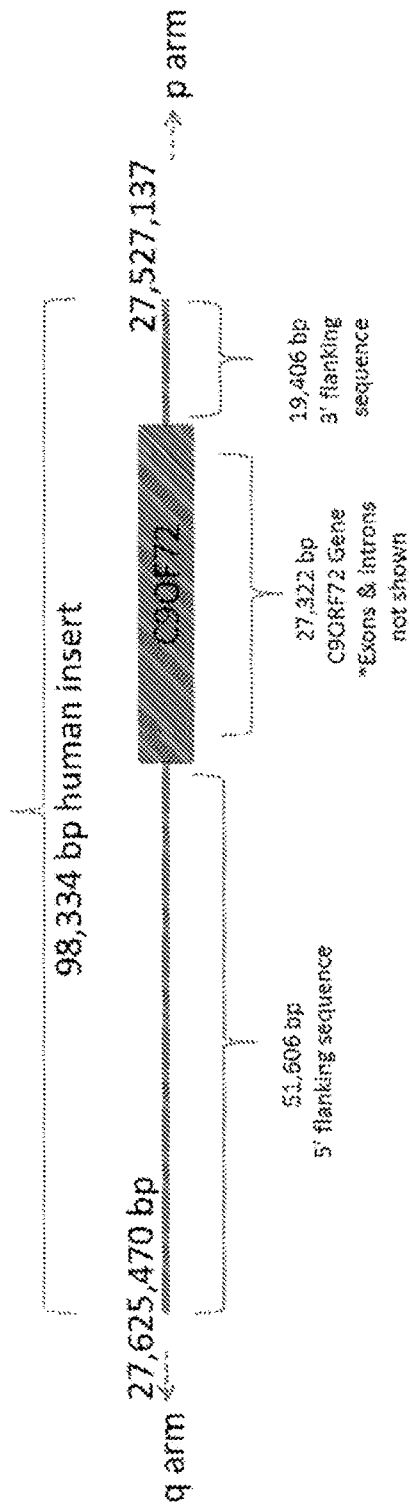

FIG. 29 is a schematic of the BAC insert used to make transgenic mice.

Figure 30:
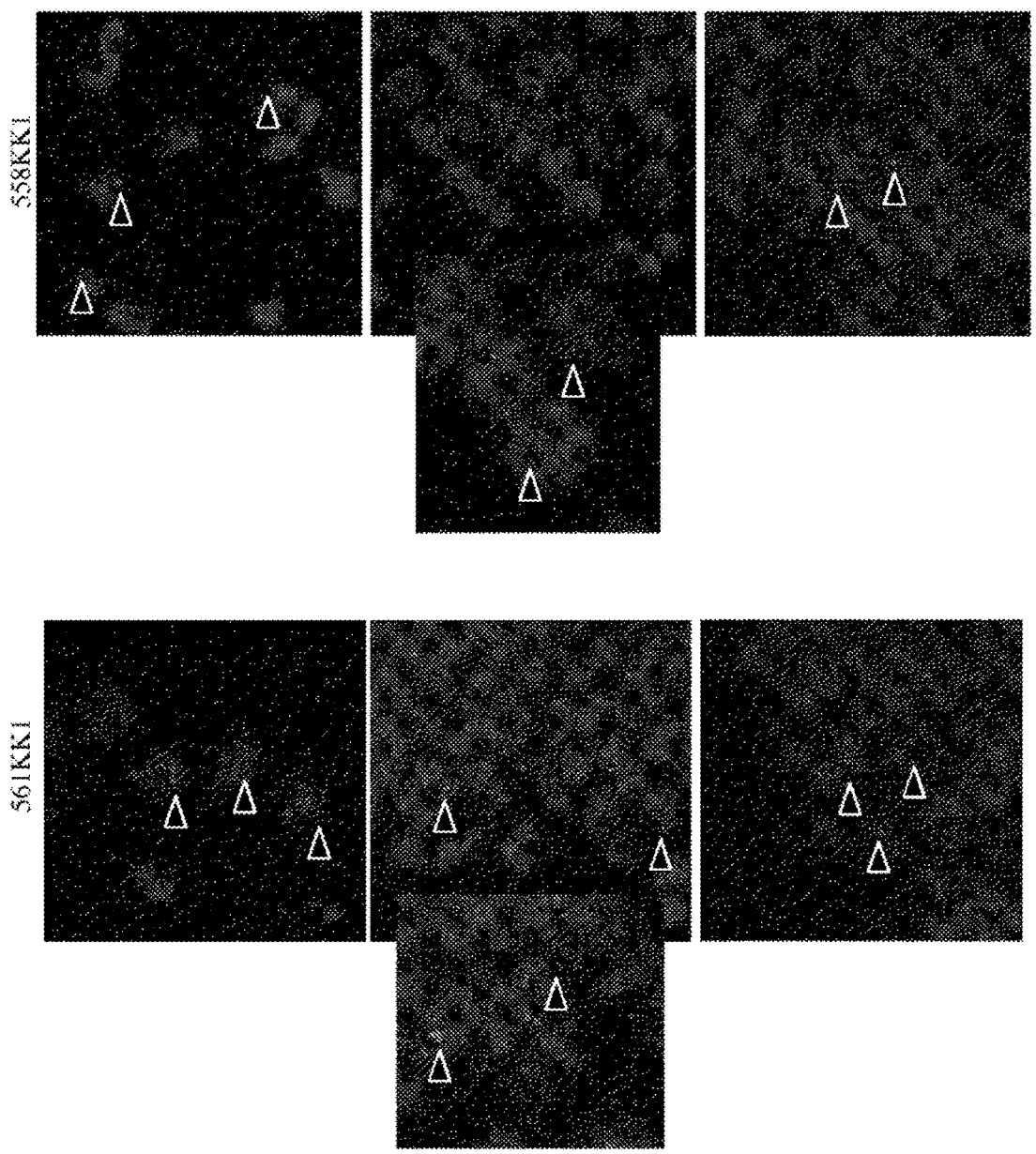

FIG. 30 is a series of photographs showing sense RNA foci in transgenic mice expressing a human C9ORF72 gene containing GGGGCC repeats. Exemplary foci are indicated by arrowheads.

Figure 31:
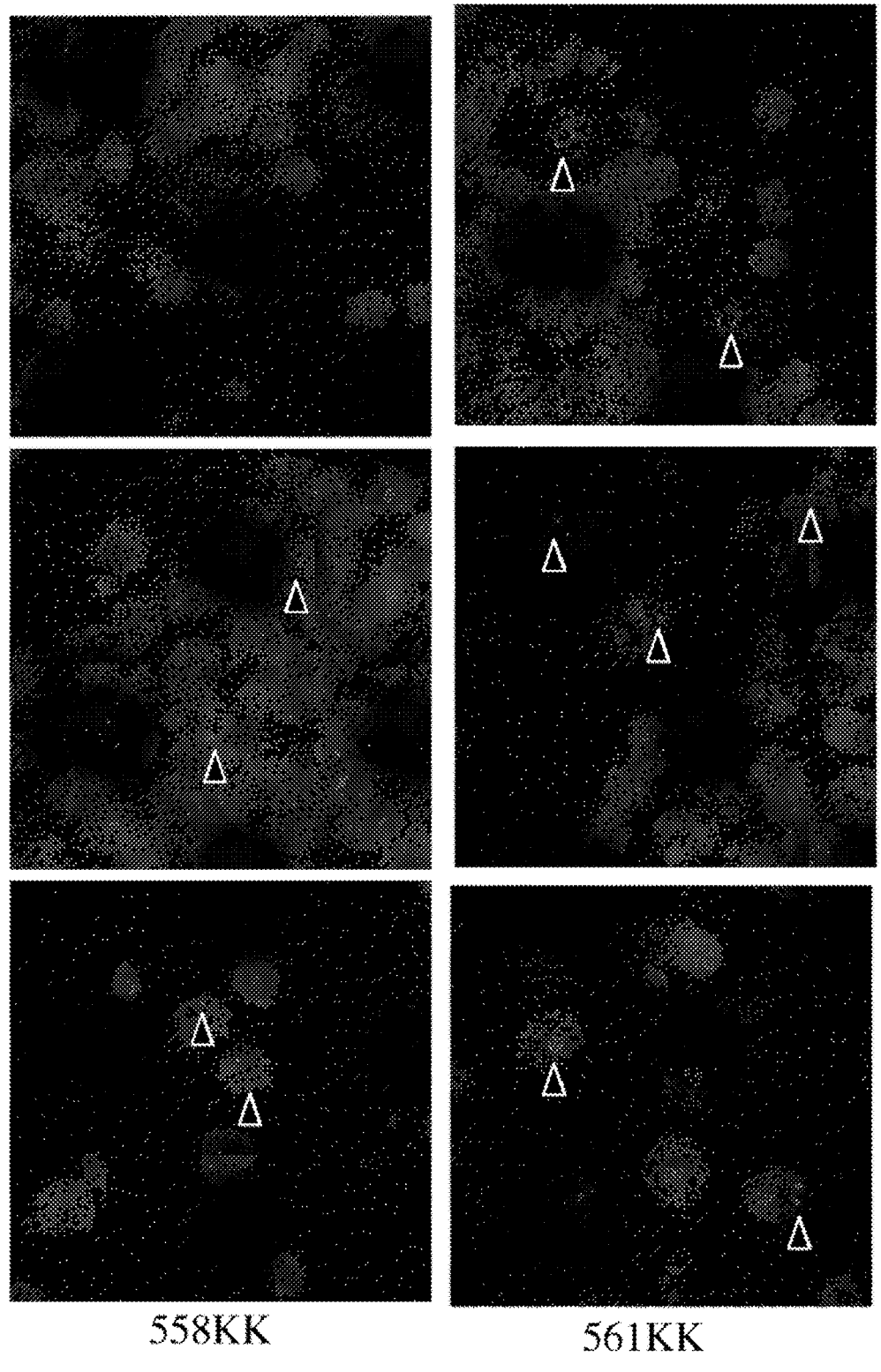

FIG. 31 is a series of photographs showing anti-sense (AS) RNA foci in transgenic mice expressing a human C9ORF72 gene containing GGGGCC repeats. Exemplary foci are indicated by arrowheads.

DETAILED DESCRIPTION OF THE INVENTION

Well-established rules of translational initiation have been used as a cornerstone in molecular biology to understand gene expression and to predict the consequences of disease causing mutations. In general, microsatellite expansion mutations (e.g., CAG, CTG) located in predicted coding- and non-coding regions have been thought to cause disease by protein gain-, or loss-, of-function or RNA gain-of-function mechanisms. It has been previously reported that the canonical rules of translation do not apply for CTG CAG repeat expansions and that CAG and CUG expansion transcripts express homopolymeric expansion proteins in all three frames without an AUG start codon (see, e.g., T. Zu et al., Non-ATG-initiated translation directed by microsatellite expansions. PNAS 108, 260 (2011)). This translation independent of an AUG start codon is termed repeat-associated non-ATG (RAN) translation. RAN translation is hairpin dependent and occurs without frameshifting or RNA editing. RAN translation has been observed from trinucleotide, tetranucleotide, and pentanucleotide repeats associated with myotonic dystrophy 1, myotonic dystrophy 2, spinocerebellar ataxia type 3, spinocerebellar ataxia type 8 and Huntington disease (see PCT publication WO/2010/115033, which is incorporated herein by reference).

Expansion of a GGGGCC hexanucleotide repeat within the intron of the C9ORF72 gene has been previously associated with both amyotrophic lateral sclerosis and frontotemporal dementia. As described herein, it has been found that this expanded hexanucleotide repeat is contained within RNA transcripts expressed in both the sense and anti-sense direction from the C9ORF72 locus. These hexanucleotide repeat-containing transcripts were found to undergo RAN translation such that poly-(Gly-Ala), poly-(Gly-Pro), poly-(Gly-Arg), poly-(Pro-Ala), or poly-(Pro-Arg) proteins were produced, depending on the frame of the hexanucleotide repeat being read from the RNA (5'-GGGGCC-3', 5'-GGGCCG-3', and 5'-GGCCGG-3' on the sense transcript, 5'-GGCCCC-3', 5'-GCCCCG-3', and 5'-CCCCGG-3' on the anti-sense transcript, see FIG. 1). In addition, the anti-sense transcript was found to be translated through ATG-initiated translation to produce Met . . . poly-(Pro-Arg) and Met . . . poly-(Gly-Pro) proteins. These RAN and ATG-initiated proteins are referred to as di-amino acid-repeat-containing proteins herein. The sense and anti-sense hexanucleotide repeat-containing transcripts are referred to herein as 5'-GGGGCC-3' hexanucleotide repeat-containing RNA (sense) and 5'-GGCCCC-3' hexanucleotide repeat-containing RNA (anti-sense).

As further described herein, these di-amino acid-repeat-containing proteins unexpectedly were found to be present in blood samples from subjects with ALS. Additionally, expression of the anti-sense 5'-GGCCCC-3' hexanucleotide repeat-containing RNA transcript was found to be highly elevated in subjects having a C9ORF72 gene containing the expanded GGGGCC hexanucleotide repeat sequence. Further, foci of both the sense and anti-sense hexanucleotide repeat-expansion-containing RNA transcripts were found to be present in subjects having a C9ORF72 gene containing the expanded GGGGCC hexanucleotide repeat sequence. Without wishing to be bound by theory or mechanism, it is believed that di-amino acid-repeat-containing proteins in the blood of subjects with ALS accumulate within the brain parenchyma over time, leading to neuroinflammatory changes, CNS dysfunction, and neuronal death. Accordingly, aspects of the disclosure relate to identification of a subject as having ALS or likely to develop ALS by providing novel assays for determining di-amino acid-repeat-containing protein levels in the blood of the subject and/or hexanucleotide repeat-containing RNA levels in a sample from the subject. Aspects of the disclosure also relate to treatment of a subject having ALS or FTD by decreasing or stabilizing di-amino acid-repeat-containing protein levels in the blood of the subject.

Identification of a Subject Having ALS or FTD or Likely to Develop ALS or FTD

Aspects of the disclosure relate to identification of a subject having ALS or FTD or likely to develop ALS or FTD based on a level of one or more di-amino acid-repeat-containing proteins in a blood sample from a subject. In some embodiments, a method comprises, determining, in a blood sample obtained from a subject, a level of one or more di-amino acid-repeat-containing proteins selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein, wherein a level of the one or more di-amino acid-repeat-containing proteins that is elevated compared to a control level indicates that the subject has ALS or FTD or is likely to develop ALS or FTD. In some embodiments, a level of one or more di-amino acid-repeat-containing proteins is determined by performing an assay. Non-limiting assays are described herein.

Other aspects of the disclosure relate to identification of a subject having ALS or FTD or likely to develop ALS or FTD based on a level of a 5'-GGGGCC-3' hexanucleotide repeat-containing RNA and/or a 5'-GGCCCC-3' hexanucleotide repeat-containing RNA in a sample from a subject. In some embodiments, identification of a subject having ALS or FTD or likely to develop ALS or FTD is based on a level of a 5'-GGCCCC-3' hexanucleotide repeat-containing RNA in a sample from a subject. The sample may be, e.g., a fluid or tissue sample obtained from the subject. In some embodiments, a method comprises, determining, in a sample obtained from a subject, a level of a 5'-GGGGCC-3' hexanucleotide repeat-containing RNA and/or a 5'-GGCCCC-3' hexanucleotide repeat-containing RNA, wherein a level of the hexanucleotide repeat-containing RNA that is elevated compared to a control level indicates that the subject has ALS or FTD or is likely to develop ALS or FTD. In some embodiments, a level of a hexanucleotide repeat-containing RNA is determined by performing an assay. Non-limiting assays are described herein.

Yet other aspects of the disclosure relate to identification of a subject having ALS or FTD or likely to develop ALS or FTD based on the presence or absence of RNA foci containing a 5'-GGGGCC-3' hexanucleotide repeat-expansion-containing RNA and/or a 5'-GGCCCC-3' hexanucleotide repeat-expansion-containing RNA in a sample from a subject, wherein the presence of the focus of the 5'-GGGGCC-3' hexanucleotide repeat-expansion-containing RNA and/or a 5'-GGCCCC-3' hexanucleotide repeat-expansion-containing RNA indicates that the subject has ALS or FTD or is likely to develop ALS or FTD. As used herein, a focus of a 5'-GGGGCC-3' hexanucleotide repeat-expansion-containing RNA and/or a 5'-GGCCCC-3' hexanucleotide repeat-expansion-containing RNA refers to an area of accumulation of the 5'-GGGGCC-3' hexanucleotide repeat-expansion-containing RNA and/or the 5'-GGCCCC-3' hexanucleotide repeat-expansion-containing RNA, which may be detectable using a nucleic acid-based assay, such as FISH. In some embodiments, the focus may be, e.g., 0.1 to 2 micrometers in diameter, 0.1 to 1.5 micrometers in diameter, or 0.1 to 1 micrometers in diameter. In some embodiments, the focus may be at least 0.1 micrometers in diameter. It is to be appreciated that a sample may contain more than one focus and that each focus may be a different size. For example, one focus may be 0.2 micrometers in diameter, while second focus may be 1 micrometer in diameter. Non-limiting examples of foci and methods detecting such foci are provided in Example 3.

It is to be understood that a subject may be identified based on a level of one or more di-amino acid-repeat-containing proteins, a level of a hexanucleotide repeat-expansion containing RNA, the presence or absence of a hexanucleotide repeat-expansion containing RNA, or any combination thereof. In some embodiments, the method further comprises identifying the subject as having ALS or FTD or likely to develop ALS or FTD if the level of the di-amino acid-repeat-containing protein or hexanucleotide repeat-containing RNA is elevated compared to a control level. In some embodiments, the method further comprises identifying the subject as having ALS or FTD or likely to develop ALS or FTD if the focus or foci of the hexanucleotide repeat-expansion-containing RNA are present in the sample. In some embodiments, the method further comprises identifying the subject as not having ALS or FTD or unlikely to develop ALS or FTD if the level of the di-amino acid-repeat-containing protein or hexanucleotide repeat-containing RNA is decreased or the same compared to a control level. In some embodiments, the method further comprises identifying the subject as not having ALS or FTD or unlikely to develop ALS or FTD if the focus or foci of the hexanucleotide repeat-expansion-containing RNA are absent in the sample.

In some embodiments, a level of one or more di-amino acid-repeat-containing proteins or the identity of a subject may be recorded. In some embodiments, recordation comprises inputting a level or identity of subject into a computer, such as a medical record database.

Other aspects of the disclosure relate to treatment of a subject identified as having ALS or FTD or likely to develop ALS or FTD. As used herein, "treat" or "treatment" refers to (a) preventing or delaying the onset of ALS or FTD; (b) reducing the severity of ALS or FTD; (c) reducing or preventing development of symptoms characteristic of ALS or FTD; (d) preventing worsening of symptoms characteristic of ALS or FTD; and/or (e) reducing or preventing recurrence of ALS or FTD symptoms in subjects that were previously symptomatic for ALS or FTD.

In some embodiments, treatment comprises administering an effective amount of a known ALS therapeutic agent, such as Riluzole (Rilutek, Sanofi-Aventis), to a subject identified as having ALS. In some embodiments, treatment comprises administering an effective amount of a known FTD therapeutic agent, such as trazodone (Desyrel, Oleptro) or a selective serotonin reuptake inhibitor (SSRI), to a subject identified as having FTD. In some embodiments, treatment comprises administering an effective amount of a therapeutic agent, such as baclofen, diazepam, phenytoin, trihexyphenidyl and/or amitriptyline, which reduces one or more symptoms of ALS or FTD in a subject identified as having ALS or FTD. In some embodiments, treatment comprises one or more of physical therapy, occupational therapy, or speech therapy. In some embodiments, treatment comprises a method as described herein for decreasing or stabilizing di-amino acid-repeat-containing protein levels in the blood of the subject, such as bone marrow transplantation or plasmapheresis. In some embodiments, treatment comprises any combination of the above-mentioned treatments or any other treatments described herein.

An effective amount is a dosage of a therapeutic agent sufficient to provide a medically desirable result, such as treatment of ALS or FTD. The effective amount will vary with the age and physical condition of the subject being treated, the severity of ALS or FTD in the subject, the duration of the treatment, the nature of any concurrent therapy, the specific route of administration and the like factors within the knowledge and expertise of the health practitioner.

Administration of a treatment may be accomplished by any method known in the art (see, e.g., Harrison's Principle of Internal Medicine, McGraw Hill Inc.). Administration may be local or systemic. Administration may be parenteral (e.g., intravenous, subcutaneous, or intradermal) or oral. Compositions for different routes of administration are well known in the art (see, e.g., Remington's Pharmaceutical Sciences by E. W. Martin). Dosage will depend on the subject and the route of administration. Dosage can be determined by the skilled artisan.

Other aspects of the disclosure relate to methods for monitoring responsiveness to a treatment in a subject having ALS or FTD or suspected of having ALS or FTD. In some embodiments, the method comprises: determining, in a blood sample obtained from the subject at a first time point, a first level of one or more di-amino acid-repeat-containing proteins selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein; and determining, in a blood sample obtained from the subject at a second time point, a second level of one or more di-amino acid-repeat-containing proteins selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein, wherein a second level that is elevated or the same compared to a first level indicates that the subject is unresponsive or likely unresponsive to treatment and wherein a second level that is decreased compared to a first level indicates that the subject is responsive or likely responsive to treatment. In some embodiments, the first blood sample is obtained before treatment of the subject and the second blood sample is obtained during or after treatment of the subject. This method may also be performed by determining a level of a hexanucleotide repeat-containing RNA or the presence or absence of a focus or foci of a hexanucleotide repeat-expansion-containing RNA in addition to or in place of the level of di-amino acid protein.

As used herein, "elevated" means that the level of one or more di-amino acid-repeat-containing proteins or a hexanucleotide repeat-containing RNA is above a control level, such as a pre-determined threshold or a level of one or more di-amino acid-repeat-containing proteins or a hexanucleotide repeat-containing RNA in a control sample. Controls and control levels are described in detail herein. An elevated level includes a level that is, for example, 1%, 5%, 10%, 20%, 30%, 40%, 50%, 60%, 70%, 80%, 90%, 100%, 150%, 200%, 300%, 400%, 500%, or more above a control level. An elevated level also includes increasing a phenomenon from a zero state (e.g., no or undetectable di-amino acid-repeat-containing protein expression or hexanucleotide repeat-containing RNA expression) to a non-zero state (e.g., some or detectable di-amino acid-repeat-containing protein expression or hexanucleotide repeat-containing RNA).

As used herein, "decreased" means that the level of one or more di-amino acid-repeat-containing proteins or a hexanucleotide repeat-containing RNA is below a control level, such as a pre-determined threshold or a level of one or more di-amino acid-repeat-containing proteins or a hexanucleotide repeat-containing RNA in a control sample. Controls and control levels are described in detail herein. A decreased level includes a level that is, for example, 1%, 5%, 10%, 20%, 30%, 40%, 50%, 60%, 70%, 80%, 90%, 100%, 150%, 200%, 300%, 400%, 500%, or more below a control level. A decreased level also includes decreasing a phenomenon from a non-zero state (e.g., some or detectable di-amino acid-repeat-containing protein expression or hexanucleotide repeat-containing RNA) to a zero state (e.g., no or undetectable di-amino acid-repeat-containing protein expression or hexanucleotide repeat-containing RNA expression).

Hexanucleotide Repeat-Containing RNAs and Di-Amino Acid Repeat-Containing Proteins As described herein, an expanded GGGGCC hexanucleotide repeat sequence within the intron of the C9ORF72 gene was found to be transcribed such that RNA transcripts containing the hexanucleotide repeat in both the sense and anti-sense direction were produced. The GenBank Gene ID for the human C9ORF72 gene is 203228. Both the sense and anti-sense hexanucleotide repeat-containing transcripts were found to undergo translation independent of an AUG start codon (repeat-associated non-ATG (RAN) translation) such that poly-(Gly-Ala), poly-(Gly-Pro), poly-(Gly-Arg), poly-(Pro-Ala), or poly-(Pro-Arg) di-amino acid repeat-containing proteins were produced, depending on the frame of the hexanucleotide repeat being read (5'-GGGGCC-3', 5'-GGGCCG-3', and 5'-GGCCGG-3' on the sense transcript, 5'-GGCCCC-3', 5'-GCCCCG-3', and 5'-CCCCGG-3' on the anti-sense transcript, see FIG. 1). In addition, the anti-sense hexanucleotide repeat-containing transcript was found to be translated through ATG-initiated translation to produce Met . . . poly-(Pro-Arg) and Met . . . poly-(Gly-Pro) proteins.

Accordingly, aspects of the invention relate to the sense and anti-sense RNAs containing an expanded hexanucleotide repeat and uses thereof. The sense RNA is a 5'-GGGGCC-3' hexanucleotide repeat-containing RNA and the anti-sense RNA is a 5'-GGCCCC-3' hexanucleotide repeat-containing RNA.

The 5'-GGGGCC-3' and 5'GGCCCC-3' hexanucleotide repeat-containing RNAs comprise a repeat nucleic acid sequence of the formula $(GGGGCC)_x$ or $(GGCCCC)_x$, respectively, where X may be at least 10, at least 20, at least 25, or at least 30, or in a range selected from 10-100,000, 10-50,000, 10-5,000, 20-1,000, 20-100,000, 20-50,000, 20-5,000, 20-1,000, 25-100,000, 25-50,000, 25-5,000, or 25-1,000. The hexanucleotide repeat-containing RNA may further comprise additional N- and/or C-terminal nucleic acids. In some embodiments, an N-terminal nucleic sequence comprises a nucleic acid sequence upstream of the 5'-GGGGCC-3' hexanucleotide repeat within the intron of the C9ORF72 for the sense transcript or a nucleotide sequence upstream of the 5'-GGCCCC-3' hexanucleotide repeat within the intron of the C9ORF72 for the anti-sense transcript. In some embodiments, a C-terminal nucleic acid sequence comprises a nucleotide sequence downstream of the 5'-GGGGCC-3' hexanucleotide repeat within the intron of the C9ORF72 for the sense transcript or a nucleotide sequence downstream of the 5'-GGCCCC-3' hexanucleotide repeat within the intron of the C9ORF72 for the anti-sense transcript.

Other aspects of the invention relate to one or more di-amino acid repeat-containing proteins and uses thereof. The one or more di-amino acid repeat-containing proteins are selected from poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) proteins.

The sense 5'-GGGGCC-3' hexanucleotide repeat-containing RNA and the anti-sense 5'-GGCCCC-3' hexanucleotide repeat-containing RNA both encode poly-(Gly-Pro) proteins. Accordingly a poly-(Gly-Pro) protein may include a protein translated from the sense strand, the anti-sense strand, or both. It is predicted that the C-terminus of the sense and anti-sense translated poly-(Gly-Pro) proteins may differ (see Table 1). Accordingly, a sense poly-(Gly-Pro) protein may comprise the poly-(Gly-Pro) a C-terminal sequence as described in Table 1, while an anti-sense poly-(Gly-Pro) protein may comprise the repeat region with no additional C-terminal sequence. Methods described herein may comprise use of a poly-(Gly-Pro) protein translated from the sense strand, the anti-sense strand, or both. Antibodies described herein may be specific for a poly-(Gly-Pro) protein translated from the sense strand, the anti-sense strand, or both.

Each di-amino acid repeat-containing protein comprises a repeat amino acid sequence, which contains a di-amino acid repeat unit of the formula $(YZ)_x$, where X can be from 2-10,000, 5-10,000, 2-5,000, 5-5,000, 2-1000, 5-1000, 5-500, 5-300, 5-200, 10-500, 10-300, or 10-200. The di-amino acid repeat unit for each di-amino acid repeat-containing protein is provided in Table 1.

TABLE 1

Di-Amino Acid-Repeat-Containing Proteins

| Di-Amino Acid-Repeat-Containing Protein | Di-Amino Acid Repeat Unit | Predicted C-terminus |
|---|---|---|
| poly-(Gly-Ala) | $(GA)_x$ or $(AG)_x$ | WSGRARGRARGGAAVAVPAPAAA EAQAVASG (SEQ ID NO: 1) or AWSGRARGRARGGAAVAVPAPAAA EAQAVASG (SEQ ID NO: 27) |
| poly-(Gly-Pro) | $(GP)_x$ or $(PG)_x$ | GRGRGGPGGGPGAGLRLRCLRPRR RRRRRWRVGE (SEQ ID NO: 2, sense), PGRGRGGPGGGPGAGLRLRCLRPR RRRRRRWRVGE (SEQ ID NO: 28, sense) or none(anti-sense) |
| poly-(Gly-Arg) | $(GR)_x$ or $(RG)_x$ | GVVGAGPGAGPGRGCGCGACARGG GGAGGGEWVSEEAASWRVAVWGSA AGKRRG (SEQ ID NO: 3) or RGVVGAGPGAGPGRGCGCGACAR GGGGAGGGEWVSEEAASWRVAVW GSAAGKRRG (SEQ ID NO: 29) |
| poly-(Pro-Ala) | $(AP)_x$ or $(PA)_x$ | PSARLLSSRACYRLRLFPSLFSSG (SEQ ID NO: 4) OR APSARLLSSRACYRLRLFPSLFS SG (SEQ ID NO: 30) |

TABLE 1-continued

Di-Amino Acid-Repeat-Containing Proteins

| Di-Amino Acid-Repeat-Containing Protein | Di-Amino Acid Repeat Unit | Predicted C-terminus |
|---|---|---|
| poly-(Pro-Arg) | $(PR)_x$ or $(RP)_x$ | PLARDS (SEQ ID NO: 5) or RPLARDS (SEQ ID NO: 31) |
| Met...poly-(Pro-Arg) | $(PR)_x$ | PLARDS (SEQ ID NO: 5) |
| Met...poly-(Gly-Pro) | $(GP)_x$ | None | x = number of repeats of the sequence in the parentheses

Each di-amino acid repeat-containing protein may further comprise an N- and/or C-terminal amino acid sequence that comprises a non-di-amino acid repeat sequence. In some embodiments, a N-terminal amino acid sequence comprises an amino acid sequence translated from a nucleotide sequence of a C9ORF72 RNA transcript, such as a nucleotide sequence upstream of the 5'-GGGGCC-3' hexanucleotide repeat within the intron of the C9ORF72 for the sense transcript or a nucleotide sequence upstream of the 5'-GGCCCC-3' hexanucleotide repeat within the intron of the C9ORF72 for the anti-sense transcript. In some embodiments, a C-terminal amino acid sequence comprises an amino acid sequence translated from a nucleotide sequence of a C9ORF72 RNA transcript, such as a nucleotide sequence downstream of the 5'-GGGGCC-3' hexanucleotide repeat within the intron of the C9ORF72 for the sense transcript or a nucleotide sequence downstream of the 5'-GGCCCC-3' hexanucleotide repeat within the intron of the C9ORF72 for the anti-sense transcript. Such a nucleotide sequence downstream of the 5'-GGGGCC-3' or 5'-GGCCCC-3' hexanucleotide repeat may be translated until a stop codon or multiple stop codons are reached.

A portion of a C9ORF72 gene sequence (sense and anti-sense) is shown below. The 5'-GGGGCC-3' or 5'-GGCCCC-3' hexanucleotide repeat is underlined and in bold. The nucleotide sequence upstream of the 5'-GGGGCC-3' or 5'-GGCCCC-3' hexanucleotide repeat precedes the underlined and bolded sequence. The nucleotide sequence downstream of the 5'-GGGGCC-3' or 5'-GGCCCC-3' hexanucleotide repeat follows the underlined and bolded sequence. It is to be understood that this 5'-GGGGCC-3' or 5'-GGCCCC-3' hexanucleotide repeat can be repeated more than the number of times present in these sequences.

C9ORF72 (partial sequence, sense)

(SEQ ID NO: 6)

CCCCATTTCGCTAGCCTCGTGAGAAAACGTCATCGCACATAGAAACA

GACAGACGTAACCTACGGTGTCCCGCTAGGAAAGAGAGGTGCGTCAAA

CAGCGACAAGTTCCGCCCACGTAAAAGATGACGCTTGGTGTGTCAGCC

GTCCCTGCTGCCCGGTTGCTTCTCTTTTGGGGCGGGGTCTAGCAAGA

GCAGGTGTGGGTTTAGGAGGTGTGTGTTTTTGTTTTTCCCACCCTCTC

TCCCCACTACTTGCTCTCACAGTACTCGCTGAGGGTGAACAAGAAAAG

ACCTGATAAAGATTAACCAGAAGAAAACAAGGAGGGAAACAACCGCAG

```
                                    -continued
CCTGTAGCAAGCTCTGGAACTCAGGAGTCGCGCGCTAGGGGCCGGGGC

CGGGGCCGGGGCGTGGTCGGGGCGGGCCCGGGGGCGGGCCCGGGGCGG

GGCTGCGGTTGCGGTGCCTGCGCCCGCGGCGGCGGAGGCGCAGGCGGT

GGCGAGTGGGTGAGTGAGGAGGCGGCATCCTGGCGGGTGGCTGTTTGG

GGTTCGGCTGCCGGGAAGAGGCGCGGGTAGAAGCGGGGGCTCTCCTCA

GAGCTCGACGCATTTTTACTTTCCCTCTCATTTCTCTGACCGAAGCTG

GGTGTCGGGCTTTCGCCTCTAGCGACTCTCTTCTGAATTGCCTGCATC

CGGGCCCCGGGCTTCCCGGCGGCGGCGGCGGCGGCGGCGGCGCAGGGA

CAAGGGATGGGGATCTGGCCTCTTCCTTGCTTTCCCGCCCTCAGTACC

CGAGCTGTCTCCTTC

C9ORF72 (partial sequence, anti-sense)
                                                  (SEQ ID NO: 7)
GAAGGAGACAGCTCGGGTACTGAGGGCGGGAAAGCAAGGAAGAGGCCA

GATCCCCATCCCTTGTCCCTGCGCCGCCGCCGCCGCCGCCGCCGCCGG

GAAGCCCGGGGCCCGGATGCAGGCAATTCCACCAGTCGCTAGAGGCGA

AAGCCCGACACCCAGCTTCGGTCAGAGAAATGAGAGGGAAAGTAAAAA

TGCGTCGAGCTCTGAGGAGAGCCCCCGCTTCTACCCGCGCCTCTTCCC

GGCAGCCGAACCCCAAACAGCCACCCGCCAGGATGCCGCCTCCTCACT

CACCCACTCGCCACCGCCTGCGCCTCCGCCGCCGCGGGCGCAGGCACC

GCAACCGCAGCCCCGCCCCGGGCCCGCCCCGGGCCCGCCCCGACCAC

GCCCCGGCCCCGGCCCCGGCCCCTAGCGCGCGACTCCTGAGTTCCAGA

GCTTGCTACAGGCTGCGGTTGTTTCCCTCCTTGTTTTCTTCTGGTTAA

TCTTTATCAGGTCTTTTCTTGTTCACCCTCAGCGAGTACTGTGAGAGC

AAGTAGTGGGGAGAGAGGGTGGGAAAAACAAAAACACACACCTCCTAA

CACCCACACCTGCTCTTGCTAGACCCGCCCCAAAAGAGAAGCAACCG

GGCAGCAGGGACGGCTGACACACCAAGCGTCATCTTTTACGTGGCGG

AACTTGTCGCTGTTTGACGCACCTCTCTTTCCTAGCGGGACACCGTAG

GTTACGTCTGTCTGTTTTCTATGTGCGATGACGTTTTCTCACGAGGCT

AGCGAAATGGGG
```

In some embodiments, a Met . . . poly-(Pro-Arg) or Met . . . poly-(Gly-Pro) protein comprises an N-terminal amino acid sequence comprising an N-terminal methionine. In some embodiments, a Met . . . poly-(Pro-Arg) protein comprises an N-terminal amino acid sequence comprising MQAIPPVARGESPTPSFGQRNERESKNASS-SEESPRFYPRLFPAAEPQTATRQDAASSL THSPPPAPP-PPRAQAPQPQPRPGPAPGPAPTT (SEQ ID NO: 41) or a fragment thereof, wherein the sequence is N-terminal to a poly-(Pro-Arg) repeat amino acid sequence. In some embodiments, a Met . . . poly-(Gly-Pro) protein comprises an N-terminal amino acid sequence comprising MRGKVK-MRRALRRAPASTRASSRQPNPKQPPARMPPPHSP-TRHRLRLRRRGRRHRN RSPAPGPPPGPPRPRP (SEQ ID NO: 42), MRRALRRAPASTRASSRQPNPKQPPARM-PPPHSPTRHRLRLRRRGRRHRNRSPAPGP PPGP-PRPRP (SEQ ID NO: 43), MPPPHSPTRHRLRLRRRGR-RHRNRSPAPGPPPGPPRPRP (SEQ ID NO: 44), or a fragment thereof, wherein the sequence is N-terminal to a poly-(Gly-Pro) repeat amino acid sequence.

In some embodiments, a C-terminal amino acid sequence comprises a C-terminus amino acid sequence shown in Table 1 or a fragment of a C-terminus amino acid sequence shown in Table 1. It is to be understood that C-terminal amino acid sequences other than those in Table 1 are also contemplated.

Exemplary di-amino acid repeat-containing proteins may comprise a sequence provided in Table 2.

TABLE 2

(GA)$_x$WSGRARGRARGGAAVAVPAPAAAEAQAVASG
(SEQ ID NO: 8)

(AG)$_x$AWSGRARGRARGGAAVAVPAPAAAEAQAVASG
(SEQ ID NO: 9)

(GP)$_x$GRGRGGPGGGPGAGLRLRCLRPRRRRRRRWRVGE
(SEQ ID NO: 10)

(PG)$_x$PGRGRGGPGGGPGAGLRLRCLRPRRRRRRRWRVGE
(SEQ ID NO: 11)

(GP)$_x$ (PG)$_x$ (GR)$_x$GVVGAGPGAGPGRGCGCGACARGGGGAGGGEWVSE
EAASWRVAVWGSAAGKRRG (SEQ ID NO: 12)

(RG)$_x$RGVVGAGPGAGPGRGCGCGACARGGGGAGGGEWVS
EEAASWRVAVWGSAAGKRRG (SEQ ID NO: 13)

(AP)$_x$APSARLLSSRACYRLRLFPSLFSSG (SEQ ID NO: 14)

(PA)$_x$PSARLLSSRACYRLRLFPSLFSSG (SEQ ID NO: 15)

(PR)$_x$PLARDS (SEQ ID NO: 16)

(RP)$_x$RPLARDS (SEQ ID NO: 17)

MQAIPPVARGESPTPSFGQRNERESKNASSSEESPRFYPRLFPAAEPQ
TATRQDAASSLTHSPPPAPPPPRAQAPQPQPRPGPAPGPAPTT(PR)$_x$
PLARDS (SEQ ID NO: 32)

MRGKVKMRRALRRAPASTRASSRQPNPKQPPARMPPPHSPTRHRLRLR
RRGRRHRNRSPAPGPPPGPPRPRP(GP)$_x$ (SEQ ID NO: 33)

MRRALRRAPASTRASSRQPNPKQPPARMPPPHSPTRHRLRLRRRGRRH
RNRSPAPGPPPGPPRPRP(GP)$_x$ (SEQ ID NO: 34)

MPPPHSPTRHRLRLRRRGRRHRNRSPAPGPPPGPPRPRP(GP)$_x$
(SEQ ID NO: 35)

$x$ = a number between 2-10,000, 5-10,000, 2-5,000, 5-5,000, 2-1000, 5-1000, 5-500, 5-300, 5-200, 10-500, 10-300, or 10-200.

In some embodiments, the one or more di-amino acid repeat-containing proteins are selected from the poly-(Pro-Ala), poly-(Gly-Pro), poly-(Pro-Arg), Met . . . poly-(Pro-Arg) or Met . . . poly-(Gly-Pro) protein. In some embodiments, the one or more di-amino acid repeat-containing proteins are selected from the poly-(Pro-Ala), poly-(Pro-Arg) protein, Met . . . poly-(Pro-Arg) or Met . . . poly-(Gly-Pro) protein.

In some embodiments, the one or more di-amino acid repeat-containing proteins is two or more, three or more, four or more, or five or more, or six or more, seven or more, or eight di-amino acid repeat-containing proteins.

Subjects

Aspects of the disclosure relate to identification and treatment of a subject, such as a human, with ALS or FTD or likely to develop ALS or FTD. In some embodiments, a subject may have ALS. In some embodiments, a subject may have one or more symptoms of ALS, such as difficulty breathing, difficulty swallowing, muscle cramps, muscle contractions, muscle weakness, paralysis, speech problems, or weight loss. In some embodiments, a subject may not have any symptoms of ALS. In some embodiments, a subject may have a family history of ALS.

In some embodiments, a subject may have frontotemporal dementia (FTD). In some embodiments, a subject may have one or more symptoms of FTD, such as lethargy, aspontaneity, disinhibition, loss of empathy and other interpersonal skills, apathy, progressive nonfluent aphasia, semantic dementia, binge eating, compulsive behavior, tremor, rigidity, muscle spasms, poor coordination, difficulty swallowing, and muscle weakness. In some embodiments, a subject may not have any symptoms of FTD. In some embodiments, a subject may have a family history of FTD.

In some embodiments, a subject may have GGGGCC hexanucleotide repeats within one or both alleles of a C9ORF72 gene (NCBI Entrez Gene ID: 203228). In some embodiments, GGGGCC hexanucleotide repeats are within a promoter and/or intron of the C9ORF72 gene. In some embodiments, the number of GGGGCC hexanucleotide repeats is greater than 25, 50, 100, 150, 200, 250, 300, 500, 5,000, 10,000 or more. The number of repeats may be detected using any assay known in the art, e.g., using as a nucleic acid-based assay such as a southern blot (see, e.g., Dejesus-Hernandez et al. Expanded GGGGCC hexanucleotide repeat in noncoding region of C9ORF72 causes chromosome 9p-linked FTD and ALS. Neuron 72, 245 (2011); Renton et al. A hexanucleotide repeat expansion in C9ORF72 is the cause of chromosome 9p21-linked ALS-FTD. Neuron 72, 257 (2011); and Gijselink et al. A C9orf72 promoter repeat expansion in a Flanders-Belgian cohort with disorders of the frontotemporal lobar degeneration-amyotrophic lateral sclerosis spectrum: A gene identification study. Lancet Neurol. 11, 54 (2011)).

Controls and Control Levels

Aspects of the disclosure relate to comparison of a level of one or more di-amino acid repeat-containing proteins and/or hexanucleotide repeat-containing RNAs to a control level. In some embodiments, the control level is a level of one or more di-amino acid repeat-containing proteins and/or hexanucleotide repeat-containing RNAs in sample, such as a fluid sample or tissue sample, obtained from a healthy subject or population of healthy subjects. In some embodiments, the sample is a blood sample. As used herein, a healthy subject is a subject that is apparently free of disease and has no history of disease, such as ALS or FTD. In some embodiments, a healthy subject is a subject that has 25 or fewer GGGGCC hexanucleotide repeats within a C9ORF72 gene.

In some embodiments, a control level is a level of one or more di-amino acid repeat-n containing proteins and/or hexanucleotide repeat-containing RNAs that is undetectable or below a background/noise level obtained using standard methods of detection (e.g., Western blot, qPCR, northern blot, or immunohistochemistry). Such a level could be obtained, for example, by measuring a level of one or more di-amino acid repeat-containing proteins and/or hexanucleotide repeat-containing RNAs in a sample that is known to be free of the di-amino acid repeat-containing proteins and/or hexanucleotide repeat-containing RNAs.

The disclosure also involves comparing the level of one or more di-amino acid repeat-containing proteins and/or hexanucleotide repeat-containing RNAs with a predetermined level or value, such that a control level need not be measured every time. The predetermined level or value can take a variety of forms. It can be single cut-off value, such as a median or mean. It can be established based upon comparative groups, such as where one defined group is known not to have ALS or FTD and another defined group is known to have ALS or FTD. It can be a range, for example, where the tested population is divided equally (or unequally) into groups, such as a subject that has 25 or fewer GGGGCC hexanucleotide repeats, a subject that has 25-50 GGGGCC hexanucleotide repeats, and a subject that has 50 or more GGGGCC hexanucleotide repeats.

Samples

Aspects of the disclosure relate to determining a level of one or more di-amino acid repeat-containing proteins in a blood sample (e.g., whole blood, plasma, or serum) obtained from a subject. The blood sample may be obtained by any method known in the art, e.g., using a needle or fingerprick device. The blood may be processed before use in the methods described herein. Such processing includes, for example, addition of an anti-coagulant, removal of blood cells, and/or freezing of the blood. However, it should be appreciated that other samples may be used, such as a tissue sample (e.g., brain tissue) or other fluid samples such as saliva, or urine.

Other aspects of the disclosure relate to determining a level of hexanucleotide repeat-containing RNA in sample obtained from a subject. The sample may be a fluid or tissue sample. In some embodiments, the tissue sample is brain tissue. In some embodiments, the fluid sample is blood (e.g., whole blood, plasma, or serum), saliva, or urine. In some embodiments, the fluid sample is a blood sample (e.g., whole blood, plasma, or serum).

Assays

Aspects of the disclosure relate to performing an assay to determine a level or presence/absence of one or more di-amino acid repeat-containing proteins and/or hexanucleotide repeat-containing RNAs. Assays known in the art for detecting proteins and RNAs (see, e.g., Molecular Cloning: A Laboratory Manual, J. Sambrook, et al., eds., Third Edition, Cold Spring Harbor Laboratory Press, Cold Spring Harbor, N.Y., 2001, Current Protocols in Molecular Biology, F. M. Ausubel, et al., eds., John Wiley & Sons, Inc., New York. Microarray technology is described in Microarray Methods and Protocols, R. Matson, CRC Press, 2009, or Current Protocols in Molecular Biology, F. M. Ausubel, et al., eds., John Wiley & Sons, Inc., New York) can be used alone or in combination with techniques and compositions described herein for measuring a di-amino acid repeat-containing protein level.

Assays for detecting protein levels include, but are not limited to, immunoassays (also referred to herein as immune-based or immuno-based assays, e.g., Western blot, immunohistochemistry and ELISA assays), Mass spectrometry, and multiplex bead-based assays. Such assays for protein level detection are well-known in the art. Other examples of protein detection and quantitation methods include multiplexed immunoassays as described for example in U.S. Pat. Nos. 6,939,720 and 8,148,171, and published US Patent Application No. 2008/0255766, and protein microarrays as described for example in published US Patent Application No. 2009/0088329, all of which are incorporated herein by reference in their entirety.

Any suitable binding partner for a di-amino acid repeat-containing protein is contemplated for detection of a di-amino acid repeat-containing protein level. In some embodiments, the binding partner is any molecule that binds specifically to a di-amino acid repeat-containing protein as described herein. As described herein, "binds specifically to a di-amino acid repeat-containing protein" means that the molecule is more likely to bind to a portion of or the entirety of a di-amino acid repeat-containing protein than to a portion of or the entirety of a non-di-amino acid repeat-containing protein.

In some embodiments, the binding partner is an antibody or antigen-binding fragment thereof, such as Fab, F(ab)2, Fv, single chain antibodies, Fab and sFab fragments, F(ab')2, Fd fragments, scFv, or dAb fragments. Methods for producing antibodies and antigen-binding fragments thereof are well known in the art (see, e.g., Sambrook et al, "Molecular Cloning: A Laboratory Manual" (2nd Ed.), Cold Spring Harbor Laboratory Press (1989); Lewin, "Genes IV", Oxford University Press, New York, (1990), and Roitt et al., "Immunology" (2nd Ed.), Gower Medical Publishing, London, N.Y. (1989), WO2006/040153, WO2006/122786, and WO2003/002609). Binding partners also include other peptide molecules and aptamers that bind specifically to a di-amino acid repeat-containing protein. Methods for producing peptide molecules and aptamers are well known in the art (see, e.g., published US Patent Application No. 2009/0075834, U.S. Pat. Nos. 7,435,542, 7,807,351, and 7,239,742). The binding partner may comprise a label including, but not limited to, a fluorescent, enzymatic, affinity or isotopic label.

In some embodiments, an assay comprises an immuno-based assay. In some embodiments, the immuno-based assay comprises an isolated antibody specific for one or more di-amino acid repeat-containing proteins. In some embodiments, the isolated antibody specific for one or more di-amino acid repeat-containing proteins is an isolated antibody as described herein in further detail. In some embodiments, the isolated antibody specific for one or more di-amino acid repeat-containing proteins is an isolated antibody specific for an antigen or sequence, or a fragment of an antigen or sequence described in Table 1, Table 2 or Table 3.

Accordingly, a di-amino acid repeat-containing binding partner (e.g., a di-amino acid repeat-containing-specific antibody) can be labeled with a detectable moiety.

Assays for detecting RNA include, but are not limited to, hybridization-based assays such as Northern blot analysis, RT-PCR, sequencing technology, RNA in situ hybridization (using e.g., DNA or RNA probes to hybridize to RNA molecules present in the sample as in FISH), in situ RT-PCR (e.g., as described in Nuovo G J, et al. Am J Surg Pathol. 1993, 17: 683-90; Komminoth P, et al. Pathol Res Pract. 1994, 190: 1017-25), and oligonucleotide microarray (e.g., by hybridization of polynucleotide sequences derived from a sample to oligonucleotides attached to a solid surface (e.g., a glass wafer) with addressable locations, such as an Affymetrix microarray (Affymetrix®, Santa Clara, Calif.)). Methods for designing nucleic acid binding partners, such as probes, are well known in the art. In some embodiments, the nucleic acid binding partners bind to a part of or an entire nucleic acid sequence of a hexanucleotide repeat-containing RNA provided herein.

Treatment

As described herein, it was found that di-amino acid repeat-containing proteins were present in samples of blood from patients with ALS. Without wishing to be bound by theory or mechanism, it is believed that di-amino acid repeat-containing proteins in the blood of subjects with ALS accumulate within the brain parenchyma over time, leading to neuroinflammatory changes, CNS dysfunction, and neuronal death. Accordingly, aspects of the disclosure relate to treatment of a subject having ALS or FTD by decreasing or stabilizing di-amino acid repeat-containing protein levels in the blood of the subject.

In some embodiments, decreasing or preventing an increase of the level of one or more di-amino acid repeat-containing proteins comprises removing the one or more (e.g., 1, 2, 3, 4, 5, 6, 7 or 8) di-amino acid repeat-containing proteins from the blood of the subject. In some embodiments, the one or more di-amino acid repeat-containing proteins from the blood of the subject is removed using a procedure selected from plasmapheresis or a bone marrow transplantation. In some embodiments, it may be advantageous to decrease or prevent an increase of the level of all di-amino acid repeat-containing proteins expressed by a subject. Accordingly, in some embodiments, a method comprises decreasing or preventing an increase of the level of all forms of di-amino acid repeat-containing proteins expressed by a subject.

In some embodiments, the one or more di-amino acid repeat-containing from the blood of the subject is removed using a hematopoietic stem cell (HSC) transplantation. HSC transplantation is the transplantation of hematopoietic stem cells, usually derived from bone marrow, peripheral blood, or umbilical cord blood, into a subject. The source of hematopoietic stem cells may be allogeneic (e.g., from a donor such as a healthy subject). Methods of HSC transplantation are well known in the art (see, e.g., Bishop M R, Pavletic S Z. Hematopoietic stem cell transplantation. In: Abeloff M D, Armitage J O, Niederhuber J E, Kastan M B, McKena W G, eds. Clinical Oncology. 4th ed. Philadelphia, Pa.: Elsevier Churchill Livingstone; 2008:chap 32; and Vose J M, Pavletic S Z. Hematopoietic stem cell transplantation. In: Goldman L, Schafer A I. Cecil Medicine. 24th ed. Philadelphia, Pa.: Saunders Elsevier; 2011:chap 181).

In order to prepare a subject for HSC transplantation, the HSCs present in the subject may be removed or depleted so that the transplanted cells can become the dominant HSC population in the subject. HSCs in the subject may be depleted, for example, by treating the subject with a chemotherapy, radiation, or both in order to cause the HSC cells of the subject to undergo apoptosis or cell cycle arrest.

In allogeneic HSC transplantation, the HSCs are obtained from a donor. The donor is preferably a healthy subject, such as a subject that is apparently free of disease and has no history of disease, such as ALS or FTD. It is preferable that the donor is HLA-compatible with the subject receiving the transplant in order to reduce the risk of graft versus host disease. HLA-compatibility can be determined, e.g., using HLA typing. HLA typing generally involves examination of at least 8 HLA markers: two A, two B, two C, and two DRB1 markers, and optionally also two DQ markers. HLA typing can be accomplished, e.g., through a blood test. HLA allele identities can be determined using serology or a nucleic acid-based assay. Generally, a match of at least 4-6 markers between host and donor is preferred. In some embodiments, the donor is a subject that has 25 or fewer GGGGCC hexanucleotide repeats within a C9ORF72 gene.

HSCs can be obtained from a donor using any method known in the art. Exemplary methods include bone marrow harvest and leukapheresis (see, e.g., Transfusion. 2003 February; 43(2):259-64. Leukapheresis after high-dose chemotherapy and autologous peripheral blood progenitor cell transplantation: a novel approach to harvest a second autograft. Schwella N, Braun A, Ahrens N, Rick O, Salama A). In a bone marrow harvest, the bone marrow is typically removed from the back of one or both hip bones of the donor. Leukapheresis involves separation of HSCs from blood obtained from the donor using, e.g., continuous flow centrifugation or filtering. The growth factor G-CSF may be administered to the donor to stimulate the growth of new HSCs so that more HSCs are present in the blood. Once obtained, the allogeneic HSCs are then administered to the subject receiving the transplant. Any suitable method of administration known in the art is contemplated, e.g., by central venous catheter.

In some embodiments, during or after HSC transplantation, the subject receiving the HSC transplant may receive additional treatments and/or therapies, such as antibiotics, antifungals, antivirals, blood transfusions and/or immunosuppressive therapies. Such treatments and/or therapies may help to prevent infection and/or graft versus host disease during a HSC transplant recovery period.

In some embodiments, the HSC transplantation is bone marrow transplantation. In some embodiments, the bone marrow transplantation is an allogeneic bone marrow transplantation.

Plasmapheresis is a medical procedure that occurs outside the body (an "extracorporeal therapy") and refers to the removal, treatment, and return of (components of) blood plasma from blood circulation. Plasmapheresis is well-known in the art and has been used to treat several diseases including Goodpasture's syndrome, myasthenia gravis, Guillain-Barre syndrome, lupus, and thrombotic thrombocytopenic purpura (see, e.g., Madore, Plasmapheresis Technical aspects and indications, Crit Care Clin 18: 375-392. 2002). During plasmapheresis, blood is initially taken out of the body, e.g., through a needle or previously implanted catheter. Plasma is then separated from the blood cells, e.g., by using a cell separator. After plasma separation, the blood cells are combined with a replacement fluid and readministered to the subject. The replacement fluid may be either the separated plasma treated to remove disease-associated components or a replacement plasma (also called plasma exchange).

Exemplary procedures used to separate the plasma from the blood cells include:

1) Discontinuous flow centrifugation: One venous catheter line is used. Typically, one or more batches of blood are removed at a time and centrifuged to separate plasma from blood cells. The blood cells are then combined with the replacement fluid and returned to the subject.

2) Continuous flow centrifugation: Two venous lines are used. Plasma is continuously spun out of the blood and the separated blood cells are fed through a line that combines with a replacement fluid before return to the subject.

3) Plasma filtration: Two venous lines are used. The plasma is filtered using standard hemodialysis equipment, e.g., a parallel-plate or hollow-fiber filter. The separated blood cells are fed through a line that combines with a replacement fluid before return to the subject. The filters usually have pores of 0.2-0.6 µm diameter, sufficient to allow passage of plasma, while retaining cells. Several membrane plasma separators are commercially available (e.g., Plasmaflo from Asahi Medical Co., Ltd., Tokyo, Japan; Plasmax from Toray Industries, Tokyo, Japan; CPS-10 from Baxter, Deerfield, Ill., USA; Plasmaflux from Fresenius Medical Care A G, Bad Homburg, Germany; Prisma TPE 2000 from Hospal, Lyon, France).

If the separated plasma is to be used as the replacement fluid, the separated plasma is first treated to decrease the levels of di-amino acid repeat-containing proteins present in the separated plasma. In some embodiments, decreasing the levels of di-amino acid repeat-containing proteins present in the separated plasma comprises contacting the separated plasma with one or more isolated antibodies specific for a di-amino acid repeat-containing protein as described herein, whereby the di-amino acid repeat-containing proteins present in the separated plasma bind to the one or more isolated antibodies. In some embodiments, a binding partner for the one or more isolated antibodies is contacted with the separated plasma. A binding partner for the one or more isolated antibodies may be, for example, a capture moiety such as biotin or streptavidin, protein A, or a secondary antibody specific for the one or more isolated antibodies. Such binding partners allow for the one or more isolated antibodies to be removed from the separated plasma.

In some embodiments, the one or more isolated antibodies are attached to a filter, column, and/or solid support. In such embodiments, the separated plasma is contacted with the filter, column, and/or solid support, whereby the di-amino acid repeat-containing proteins bind to the isolated antibodies attached to the filter, column and/or solid support. Without wishing to be bound by theory, it is believed that the di-amino acid repeat-containing proteins may form aggregates in the blood. Accordingly, the di-amino acid repeat-containing proteins may be removed from the separated plasma using a filter, such that the aggregates are isolated from the separated plasma.

In some embodiments, a subject expressing one or more di-amino acid repeat-containing proteins may develop autoantibodies. In some embodiments, autoantibodies to one or more di-amino acid repeat-containing proteins may be removed from the separated plasma. Autoantibodies may be removed using any method known in the art, e.g., using a binding partner (e.g., bound to a solid support or attached to a tag) that recognizes the autoantibodies. In some embodiments, the binding partner may be one or more di-amino acid repeat-containing proteins as described herein.

If plasma exchange is to be used, the subject receives replacement plasma. Replacement plasma may be, e.g., donor plasma or a solution of albumin (e.g., 5-70% albumin in saline). An exemplary replacement plasma is 5% albumin combined with 0.9% saline in a 50%:50% (vol:vol) solution. Medication to keep the blood from clotting (e.g., an anticoagulant such as citrate, acid-citrate dextrose or heparin) may be given to the subject or contacted with the blood of the subject during the procedure.

In some embodiments, decreasing or preventing an increase of the level of one or more di-amino acid repeat-containing proteins comprises decreasing a level of a hexanucleotide repeat-containing RNA. Decreasing a level of a hexanucleotide repeat-containing RNA may comprise administration of an effective amount of an inhibitory nucleic acid molecule such as an shRNA, an siRNA, miRNA, or an antisense nucleic acid molecule that targets the hexanucleotide repeat-containing RNA.

Methods for producing shRNAs, siRNAs, miRNAs, and antisense nucleic acid molecules are well known in the art (see e.g., Sambrook, Fritsch and Maniatis, MOLECULAR CLONING: A LABORATORY MANUAL, (Current Edition); CURRENT PROTOCOLS IN MOLECULAR BIOLOGY (F. M. Ausubel et al. eds., (Current Edition)); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition). In some embodiments, a nucleic acid inhibitor comprises or corresponds to at least a portion of sequence of a target hexanucleotide repeat-containing RNA sequence or comprises at least a portion of a sequence complementary to a target hexanucleotide repeat-containing RNA sequence.

In some embodiments, treatment may comprise decreasing or stabilizing a level of an autoantibody to one or more di-amino acid repeat-containing proteins in a subject. A level of autoantibody may be decreased or stabilized using any method known in the art. In some embodiments, decreasing or stabilizing a level of an autoantibody comprises administration of an effective amount of atacicept, belimumab, blisibimod, BR3-Fc, rituximab, ocrelizumab, atumumab, epratuzumab, corticosteroid (e.g., prednisone), mycophenolic acid, methotrexate, cyclophosphamide, azathioprine, and/or cyclosporin. In some embodiments, decreasing or stabilizing a level of an autoantibody comprises plasmapheresis.

Antibodies

Aspects of the disclosure relate to isolated antibodies specific for a di-amino acid repeat-containing protein (e.g., a RAN protein) selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein. The isolated antibody may recognize a region or regions of the di-amino acid repeat-containing protein (such as a repeat sequence or the C-terminus) or may recognize the entire di-amino acid repeat-containing protein.

An antibody that "specifically binds" to a target or an epitope is a term understood in the art, and methods to determine such specific binding are also known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen if it binds with greater affinity, avidity, more readily, and/or with greater duration than it binds to other substances. For example, an antibody that specifically binds to a poly-(Gly-Ala) protein or an epitope therein is an antibody that binds this target antigen with greater affinity, avidity, more readily, and/or with greater duration than it binds to other antigens or other epitopes in the same antigen. It is also understood by reading this definition that, for example, an antibody that specifically binds to a first target antigen may or may not specifically bind to a second target antigen. As such, "specific binding" does not necessarily require (although it can include) exclusive binding. Generally, but not necessarily, reference to binding means specific binding. In some embodiments, antibodies described herein have a suitable binding affinity to a di-amino acid repeat-containing protein (e.g., a RAN protein). As used herein, "binding affinity" refers to the apparent association constant or $K_A$. The $K_A$ is the reciprocal of the dissociation constant ($K_D$). The antibody described herein may have a binding affinity ($K_D$) of at least $10^{-5}$, $10^{-6}$, $10^{-7}$, $10^{-8}$, $10^{-9}$, $10^{-10}$ M, or lower. An increased binding affinity corresponds to a decreased $K_D$. Higher affinity binding of an antibody to a first target relative to a second target can be indicated by a higher $K_A$ (or a smaller numerical value $K_D$) for binding the first target than the $K_A$ (or numerical value $K_D$) for binding the second target. In such cases, the antibody has specificity for the first target (e.g., a protein in a first conformation or mimic thereof) relative to the second target (e.g., the same protein in a second conformation or mimic thereof; or a second protein). Differences in binding affinity (e.g., for specificity or other comparisons) can be at least 1.5, 2, 3, 4, 5, 10, 15, 20, 37.5, 50, 70, 80, 91, 100, 500, 1000, 10,000 or $10^5$ fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in, e.g., TRIS-buffer (50 mM TRIS, 150 mM NaCl, 5 mM CaCl2 at pH7.5). These techniques can be used to measure the concentration of bound binding protein as a function of target protein concentration. The concentration of bound binding protein ([Bound]) is related to the concentration of free target protein ([Free]) and the concentration of binding sites for the binding protein on the target where (N) is the number of binding sites per target molecule by the following equation:

$$[\text{Bound}]=[N][\text{Free}]/(Kd+[\text{Free}])$$

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

In some embodiments, the isolated antibody is specific for a di-amino acid repeat-containing protein selected from a poly-(Pro-Ala) poly-(Pro-Arg), Met . . . poly-(Pro-Arg) or Met . . . poly-(Gly-Pro) protein.

In some embodiments, the isolated antibody is specific for an antigen comprising a di-amino acid repeat and/or C-terminus sequence or fragment thereof as defined in Table 1. In some embodiments, the isolated antibody is specific for an antigen comprising a sequence or fragment of a sequence defined in Table 2.

In some embodiments, the isolated antibody is specific for an antigen in Table 3 or in FIG. 28. In some embodiments, an antigen in Table 3 does not contain an N- and/or C-terminal modification.

TABLE 3

Di-Amino Acid Repeat-Containing Protein Antigens

| di-amino acid repeat-containing protein | Label | Antigen | Antigen location in di-amino acid repeat-containing protein |
|---|---|---|---|
| Poly-(Gly-Arg) | GGGGCC F1 repeat | Ac-RGRGRGRGRGRGRGRGRC-amide (SEQ ID NO: 18) | Repeat sequence |
| Poly-(Pro-Arg) | GGGGCC-AS F2 repeat | Ac-RPRPRPRPRPRPRPRPRC-amide (SEQ ID NO: 19) | Repeat sequence |
| Poly-(Pro-Ala) | GGGGCC-AS F1 repeat | H2N-APAPAPAPAPAPAPAPACKKKK-amide (SEQ ID NO: 20) | Repeat sequence |

TABLE 3-continued

Di-Amino Acid Repeat-Containing Protein Antigens

| di-amino acid repeat-containing protein | Label | Antigen | Antigen location in di-amino acid repeat-containing protein |
|---|---|---|---|
| Poly-(Gly-Pro) | GGGGCC F3 repeat | H2N-GPGPGPGPGPGPGPGPGCKK-amide (SEQ ID NO: 21) | Repeat sequence |
| Poly-(Gly-Pro) | GGGGCC F3 CT | Ac-CRRRRWRVGE-OH (SEQ ID NO: 22) | C-terminus |
| Poly-(Pro-Ala) | GGGGCC-AS F1 CT | Ac-CYRLRLFPSLFSSG-OH (SEQ ID NO: 23) | C-terminus |
| Poly-(Gly-Arg) | GGGGCC F1 CT | Ac-CRVAVWGSAAGKRRG-OH (SEQ ID NO: 24) | C-terminus |
| Poly-(Pro-Arg) | GGGGCC-AS F2 CT | Ac-CRPRPLARDS-OH (SEQ ID NO: 25) | C-terminus |
| Poly-(Gly-Ala) | GGGGCC F2 CT | Ac-CSGRARGRARGGA-amide (SEQ ID NO: 26) | C-terminus |

F1 = reading frame 1, F2 = reading frame 2, F3 = reading frame 3, AS F1 = anti-sense reading frame 1, AS F2 = anti-sense reading frame 2, AS F3 = anti-sense reading frame 3.

An isolated antibody may be a monoclonal or polyclonal antibody, or an antigen-binding fragment thereof. An antigen-binding fragment thereof includes, for example, an Fab, F(ab)2, F(ab')2, Fv, single chain antibody, Fab fragment, sFab fragment, Fd fragment, scFv, or dAb fragment. Methods for producing polyclonal and monoclonal antibodies and antigen-binding fragments thereof are well known in the art (see, e.g., Sambrook et al, "Molecular Cloning: A Laboratory Manual" (2nd Ed.), Cold Spring Harbor Laboratory Press (1989); Lewin, "Genes IV", Oxford University Press, New York, (1990), and Roitt et al., "Immunology" (2nd Ed.), Gower Medical Publishing, London, N.Y. (1989), WO2006/040153, WO2006/122786, and WO2003/002609). Also encompassed are antibodies made by recombinant means such as chimeric antibodies (variable region and constant region derived from different species) and CDR-grafted antibodies (complementary determining region derived from a different species) as described in U.S. Pat. Nos. 4,816,567 and 5,225,539, which are incorporated herein by reference in their entirety. Also encompassed are humanized antibodies, typically produced by recombinant methods, wherein the human sequences comprise part or all of the antibody. Also included are fully human antibodies, such as those produced in genetically-altered mice (see PCT Application No. 93/12227, which is incorporated herein by reference in its entirety).

In some embodiments, an isolated antibody specific for a di-amino acid repeat-containing protein is a rabbit polyclonal antibody as listed in Table 4.

TABLE 4

Di-Amino Acid Repeat-Containing Protein Rabbit Polyclonal Antibodies

| Antigen | Animal | Titer |
|---|---|---|
| GGGGCC F1 repeat | H3147 | 1,575,500 |
| GGGGCC F1 repeat | H3148 | 1,956,500 |
| GGGGCC-AS F2 repeat | H3149 | 2,399,600 |
| GGGGCC-AS F2 repeat | H3150 | 3,225,000 |
| GGGGCC-AS F1 repeat | H3151 | 660,200 |
| GGGGCC-AS F1 repeat | H3152 | 2,082,600 |
| GGGGCC F3 repeat | H3154 | 752,300 |
| GGGGCC F3 repeat | H3155 | 590,500 |
| GGGGCC F3 CT | H3156 | 231,300 |
| GGGGCC F3 CT | H3157 | 616,700 |
| GGGGCC-AS F1 CT | H3158 | 6,300 |
| GGGGCC-AS F1 CT | H3159 | 32,800 |
| GGGGCC F1 CT | H3160 | 573,900 |
| GGGGCC F1 CT | H3161 | 363,000 |
| GGGGCC-AS F2 CT | H3162 | 2,261,700 |
| GGGGCC-AS F2 CT | H3163 | 176,300 |
| GGGGCC F2 CT | H3164 | 1,549,500 |
| GGGGCC F2 CT | H3165 | 115,700 |

Antibodies may be produced in bacterial cells, e.g., *E. coli*, or eukaryotic cells, such as yeast cells or mammalian cells. In one embodiment, antibodies are produced in mammalian cells. Mammalian host cells for expressing the antibodies or antigen-binding fragments thereof include Chinese Hamster Ovary (CHO cells) (including dhfr-CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601 621), lymphocytic cell lines, e.g., NS0 myeloma cells and SP2 cells, COS cells, and a cell from a transgenic animal, e.g., a transgenic mammal. Antibodies can also be produced by a transgenic animal. For example, U.S. Pat. No.

5,849,992 describes a method of expressing an antibody in the mammary gland of a transgenic mammal.

Isolated antibodies of the disclosure may also have a detectable label attached thereto. The label may be, for example, a fluorescent, enzymatic, affinity or isotopic label. Examples include fluorescein isothiocyanate (FITC) for detection by fluorescence, horseradish peroxidase which allows detection by cleavage of a chromogenic substrate, radioisotopes such as $I^{125}$ for detection by autoradiography and avidin/biotin for antibody detection and affinity purification of antigens and antigen-bearing cells.

Also encompassed by the disclosure are hybridoma cell lines producing a monoclonal antibody specific for a di-amino acid repeat-containing protein selected from a poly-(Gly-Ala), poly-(Gly-Pro), poly-(Gly-Arg), poly-(Pro-Ala), poly-(Pro-Arg) protein, Met . . . poly-(Pro-Arg), Met . . . poly-(Gly-Pro), a C-terminal peptide of a di-amino acid repeat-containing protein as described herein, and/or a combination of two or more thereof.

In some embodiments, an isolated antibody is an isolated auto-antibody obtained from a subject having ALS, wherein the isolated auto-antibody is specific for one or more di-amino acid repeat-containing proteins as described herein.

In some embodiments, an isolated antibody described herein is contained within a buffered solution. In some embodiments, an isolated antibody described herein is attached to a solid support (e.g., the surface of a plate or a bead).

Transgenic Mouse

In another aspect, the disclosure relates to a transgenic mouse comprising a human C9ORF72 gene comprising a GGGGCC hexanucleotide repeat sequence. In some embodiments, the mouse comprises a human C9ORF72 gene comprising a GGGGCC hexanucleotide repeat sequence and flanking human sequences on the 5' and 3' end of the human C9ORF72 gene. In some embodiments, the flanking human sequences on the 5' and 3' end are each independently at least 1 kilobases (kB), at least 5 kB, at least 10 kB, at least 20 kB, at least 30 kB, at least 40 kB, or at least 50 kB in length. In some embodiments, the flanking human sequences on the 5' and 3' end each independently comprise a promoter capable of driving transcription of the human C9ORF72 gene in the sense and anti-sense direction, respectively. Accordingly, in some embodiments, the transgenic mouse expresses both sense and anti-sense transcripts (e.g., 5'-GGGGCC-3' and 5'GGCCCC-3' hexanucleotide repeat-containing RNAs described herein). In some embodiments, the human C9ORF72 gene and flanking sequences comprise the sequence below, wherein (GGGGCC)$_n$ indicates the location of the GGGGCC hexanucleotide repeat sequence:

Chr9:27,527,137-27,625,470 (reverse complement)
(SEQ ID NO. 63)
AAGCTTGATAATATTATCAAATATTAGATAAATGTAA
TATTAGAAGAAACTTTTTGAAAAGATATATAAAAAT
AATTTCATTCAAAATTTTTATATTTAATTTAAATTTTT
AATGAAAATATATCTAAGTTTTGTACGCTTTAAATGT
AATTATGTTTGATAATTTAATCATTTACTATTCGTTCT
CTATTGCTGCCCTAACAAATTCACATTACAGTTCAGTGGC
TTACAAAACACAAATTTATTATCTTACCATTCTGTGAG
TCAAAATTCCAAAATAGGTGTCACTAGGCTAAAATGA
AGGACTGCATTTCTTCCTGCAGGCTCCAGGAGAGATCT
ATGTCTTACTCTTTTCGGCTTCTAAAGGCTGCCCACA
TTCCTCGACTAGTGGCGTCCCTCCTTCGTCTCTAAACC
CAGCAACAACAGGTTGAGTCCTCATGTCACATCTTTC
TTACCTTTCTGTCATCTCATCTCGCTGACTGCTGCTGG
GAAAAATTCTCCACTTTTAAGGGCTATCATGATTAGA
CTATGCCCACTAGATAATACAAGATCTCAGATCCTTAA
CTTCCATCACATCTGCAAAGTCGCTTTTGCCTCATAA
AAGAGTCTGAGGTTTAGACGGGAGATCTTAAGGGGGCT
ATTAATATGCCTACCATAATCACTGAGAATAAGTACA
AGTTAAGATTATAATAGCAATAGAATATACAAACGTGA
AGCTCCAAAGAACAACAACAACAAAAAAAGGTGAACA
GGAAAAAGAAACTGAAAATCTTTAAAAAGGCAGTCTGT
TTAAATCTATAAAAACTGGAAAAAAATGAGAGTGGAC
AAATATCTGGTAAGCATGATGGACTTAAAATTTGTGAC
TAGGGCATTACATTTTTTATATTAATATAATGAAGAT
TGAATTACTGATCAAAACAATTAAAAAGCAAGAGAACT
ATTCTCATCAAATCTGCAACACGAAAAGTTCAGACAA
AATTCCAACAACTTCACATTCTGAACTAAATGAGGACT
AATTACCAGTTCGAGCAATGAGAATATATGAGGTCCT
CCGTTTGCACTTTGCCAGGGATCTGAAAACGTTGGGAG
TAGGTCGGCTTCACCCTGAAGCCAGACCATCGACAGC
CAGTTTTCCCTCCCTTCTCCACCCACAGGTCTTAGGCC
CTCATCCTTCCCAGCCTCAGAACTAGTCTCCAAAGAA
GAGGAAAGTTAGAGGAGAGAGTAAATCGTTGAATAGGA
TGAAGGAGATGTGGGAAAAAGAAAAAGAGAGGCTGCA
AGAGAGAGGGTCCCAGGGATAACTCTGCTCTTGGAAGG
GTGGCCACAGTCATGTGGTCCCAAGAGGCAACAACAA
GCTTAGGAAGCCAGAGAAACCAGTTACAATCACTGCTA
CTCTTTTCGATTCTGTGTTGTTTAAGAAATATCACCC
GCCAGGAGTTCTCCAGAAACATTTTCCCTGATTCCATG
TAAGTGCTCAACCAGTGAATGGTAATCCCATTTTGGT
TTAGTCTGTACCATCCCCTATTCCAAAATAAAGGGAAA
AATGGTGGGTTTATATCTTAAATTTTCTACTTTACTA
AACTCAAGGGAAATAGCCAAGCAAAAACGAAAGCTGAG
ACTCTTGCTAATTATCCTTTCCATAGAATGTTTGCTA
AAATTCCTTGTCAAGGAAGGAATAACAAAGCTAGTCCA
CGCTCTGTATAGGGTGTTTCCAATTAGTTATACTTTA
AAGTATAAGTATTTAACAAAATCTATAAATTTTGTTAA
TTATTTACTTGTAGTGAAAAATGAGCCATTCTCAAGC
AAATCACTTTTTATTACACATTCCAGAGAATAACCATA
AAAGGACATTTATTATAGCAAAAATAACCACATCTGG
ATGGAACTTCAATCACCAGTATTTACTAAATAAATGCC
CAGAAAAAAATAGTTCATCTTTAATTTCAGTCATCA
TTAATAAAAGCTGAAGTACCTCTTCAGATCTTTTGATC
ATTTTCTGTTGGATTTGTTTTCTTTTTACTGAGTTGCA
AATGCTCTTTATATATTTTGGATACAAAGCTTTATCAC
ATAGGCATTTTGCAAGTATTTTTTCCAAGTTTTTTTA
TCTTTTCATTTATTTAATAATATCTTTCAAAGAACGGG
AATTTTATAATTTTTATGAAGTCCATTTATAATTTTT
TCTTTTATGGGTTGGTGGGGTTGGGGGTTGTGTTGTC
CTAAGAAATCTTGGCTCAACACAAAAAGATTAGTTTC
TATATTTTCTTCTAGAAGTTTTATAGTACGATCTCAGA
TCCATTTCAGATGATGAATAAGCACATAAAAAAAGGA
TACTCATCGTTAGTCATTAGAGAAATGCATATTAAAAC
CATAAGGAAATACTACTATATACATATATTAGATAGG
ATGAAGAGCAACTGGAATCTCATACAGTGCTGATTGAA
ATGCAAAATGGCAAAACAACTTTAGAAACCAATTTGG
AAGCAGCTGTACTGACATGGAATTTTGAGCTGGAAGAA
TCTTAGAAAAGAATACTTTACCACCTCCCCCATTCT
CTTCACCCTGGGGAACTGTTAAATGAGGAAATTGTGGT
TCAAGGAGGAACTTGTCTATATGCTTTCTCAGCTTTC
CCGTGGTAATTACCATCTTGATAATATAACGTAATGTA
TGTATATGTTATCAAATAATATAATATCTTCATCATA
TATTTATCATCTTCATAATGTTAGCTGTCTAGTGGTAA
CTTTTTTTGCTCTTTATTGCCTCCCTCTTTTTTCCC
TCTTTGTTGTTTTTTGTCATACAATTATGATATATGTG
TATATATTCTCACTGTAAAGATGTAAACAACACAAAG
ATTATTGAACAAATCACGAAAGTAACCCTTCCTTCATT
CTTACCCTATCCAACCCTCATCTCCTCAGAAGAATAC
ACCATTTTAGTTGTAAATGTTTTTCTAGCTCTTTTTCA
ATGTTTCTACCTATATGCATGTATGTATAATGTATAT
ACATACATATATACATACATATTGATATATACATATAT
AGAGGTATGGTTTTTTAACTTAAATGGAATTGCATTG
TGGATATTGTCCTATGACTTGCTTTCAACCAAATTATA
TGTCTTGGAAATACATACATATATTTAAAAAATATGT
TATGTATATGTAACATACTATATGTGCATAATATATAT
TACATAGATATAATAAGGCCTAGGAAGAAATTGTGTG
CAACCTCTAGTCATCTTCCTCTATATCTACTGTACAT
ACATACAACCCATTCTTTTTTTAATTTTTTTATTTTT
TTAGACAGAATCTTGCTCTGTCGCCCAGGCTGGAGTGC
AGTGGCACAATCTCGGCTCACTGCAAGCTCCACCTCC
TGGGTTCACGCCATTCTCCTGCCTCAGCCTCCCAAGTA
GCTGGGAATACAGGCACCTGCCATCAGGCCCAGCTAA
TTTTTTTTTGTATTTTTAGTACAGATGGGGTTTCACCG
TGTTAGCCAGGATGGTCTCCATCTCCTGACCTCGTGA
TCCGCCCACCTCATCCTCCCAAAGTGCTGGGATTTACA
GGCGTGAGCCACCGCGCCCAGCCACAACTCATTGCAG -continued

```
AGTAGTCCAAAATATGGATGGACTGTAGCTTAATTACT
TATTCTCCCATTGATAGACACTTAGGACTTTTCTAAT
TTTTTATAATTTAAAAATATGCTGCAATTAACAAACATT
CTTGTGTATCTTTTTGCTGTATGTATGCATATTTCTT
TAGTATGGGTTTTGGAAGAGGAATCACAAAGGAGGCAT
AGAATATAAATATTTTTATTTTGAAAAATACAGTTGT
AATTTAATAACCCACCAAAAGACTCTAACAGTTTAGAT
TCACATCAACAGTGTAAGAACATGTCTGTTTTACTGC
ATCCTTACCCCCACTGGTTATAATACTTTTAATTAACA
ATCTTATGGATGAAGAATACTATCGCAATGTTGTTTT
AATGCATTTTTCCAATTACTAGTGAGATTGAACATTAA
TTCTTTTATTTTATGGATCACTGGCTTTTCTCCTTCT
GTGAACTACCTGTTCACATCCTCTGCTTTTCAGCTCTT
GAGCTGTTATCTTTTTCTTATTGATTTATATGAGCTC
TTTATATATTCAAGATGTTAATCATTTGTATTTTATGT
ATATGGCAATGATTTTCTTCCAAACCAATGCTTGTCT
TTTATTTATTTATTTATTTATTTATTTATTGAGACCG
AGTCTCGCTCTGTCGCCCAGGCTGGAGTGCAGTGGCG
CGATCTCGGCTCACTGCAAGCTCCGCCTCCCGGGTTCA
CGCCATTCTCCTGCCTCAGCCTCCTGAGTAGGTGGGA
CTACAGGCGCCCGCTGCCACACCCGGCTAATTTTTTGT
ATTTTTAGTAGAGACAGGGTTTCACCGTGTTAGCCAG
GATGCTCTCTATCTCCTGACCTCGTGATCCGCCCGCCT
CGGCCTTCCAAAGTGGTCGGATTACAGGCATGAGCCA
CCACGCCTGGCCAATGCTTGTCTTTTTATCTCTGTTTA
TGGCATCTTTCATACATATGGACATTTTTATTTTTATT
TTTTATGTTGATTTATTCTTGAATTGTATACATGTTAA
TTATACCTAAGTTATTGTAATACCCTTAAAGCCAAGT
TCTACACATATATTTAATTTGCTTTCCCAATAGGTCTC
TGAGGGAACACATTTTTTACAAATCATTTGTTTCATC
TTTTTTAGGTGTTGATCAATTATTAAGGAGTTTGAAAT
AATCATTTAAACGGAATTCTTCAGATGAAAACATAAA
GACATTTATCGGGTCAGAGCATTGGTCGGTTCACATAC
TCAGGATCAGTGGCCTGGGTGGGCAGGCACTGGGTGA
ATGGAGAGCTGCAGGTATTGGAAGAGAGCCCAGTTGGA
TATGTAGTTTCCAAAGATCATCAAGGCAGACAACCAA
AGGGAAACCGTGGGAAACACCTGCTTTGGGCATCTAA
GATGAGATGATAAAGTAAGGAAAGAGTTGAGCCCAAC
ACAGTGATAGCCAATCTGAAAGCGGGCAGAACTGACAA
GACCAAACAAGTAGGTGAACTGGCTGCAGGCAGCCAG
CCACCACAGGGACAGCGTGTACTCCAGGGACAAGCTCA
AGGCTATAGGTAGTTAGTTCAAGGCTACTAGGGTGAG
AAGAGCAGGAACTGAGTTCTATACCAGTGCTTCTCAAA
ACTAATGTGCATCCTAATCACCTGGAAATCTTGTAAA
AATGTAGATTCTGATTCAGTGAGTCTGAAGCAGAGCTT
AAGATACTACATGCTTAACAAGAGCCTAGTTGATGCT
GACACTGCTGGTCCCTGGAGCTCTCTTTGAGTAGCAGG
CTTCTGGAAGGCTTGTGTCACTAAGCACAGAGAAGCC
TCACTTATCAAATCTGCACCAAAACAGGAAAACTAATG
TGAAGAATAATGTGATGCACACGTCAGAGCATGAGGC
AGTTGCTTTGTCCCTGAGGTTGCACTTCCAGATGGCTTC
CTAAGATGCGACAGGCTGATCTTGTGCGTGGGGGTCC
CGGAGGCTTGGGCCACGGGAGAGACAGGACCTCAGAGG
CTGGGAGACAGGCAGAGACAGAAGAGTGACATCCTGC
TGCTTTTGAATTTGCATTCTGTAGAATAATAACAGC
AGTAAACTGTTACACAATATCTATTCTCAGCATCTTG
AAGCCCTTTCACATATTGTTACTTCCATTAATGGGGCC
CTTTGCTGCTATTTCTACTTTTCTCTTCAGCTATCAA
CAATATGGCTTTCCACACCTCCATCACAGTAGCCAG
ATGAAATAAAATGTGCCAGAATGAAAACTTGTTCATT
TGTCTACTTTTTGCCAAGACTAGACAGGCAGGAAATTG
AATGTATTTTACAGAAAAGGTTTTCAAAACTTTTTC
CCCTCTGTGGCTCATTTAGGTAAACTAAAAGGCATAAG
ACCCACCTAAACATGGGTTCCCGCTTTTTATTGGAG
AAAGAACATAGTACTTTAAAAAAATACATAAAATAATA
AAAAGGAAAGACAAAGATAATGAAGGTTGTACATGGT
ACCAAATTTTTGTATCCCATAATAACACATGAGTAGAT
CACTACTAAGTAGGTTTTAGTGACATATAGGAAACAT
TAAAATCTACAGAAATTTGCATTATTTTCTGTCAAAAA
GGATCATTTCACAGCCTTTCAGGGGAACCCATTGCC
CACAGGAACTCATGCATTCCATGCTTTGAGGATCACTA
GATCTAAGAAGCCTTCCTTGGAGGTTCTAGCCTCCAA
CCCTTATTTTAGTAAAAGAAGCTCCAGTTTTATCTGTT
TCTAAGTCAGACTACCACACAACATTGGGCTTAAAGA
AAGGTTTCCAGGGCTAAAGCAGACTTTGAGGATTACTA
ATTCCGAGTTAAATTTCTGTGTATTATCTCTGGATTT
GACTTATTCACACTGGACTATCACTCATAAATATACAT
AATACAGAGTTAACTATTTAAATTTATAAAGAGAGTA
TTTTCCTTTTTTATGAGCAAAACATGCTGCCAACTACT
TGGACCACATACTGATCCATAAATACTGACAGCTTTG
TAATTGGAAATAATAAATACACACTAATGAAGCATCTC
AAAAGGGAAGAGCCACAGGTAATCTGAGTGATTAGGC
ATTCATGTTAGGTTAGGCTTTGATCATTGTTTTTAATC
GCAATTTCATTGCAGTGCATCTATAAATCCATGTCCA
GAAGTATGAAGTGGTTCTATAGTAAGAATAAGATGCTA
CAGATAATGCGACTAAATAAGACACTATAGGTAATGA
CACAGATTCAAGTCTTATTGTTGATGGGAAGAGGTCAA
TAATGGATGATATAATATACTACAGCAATGAGAATTA
TTGAATGTTTTCCAGACTCACTTGTATAATTGGCCATA
ACAGCAAACAAAAAACAGGTTCTGATAGCAAAATGAT
ATACAGTACTAACAAAGGTGAATCTTGAGGTGAACCTT
CTCTTTATAAGTTTAAATAGTTTACCCCCGACCTTTT
CCCATAGTAGAACAGCCTAAAAAGTATCTTTCAGTAGA
ATGCTAGTGCTTATGAGGTTTTCTTAAGATATCATTT
TTCAATTAAAATTTATTTCACAAAAGACTCACATCCTT
GCCAGCCTTCAGGGTGAGTGTTGATTCAGGCTGTGTC
CAACGGCAACGATGAGTGAACTTCTCACCCTCAGAATC
ACATGAGCATTCCTGAGATGTTTTATCAGAGTGATAC
CAACTTCATTATTAGAATATTGAGTCCCTATTTCCTAT
ATTCAATGTCCTTTCAAGCCCTAACTTTGTCCGGGTT
GAAGGCAAAGATCCAAATAATCACATTTGTCTTTGATA
ACTGAAACTGGGAGAACTGGGACTGTCTCAAGAGTTC
TACGTGACTGTAGGTTGCAAGTACTGTGGTTGCATCTC
CAAATATTAACCAATCCCAGTGACAATTCAATGGGGT
CTCCTGAACCATGATCCTCATGTCTCCAGTGAAGGAAA
TGGGCAAAGGGGATTCAAAAATCCCTTTTGGAGGAAT
AGGAAACTTCTGCTTTCCTTCATTTCATAACATTTGCG
ATGGAACAAAGGCTTTTTTAGAATGGAGCAACCAGAT
CCTTTTTTGGGGGAATCAGCTTAAATGTCCCTTCTTCT
CATACTACTTTTATCTATGTGATCCTATTCTTTTCTG
TTGTGGATTGAATCATGTCCCTCAAAAAGATTGAATTT
AGAGTGTGCTCTAAATTCAATGTGGAGAAATTTGGAC
ACAGAGGCAGACACACAGGGAGAACCCCGTGTGACAAT
GGAGGAAGAGGATGCATTTATGCTGCCACAAGCCAAG
GAACACCAAAGATTGTCAGCAGCCACCAGAAGCTAGGA
TAAAGGCATGGCACATCACTCCCTCTGAGCCCCCAAA
AGGAGCCAAGACTGCTAATACTCTGATCTCGGACTTCT
GGCCTGAAACAGTGAGAGAATAAGGTTCTGTTGTTTC
AAGCTACCCAGCTTGCGGTATTTTGTCACAGAAGCACA
AGGAATCAAGTACATTTTCTTTCTCAGCACTTGTGAT
AATTTGATTTTTTCTTTACTCAGTGGTTGTTTCACACC
TATGTCCCCATCAGACTGTAAGCTTAAAGAGACCTGG
ATCTGGTCTGTCTTCACCACTGTTGATTCATTACCAGC
ACAGTCCCTGGCCCATGGTCACTGAATAAACGTTTGT
TGAGAGAATGAATGTGCTTAACCAGAAGTACTATTGAC
CTATTAGGCCAAGTTCAAGGTGCCTAACAGCTCAGCT
GTGAAGGATACCTCTCCTTTCAGTCCTCTGTTACATAT
GTCCCTGATAGATGTGTTATTTGTATCTCCTCCTGG
CCTCAAGTTTGTTTGAGGGCAGGACCCTTTTTTGTATA
TCTGTAGAGCTTCGTAGTACCTAAATACTACTTTGCA
TATATAATAAAGTTTCGATAAATATTCATTAAATAAAG
AAATAAATGAAATGACTAAGTTTTCTAAGATGTTACA
ACTAGATTGAAGATATTTAGCTCATTATTTAACAAGAA
AACTATGGTTAATTATGGTGTCCTGTGTGAAATGGT
TATAGTTTGTTTTTTAATTAATATAAGCATGTATGTGC
ATTATCAGTATACACAATTTGTGGTATGATGAGTGTTTG
TGTCCCTGCACACAGACCACGGAAATCCTGAGAAACAA
ACTGCCACCCCAGAGCAGGTGCCTAACACAGAGACTT
TTAATCCTTAAAGTTTTTCTATAACTAAGCAATGTTTT
TTCAAATGCAATAACACTGATATGCAGACATATTGAT
TGTCCACTCACAAAGCATTCCTCAATATCATTACAAC
ATGCCTCTTTGAATGTCATTAAAAATAGATGTCTCAT
TTTTCTAGGACAAGTTGGCTGAAGTTCTGCTTGAAAAC
TGGTAATAGAAAATACAATTTCTCAACCCGCTTTGGC
CTTTTAATTCTGTTCTACAACCTTGCCAGTTCACTTTC
AAAGTCAAGGGATGCATCTTGCAAAACCATGACATCT
TTTGAGTAACTCCTTCTGTTCTTAACACATATTCCCAG
GAGCTTAATAAATATTGTTTTGCAACTTGTTTAGTG
GCAAAATAAGATCCTTGGTGTATGCTTATCCTCTGC
TTTGCTATTAGAGAAGATATATTCAGACTGTTTTAAA
CAAATTAATTCAAGGGCAGGGAACAGTCCTAAAACCTG
TTAAAATTCAAATACTTGGTCACTGTATGTGCAGCAT
GTGTGTTCTAGAAAGTCCTATTATTTTAAAATATAAAT
TGAATCTTGTTGAGAAATTAATGTCATATGAATATAT
TAATAACTGAAATGCTGCCAAGTTTACAAAAAGCCCTC
AATGAAACTGTGACCTTGTATAGACAAGGGCCTGTGG
AGGGACATTTTTAAACCATCTCTTTTTTATTTCCTCA
TGAGATCTACAATGTAAGTGCATTAAAGTTGATGAAT
GAATTGCAGTGCAACTTTTCCTGCCTCTTTTGCCTTTC
ATTTGTCTATATTTCAAGCTTCACTGAAGTGATAGAT
TTTGGGCTTTGCCACATTGTCCTCTGATTGCTTCCCTC
TGCTCCTCCTTTTCCTAGTGAATCTTTGTTTTACTGG
```

```
TGGAAAAATCTACATCTTTGTATCTTGGCATTTTACTT
TCACATTATCTCATAGATTTTATTTCAAGTTGCTATA
AAGTTATCAACTTTTATTTTTAACTAATATTATTTTTA
ACAATTAGAAAATTGTTGACCAGGTAATTCCAGCACT
TTGGGAAGCTGAAGCGGGAGGATCACGTGAGCCCAGGA
GCTCGAGACCAGCCTGGGCAATGCAAGGAGACTGTCT
CTACAAAATATAAAAATACATTAGCCAGGTTTGGCGGT
GCATGCCTGGGGTCCAGCTATTCAGGAAGCTGAGGTG
GGAGGATCACTTGAGCTGGAGAGGTTGAGGCTGCAGTG
AGCAGTGATCGCACCACTGCACTCCAGTCTGGGTGAC
AGAGGGAGACCCTATCTCGAAAAAAAGGAAAAGAAGAG
GATTTTGCTGGCAAGATGGCTGAATAGGAATAGCTCC
GTTCTGCAGCTCCCAGTGAGATCAATGCAGAAGGCAGG
TGATTTCTGCATTTCCAACAGAGGTACCTGGTTCATC
TCACTGGGACTGGTTGGACGGTGGGTGCAGCCCATGGA
GGGTGAGCAGAAGTAGGGTGGGGCGTTGCCTCACTCA
GGAAGTGCAAGGGGTCCCTCTTCTAGCCAAGTGAAGCC
GTCAGGGACTGTGCCATAAGACAGTGCACTCTGGTC
CAGGCTTTTCCCACAGTCTTTGCAACCCACAGACCAGG
AGATAACAAGCGGTGCCTATGCCACCAGGGCCCGGGG
TTTCAAGCACAAAACTGGGTGGCCATTTGGGCAGACAT
CAAGCTAGCTGCAGGAGTTTTATTTTCATACCCCAG
TGGTGCCTGGAACGCCAGTGAGACAGAACCGTTCACTC
CCCTGGATAAGGGGCAGAATCAGGGAGCCAAGTGGT
CTGGCTTGGCGGGTCCCACACCCACGGCGCCCAGCAAG
CTAAGATCCACTGGCTTGAAACTCTCAGCTTCCAGCAC
AGCAGTCTGAGGTCCACCTGAGACGCCCGGGCTTGGTG
TGGGGAGGGGCATCCACCATTGCTGAGGCTTGAGTAG
GCGGTTTTACCCTCACGGTGTAAACAAAGCTGCCTGGA
AGGTCCAGCTGGGCACAGCCCACCACAGCTCACCAAG
GCCGCTGTGGCCAGAGTGCCCCTCTGGATTCCTCCTCT
CTGGGCAAGGCATCTCTGAAAAAAAGGCAGCAGCGCC
AGTCAGAGACTTATAGATAAAACCCCCATCACCCTGGG
ACAGAGCTATTCCAGGGAAGGAGTGGCTGTGGGTGCAG
TTTCAGCAGATTTAAACGTTCCTGCCTGACAGCTCTGA
GAGAGCAACAGATCTCCCAGCACAGCGTTCAAGCTCT
GTTAAAGATCAGACTGCCTCCTCAAGTGGGTCCCTGAC
TCCCATGTCTCCTGATTGAGAGACACCTCCCAGTAGG
GGCTGACAAACACCTCATAAAGGAGAGCTCCAGCTGGC
ATCTGGCAGGTGCCCCTCTGGGACGAAGCTTCCAGAG
GAAGGAACAGGCAGCAATCTTTGCTGTTCTGCAGTCTC
AGCTGATGATACCCAGTCAAACAGGTCCTGGAGTGGA
CCTCCAGCAAACTCCAGCAGACCTGCAGCAGAGGGGCC
TGACCGTTAGAAGGAAAATTAACAAATAGAAAGGAAT
AGTATCAACATCAACAAAAAGGACGTCCACTCAGAGAC
CCCATCCAAAAGTCACCAACATCAAAGACCAAAGGTA
GATAAATCCACAAAGATGGGGAGAAACCAGTGCAAAAA
AGTCTGAAAATTCCAAAAACCAGAACGCCTCTTCTCC
TCCAAAGAATCACCACTCCTCACTAGCAAGGTAACAAA
ACTGGACAGAGAATGAGTTTGACAAATTCACAGAATT
AGTGTTCAGAAGGTGGGCAATAACAAACTCCTCCAAGC
TAACGGAGCATGCAAGGAAGCTAAGAACCTTGAAAAA
AGTTAGAGCAATTGCTAACTAGAATAACCAGTTTAGAG
AAGAACATAAATGACCTGATGGAGCTGAAAAACACAG
CACGAGAACTTTGTGAAGCATACACAAGTATCAATAGC
CAAATCGATCACGTGGAAGAAAGGATATCAGAGATTA
AAGATCAACTTAATGAAATAAATTGAGAAGACAAGATT
AGAGAAAAAAGAATGAAAAGGAATGAACAAAGCCTCC
AAGCAATATAGGACTATGTGAAAAGACCAAATCTATGT
TTGACTGGTGTACCAGAAAGTGACGGGGAGCATGGAA
CCAAGCTGGAAAACACTCTTCAGGATATTATCCAGGAG
AACGTCCCAACCTAGCAAAACAGGCCAACATTTAAA
TTCAAGAAATACAGACAACACCACAAAGATACTCCTCG
AGAAGACCAACCCCAAGACACATAATCGTCAGATTCA
CCAAGGTTGAAATGAAGAAAAAATGTTAAGGGCAGCC
AGAGAGAAAGGTCAGGTTACCCACAAAGGAAGCCCAT
CAGACTAACAGCAGATCTCTCTGCAGAAACCCTACAAG
CCAGAAGAGATGGGGGCCAATATTCAACATTTTTAA
AGAAAAGAATTTTCAACCCAGAATTTCATGTCCAGCCA
AACTAAGCTTCATAAGTGAAGGAGAAATAAAATCCTT
TACAGACAACCAAATGCTGAGAGATTTTGTCAACAGCA
AGCGTGCCTTACAAGAGCTCCTGAAGGAAGCACTAAA
CGTGGAAAGGAACAATCGGTACCAGCCACTGCAAAAGC
ACACCAAATTTTAAAGTCCATTGACACTATGAAAAAA
CTGCATCAACTAACAGGCAAAATAACCAGCTAGCATCA
TAATGACAGGATCAAATTAACCTTAATTAAGTTAGCC
TTAAATGTAAACGGGCTAAATGCCCCAGTTAAAAGACA
CAGACTGGCCACCTGTATAAAGAGTAAAGACCCATCA
GTGTGCTATATTCAGGAGACCCATCTCACATGAAAGA
CACACATAGGCTCAAAATAAAGGGATGGAGGAATATT
TACTAAGCAAATGGGAAGCAAAGAAAACAAAAAGCAGG
```

```
GGTTGCAATCCTAGTCTCTGATAAAACAGACTTTAAA
CCAACAAAGATCAAAATAGACAAACAAGGGCATTACAT
AATGGTAAAGGGATCAATGCAACAAGAACAGCTAACT
ATCCTAAATATATATGCACCCAATACAGGAGCACCCAG
ATTCATAAAGCAAGTTCTTAGAGACCTACAAAGAGAC
TTAGACTCCCACACAATAATAATGGGAGACTTTAACAC
TCCACTGTCAATATTAGACAGATCAATGAGATAGGAA
ATTAACAAGGATACTCAGGACTTGAACTCAGTTCTGGA
TCAAGTGGTCCTAATAGATACCTACAGAACTCTCCAC
CCCAAATCAACAGAATTTACATTCTTCTCAGCACCACA
TCGCACTTATTCTAAAATTCACCACATAGTTGGAAGT
AAAACACTCCTCAGCAAATGCAAAAGAACGGAAATCAT
AACAGTCTTTAGACCACAGTGCAGTCAAATTAGAAC
TCAGGATTAAGAAACTCACTCAAAACCGCACAACTACA
TGGAAACTGAACCTGTTCCTGAATGACTACTGGGTAA
ATAATGAAATGAAGGGCAAAATAAAGAAGTTCTTTGAA
ACCAATGACAACAAACACACAATGTACCAGAATCTCT
GGGACACATTTAAACAGTGTTAAGAGGGAAATTTATA
GCACTAGATGCCCAAAAAAGAAAGCAGAAAAGATCTA
AAATCGACACCCTAGCATCACAATTAAAAGAACTAGAG
AAGCAAGAGCAAACAAATTCAAAAGCTAGCAGAAGAC
AATAAATAAGATCAGAGCAGAACTGAAGAGGAGAGA
CATGAAAAACCCTTCAAAAAAATCAATGAATCCAGGA
GCTGGTTTTTTGAAGAGATTGACAAAACAGATAGACCA
CTAGCCAGACAATAAAGAAGGAGAGAAGAATCAAATA
GATGCAATAAAAAATGATAAAGGGGTATCACCACTGA
TCCCACAGAAATACAAACTACCATCAGAGAGAATACT
ATAAACAACTACACAAATAAACTAGAAAATCTAGAAGA
AATGGATAAATTCCTGGACACATACACCCTCCCAAGT
CTAAACCAGGAAGAAGTTGAATCCCTGAATAGACCAAT
AACAAGTTCTGAAATTCAGGTAGTAATTAATAGCCTA
CCAACCAAAAAAGTCCAGGACCAGACAGATTCACAGC
CGAATTCTATCAGAGGTACAAACAGGAGCTGGTACCA
TTCCTTCTGAAACTATTCCAATAGAAAAAGAGGGAATC
CTCCCTAACTGATTGTATGAAGCCAGCATCATCGTGA
TACCAAAACCTGGCAGAGACACAACAAAAAAAAGAAAT
TTTCAGGCCAATATCCCTGATGAACATTGATGCGAAAA
ATCCTCAATAAAATACTGGCAAGCGGAATCCAGCAGCG
CATCAAAAAGCTTATCCGCCAGGATCAAGTCGGCTTC
ATCTCTGGGATGCAAGGCTGGTTCAACATACGCAAATC
AATAAACCATCATTCTCAGCAAATTATCACAAGGACA
GAAAACCAAACACCGCATGTTCTCACTCATAAGAGGGA
GTTGAACAATGAGAACACGTGGACCCAAGGAGGGGAA
CATCACATATGCGGCCTGTCGAGGGATTTGGGGTTGA
GGGAGTGATAGCATTAGGAGAAATACCTAATGTAGGT
AACAGGTTGATGGGTGCAGCAAACCACAATGCGATGTG
TATACCTACCTAACAAACCTGCACGTTCTGCACATGC
ACTCCAGAACTTAAAGTATAATAATAAAAGGCGCTGCC
TCAGGATGTAAAGTGTAACAAGGGGGCTGGGGTGGGC
AGCGTGGGCCTCTGAGACCTTTGGTTGCCCGTGTCCGC
AGCTCGCCCCGCAGCCGGCTCCACAATGGTCCGCTCC
GTTTGCCACGTGCGGATTCGGGTTCCAGACTGAAGGCT
GCGTGTTCTCTGCCGCCCACAGCCCAAGTTTATTGTG
GCAACCGCCGGAGCAGCCTTCCCCGCTGTGGAGGAGCC
TGGGGCTACCCCTCAGCGGTATTTGGGGCTGGTCCTG
GGGGAGCTAAGCAGGGTTGTGGCAGCACTGCCTGAAAG
TGTGAGACCAGACTCTAATCCTTATGGTTTTCCATGG
GAGTTGGTGATATGTGCAGCTGTACATGGATTTTTGC
TGTTCTCTTTTTTGTGTGGAGAAGTTTTAGATCGT
TGGGAGTCGGCTTTATGTGGGAAGAGAAAAAAAGCTTG
CTGTAATGCTTTCTGGACTAATTGAAGAAAAGCATAA
ACTACTTGAAAAATTTAGCCATGTTCAAAAAGAGTATG
AAGGCTATGAAGTAGAGTCATCTTTAAAGAATGCCAG
CTTTGAGAAGGAGGCAACCTGTGAAAAGCTAAACAGGT
CCAATTCTGAACTTGAGGATGAAATACTCTGTCTAGA
AAAAGAGTTAAATAAGAGAAATCTAAACATTCTGAAC
AAGGTGAATTGATGGTGGATATTTGCAAAAGGATACA
GTCTCTAGAAGATGAGTCAAAATCCCTCAAATGACAAG
TAGCTGAAGCCAAAATGAACTTGACGATATTTCAAAT
GAATGAAGAACGACTGAAGATAGCAATAAAAGATGCTT
TGAATGAAAATTCTCAACTCCAGGAAAACGAGAGACA
GCTTTTGCAAGAGCTGGTAGGTATGGAAAGAACAAGTGA
GTGAACTTAATAAACAGAAAATAACATTTGAAGACTC
CAAAGTACATGCAGAACAAGTTCTAAATGATAAAGAAA
ATCACATCAAGACTCTGAACGCTTGCTAAAAATGAAA
GATCAGGCTGCTATGCTTGGAGAAGACATAACGGATGA
TGGTAACTTGGAATTAGAAATGAACAGTGAATCGGAA
AATGGTGCTTACTTAGATAATCCTCCGAAAGGAGCTCT
GAAGAAACTGATTTATGCTGCTAAGTTAAATGCTTCT
TTAAAAACCTTACAAGGAGAAAGAAACCAAATTTATAG
TCAGTTATCTGAAGTTGATAAAGGAAGAGCTTACAGA
```

-continued

```
GCATATTAAAAATCTTCAGACTGAACAAGCATCTTTGC
AGTCAGAAAACACACATTTTGAAAGTGAGAATCAGAA
GCTTCAACAAAAACTTAAAGTAATGATTGAATTTTATC
AAGAAAATGAAATGAAACTCCAGAGGAAATTAACAGT
AGATGAAATTACCGGTTAGAAAAGGAAGAAAAACTTTC
TAAAGTACACGAAAAGATCAGCCGTGCCACTGAAGAG
TTGGAGACCTATAGAAAGTGAGCCAAAGATCTTGAAGA
AGAGTTGGCGAGAACTATTCATTCTTATCAAGGATGG
ATTATTTCCCACGAGAAAAAAGCACATAATAATTGGTT
GGCAGCTTGGACTGCTGAAAGAAACCTCAATGGTTTA
AGGAAAGAAAGTGCTCACAACAGACAAAAATTAACTGA
AGCAGAGTTTAAATTTGAACTTTTAGAAAAGATCCT
TATGCACTTCATGTTCCAAATACAGCATTTGGCAGAGA
GCATTCCCATATGGTCCCTCACCACTGGGTCGGCCT
TCATCCTAAACAAGAGCTTTTCTCTGAGGGCCCACTGA
GACTCTCATCTTTGCTAACAGGAGGAGGAGGAAGAGG
CTCAAGAGGTCCAGGGAATCCTCTGGACCATCAGATTA
CCAATGAAAGAGGAGAATCAAGATGTGACAGGTTAAC
CAATCCTCACAGGGCTTCTCTGACACTGGGTCCCTGTC
ACCTCCATGGGAACAGGACCGTAGGATGATGTTTCTT
CCACCAGGACAATCATATCCTGATTCAGCTCTTCCTCC
ACAAAGGCAAGACAGATTTTATTCTAATTCTGGCACA
CTGTCTGGACCAGCAGAACTCAGAAGGTTTAATATGAC
TTCTTTGGATAAAGTGGATGGGTCAATGCTTTCAGAA
ATGGAATCCAGCAGAAATGATACCAAAGATGACCTTGG
TAATTTAAATGTGCCTGATTCATCTCTCCCTGCTGA
AATGAAGCAACTGGCCCTTACTTTTCTCCTCCACCTCT
TGCTCCAATCAGAGGTCCATTGTTTCCGGGGATACA
AGGAGCCTGTTCATGAGAAGAGGACCTCCTTTCCCCCC
ACCTCCTCCAGGAACCATGTTTGGAGCTTCTCAAGAT
TATTTTCCACCAAGGGATTTCCCAGATCCACCACATGC
TCCATTTGCAATGAGAAATGTCTATCCAGCGAGGCGT
TTCCTCCTTACCTTCCCCCAAAACCTGGATTTTTCCCC
ATAAACCCCACATTCTGAAGGTAGAAGTGAGTTCCCT
GCAGGGCTGATTCTGCCTTCAAATGAGCCTGCTACTGA
ACATCCAGAACCACAGCAAGAAACCTGACAATATTTT
TGCTCTCTTCAAAAGTAATTTTGACTGATCTCATTTTC
AGTTTAAGTAACTGCTGTTACTTAAGTGATTACACTT
TTGCTCCCACTGAAGCTTAATGATTTATAATTCTCAG
GATAGTGTTTTCTAAATAAAGATGATTTAAATATGAA
TCTTATGAGTAAATTATTTCCATTTTATGTTATTCTGG
ATAGTATAACTATTTTAATTTGATAAACTAATCCACG
ATTATATAAACAATAATGGGAGTTTTATATATGTAATC
TTGCAGGTAGGGAGGCTTTAAATTATAAAGGTTGTGT
CTTTATGCCAAGAACTGTATTAACTGTGGTTGTAGACA
AATGTGAAAGTAATTTTATGCTTCATTAAATAAATTT
TAGTTGATTTTTTTTTAAAAAAAGAAAATTGGTTAATCT
ATCATTTAGGTGCATCATCAGTTGTTTAACCATTCTC
TCTTACTGAACATTGGGTTGTTTAAAAAGTGTTGTTAT
TTTTGAATCATGGTTCAGTGAACAATTTTGGACACAT
AACTTTTTATCTGATGAGTTTATTTCCTAAGGATCCAGC
TCAGAAACTCAGCACATAAACCTAATAAGAAAAAAAC
AATTTGAAGTGGCTAACCTCTTATCCCAATAAAAATGT
TGTATTTATGTTTGGATTTAGATGCCTTTCAGTGGTC
ATACCTTCACCTAACTTTTATGGATTCTACTTTTAACA
TGTAGAGTGACTGTTTAAATCACCTAAACTCACTGAG
TTTTAAGTTCCTTTTTATTCAACAAGACTGGATTGTAT
GTTCCAGCTCCTCAAACTTAGTTACCAACCACCATCC
TAGAGAGTGAATTCACATGAGGCCTGTCCAGAAGAAC
AATCTCCCTTTCAGTGTCCTCATGCATGCAGTGACCA
GAGACCAACCTTGATAAATTATGGAAAAGTACAGCAC
ATTCTGGAAGAGCCATGAAAGATCCAGATCATCTGGT
GCTGGATAAGAATATTAATGGACAGGCTGGGCGCGGTG
GCTCACGCCTGTAATCCTAGCACTTTGGGAGGCCGAG
GCGGGCGGAACATGAGGTCAGGAGATCGAGACCATCCT
GGCTAACACGGTGAAACCCCGTCTCTACTGAAAATAC
AAAAAATTAGCCGGGCATGGTGGCGGGCGCCTGTAGTC
CCAGCTACACAGGAGGCTGAGGCAGGAGAATGGCGTG
AACCCGGGAGGCAGAGCTTGTAGTGAGCCCAGATGGCG
CCATTGCACTTCAGCCTGGGCGACAGAGTGAGACTCC
GTTTCAAAAAAAAAAAAAAAAGAATATTAATGGACAAA
AAGATTAATGAAAGAACATATTGAAGCATCCAATTAC
CTGGTGTCTGCTCAAATGAGGAATCGGTGAGATAGGTC
AGTTAGCAGTCAAGATTTATAAAAGAGACGATGGCCT
TGGGAGGGGCTGCCCTACTCGACTTTTTAATGGCTAGA
AGCTATTAAGGGCTAAGCCAGACCCTTCAGTATGGT
TCAGTGAGGATCCCAATTTGGGGTCCAAAAGTAAATGA
CAACTCCCAGGAACCATTAAGAATAAAAATCATGGAG
CATTACTGAGAATTTATGTTATCTAAGTCTGAGGAAAA
TTAATGTTAAGGAAGCTTTCAAAAGTCTAATATTTAC
ACCGAATTCCAGGGCACCATGCTCTAAGACAAAGCACT
CTGGTCCTGCCCCTCTCCTTTCCTCATGTTTTTTGGT
TCTTGGGATCCTTAAGGGTCAATGTTATTCTTAAAATA
CAGAGCATCCTGGAAACTAAAAAAGTGGAAGATATTC
AAATTCTAATGAATGTACTGGCAGTATTGTAGATCATG
GAGTATAACATAAAGACAAGAATCCCTAGCCTCTTCC
ACCATACTTTGTAATGGTAAGGAGAAAGGATAGAATTT
TGAGAAGTCTGGGAAGACAATGTATGATAACATCTGG
AGAAGCTCTGCATAAGTTACTTTTGTTCAGGCTTAAGA
AAAATTCTAGCTTGCCCCTGCACTGTCATCAGGTATC
ATGAAAGTAAATAAAACCTTTAAAGATTCTTCAAGCCA
GCAGACTTCTATCTTCTCTATACTATCCTGTGATCCT
AAACTCTTAACAGTTACTACGTATAATTTCCCTACATT
TGCTACTAGTATTTTATCATACACAATATTACACTCA
ATATTTCAAAAGTGGATGATTCATCTCCCGAAGAGACT
GCAAAATTCATGAGTTAAGATTTGAGAATACTATTTT
AGACAAGATTTAGTCAGATTTTAGAGAGTTAGAAACCT
GTAACAATTCTCTAACAATACTGCTTCTCCTTTTGTG
TATTAAGGAATTTTTGTCTATCAAAGATAGTACGAGGT
AGACCAGAAGATAACTTGCCTTCAAAATGTCTGGAAT
GTAAAATGGCAACAGTAGTATTTGGGGACTTCGTAGGG
GATGGCCAATATACACCCATTCTTAGAGGGTACTGATG
ATATAAATGTAATACAAAATCAAGTGGTCTTCCATCAC
CATATAATGTTTAAAATGGCAAAGAGGGAGCAGAACA
AACACCCTTTGCAAATCTCTTCATAGAATCTACCGTAA
TAAACTTGTACTTGCTTAAAGTGTGTCTCTTCAGTGG
TCTTATTACCACATCTTTGGGGAAAATGAGGCTGCTTA
AAAGATTAACACATTACATTTTACATATCTGTGGC
AGAGAAAACACTATGTATTCACCAAACCACTTCTTTTC
CTTCCCAGTCACTCGGGAAGAGGTCATTTCTTTGTCC
CCTTTCATCTAATTGAGGTGCCGTGACTACTTCTAGAC
AGGCAATGTGAGCAGAAGGTATGCACTCACACGTATAG
GCCTGGTCTTCAAAAATCCCTCAGATATGATCTTCTTC
TCTCGTCTCTTTCATGGACAAACTACAGGCCATGTAA
TAAGGATGGTGGGGTTCCAAACTGAAAGAGCCTGGATT
TCTGATTTACTGTTTTGAGAAGAGTTCACCAGGGAAA
CAGCCTGGAAATACGCACAGGAAAATATGCACAGGACC
CTGTGTGAGCAAGATATAAAGATCTATTACATGGTGC
CATTAAGGTGAGAGTATTGTGCTTATAGTATCCAGCAT
TAATTATCCTCACTACTACAACTTCTTTTGTATCCATC
ATGTGGAAAAGTAGAGTATTTAATAAATGATTATTGAG
TTTATTACCTTTTTTATATTCCAATCATTGCTAATTG
TACGTTACCTCATTTCAAGGTAAAGGTGACCAAGGGCT
AAAGCAGTGCTATCCAAACCAAGCCAGACATCAAAT
CACACAAAACCTTTTGAAAATACAACTTTGAAGATGCC
ATTCACATAGATATTTATTCAGTGGGTTTTCAAATGG
AACCCTGGAATCTACAGTCTTTAACAAGGCTTCCCAAG
TTATTCTGATATACAGCAGGCAAATCTGAGAACCACT
GGACAAGAAGAAAATAAAGGCTATATCTTTCGACAACA
AAGACAATGCCTTAAACATAGAATGTATTCAATTAAA
GCTTGTAGAAAGATAGGTTTGTGAACAGGCACAGGGAC
TAGCCTCAGCAAAATTAATAAGGGCAGCAATGTTTTT
CACTGAAACCATTATTCCCCCTATTTTATTTCTTCTGG
GGCTCTGTGTTTCCTTTCTCCTATCAAAATCCATTCT
AAGGTTGGAGGTTGGGGGTATCTCTTGCCTACTCCATA
CAGCAAGGAATAAAATTAGTATTTCTCGAACTATCTG
TGACAGCAGACCCATTGTAGGCCAGTACTTTTGTAAAA
TGCAATAAAAATTAACTTCTAGAGAATGAAATTTTAA
AATCACAGACATTCAAAATACAAATTCCAATTTTTTA
TTATTAACTGTAAGAAATTTAAAATTAAATCTCAATA
AATAAAATTAAAGCAAACATAAGATAGAAAAAAATAAG
CATTATGGATTGGCCCAGTCTGCAAACTGTATACACT
TTGCCAAACATGGGCATAAATTACTAAGAAGCAAATC
TTCCATCTGTAAACATTTCCATTTCCATTGACAATAT
GTGTGAGGGAAAGGAGGGATGCTTCTGTTTTAGAATGC
CAGGCGTCAGCTCAACAAGTGACAAATACGTATTGAGA
CTGAGATCTCCCCAGCCTCTCAGTAGTCAGCAAGAACA
TGTTGAGGCCTCTGTTTTTGACTAAAAAATTGGCCAG
TGCATGGGCAACATGCATAGGTCCTGAATGAAAAAAT
AGCAGCAGCAGAAATTTAAAAGAATTTTCACAGCTAG
GCCACAGTAAATTCTCAAGCCCTTCATCAGAAGCCACT
GTGGGGCCTCATTTATGCCTTTGTTTTTATTAAATTG
GATGTGATCTTAAGATTCTTCTGTCAAAATTCCACTAG
CATGTGAAGGCACCAAAAGTTTAAAATGTAAAATTAA
CCCAAGTTAAGCTATTCCATTATTAAGCAATAGCAGAT
ATATTTGTTATTATATGAGAAGAAAGTTAACAGGGAG
CTAAGATTGATTGTACTGATAAGAAACAGAAACAGAC
TTTAAAATTAAATAAATGAATTATTTATTTAATAAGA
ACCAATTGACAGATTCTCGATAAAGACTGTAAGATGTC
TTAAAACATTAGGTGTATGGAGATAACATTTGTAACT
TTGACAATTTATATGATGAGAAAAATCAAGGAATGTTA
TTGTTTATTGGCAGAGTTCTAGAATTACAATTCCATC
```

```
ATTCTGTTTTGGGGAAGTTTCCCTTGAAGTAAATGATA
ACAGGGCTTGAAATAGTACACCTCAGCATTTTGTTTA
TAAAACTGTGGAATAGGTAAGGTTTGTATTGTAACTGA
ACCCAGGTTCAGCTGCTTGCTGCTCTAAAGCTAGACA
TAAGAGGAGAAGGTTGGTGGGAGGAAAAGCGATTTTAA
TCGGAGAAGCAGCAAACCAAGAAGATGGTGAACAATA
GTCACAGAACCATCTTAAATTTTAAAATTTACCATAGA
GTGTTCAAAGGAAAACTTGGTATGGGAGGCATGCAGG
AGGGGTGCAGGGGGCGGGGTCTGTGTGTCTTGTTCCAA
TGGCTATCTCAGATAGTCACCCATCTGGAGGTCTAGT
TGGTATTATTTTGAATTCAGCCCAGTGGTGGTGGACTG
TCAGTGACTCCTCGCTAAGCAGGAGGATTCTGCACTC
AGGGCTCCATGCATGGTTTGTTTCAAGATTGGCCTCTG
GAATTTCTCAAGCAAGAACATAATTAAATAAGCAGGC
ATTGCCAGAGGGGAGTGTCTGGAAAGGAAAGGAATGAA
GAGATGAAAGGAAAGTGGGTGGTTAAACTATATTTTT
AAAACTGAGGTTCCCAGTTATAGTATGTTTCGCACGCT
CCCCCCATTTTAGCACCCCTGACAGAATTTAGTAATC
TCCTCATCTTGTCCTCTACTTCAGGTCCCCTATCTGTC
CTTGTACTCTCCAGGGTTTCCTTTTCTTCTTCACGAC
CTTCCTTCCCTGCAATTTTATAAGCTATTCCTATCCCA
GTGATTTAGTTTCAGCTATAAAACTGTGTCTTTGCC
ATTGTAATCAAATTGAAGGGCCTCTGCTTCATGGTTGG
ATTCTGTGACCAGGAGACTCTTACGAGGAGTTGGCCA
GGTCTCTGTTAGGAAAGCAAAAAAGAACAATGGAGGCA
ATTATCCCATTGTATTTCAGCTATAAATCCTATTTTGC
CTGAATTGTCTGAACGATGAGTATTCTGTGAAAATGCT
GCTCTCTAGTGCAATAGAACTGCAAATAATGCACATC
TATTTCTTATAATCTCATCCAACATACCCACAGAGATT
CAGATCTAACAAAACAGAGGTGATTTGGTTATTGAAT
CATAATATAAATATGGGGAAGAGGAGGGAAATTTCAAG
CCTGAGGAAACTGTAGTAGGAGTAAGTATGCTGTGTT
TAAGAGGTCACAGATAAAATTAATATTACCAATCCATC
AATAGGCAATTACTAATAGCTTACTACACACACAGGA
ATAAAATGTGAAGACAGAGGAAGTGTAAAATGGAGCCG
CCAACTCTACGGAGTTGTTTGCAATTTGGTCTGGTAG
AAAGCTATGAAATAAGGAAGTACATGATTGAGAGCTAG
AGAATGTGGCACAGGCTCTGAACCCGGACCGTTCAAT
GTAGTAAGCTCTAGCCACACTGGACACTTGCAATGTGG
CTTGTCCAAACTGACATGTGCTTTAAGTATAAAATAT
AATCCAGATTTCTAAGACTTCAAAAAAAATGGAAATAT
CTCATTAATAATCTTAAGTTTATTACAGGTAGAAATG
ATAGATTAAATAAACTATATTGTCAAAATTCATTTGAT
CTGTTTCTACAGTATAACAAACTTACTTGTGTGGTTT
GCATTTTATTTCTACTGGATAACATGGCTTTAAAAATG
GTATTTTAGAGGAAGGAAAGCTTGGTAGAGAATGGAC
TAATCCGGATCCCTGAAAAATGGACCTTGAATGGGT
CTTGATGACTTGGAGAGGCAGAGAGAGAAAAAGAAAA
GTCAAACATAGGGAATTGGTTGATAAAATGAAGGTGAG
GGGAGAAGGAACAGAGGGAGGAGAAGATCCAGTTTGA
GGGATATTACAGCGAGCAGCCTGGAGAAGAAGGATAAG
AAAGGAGAGAAAAAATGCAAGGGAAGTAACCCTTCAA
AGCCAGTCAGAAGTTTCTGGGTTCCTCAGCAGCCAGAA
AAGAAGCCGTTGAAAAGATCTGAGTAACGGAGATTCT
GGACGAAAACTGAAGTTATGGAAGGGAAGTTTAGACAT
GGGTTATTAAACGCTTTAGCGCATTAGAAGTTTCTTA
TGTAATCACTAAATTCAGATCCTGAAATAATGCCACAA
GAACTATACAGCTCAGCCACCCAATTCAATAAGAAGT
TACAGCACAGTCTCACACATATCCAATTAACCTTGGCC
TTTAGTCAACATCTGGGTTCTTTTTGTCATTTTCAAA
TACTATCACCCAGAGGTGCTATGATTTATATTGGGGAG
GGGATTAAAAGAAAATAAGTAAGTTGGTGATAAGAAA
AAGCTTTCAGATGATTCCATCTGAATTAACAGCCCTCT
TTAGTTGTCTAGGAAAGAGGATGCTTTTTCTTGAAAG
TGCTTTGAAATGATGATGTGCTTGTTAGTAAACATCAA
TTATTTTCAAATCGTAATGTTTGCAAGTTTGTCTTCC
TGTAGCTCACCCTTTATGTAGGTCCAGAATATGATTGT
CACAAATATCTGGGTGACAATGTCAAGTATGAAATGTGGT
CATAAAGTAAGTGATTATTTCTAAACTCATCTTTGTCA
CTCGTAGTGCTTCACAAAGCACCTTTTCCTGGACTAC
AATTCATTTTAATTGATCCCATCAGCACTATATCTGTA
TCCTGAGTGACTTCACATACCCTCTATTTCAAGAGA
AACCAATCAGGTTATGGGTTTGTTAGTAATAAAAATTA
CCAAGGAGCAGTTTGTGGATGGTAAAAGCAATGCAAA
TTCTAAAGAGAAGTCATAAGAGCAATAATAAGCATCCT
CCTCACTTCTTGGAAGTGAACATTCCAAGCTCCCTG
AAGCAACACTTAACCTATCATATTAAACAGTAATGGAC
AAATATTAGAAATGTTGATGTCAGCTTTCAGAATCTG
TGGGCATCAAACATCACTTAAGTTCTCCGAAGTATTC
TCTGTCAAGTTTCCTTCACAGTATTCTTTTCCTACT
AGGACAGAGCCTTAAGCCCTAGAAGAATAATTTTGCTT
GTGTGTTAATTATTTGTTTACTGGTTCATTCCAGAGT
GTGAGCTGGAAAAAGGGGGAAGTGTCATAAATAGTTTT
TTATGGCCCATGGTTTTTCAACTACGTCACTATTGGT
AGCAGTTTCCACTGCAGGATCTATTTGCAAAGCCTAGG
AAATTAGCATTAAGCAAGCTGCTAGGAAGACTTCAAC
AGTAACTAGGCCACAGGCCTCACACATTTTTCCTCCAC
CCCAGCCTCCTCTGGAGAGTACTTGCTAAACCTCTGT
GACACATAATGAAGCAAAGAAAGTGATAGAACAACAGA
ATTACACGGCAGATCCTTGTTTCTTCTTCTCTCTCT
AAAGAATTCCTTGGACTGAAAAGCAGTTTATTTTGGAG
GAGTGAGAAAGTGGTGACAGAATTAGAAGGGCCTGGG
AGGGGCTTCATTTTAGGAGACAGTTTTAGGCTGAAAAGA
GATTTCATGAGTGTGATTTACCTGAGGTGACTTTTGG
GGGCTCTTATAAAAAGGAAGTTCATGCTGAATGGGAGG
TGGCTTCTGAGATGCAGATTCTGGTGAGCTAAGAGGG
CTCGGTAAAGAGGAGGCAGGAGTTAAGTAGCGTGAACT
ATGCAGTAGCAGCCTTCTTCCCCCCTTGCTTGGGGCA
GGTCATCACAACCCTTCTCAATAAAGGGGTTCCAGGAAC
CACTAGGAATAAATGGGCATTTGCACTTCAGGTGAAA
CCCATTTGTCATAACTGCTTGGACTTTAAGCTTACAAA
TAAAAGAACCACATATTTCCCTTTGCAGCTTGATTT
AGTTAATGTCATTTTGAGAAAGAAAGAAGACATTGTTA
TCCCGTCCCTTTTTTTTTTTTTTTTTTTTTTTTTTATGA
AGAGACTGGGACTCAGAGAAGTCAAGTGATTTTCCCAG
AACCAGAAAACACAGAAGTAGCAGAGCTGAGATGACT
ACTCCGGTCTTCTGATTCCAAATTCCAAATTCATTCTT
CTAAGCGATTTCCCAAAACGGGAAATGGGTTTATCTT
CTATTTATGGGAAGTGATAGTGGTATTCTATTTAGAGA
ACTTATATAAAATCTTACTTTAAAATAAATAATATTT
CAAAAAGTAAGCTTAATTTAAAGAAAAATAATCAAGAAA
GTCTGGTATATTTTTACAAATATACCAAATGACCTTG
CTCTAAAATACATCTACTTTCCAGCAAGCCAAAGTGAA
ACAATTTGAAATAAGTGGCATTTACTGACCACTCCCT
AAAGTTCACACAAAGAGGTAGTACTCTAACTTAAATA
TACAAGGTGAAGAAATAGCTTACTCAGCCTGTTGGGC
TTCCTCTTCTACACTCTTGGGAAATGCCCTCCGTGTTA
ACCAAGAATTCTCAGGCCTTGGAGGGAGTTTTCCATT
CTCAGTAAACTGAGATTGCAGTTGCGGAAATTAAGAGG
TATCTGTCCAGCCTTCATTCCCTTAAGGTCAGGATC
TGTGCTTTTAATAATGACAATTAGCTAACATATACAAT
TAAGCCATGCAAATGAAGTAAGAGAAAGCTAGAGGAG
AAATTCAGGAGCCAGTTGCCTTTTCCAGACATCTTGTA
CAAATAGTGTTAAGGATACTAATTCAAAAGATGGGAT
TCTTCGCTTGAACCCAGGAGGTGGAGTTTGCAGTGAGC
GGAGATCGCTCCACTGCACTCCAGCCTGGGTGACAAA
GTGAGACCCCATCCAAAAAAAAAAAAAAAAAAAAAA
AAAGATGGGATTCTTTTTTAAAAAATAAATTTTACT
GCGTATTTTAAGGTATACAACGTGATGTTATAAGATG
GATATAGATAGTGAAAAGGTAACTGTAGTGAAGCAAA
TTAACATATTCATCATCTCACATAGTTATCTTTTATTT
GTTTTGTTTTGAGGGATTTTTAAGATAGTAGAAAGG
AATGGTAGACAATAAACATTTGAGGGAAAGTGGGGCTT
TGTAGAACTCCTAAAATGACAGCACGCACAAATGTCC
CCATTATGTCTAAAGGGTAACTCGTTCCTACTTCTAGG
GACAGCTGAGGGACATCAATGTAAATTTCTAAATGAC
TTCCTGAACTTTTTATTTTTATTTTTTGTATTTTTAGA
GGAAATTATAATAACATCAAGCCACCTCTGGACCATA
TCGCTGCTGATATCATCAGCAAATGGCACTATTCCTAA
ATCCTAAGATGCACTTTTCCCTTCACATTTCAACATT
TGTGAAACTCGATTGTACCTACACCTGATTTTATATAC
AATGCAGCCTTTCCTTTTCTTTTGTCATTGCATCTTA
CGCCTGATTTCTCCTTGGAATTGAGTAAATATAATGCT
TACATGTGTTAATAAGAATTGAGGTCACTCATAATTT
TTGAAATATGCCACCAAATATAAGCCTTTCTACATATT
GTTGACTTTGAAGTCATTTCTTTTTTTAACTACTAAA
CAATAACACTTTTTGTTGAGAAAAATTGCATATGAACA
AGAGACCAAGCAGGTAGAGAGAAAAAACTTTTAATA
ATCAAGAGAATGTTACTGTGTCCCAAAGCTAAAGTCA
CCTTACTATCAAGAGAAGGACAGGAACAGAGAGAA
CCAGGTAAATTACGAATTGAAAATTCCATGGTTCATTT
ATCTTTATTTTTAATAATTCCATTTGTGTGATTGTGT
TGACCACAAGGTCATAATGTTACTCTTCATACTGACTT
CTCATGTAAATTATAAATAAGTTTTTATGCTAATGAT
TTATGGAGTAAGCTATTCATCTTTCCGACAGAGAGTTA
CCTACAAAGAAATAATTATTCTACCTCTGAGATGAAA
TATCATGAAAGGAGTGGTTTCCAGATATTTTGACTTT
AAAAGCTTAAAGAATATATGTAGTATAAAATTCTAAA
GCAGGCAAAATTAATCCTTTTAGCAATCAAGATAGCGG
CTACTTTTGGTGAGAAGGACAAGGTAGTGATAGAGAA
GGGGCTCAGGGGTCTTTCCTGAAGACAGTGAGGTGGGC
AATGGTATTTTCCTTGACCTGGATGGTGATTAAACAG
```

-continued

```
ATGTGTTTACTTTGTGATAATTGACTAGGCTGTGCACC
TATGAACTGCATACTTTTCCATATATGTACTGTATTC
TTATACTTAAAAAGAAGTTTAAAAATAAATGCAACAGA
TATAGGACTTCCTATATTACTCGTTGACCAAAAAAAT
GGATTCATTTTTCTTTCAGGTAAAACGTACTAGTGGTT
TTAATATTATATTGACCAGGGAGTAAATGTTTACCTT
AGGAACCTTAATCTTGATGTTCTCCAAAGTCATTATCT
GTTCTTTCTGATTATCAGAATAGAGTATATCTCTATA
TAAATGAAAATTTCTGGTCATTCTCAAAAAATAACACT
AAGCATGAAAATCAGAAATATTGATCTTGTTTTGTAA
TGATGTTTCTATTGATGTGAAGTAGTTTCTAGTAGAGT
TGCTGTCCTAACACACAAATGAAATTGCACTGTTTGG
AAGACACAACTGTGAATGACTTGCTTCAGTAAGGAATT
TCCAACATGATGGTTTAGGGATAGAGGTGCTCGATTC
CTCTGTCTCCGGTTACCCAGGTTATTGAGGACAGGGAG
GTCAATAAGTAATGCCCTCCTCCCACCCATAGCACAA
AACAGAGCGGGGTTCAGAGAATAGGTAAGGCTTTGGCC
AGGGTGTTGAGGAGACTTACATCCCTGGGAACCAGTC
AGAATGGGGGCGCTGAAAACAATGTTTTAAATTCTAGC
ACCCAGCAACATATGTGTGAAGATTAAATGTACTCGT
GCTAAATTCACTTGCTCCATTACTGAATTTGGGTGGTG
TCTGTTAAAGATGGGAACAAAGGCATTCAGGTCCTGG
TATCTTCTACCACTCCCAGCATGAACAGACTCATGTCA
GTGGGTAAGGGATGGTATTTCCCGAGAAGGCTTTGAA
CTCTTGTAGTGGGTCAAATAATGGCCCCCCACTTAAAA
ATGTTCATGTCCAAATCCCTGGAAGCTGTGAAAAGGG
GTTTTTGCACATGTAATTAAGTCAAAGATATTGAAATT
AGATCATCCTGGATTACATAGGTGGGCCCTACATTTA
ATGACAAGTATCCTCATAACAGAAGAGGAGAAGGTGAT
GTGAGATTTGGAGCAGCAGAGATTGCAGTGATGTGGC
CACCAATCAAGGAAACCAAGGACTTCCAGCAGCCACCA
GAAGCTGGAAGAGGCAAGGAAGGACTCTTCCCTAAAG
CCTTTAAAGGAGCACAGCCCTACTAACACCTTGCTTTT
GGGCTCTGGCCCGCAAAACTGTGAAAGGATACATTGC
TGTTATTTGAAGCCACAGTTCGTAGTAAATTTATTACA
GCAGCCCTAGAAACTGATACAACTCCTAAATACACCC
TTAGCAACACTGCTCAACAAGAAGTAGGCAATTTCCTC
CTGACTGAAAAATACTGATACTGTTATGGGATCCTTG
GGGGTGTTGCTTTTCTGTCCAGAAACCCTCTGTGGCGGT
GGCACCTTTGCATGAGTTTTGCTCGGGTCCACTGGGC
CCACTCATCCTGGCAGGCTGCGCTCAGCTGACACTACT
GGCGTGGATCCCATGCCTCCAAAGAGACTGGAGCGAA
GCGGTGAGGGATGTGTGAGGAAGTGAGCGTGGGGTCTG
GCACACAGTCAGGCTCAATGGCTGCTACAGCGGGATG
GGCAGCTTCAGGTGCTGGCACGGGTGCTGGCTCACTGC
AAGGCTGTGGCTGCACCAAGCAGCGCAGCAACGGAAC
GCATTGGTGCCTGGAAACTTGGAGCTCCAGGAACCTC
AGGGCTCCAAAAGGCAAATCACAGCCCTAGCTTCGGG
AGCTCCCAGGTCTGGGCTGCCAAAGGGCTGCAGCTCTT
CTCTCCTCTCTCTCTTCGCTCCTCTCCCTTTCTCT
CTTCACTCCTCCCTCTTTCTCTTCACTCCTCCTGTC
GCCTATGAACAGCGAATTCAACCTTCCAGTTTTCAGA
CTAGGAATGCTGGAGTTGTCCTTGATTACTCTGAATTG
TTCACTCCGCATATGGGCACTGAGGATACGTTGATGA
ACTACACAGACAAAAAGGATAGAAATTCCTGTCAAGAC
TACATTCAATAGGGATGAAGCAGGCAATAATGAATAA
ACATACTAAGTTGAATATGACTATTTAAATATATATAA
CACATATGACTTGTATAATGTTAAATATTTTAAGTTT
TTTAAATTCTTCCCTTCATAGATTTTACATTATAGTAG
AAGAGGCATTTTGTTGTTGTTCTTTTTGTTTTGGAT
TCAGAGGGTAAATGTGCGGGGTTGTTACATGGGTATAT
TGCATAATGCTGATGATGGTCCCATCACCCAGGTGGT
AAACATAGTACGTAATAGGTGAATTTTTAGCCCGTGCT
TCCCTCTCCCATCTAGTCGTCCTGAGTGTTTATCGTT
GCTACGTTTATGTCAATGTGTATTCAATATTTAGCTCC
CACTTATAATTGAGAATATGCAGTATTTCGTTTTTTG
TTCTCGTGTTAATTTGTTTAGGATAATGGCCTACAAAG
AACATGATTTCATTATTTTTATGAGTACTAGTATTT
CATGGTGTATATGTACCACGGTTTCTTTATACAATCCC
ACTGTTGATGGGCACCTAGGTTGATTCTATTGCTGTT
GTGAATAGGGCTGCAATGAACATACAAGTGCATGTATC
TTTTTGGTAACAAAAATTTATATTTGATTACCCAG
TAGAATTGCTGGGTTGAATAATAGTTTTGGTTTAAGTT
CTCTGAGAAATCTCCAAACTGCTTTCCACAGTAGCTG
AACTAATTTACATTTCCACTAGCAGTGTATAAGCGTTC
TCTTTTTCTCCACAATCTTTTCACCAGCATCTGTTATG
TTTTGGCTTTTTAATAGCCTTTTGATGACTGTGAAATG
GTATCTCACTGTGGTTTGGATTTCCATTTCTCTAATG
ATTAGTGAATGTTGAGCATTTTTTTCATATGTTTATTG
GCCGTTTGTATGTCTTCTTTTGATAAGCGTCTGTTCA
TGTCCTTTACACATTTTCAATTAAAATATTTGTTTTTT
```

```
GCTTGCTGATTTAAGTTCTTTGTATATTCTGGAAATT
AGATCTTTGTCAGATGCATAGTTTGCAAATATTTTCTC
CCATTCTGTAGCCTGTTTACTCTGTTGGTAATTTCTT
TTGCTGTACAGAAACTCTTTAATTAGGTCCCACTTGCC
TATTTTTAGTTTTGTTGCAATTATTCTCTGGAACTTA
GCCATAAATTGTTTGCCAAAGCCAACGTGGAGAAGGAT
ATTTTCTAGGTTTTCTTCTAGGATTTTATAGTTTAAG
TTTTACATTTAAATCTTTAATCCATCTTGAGTTAATTT
TTGTATATGTTGAAGAGCAGGAGTCTAATTTCATTCT
TCTGCATAGGCTAGCCATTATCTTGGCACCCATTTATT
GAATAGAGAGTCCTTTCCTTATTGCTTATTTCTGTCA
ATTTTGTTGAATATCAGATCGTCGTAGGTGTATGGGTC
CATTTCTGGGTTTTCTATTCTGTTCTATTTGTCTCTG
TGTCTGTTTTTGTACCAGAACCATGCTGCTTGGTTACT
GTAGCCTTTTAGTATAGTTTGAAGTTGGGTAATGTGA
TGTCTCTGGCTTCGTTCTTTTTGCTTAGGATTGCTTTG
GCTATTCAGGCTCCTTTTTGGTTCCATATGAATTTTA
GAATATTTTTCTGATTCTGTGAAAAATGACTTGATATT
TTGCTAGGGATAGCATTGGAGTGGTAACTTGCTTTGG
ACAGTGTGGCCATTTTAATGATATTGATTATTCCAATC
CATGAGCATGGAGTATTTTTATATTTATTCAGTCATC
TTGATTTCTTTCAGCAGTGTTTTGTAGTTCACCCTGTA
GAACATTTCACTTCCATGGTTAGATGTATTCCTATTT
TGTGGCTATTGTAAATGGCATTGTATTTTTTTTATTT
GGCCCTAAACTAGAATGTTATTGGTGTATAGAATTGC
TACTGATTTTTGTACATTGATTTTGTATCCTTAAACTT
TACTGAAGTTATTTATCAGTTCTAGGAGACTTTTGGA
GAAGTCTTTAGGGTTTTCTATGTATGAAATCATATCAT
CAGCAAAGAGAGACAGTTTGACTTCTTCTTCTTTTTG
GATGCCATTTATTTCTTTCTCTTGCCTAGTTGCTCTGA
CTAGGCTTCCAGGGCAATGCTGAATAGGAGTGGTGA
GAGTGGGCATCCTTGTCTTGTTCCAGTACTCAAGAGAA
ATGCTTCCAGCATTTACCTGTTTAGTATGATGTTGGC
TGTGGTTTGCTAGGTGGATCTTATTATTCTAAGGTA
TATTCCTTTGATGCCTAGCCTGTCGAGGGTTTTTAAT
CATGAATGGATATTGAATTTTATTGAAGGTTTTTTCTG
AAACTATTGAGATGATCATATGGTTTTTGTTTTTTCA
TTCTGTTTATGTGGTGAATCACACTTATTGATTTGTTA
TGTTGAACCAGCCTTGCATCCCAGGAATAAAGCCTAC
TTGATTGTTGTGAATTAACTTTTTGATGTGCTTCTTGA
TTTAGTTTGCTCATATTTTGTTGAGGATTTTCGTGTT
TATGTTAATCAGAGATATTGTCCTGAAGTTTTCTTTTT
TCATTGTGTCTCTGGCAGATTTTGATATCAGGATGAT
GCTGGCATTGTAGAATGAGTTAGGGAGGAGCCCCTCTC
CTTAATATTATGGAATAGTTTCAGTAAGATTACTATC
AGTTCTTCTTTGTATGCTTGGTAGAATTCAGTTGTGAA
TCCATCTGGTCCAGGGCTAAATTTGGTTGGTAGGTTT
TTTATTACTGATTCAATTTTGGAACTTGTTATAGGTCT
GTTCAAGTTTTCACTTCCGTCCTGGTTCAATCTTGGG
AGGTTGTATGTTTCCAGGAATTTATCCATTTCCTCTAG
ATTTCCTACTTTGTGTGCATAGAGGTGTTCATAACGG
TCTCTGAAAATCTTTGGCATTTCTGTGGGATTGGTCGT
AATGTCATTTTTGTCATTTCTTGTGCTTTTTGGAACT
TCTGTCTGTTTTTCCTCGTTTTTCTAGCTAGCAGTCTA
TTAGTCTTGTTTATTCTTATGAAAAACCAACTCTTTG
TTTCACTAACATTTTATGGACTTTTGCATCTCAATTTT
ATTTAGTCATTATCTGATTTTAGTTATGTCTTTTCCT
CTGCTAGCTGTGAGATTGAATTGTGCTCTTTTTTCTA
GTTCCTCTAGTGTTTGTTAGATTGTTTAGTTGAGAT
CTTTCTAACCTCTTGTGAAGGCATTTTAGCACTATAA
ACTTTCCTCTTAACACTGCTTTTGCTACATCCCAAAG
ATTTTGGAAAGTTGTGTCTCTATTTTCATTAATTTCAA
ATAATTTTTTGATTTCTGCCTTAATTTCATTGTTCAC
CCAACAGTTATTCGGGAGCATGTGGCTTAATTTCCATG
CTTTTGTGTAGTTTTGAGAGATCTTCTTGGTATTGA
TTCTATTGTTATTTCACTATGATTTGAGAGTGGCCTTT
GTATGATTTTAATTTTTTTAATTTATTGAGACTTGC
TTTATGACTGAAGCTATGTCTCCTTAGAATACGTT
CCATGCATATGAGAAGAATGTGTGTTCTGTCATTG
TTGGCTTGAGTATCCTAGAGAGGTCTATTAGGTCCAAC
TGGTCAAGTGTCAAGTTTAATTCCAGAATTCCTTCGT
CAGTTTTCTGCCTCAGTGATCTGTCTAATGCTATCAGT
GGAGTGATAAAGCCCCACTAATATTGTGCTGCCATC
TACGTTTATTGTAGGCCAATAATTTGTTTTATGAATC
TGAGTGCTCCAGTGTTGGGTGCATATATGTTTAGAAT
AGTTAAGTCTTTTCTTTTCAGATTGAACCTTTTATCATT
TATAATGCCCTTCTTTGTCCTTCCTGATTGTTGTTGG
TTTAAAGTATGTTTAATCTGATTTAAGGGTAGCAACT
CCTGCTCTTTTTGTTTTTCATTTGCATGGTAGATCT
TTCTTCATTCTTTCACTTTGAGCCTGTGAGTGTCATTC
ATGTAGGATGCATCTTCTGAAAACAGCAGACAGTTGT
```

```
GTCTTGTCTTTTTATCCAGCTTACCACTTTATGCATTT
TAAAGGGAGAGTGTAGACTGTTTACATTTAGGGTTAG
CATTGACATGTGAGATTTTGCTCCTGTCATTGTGTTGT
TTAGCTGGTTGTTTTGTAGACTTCATTGTGTAATAAG
TGTATTTTTATTGGTAGCAGGTTTCGTCTTTCATTTCC
ATGTTTAGCAATCACTTACGGATTTCCTGTAAGAATC
ATCTGGTGGTAATGAATCTCCTTGGTGCTTGCTTGTCT
GAGAAGGATTGTATTTCTCCTTCACTTATGAAACTCA
GTTTGGTGGGATATGAGTTCTTGGTTGAAATTTATTTT
CTTTAATAATGCTGAAAATATAGGCCCCCCCATATCT
TCTGGCTTGTAAGGTTTCTGCTGACAGAACTGTTGCTG
GCCTGATGAGGTTCTTTTTGTAGGTGACCTGACCTTT
CTCACTAGCTGCCTTAACAATTTTTTCTTTTGCATTGA
CCTTGGTGAATCTGATGACTATGTGACTTGGCAATGG
TTGTCTTGTATAGTGTCTCACAGGAGTTCTCTGTATTT
CTTGAATTTGTATGCCCACCTCTCTGGTGAGATAGGG
GAAATTTTCATGGACTGCATCCTCAGATGTATGTTCTA
AGTTGCTTACTCTCTTTCTCAGGAATGACTGTGAGTC
ATAGACTTGGTCTCTTTACATAACCTCATAAATCTTGA
AGGTTTTGTTCATGTTTTAAATTCTTTTTTCTTTATT
TTTGTCCAACCAAGTTGATTCAAATAACTGGTCTTCAA
ACTCTGAGATTCTTTCCTCAGCTTGGCTGGTCTGTTCTGCT
GTTAATGCCTCTGACTATATTATGAAATTTTTGAAGTT
GATCCCTCAATTTCTGAAGTTCAGTTTTGTTCTTTCT
TAAAATAGCTATTTCATCTTTAAGCTCTTTGATCATTT
TTCTGGATTCCTTGAGTTCCTTGTATTGGGTTTCAAT
GATCTCCTGGATCTTGATGTACTTCCTTGCCATCCAGA
TTCTGAATTCTATGTATGTCATTTGAGTCATTTTAAT
CTGGTTAAAATCCTTTGCTGGAGGACTTGTGTGTTTGT
CTGGAGGTAAGGAGACACCAGCTTTTTTGAATTGCTA
GAGTTCTTGAGATGACTCTTTAACATATGAGGGCTGGT
GTTCCATTAACAATAGTGTACATTGAGTATAGTCAGT
TGGCTTCATTCTGAGTGCTTTCAAAGGGCCAAAGCTCT
GTACAGCATCTTTATTTGTGGCTAGATTTTGCTTTA
GGTTTCACAGGTGCTGTATATTGTGAAAAATGTTTTTGG
TGTTGTCATTTGGGGTGCAATCCAGTAGGTGATGCTT
AAGAGTGGTAGCTGGCAGATAGGCTCTTACTCAGTCCA
CAGCTCTTTTGTATTTTGGTGCAGTCCTCAGTAGTGC
TCTGTGGTGGTAGGGAGAGATGACCCCCTCACCAGATA
CATTCCTGGGCCTTGGGGGAGCCCTCTCTTATTACTG
GCACTGCACCTGCATTTCATTTATTAGGTGTCCTGGGC
TGCAGGGTGCCCTCAGGCAGAGGCTGCGGCTGGAAAA
TAGACCATACCCTTCCCTGGCTGGCCCTGCACAAGGAG
GCACACCCTGTTCCTGAGCCAGTCCATGAACCCAGCT
GTCTCACCCCTCTCAGTGTTCTGAGAGTAGGGGATCCC
CCACTGCTTGAGCACCATGAGCCCCTCCTGGCTACAG
GCAGTGGGGGTGGGTATAGTTCTCAACCCACTGTCCA
ACTGATTTCCAGGGTAACAGAGAGCTGTGCCTGCCCA
CAGAGTTCAGGCAGAGGCCAGGCCATTGTGCTGGAAGC
TGATGCTAAGCCTTGTCTGATGATGGGAGTGAAGCA
ATGTAACGGCTCCCTAACTGTGGCTTCTCTCAGGGCTA
TGGCAGCTGGCATGAGACTGCTCCAGGTCCAAGGCCT
GTGGGACTTCCTGTGGACTTGAGTTTTGCCTCTGCAAA
CACTCCAGCAACTCTCTATGTCAGTCTAGAGGCCCAG
GGACACGGATCAGGTATTGGGATGAAGGGGTTCTCCAG
TTCCCAGGATTTCACAGGTCCCTGTGGAAAGTGAGGA
TCCCCCAGGGGCTCTCACTCACTCACCCTTTCTCTATG
TTGGGGAGCTTCCCCTGGCTCCATGCCCATCTTGGGT
GGCCAGCTGCCCAGCTTCACTCTTCCCTGTTCTCTGTG
TCCCCTCACTCCCTTAATTGTCCTGATATCGTTCCTT
AGGTGATCTACTTGCAGAGGCAGTGTTTACTCGCCACT
TGTTTTCTCTCGTGAGAGTAGCACACACTAGCTGCT
ACTCATCTAGCATCTTGAATTCTTCCCATCTGAAAAAG
TTTCAACTGCAATCACAGTTAAAGAAATACAAAAACA
ATAGCACTCTAAGTTACAACTTCTCACCTATAGAATTC
AAAAACATCCAAATGATTAACTAAACATTTGTTTGGT
AGATCTGTGGGAAAACATGAATTCCTTGTGAATTACTG
GAGAAAATGAAAATGATGCAACACTTATGAAGAAAA
TTTGGGATTTTTGGGGGGAGGGGAACAATATATTTA
AAACTATAAATGCATTTATCCTAGCAATTCTATGAAT
GGGGATTTATCTTAGGGTACACCTGCACACTTAGGAAA
TAATGTATGCAGTCATTCATTACAGATTTGTTTGTAA
TAGCAACAACCTGAAAAGCAACTCATATATCCATCCAT
CACACAGGGACTGGTTTCATGACTACGGTTCATGAAT
ACTCTGCAGCCCTTAGAAAGAATGAGGAAGTGGCCGGG
CGTGGTGGCTCATGCCTGTAATCCCAGCACTTTGGGA
GGCCGAGGCGGGTGGATCACGAGGTCAGGAGATCAAGA
CCATCCTGGCTAACACGGTGAAACCCCGTCTCTACTA
AAAACAATACAAAAAATTAGCCAGGCAGGCGCCTATA
GTCCCAGCTATTCGGGAGGCTGAGGCCGGAGAATGGC
ATGAACCCGGGAGGCAGAGCTTGCAGTGAGCCGAGATA
ACGCCACTGCACTCCATCCAGCCTGGGCGACAGAGCG
AGACTCCGTCAAAAAAAAAAAAAAGAGGAAGTTCTCT
ATGCGCTGACATGGAAGGAAGACAGATGGTTGAATGA
AAAAAGTACATAATTAGCCATAAAGTGTAAGACTTTTT
GTCTAAAAAAGAAGGTGATATAATTGCATATTTATA
TTTTCTTCCATTTATATTAAGAGATAATAAAGGTACAC
AAATTGGCTAGAATAAAGTGGTTTCCTATAAAGGGTA
AGAGTAATTGAGTGGATGAAGACTAGGGTTAGGGATAG
ATTTCTCAGTGTATTCATTTTAATATATGTATTCATT
TTATATATGTACTAATTTTTATATATGTATTTATTTTA
TATTTTGATTTCTTAACATAAATATATTATTCCTTC
ATAAAATTAAACTTGATCACATTTTTGATTACTAGATAT
GTAGAAAGCATTATGTTCAGTACCACAGTAATACTTT
CAAACCAGCTACAATTAGTATTTATGAGCATCTATGTG
CCAGACATTGTGTTCTGCTTTGGTTGGTGGGGGTAGA
GGAGGAAAGGAAACCATGGCTTACATAGGAGTGGAAGT
CTTGTCTTTCACTTTGCACCTCTCTCCTTCAGACCTA
GCATAAATATGACCTTAGGGGAGGCAGAACACATATGA
TAAAGAGATAACTAGCAAGAGACATAATAGTAGCTAA
ATAAATACTGAAGGAAAAATTCAGGAAGAGGTAGGAAG
GATATGCCTCATCACTTCCACCTGTTAAGAAAAACTT
TAGACATTCTTGCCAATATTCCTTATTGCCTGTCTTTT
GAACAAATGCCATTATCACTAGAGTGAAATGATATTT
CATTGTAGTTTTGATTTGCATTTCTCTCATGATCGGTG
ATGTTGAGCACCTTTTTATATACCTGTTTGCCATTTG
TATGTCTTCTCTTGAAAAATGTCTATTCAGATCTTTGC
CCATTTTTAAATGGCGTAATACATTTTTTCCTATTGA
GTTGTTTGAGTTCTTTATATATTCTGGTTATTAATCCC
TTGTCAGATGAATAATTTGCAAATATTTTCTCCCATT
CTGAGGATTACCAGAGGCTCAGAGGGGTAATGGTGGTG
GGGGAGAATAAAAATGGTTAATGAGTACAAAAATATA
GATAGGAGTAATAAGATCTAGTATCTGATAGCACAACA
GGGTAATTACAGCCAACAAAAATTTATTGTGCATTTC
AAAATAACTAAGAGTAATCAAATTTAACAGAGATTTAATTGGGCA
AAGAATGATTTGAGGATCAGGCAACCCCCAGAAACAGA
AGAGGTTCAAAGCAACTCAGTGCTGTCACATGGTTGG
AGAGGATTTATGGGCAGAAAAGGGAAAGAGAGATACAG
AAAATGGAAGGATTACAGTGTACACAAACAGCTGGATTGGTT
ACAGCTTGCCATTTGCGTTATTTGAACATAATCTGAAC
AGTTGGCTGTCTTTGCTTGACCAAAACTTGGTGTTTG
GTACAAGAGCAGATTACAGTCTATTTACACATCCAGTT
AGTTTACAGTTCACTATACACGAAGAAGAAACCTTTA
AGCAGAACTTAAAATATGCAAAGAGGAAGCTTTAAGTT
AAACTTAATTTAACACACCCAATTATCAAAAAATGAG
TAGCTCTGCAAAAGTGGATTTTCCTGGTCATCTTTGGT
ACTTCCTTAAAAAAGAGAAAAGTAGTACTCACGATAA
AAAAAAAAAAGTCCTCAAGTCTTTATTTTATTCCTTTC
CAATTTAAAATGTTACATCATCTGAGGAAGGTTTTTC
CCTTTGACCGCTTTCATAGACATTTCTTCTGCATGGGT
TGGGCAGAATCAGAAGAGTAATTGTAACTTTCTGTTC
TTGTCCTACAGTTACAAAGCGGTTTCACTTTGTAAATG
CTCTTTGGATGGCAGGAACCAAGCAGCCATGAAAAGA
GGAGTTACACCTTTAAAGGAGTCATTCCATCATGACTC
TCAGGACTGGAACATGACATACCTGAATGGCCTCTTT
GGCACAGATAGGCACACCCTTGAAAGGTGTTCCAAGCTA
GGAACTCACTACCACTGTTACATCGATGCAACTCTGT
GAGAAGTTTTTATCTGGTGATGGAAAATCTCATCTCTT
CAACACACTGACTACTACCAGTCTCAGAACCCTGTAA
ACAAGATTCATTCATCTCAAATTGGGTTAAAGCAGTCA
CCCTGCCTTACATTAGTTTGGAATAAGGATGTGGGGA
TGGTGGTAGAGGAGGGGAGTGGATGATGATTTTTAT
TGTTATTTGATTCTAAAGAAACTTCTATACATTTTGC
ATTTAAAATAATTTGAGGTCACACAAGTGGTTGGATTAA
TTCAAAATAGGATATTATATCCTATTATATTAAATAT
ACTATTTAATCATCTTGTTGACCAAATGCAACTTAAAC
ATGTAAAATGGTAAATAGCATAATAATTGTCTTCTAA
GCCTGCACTATAAAGTATTTCAGTGGCCTCATTATTAA
AGGACCAAGGTGCCCAAAGAAACAAAATTTAGTAATC
ATAAACAAGAGACAAACCTACTTCTTTTCCCCCAGAGT
TCTGGCCACATTGAAATAAGGTGTTTGAATGCTTAAT
AAGAATTATTTTGAGGTCACAAGTGGCTCATGCCTGTA
ATCTCAGCACTTTGGGATGCCAAGGTGAGCAGATCAC
TTGAGGCCAGGAGTTCAAGACCAGCGTGGCCAACGTGG
TGAAACCCCATCTCTACTAAAAATACAAAATTAGCC
CGGTGTGGTGGTACACGCCTATAGTCCCAGCTACTCGG
GAGACTGAGGTGGGAGAATCACTTGAACCCGGGAGGC
```

```
CAAGGCTGCAATATCGAGATCACACCACTGCACTCTAG
CCTGGGCAACAGAGTGAGAGTGAGACTCTTTCTCGGA
AAAAAAAAAAAAGAATTATTTGAACAAAGTGCTGTCA
CCTAAGTTAGCAAAACTCCAAGCAAGGTTTTTGGCTC
TGTAAGGAAAGAATTAGCCTACTCATTTGGAAATTTAG
TGGTGTTTGTAATGCAGAAAGTGACAGTGAGACTGGA
AAGGGATTGGCTTTGGGGCTTGTTCTGCTTTATAAATA
ATAATGAATCTTCTCCAACATGAAGTAATGTGAATTA
AAAAAAAAAAATCTGTCCTTAGAGTACAAAATTACTTC
ATAACCCAATCTGCATTTCTCCACTCCAAGCATATTT
TCTGGGAGTTCTACTTAGAGAGTGAAAGCTGCTGTGTG
TGTGATAATTAATTTTAACAAACACTTGGCAAACTGA
GCTGGACTATGTATAAGCTACCCTAGACTAAGCATGAA
TTTGAACTGCACTTTTTATGGTGTTTTTTCCACAATG
ACATTATTTAGGCATTTAAAGTTATCTGAACTGCAATT
TTTTGTTCTTTTTTTTTAATTTGACTTTTTAAAAAA
AATTATTCCTGAATAAAGAGGCAGTTTGTAAAAACTCG
AGAACTGTGAGAGATAATTGGATCTTTGTGTAGCAAA
ACTAGAAGGGTGTTGGGTATCTGCTCTTTATCAAATGG
ACCACTTACTTTTCTTTTCTTTTTTGCCCTGTGTTCA
GAAAACAAATGTGCGTGTCTCCTGATTTATAATGTATA
GTTCATTAATGGAGAAAGTGCTTGAGAATTAGATCCT
AATGTCATTTCCCATGCAGCATCTTCATTCTTTTCTAA
AGCACTATTTGGTAAAAACAACTGATAGTCGTCAGAG
GTGATCAGCAATGTTTGAGCACTATTTCCTTTTTATAT
CCTGCACATGGATATGGACAGGACAAACAAATCATTT
CCAAGTAAGAAAATAAATTTTGAGGGAGTTAATACTAT
AATTTGAAGTAATAACCTCCTATTTATCCATCTAGT
TTGTTGTTCTGTACTAAATTATTTGTGCATGTCTCTGT
GTCTATAATTTATGTGAAACTTTGCACAATCTTAAAT
AGGACAAAATAGACATTCTGTAATTTCCCAGGCAAGCT
ATTTAAGGTGACTATCTCTCTACATATTTGAGATGAA
AAACAATAACATGACAATCCATCCCTTCTTAGGTTTTT
GTAAGCAGACTTACTACCTGTGACTCAGTTTTGTTCT
CACAGGGTACTAATTAATCCTTCACGATAATAACTTGT
CAAATTCCATTACTTCTGTAAAGGCAATACTTTATAT
TTGTTTGTATTCAAATTTTAAACTGATGTTAAATGCCG
TGGGTGCAACTGCAGGTTAAAAATATGTGTTTGAATC
TCTTATTCTTTTTGCTTGGCAATGTATGAAATAACTGC
TCTTTCTAGAAATCTTGATGATGAAGTGGCCTGTTGT
TTTGTCACCTAAAAATGCAATAATGTTCAAATTAAGCT
TTTCTTTATTAACATCACTTGATTGTGTGCCATATTT
AGAGCTTAGTGAAATTTTAATCTACACATTGATTAAAT
ACATTTTATTTATTCTTGTTTCTAATGGGAACTTTCT
TTGTTTCTAATGGGAACTTTCTTAAATTAAATTACATC
CAACATTTATTAAAGACCTAAAACATAGGCAATTACT
GTGCTTAGAGGAAAAGCGCAGACGAAAGTGAATCAGAC
AAGTTCCCTGCCCTCCGGAAGCTTTCAGTCTAGTGAT
GAGAAAGACGTATACACACCTTATGTTGATTTAAAAA
AAAAAAAAGCTCTTACCTGGTTGCTGGCATATGAAAGT
GTTAGTTACAGATCTGCCCCAACATAAAGGTGTCACCT
CGAGTAAATCTCTTTCCCTTTCCCTTTCAATCTCTTC
ATCTATAAACTAGGGGTTGGGAATACATTTATTAACAA
ACACAAATTGAGCGTCTACCATGTGATAATAGTAGCT
AAACTTACTGAGCAATTACCATGGGGCAGGTATCAAGA
TAAACCCTTTATGATGGTAACCTCATTTAATCCTCAA
AGCAATTCCATTTTCAAGAGGAGGAAATTGAGGCTCAA
AAATGTTAAGTAACTCCCCAAGGATGCAAAGTGATT
GAGCCAGAATTCAAGACTAGGTTGGTTTGACTCCAAA
CTCATGCCATTAAACCCTATTGTGTCACTGCAAACAA
CTCTAATAGTTTCAAATTATTAGTTCTATTAATATTAT
ATTACCATTATTTGCCCCCAAAATGTAAAATGTAAAT
ACAAAGAGTTTGGTTTTTGTATTACTAGTGGAGGTTAA
AGGTGCACAATGGAATTATTCAAACTGGGAAAATCCA
GGAAGACTTCATGGAGGAGGCAGCATATGGCTGCAGTT
AATAAGGTTTGCTCACACAAATGGAGAGGTGAGGAC
ATTTCAGGCAGAGAATTATATGAGAGGTTACAGAGC
AGTAAACAGTCTGCGTCTGCAAGATCAAAGGGAAAG
GGCGGTAAGAGAGAAGCTTGAAAGTCAAGTGGAGCCAG
ATTGTGAAAAACTAGAGAGTCATGCCAAGGACCTTG
ACATATAGAAAATGGGAAGCCCCTGAAAGGTGAAGAAC
ATGAGAGTGAAATGATTAGTACTTTTTGGTTTAGGA
CTTGTTTCTTTTGTGTTTTGGTTGCTTTCTTGTTTGT
TTGTTTGTGGTTTTAAATTTACAACCAATAAGAAT
ATTTAGTAAGGTTTCCAAATACATCATGAATATATAAA
ACTAGCCTGACTCAAGGATAATAATTCTGGGTAGTTG
GAGTGAAGTTTCAATCAGCTACGTGGCATTTGCTAATC
ATCTGATATGAGCTAACAATAAAGGAGTTAACAAATA
AACTGTCAGCCTACAGTCCAGGGTCTCAAATAGCATGT
GACATAGTTGAGAAGCAGTTTTCCATATCATCATGA
AATAACTAAAGAAACTACTTACAAAGCACTATACCAGT
```

```
AACTACAATAAAATACAACTATACATGCAAAATAATG
CTGAAAGCTGCAAGTAGAGGGGTAAAGCTAGGCCAGTT
GCTCAGGGAACCATTCTGAAGTGGATTTGGGAAGTAT
GTCTAGAAGGGGAGCCATTGCTGTGAGAGTGCTGAGGC
TCATCTGCTACTAGTCCCCCACTACTCAGGCATATGG
TAGGTCAGTAACAAAACCATCATTGTGCACTGTTCTTT
CCATCTAAATTCCATCAAATTATGACCAACCTATCAA
GGTACTAGTTCAAATTCTCTCTTCCTCTATAAGCTAGT
GGTCTTCTCTAAAAATTTAAGAAGATCGTGCTCATCTT
CCTACTTCTTGTTCTCTTTCTTCTGTGTTTTCTGAGGC
TGCAATGAACTAGGAACTTCCTCTCCCCAGAACTCTG
TATTCCAGGCCTTAGATCACTCAAAACTGTTGCTTATA
AAGTGCAGAGAATCAACAGAGAAGGAATAGAAGGTTAA
TGTCTGGTCAAAGATGTGATTCTCTTGTTGAAAAGTTC
ATTAGCTTATTATTTATAGAATCATAAGTCCCAGGAA
AAACCAAAAGGAAATATATATTGGATCCTAATGATATT
CTCTTTTTTTCTTTTTTCTTTTCCCCCACTCCATTGC
CCAGGCTGGAGTTGCAGTGGCATAATCTCAGCTCACTGC
AACCCTCCACCTCCCGGGTTCAAGGGACTCTCCTGCCT
CAGCCTTCCAAGTAGATGGGATTACAGGCATGTGCCAC
CACATCTGGCTAATTTTTTTTTGTATTTTAGTAGAG
ATGGGGTTTCACCATGTTAGTCAGGCTGGTGTTGAACT
CCTGACCTCAAATGATCCACCAGCCTCGGCCTCCCAG
TGTGCTGGGATTGCAGGCGTGAGCCACCACACCCGGCC
TGATATTCTCTTGCAAGGGCATTGTTTACATTGTCTA
TCATCAGAACTGTAGAGTGTTGGCTCCAGGCACAGAAC
CCCTAGAGTTTTGTAAACCATTTATATCACACTGGCA
ACCAGAAGTAACTTTATATACTCAAGAATCAAGATTTC
ACCTAGAAGTACCTCAGGTAGGTGTTGGTTCATTCAC
ATTCCAACCAAAAGATAATGTACCATAAAGTGCATACC
GCCTAGTCCGTAATGATTAAGGCAACCACATAAAATC
TCATTATTTAAAAGAAATTAAGTCCAGGCACGGTGGCT
CACACCTGTAATCTCAGCACTTCGGGAGGCCAAGGAG
GGCAGATCACCTGAGGTCGGGAGTTTGAGACCAGCCTG
ATCAACATGGAGAAATCCCATCTCTACTAAAAATACA
AAATTAGCCGGGCATGGTGGTGCATGCCTATAATCCCA
GCTACTCAGGAGGCTGAGGCAGGAGAATCACTTGAAC
CCAGGAGGTGGAGGTTGAGATCGTGCCATTGCACTCCA
GCCTGGACAACAAGAGTGAAACTCTGTCTCAAAAAAG
AAAAAAGAAAAAGAAATTAAATGCACTATGGTTTATG
GAGCGGTATTCCTCCTCCATGTCCTACATAAGATCTT
TCACATGCCAGTCACAGTTAAATCTAATTTGCTGTAAT
CTGGATAAATGGGAGCTAATCAACAAGCTCTCAGCTC
TAGCTCTGAATCAGCAGCAGATATTGCATTTTTGAAAT
ACACTAATAGCAAGAATGCCTTCCTGACAACAACTGG
CATTTTTGACACAGCAGGAAGTTTATCTGGATTCTGAT
ATAATAGTTATTCAGAATCATACATAGGTACATAGTTT
AAAAGGCTAATAAGTCATTTGTTATTGCTTTTATTATC
TCTGCATAGTTAGTAAAATTGAGATTAGAACCACTTC
TCGAATGTACTGTTCTAAATCCTTAGCTTGCTTGATCA
CACATGACCCTCACAATGATCCTAGGAGAAATTATTC
TGCATGCCATTTTGTAGCTGGGGAAACTGAGGCACAGA
GAAATACAGTACTGCCCAAAATGTCATAACTAATCAA
AGGCAAAGACAATACTCACACCAGCTCTGATTCCAGAG
CCCACTCTCTTAACCATATGCTTTTCTGCTTCCCTAG
TTGTAGAGTCTTTTTGTATGACTGCATTAATTATATGT
GAAGAGTTCAAAAATTTCTATATAAGGTCTTTTAAGG
GTGTCATTCTGGTTGAAAATGGAGGACTAGGCTTCTCA
CTTGAAGACATATTTCTGTAGAAAAACCTATTTTCAT
TTAGATGCTACAGTTACTTGTGATGTGGTTAATAAACCAG
TTAACAGAGTATGAAAGGATAAGGGTTAAAGCCCTC
CCAAGCCATCTTTCATGCTGCTAATATGAATCACATTA
CTAGATACTTAAATCATTTTCTCTTTGGTTCCCAG
AAGACTGCATATATGCTAGAATATTTGTCTCCTCTTT
TACCCTTTCAGGCAATAAAGTATTTTGGACCACTGTA
CTATGTTATAATTATTGTTTCTCCTGATTTTTTGC
TCCAATCTAATGAAAGACATACAAGCTACTATACTGC
TACACAATGACTAAATACCTGTTGATTAGGTGGGGGG
AAGATACACAGTCACTGGCTAGAAAGCATCATGCATA
CAGAGCCATTTTCACCATATATTTTATTTCTCATGATC
ATGTAGAATTTAGGCTTTGGTGTTGATTATTTCTCTC
TTAGGAACATGTTTCAGGGTTGATCTATTCACAAAA
AAACAGAAAAACCTATTCGAGAAAAGGAAAATTATTT
GTCTGTAGGCCAAATTTTGAAGTAGGAAAACCTGCTTT
TGGAGTTGTATTCCCTCCCAGGCACTTAATCCAAGT
TCCAGTCTTATTCTAAACTGGGGATGCTTGTATTAACC
ACCATAGGGTTATCTGAGATGAGTTATCATCAACTT
GGTACCAGGTTGTTGTCCTCTGGACTCAGTGAGCTCTA
GAATTGCATGAACTGGCCTAATTTATCAAAGTATGT
AGCCTTGGGTAAATAATTCAAGCTCTCAGAGGTCCAGT
TATCTCCTCTGTAAAACATATCTACATCCTAGGGATG
```

```
ACAATATCTACATCCTAGAGATGTCAGGAGGATTAAGT
GTAATTTTTTTTAATTGTATGTATTTAAAATGGGCAA
CATAATGTTTTGATATACACGTGTATAGTGATTACTAC
AGTCAAGCAAATTAACATATCCATCATTTCATAGCTA
CCTTTTATGTATGTGATAAGATTATCTAAAATCTATTC
TCTTACCAAATTTCCAGTATACAATATTGATATGGTT
TGATCCATATCCCCATCCAAATCTCATGTTCAGTTGCA
ATCCCCAACGTTGGAGATGGAGCCTGGTTGGAGGTGA
TTGGATCACAGGGGTGGCTTCTAATGGTTCAGCACCAT
CCTTTCTTGGTACTGTATAGTGAGTAAGTTCTCACGA
GATCTGGTTGTTTAAAAGTGTGTAACACCTCCCCCACT
TTCCCTCTCTCTGTTCCTCCTGCTCCCGCTATGTGAA
GTGCCAGCTCCCTCTTTGCCTTCCGCCATGATTGTAAG
TTCTCTGAGGCATCCCCAGAAGCTGATGCTGCCATGC
TTCCTATACAGCCTGCAGAACCATGAGTCAATTAAACC
TCTTTTCTTTGTAAATTACCCAGTCTCAAGTATTTCT
TTATAGCAATGCAAGAATGGACTAATACAGAAAATTGT
TACTGAGAAGAAGGGCATTGCTATAAAGATACCTGAA
AATGTAGAAGTGACTTTGGAACCGGCTAACAGGCAGAA
GTTGAAACATTTTAGAGGGCTCAGAAGAAGACAGAAA
GATGAGAGAAAGTTTGGAACTCGCTAGGAACTTGTTGA
GTGGTTGTAACCAAAATACTGATAGTGATATAGACAG
TGAAGTCCAGGCTGAGGAGGTCTCAGATGGAAATGAGA
AATTTATTGGGAATGAGTAAAGGTCAGGTTTGCTATG
CTTTAGCAAAGAGCTTAGCTGCATTGTTCCTCTGTTCT
AGGGATCTGTGAAATCTTAGACTTAAGAATGATGATT
TAGGGTATCTGGCAGAAGAAATTTCTAAGCAGCAGAGT
GTTCAAGAAGTAACCTAGCTGCTTCTAATAGCCTATG
CTCATAGGCATGAGCACAGAAATGACCTGAAATTGGAA
CTTACACTTAAAAGGGAAGCAGAGCATAAAAGTTTGT
AAATTTTGCAGCCTGGCCATGTGGTAGTAAAGAAAGC
TCGTTCTCAGGAGAGGAAGTCAAGCAGGCTGCATAAA
TTTGCATAACTAAAAGGAAGGCAAGGGCTGATAACCAA
AACAATGGGGAGAAAGACTCATAGGACTAACAGGCAT
TTTATTTTATTTTATTTTTATTTTTATTATTATTATACT
TTAAGTTTTAGGGTACATGTGCACAATGTGCAGGTTA
GTTGCATATGTATACATGTGCCATGCTGGTGTGCTGCA
CCCATTAACTCGTCATTTAGCATTAGGTATATCTCCT
AATGCTATCCCTCCCCCCTCCCCCCACCCCAACAGTC
CCCAGAGTGTGATGTTCCCCTTCCTGTGTCCATGTGT
TCTCATTGTTCAATTCCCACCTATGAGTGAGAACATGT
GGTGTTTGGTTTTTGACCTTGCAATAGTTTACTGAG
AATGACGATTTCCAATTTCATCCATGTCCCTACAAGG
ACATGAACTCATCATTTTTATGGCTGCATAGTATTC
CATGGTGTATATGTGCCACATTTTCTTAATCCAGTCTA
TCACTGTTGGACATTTGGGTTGGTTCCAAGTCTTTGC
TATTGTGAATAGTGCCACAATAAACATAGTGTGCATGT
GTCTTTATAGCAGCAGGATTTATAGTCCTTTGGGTAT
ATACCCAGTGATGGGATGGCTGGGTCAAATGGTATTTC
TAGTTCTAGATCCCTGAGGAATCGCCACACTGACTTC
CACAATGGTTGAACTAGTTTACAGTCCCACCAACAGTG
TAAAAGTGTTCCTAATAGGCATTTTAGGCTTTCATGG
TGGTCCCTCTCATCACAGGCCCCGAGGCCTAGGAGGAC
TGAATCATTTCCTGGGCCAGGCCTAGGGCCCCTGCTC
CCTCTTACAGCCTTGGGACTCTGCTCCCTGAATCCCAG
CTGCTCAAAGGGGCCCAGGTACTGTTACAGTAGGTAG
CTAATCAGGCATGAGTGGGGTAAGAGAGAAGTCCCCAC
CACCCACCAGGAATGTCAGGCAACCATCAGATGATGG
TCAGGCAGTTGTCATACTGCCTCTCTAAAATAGTAATT
GGTTGCAGCCAGCACCAGGGAGAGGCAACTTCTCAAT
AGATAGAAACACCTGAAATTGGTAACTGGGCGCTTCCA
ATAAGATCTCAGGAACTGAGAGAGTGGGCTTAACATG
CACATTAAGAGGCAAAATGGTGAAGTATGACCTTTGGG
GGCATTCCACCGGAAAAGGGAGAAAGAAAGCCTCAGGTAA
GCATGTATACAACTCCAGTAAACACACTGCACACGCTC
ACCTTCCAAGTGCAAGCAGGGCACCATGCATGCGGCA
AGCTCACCCTTAGGGAAGGACCAAGGGAAAGGGGCACA
AGATGTCAGAAGTAGGCCAGTGTATAAGATCCTAGGT
TCAAGGTCAAACAGGGCACTTGACCTCCAAGGTGCCCA
CTTGGGCCTCTTCCAAATGTACTTTCCTTTCATTCCT
GTTCTAAAGCTTTTTAATAAACTTTTACTCCTGCTCTG
AAACTTGTCGCGCAGTCTCTTTTTCTGCCTTATGCCTCT
TGGTCAAATTCTTTCTTCTGAGGAGGCAAGAATTGAGG
TTGCTGCAGACCCACATGGATTTGCAGCTGGTAACTC
AGATAACTTTCACCAGTAAGAATACAGTTCAGGCTGCT
GCTTCACAGGGTGCCAGGCATAAGCCTTGGTGGCTTC
CATAAGCTGTGAAGCCGGCGGGCGCACATAATGCAAGA
GTTGAGGCTTAAGAAGCTCTGCCTAGATTTTAGAGGA
TGTATGAAAAGCCTGGATGTCCAGACAGAAGCCTGTT
ACTGGGGTGGAATCCTCATGGAGAACATCTACTAGGG
AAGCAAGGAGAAGAAATGTGGGGTTGCAGCCCCCACAG
AGAGTCCCCTGGGGCACTGCCTAGCAGAGCTATGACA
AGACAGCCACCGTCCTCCAGACCCCAGAATGGTAGATC
CACCAACAACTTGCACCCTGCAGCCTGGAAAAGCTGC
AAGCACTCAATGCTAGCCCATGAGAGCAGCTGTGGGAG
ATGAACCCTGGAAAACCACAGGGGTGGTTCTGCCCAA
GGTTTTGGGAGCCCACTCATTGCATCAGTGTTCCCTGG
GTGTGAGTCAAAGGAGATTATTTCAGAGCTTTAACAT
TTAATGACTGCCCGGCTGGCTTTCAGACTTGCAATGGG
GCCCTATAGCTCTTTCTTTTTGGCAGATTTCTCCCTT
TCGGAATGGCAGTATCTGCCCAATGCCTATACCCCCAT
TGTATCTTTGAAGCAATTACCTTGTTTTTGATTTTAC
AGGTTCATAGGTAGAAGGGACTAGCTTCGTCTCAGGTG
AGACTTGGGACTTTGGACTTTTGAATGAATGCTGGAT
CGAGTTAAGACTTTGGGGAACTGTTGGTAAGGCACGAC
AGTATTTTGCAATATGAGAAGGACATTAGATTTGGGA
GGGGCCAGAGTTGGAATAACATGGTTTGGATCTCTGTC
CCCACCCAAATCTCATGTTCAACTGTAATCCCCAGTG
TTGGAGGTTGGGCCTGGTGGGAGGTGAGTGGATTATGG
GGTGGCTTCTAATGGTTTTGTACAGTCCCCTCTTGGT
ACTATATAGTGAGTTCTGACAAGATCTAGTTGTTTAAA
CGTATGTAGCACCTCCCATTTCTCTCTTCCCCCAGTT
CCTGCCATGTGAAGTCTGGGGTCTCCCTATGCCTTCCA
TCATGATTTTAAGTTCCCTATGCCTGCCCAGAAGCT
GATCCAGCCATGCTTCTTGTACAGCCTGCAGAACTGTG
AGCCATTAAACTTTTCTTTATAAATTACCCAGTTTCA
GTTATTTCTTTATAGCAGTGTAAGAATGGACTAACACA
ATTATTAACGCTAGTCCTCATGTTGTACATTAAATCT
CTAGATGTATTAGACGTAACTGCAACTTTGTACCCTAC
CCTACAATTTTCTTTCCCCCAAGCCCCCCAACCAAG
GGTCTACTCTGTTTCTATAAATTCAGTTGTTTTTTAAT
TCCACGTATAAGTGAAGTACAACTCAGTGTAGAAACT
TGGTAAATGCTAGCTACTTGTTATAAGCTGTCAGTCAA
AATAAAAATACAGAGATGAATCTCTAAATTAAGTGAT
TTATTTGGGAAGAAAGAATTGCAATTAGGGCATACATG
TAGATCAGATGGTCTTCGGTATATCCACACAACAAAG
AAAAGGGGGAGGTTTTGTTAAAAAGAGAAATGTTACA
TAGTGCTCTTTGAGAAAATTCATTGGCACTATTAAGG
ATCTGAGGAGCTGGTGAGTTTCAACTGGTGAGTGATGG
TGGTAGATAAAATTAGAGCTGCAGCAGGTCATTTTAG
CAACTATTAGATAAAACTGGTCTCAGGTCACAACGGGC
AGTTGCAGCAGCTGGACTTGGAGAGAATTACACTGTG
GGAGCAGTGTCATTTGTCCTAAGTGCTTTTCTACCCCC
TACCCCCACTATTTTAGTTGGGTATAAAAAGAATGAC
CCAATTTGTATGATCAACTTTCACAAAGCATAGAACAG
TAGGAAAAGGGTCTGTTTCTGCAGAAGGTGTAGACGT
TGAGAGCCATTTTGTGTATTTATTCCTCCCTTTCTTCC
TCGGTGAATGATTTCAATGTTCTGTGTGATTTTTAGT
GATGAAAAAGATTAAATGCTACTCACTGTAGTAAGTGC
CATCTCACACTTGCAGATCAAAAGGCACACAGTTTAA
AAAACCTTTGTTTTTTTACACATCTGAGTGGTGTAAAT
GCTACTCATCTGTAGTAAGTGGAATCTATACACCTGC
AGACCAAAAGACGCAAGGTTTCAAAAATCTTTGTGTTT
TTTACACATCAAACAGAATGGTACGTTTTTCAAAAGT
TAAAAAAAAAACAACTCATCCACATATTGCAACTAGCAA
AAATGACATTTCCCAGTGTGAAAATCATGCTTGAGAG
AATTCTTACATGTAAAAGGCAAAATTGCGATGACTTTGC
AGGGGACCGTGGGATTCCCGCCCGCAGTGCCGGAGCT
GTCCCCTACCAGGGTTTGCAGTGGAGTTTTGAATGCAC
TTAACAGTGTCTTACGGTAAAACAAAATTTCATCCA
CCAATTATGTGTTGAGCGCCCACTGCCTACCAAGCACA
AACAAAACCATTCAAAACCACGAAATCGTCTTCACTT
TCTCCAGATCCAGCAGCCTCCCCTATTAAGGTTCGCAC
ACGCTATTGCGCCAACGCTCCTCCAGAGCGGGTCTTA
AGATAAAAGAACAGGACAAGTTGCCCCGACCCCCATTTCG
CTAGCCTCGTGAGAAAACGTCATCGCACATAGAAACAC
AGACAGACGTAACCTACGGTGTCCCGCTAGGAAAGAGA
GGTGCGTCAAACAGCGACAAGTTCCGCCCACGTAAAA
GATGACGCTGTGGCACCGTCCCTGCTGCCAGGTGGT
TGCTTCTCTTTTGGGGCGGGGTCTAGCAAGAGCAGG
TGTGGGTTTAGGAGGTGTGTGTTTTTGTTTTTCCCACC
CTCTCTCCCCACTACTTGCTCTCACAGTACTCGCTGA
GGGTGAACAAGAAAAGACCTGATAAAGATTAACCAGAA
GAAAACAAGGAGGGAAACAACCCAGCCTGTAGCAAG
CTCTGGAACTCAGGAGTCGCGCGCTAGGGGCC
(GGGGCC)ₙ
GGGGCCGGGGCGTGGTCGGGGCGGGCCCGGGGCGGG
CCCGGGGCGGGGCTGCGGTTGCGGTGCCTGCGCCCGCG
GCGGCGGAGGCGCAGGCGGTGGCGAGTGGGTGAGTGA
GGAGGCGGCATCCTGGCGGGTGGCTGTTTGGGGTTCGG
CTGCCGGGAAGAGGCGCGGGTAGAAGCGGGGGCTCTC
CTCAGAGCTCGACGCATTTTTACTTTCCCTCTCATTTC
```

```
TCTGACCGAAGCTGGGTGTCGGGCTTTCGCCTCTAGC
GACTGGTGGAATTGCCTGCATCCGGGCCCCGGGCTTCC
CGGCGGCGGCGGCGGCGGCGGCGCAGGGACAAGG
GATGGGGATCTGGCCTCTTCCTTGCTTTCCCGCCCTCA
GTACCCGAGCTGTCTCCTTCCCGGGACCCGCTGGGA
GCGCTGCCGCTGCGGGCTCGAGAAAAGGGAGCCTCGGG
TACTGAGAGGCCTCGCCTGGGGGAAGGCCGGAGGGTG
GGCGGCGCGCGGCTTCTGCGGACCAAGTCGGGGTTCGC
TAGGAACCCGAGACGGTCCCTGCCGGCGAGGAGATCA
TGCGGGATGAGATGGGGGTGTGGAGCAGCCTGCACAAT
TTCAGCCCAAGCTTCTAGAGAGTGGTGATGACTTGCA
TATGAGGGCAGCAATGCAAGTCGGTGTGCTCCCCATTC
TGTGGGACATGACCTGGTTGCTTCACAGCTCCGAGAT
GACACAGACTTGCTTAAAGGAAGTGACTATTGTGACTT
GGGCATCACTTGACTGATGGTAATCAGTTGTCTAAAG
AAGTGCACAGATTACATGTCCGTGTGCTCATTGGGTCT
ATCTGGCCGCGTTGAACACCACCAGGCTTTGTATTCA
GAAACAGGAGGGAGGTCCTGCACTTTCCCAGGAGGGGT
GGCCCTTTCAGATGCAATCGAGATTGTTAGGCTCTGG
GAGAGTAGTTGCCTGGTTGTGGCAGTTGGTAAATTTCT
ATTCAAACAGTTGCCATGCACCAGTTGTTCACAACAA
GGGTACGTAATCTGTCTGGCATTACTTCTACTTTTGTA
CAAAGGATCAAAAAAAAAAAAGATACTGTTAAGATAT
GATTTTTCTCAGACTTTGGGAAACTTTTAACATAATCT
GTGAATATCACAGAAACAAGACTATCATATAGGGGAT
ATTAATAACCTGGAGTCAGAATACTTGAAATACGGTGT
CATTTGACACGGGCATTGTTGTCACCACCTCTGCCAA
GGCCTGCCACTTTAGGAAAACCCTGAATCAGTTGGAAA
CTGCTACATGCTGATAGTACATCTGAAACAAGAACGA
GAGTAATTACCACATTCCAGATTGTTCACTAAGCCAGC
ATTTACCTGCTCCAGGAAAAAATTACAAGCACCTTAT
GAAGTTGATAAAATATTTTGTTTGGCTATGTTGGCACT
CCACAATTTGCTTTCAGAGAAACAAAGTAAACCAAGG
AGGACTTCTGTTTTTCAAGTCTGCCCTCGGGTTCTATT
CTACGTTAATTAGATAGTTCCCAGGAGGACTAGGTTA
GCCTACCTATTGTCTGAGAAACTTGGAACTGTGAGAAA
TGGCCAGATAGTGATATGAACTTCACCTTCCAGTCTT
CCCTGATGTTGAAGATTGAGAAAGTGTTGTGAACTTTC
TGGTACTGTAAACAGTTCACTGTCCTTGAAGTGGTCC
TGGGCAGCTCCTGTTGTGGAAAGTGGACGGTTTAGGAT
CCTGCTTCTCTTTGGGCTGGGAGAAAATAAACAGCAT
GGTTACAAGTATTGAGAGCCAGGTTGGAGAAGGTGGCT
TACACCTGTAATGCCAGAGCTTTGGGAGGCGGAGGCA
AGAGGATCACTTGAAGCCAGGAGTTCAAGCTCAACCTG
GGCAACGTAGACCCGTCTCTACAAAAAATTAAAAAC
TTAGCCGGGCGTGGTGATGTGCACCTGTAGTCCTAGCT
ACTTGGGAGGCTGAGGCAGGAGGGTCATTTGAGCCCA
AGAGTTTGAAGTTACCGAGAGCTATGATCCTGCCAGTG
CATTCCAGCCTGGATGACAAAACGAGACCCTGTCTCT
AAAAAACAAGAAGTGAGGGCTTTATGATTGTAGAATTT
TCACTACAATAGCAGTGGACCAACCACCTTTCTAAAT
ACCAATCAGGGAAGAGATGGTTGATTTTTTAACAGACG
TTTAAAGAAAAAGCAAAACCTCAAACTTAGCACTCTA
CTAACAGTTTTAGCAGATGTTAATTAATGTAATCATGT
CTGCATGTATGGGATTATTTCCAGAAAGTGTATTGGG
AAACCTCTCATGAACCCTGTGAGCAAGCCACCGTCTCA
CTCAATTTGAATCTTGGCTTCCCTCAAAAGACTGGCT
AATGTTTGGTAACTCTCTGGAGTAGACAGCACTACATG
TACGTAAGATAGGTACATAAACAACTATTGGTTTTGA
GCTGATTTTTTTCAGCTGCATTTGCATGTATGGATTTT
TCTCACCAAAGACGATGACTTCAAGTATTAGTAAAAT
AATTGTACAGCTCTCCTGATTATACTTCTCTGTGACAT
TTCATTTCCCAGGCTATTTCTTTTGGTAGGATTTAAA
ACTAAGCAATTCAGTATGACTCTTTGTCCTTCATTTTCT
TTCTTATTCTTTTTGTTTGTTTGTTTGTTTGTTTTTT
TCTTGAGGCAGAGTCTCTCTGTCGCCCAGGCTGGAG
TGCAGTGGCGCCATCTCAGCTCATTGCAACCTCTGCC
ACCTCCGGGTTCAAGAGATTCTCCTGCCTCAGCCTCCC
GAGTAGCTGGGATTACAGGTGTCCACCACCACACCCG
GCTAATTTTTGTATTTTTAGTAGAGGTGGGGTTTCAC
CATGTTGGCCAGGCTGGTCTTGAGCTCCTGACCTCAG
GTGATCCACCTGCCTCGGCCTTCCAGAAGAGCTGGGATA
ACAGGTGTGACCCACCATGCCCGGCCCATTTTTTTTT
TCTTATTCTGTTAGGAGTGAGAGTGTAACTAGACAGTAT
AATAGTTCAATTTTCACAACGTGGTAAAAGTTTCCCT
ATAATTCAATCAGATTTTGCTCAGGGTTCAGTTCTGT
TTTAGGAAATACTTTTATTTTCAGTTTAATGATGAAA
TATTAGAGTTGTAATATTGCCTTTATGATTATCCACCT
TTTTAACCTAAAAGAATGAAAGAAAAATATGTTTGCA
ATATAATTTTATGGTTGTATGTTAACTTAATTCATTAT
GTTGGCCTCCAGTTTGCTGTTGTTAGTTATGACAGCA
GTAGTGTCATTACCATTTCAATTCAGATTACATTCCTA
TATTTGATCATTGTAAACTGACTGCTTACATTGTATT
AAAAACAGTGGATATTTTAAAGAAGCTGTACGGCTTAT
ATCTAGTGCTGTCTCTTAAGACTATTAAATTGATACA
ACATATTTAAAAGTAAATATTACCTAAATGAATTTTTG
AAATTACAAATACACGTGTTAAAACTGTCGTTGTGTT
CAACCATTTCTGTACATACTTAGAGTTAACTGTTTTGC
CAGGCTCTGTATGCCTACTCATAATATGATAAAAGCA
CTCATCTAATGCTCTGTAAATAGAAGTCAGTGCTTTCC
ATCAGACTGAACTCTCTTGACAAGATGTGGATGAAAT
TCTTTAAGTAAAATTGTTTACTTTGTCATACATTTACA
GATCAAATGTTAGCTCCCAAAGCAATCATATGGCAAA
GATAGGTATATCATAGTTTGCCTATTAGCTGCTTTGTA
TTGCTATTATTATAAATAGACTTCACAGTTTTAGACT
TGCTTAGGTGAAATTGCAATTCTTTTTACTTTCAGTCT
TAGATAACAAGTCTTCAATTATAGTACAATCACACAT
TGCTTAGGAATGCATCATTAGGCGATTTTGTCATTATG
CAAACATCATAGAGTGTACTTACACAAACCTAGATAG
TATAGCCTTTATGTACCTAGGCCGTATGGTATAGTCTG
TTGCTCCTAGGCCACAAACCTGTACAACTGTTACTGT
ACTGAATACTATAGACAGTTGTAACACAGTGGTAAATA
TTTATCTAAATATATGCAAACAGAGAAAAAGGTACAGT
AAAAGTATGGTATAAAAGATAATGGTATACCTGTGTAG
GCCACTTACCACGAATGGAGCTTGCAGGACTAGAAGT
TGCTCTGGGTGAGTCAGTGAGTGAGTGGTGAATTAATG
TGAAGGCCTAGAACTGTACACCACTGTAGACTATA
AACACAGTACGCTGAAGCTACACCAAATTTATCTTAAC
AGTTTTTCTTCAATAAAAAATTATAACTTTTTAACTT
TGTAAACTTTTTAATTTTTTAACTTTTAAAATACTTAG
CTTGAAACACAAATACATTGTATAGCTATACAAAAAT
ATTTTTCTTTGTATCCTTATTCTAGAAGCTTTTTTCT
ATTTTCTATTTTAAATTTTTTTTTTTACTTGTTAGTC
GTTTTTGTTAAAAACTAAAACACACACTTTCACCTA
GGCATAGCAGGATTAGGATCATCAGTATCACTCCCT
TCCACCTCACTGCCTTCCACCTCCACATCTTGTCCCAC
TGGAAGGTTTTTAGGGGCAATAACACACATGTAGCTG
TCACCTATGATAACAGTGCTTTCTGTTGAATACCTCCT
GAAGGACTTGCCTGAGGCGTGTTTTACATTTAACTTAA
AAAAAAAAAAGTAGAAGGAGTGCACTCTAAAATAACA
ATAAAAGGCATAGTATAGTGAATACATAAACAGCAA
TGTAGTAGTTTATTATCAAGTGTTGTACACTGTAATAA
TTGTATGTGCTATACTTTAAATAACTTGCAAAATAGT
ACTAAGACCTTATGATGGTTACAGTGTCACTAAGGCAA
TAGCATATTTTCAGGTCCATTGTAATCTAATGGGACT
ACCATCATATATGCAGTCTACCATTGACTGAAACGTTA
CATGGCACATAACTGTATTTGCAAGAATGATTTGTTT
TACATTAATATCACATAGGATGTACCTTTTTAGAGTGG
TATGTTTATGTGGATTAAGATGTACAAGTTGAGCAAG
GGGACCAAGAGCCCTGGGTTCTGTCTTGGATGTGAGCG
TTTATGTTCTTCTCCTCATGTCTGTTTTCTCATTAAA
TTCAAAGGCTTGAACGGGCCCTATTTAGCCCTTCTGTT
TTCTACGTGTTCTAAATAACTAAAGCTTTTAAATTCT
AGCCATTTAGTGTAGAACTCTCTTTGCAGTGATGAAAT
GCTGTATTGGTTTCTTGGCTAGCATATTAAATATTTT
TATCTTTGTCTTGATACTTCAATGTCGTTTTAAACATC
AGGATCGGGCTTCAGTATTCTCATAACCAGAGAGTTC
ACTGAGGATACAGGACTGTTTGCCCATTTTTGTTATG
GCTCCAGACTTGTGGTATTTCCATGTCTTTTTTTTTT
TTTTTTTTTGACCTTTTAGCGGCTTTAAAGTATTTC
TGTTGTTAGGTGTTGTATTACTTTTCTAAGATTACTT
AACAAAGCACCACAAACTGAGTGGCTTTAAACAACAGC
AATTTATTCTCTCACAATTCTAGAAGCTAGAAGTCCG
AAATCAAAGTGTTGACAGGGGCATGATCTTCAAGAGAG
AAGACTCTTTCCTTGCTCTTCCTGGCTTCTGGTGGT
TACCAGCAATCCTGAGTGTTCCTTTCTTGCCTTGGTAGT
TTCAACAATCCAGTATCTGCCTTTTGTCTTCACATGG
CTGTCTACCATTTGTCTCTGTGTCTCCAAATCTCTCTC
CTTATAAACACAGCAGTTATTCATTTGGATTAGGCCCACTC
TAATCCAGTATGACCCCATTTTAACATGATTACTTA
TTTCTAGATAAGGTCACATTCACGTACACCAAGGGTT
AGGAATTGAACATATCTTTTTGGGGGACACAATTCAAC
CCACAAGTGTCAGTCTCTAGCTGAGCCTTTCCCTTCC
TGTTTTTCTCCTTTTTAGTTGCTATGGGTTAGGGGCCA
AATCTCCAGTCATACTAGAATTGCACATGGACTGGAT
ATTTGGGAATACTGCGGGTCTATTCTATGAGCTTTAGT
ATGTAACATTTAATACAGTGTAAGAAGCCCTTTTT
TAAGTTATTCTTTGAATTTCTAAATGTATGCCCTGAA
TATAAGTAACAAGTTACCATGTCTTGTAAAATGATCA
TATCAACAAACATTTAATGTGCACCTACTGTGCTAGTT
GAATGTCTTTATCCTGATAGGAGATAACAGGATTCCA
CATCTTTGACTTAAGAGGACAAACCAAATATGTCTAAA
```

```
TCATTTGGGGTTTTGATGGATATCTTTAAATTGCTGA
ACCTAATCATTGGTTTCATATGTCATTGTTTAGATATC
TCCGGAGCATTTGGATAATGTGACAGTTGGAATGCAG
TGATGTCGACTCTTTGCCCACCGCCATCTCCAGCTGTT
GCCAAGACAGAGATTGCTTTAAGTGGCAAATCACCTT
TATTAGCAGCTACTTTTGCTTACTGGGACAATATTCTT
GGTCCTAGAGTAAGGCACATTTGGGCTCCAAAGACAG
AACAGGTACTTCTCAGTGATGGAGAAATAACTTTTCTT
GCCAACCACACTCTAAATGGAGAAATCCTTCGAAATG
CAGAGAGTGGTGCTATAGATGTAAAGTTTTTTGTCTTG
TCTGAAAAGGGAGTGATTATTGTTTCATTAATCTTTG
ATGGAAACTGGAATGGGGATCGCAGCACATATGGACTA
TCAATTATACTTCCACAGACAGAACTTAGTTTCTACC
TCCCACTTCATAGAGTGTGTGTTGATAGATTAACACAT
ATAATCCGGAAAGGAAGAATATGGATGCATAAGGTAA
GTGATTTTTCAGCTTATTAATCATGTTAACCTATCTGT
TGAAAGCTTATTTTCTGGTACATATAAATCTTATTTT
TTTAATTATATGCAGTGAACATCAAACAATAAATGTTA
TTTATTTTGCATTTACCCTATTAGATACAAATACATC
TGGTCTGATACCTGTCATCTTCATATTAACTGTGGAAG
GTACGAAATGGTAGCTCCACATTATAGATGAAAAGCT
AAAGCTTAGACAAATAAAGAAACTTTTAGACCCTGGAT
TCTTCTTGGGAGCCTTTGACTCTAATACCTTTTGTTT
CCCTTTCATTGCACAATTCTGTCTTTTGCTTACTACTA
TGTGTAAGTATAACAGTTCAAAGTAATAGTTTCATAA
GCTGTTGGTCATGTAGCCTTTGGTCTCTTTAACCTCTT
TGCCAAGTTCCCAGGTTCATAAAATGAGGAGGTTGAA
TGGAATGGTTCCCAAGAGAATTCCTTTTAATCTTACAG
AAATTATTGTTTTCCTAAATCCTGTAGTTGAATATAT
AATGCTATTTACATTTCAGTATAGTTTTGATGTATCTA
AAGAACACATTGAATTCTCCTTCCTGTGTTCCAGTTT
GATACTAACCTGAAAGTCCATTAAGCATTACCAGTTTT
AAAAGGCTTTTGCCCAATAGTAAGGAAAAATAATATC
TTTTAAAAGAATAATTTTTTACTATGTTTGCAGGCTTA
CTTCCTTTTTTCTCACATTATGAAACTCTTAAAATCA
GGAGAATCTTTTAAACAACATCATAATGTTTAATTTGA
AAAGTGCAAGTCATTCTTTTCCTTTTTGAAACTATGC
AGATGTTACATTGACTGTTTTCTGTGAAGTTATCTTTT
TTTCACTGCAGAATAAAGGTTGTTTTGATTTTATTTT
GTATTGTTTATGAGAACATGCATTTGTTGGGTTAATTT
CCTACCCCTGCCCCCATTTTTTCCCTAAAGTAGAAAG
TATTTTTCTTGTGAACTAAATTACTACACAAGAACATG
TCTATTGAAAAATAAGCAAGTATCAAAATGTTGTGGG
TTGTTTTTTTAAATAAATTTTCTCTTGCTCAGGAAAGA
CAAGAAAATGTCCAGAAGATTATCTTAGAAGGCACAG
AGAGAATGGAAGATCAGGTATATGCAAATTGCATACTG
TCAAATGTTTTTCTCACAGCATATCTGTATAAGGT
TGATGGCTACATTTGTCAAGGCCTTGGAGACATACGAA
TAAGCCTTTAATGGAGCTTTTATGGAGGTGTACAGAA
TAAACTGGAGGAAGATTTCCATATCTTAAACCCAAAGA
GTTAAATCAGTAAACAAAGGAAAATAGTAATTGCATC
TACAAATTAATATTTGCTCCCTTTTTTTTTCTGTTTGC
CCAGAATAAATTTTGGATAACTTGTTCATAGTAAAA
TAAAAAAAATTGTCTCTGATATGTTCTTTAAGGTACTA
CTTCTCGAACCTTTCCCTAGAAGTAGCTGTAACAGAA
GGAGAGCATATGTACCCCTGAGGTATCTGTCTGGGGTG
TAGGCCCAGGTCCACACAATATTTCTTCTAAGTCTTA
TGTTGTATCGTTAAGACTCATGCAATTTACATTTTATT
CCATAACTATTTTAGTATTAAAATTTGCTTGGTCAGTGATAT
TTCCTTACCCTCTCCTCTAGGAAAATGTGCCATGTTTAT
CCCTTGGCTTTGAATGCCCCTCAGGAACAGACACTAA
GAGTTTGAGAAGCATGGTTACAAGGGTGTGGCTTCCCC
TGCGGAAACTAAGTACAGACTATTTCACTGTAAAGCA
GAGAAGTTCTTTTGAAGGAGAATCTCCAGTGAAGAAAG
AGTTCTTCACTTTTACTTCCATTTCCTCTTGTGGGTG
ACCCTCAATGCTCCTTGTAAAACTCCAATATTTTAAAC
ATGGCTGTTTTGCCTTTCTTTGCTTCTTTTTAGCATG
AATGAGACAGATGATACTTTAAAAAAGTAATTAAAAAA
AAAAACTTGTGAAAATACATGGCCATAATACAGAACC
CAATACAATGATCTCCTTTACCAAATTGTTATGTTTGT
ACTTTTGTAGATAGCTTTCCAATTCAGAGACAGTTAT
TCTGTGTAAAGGTCTGACTTAACAAGAAAAGATTTCCC
TTTACCCAAAGAATCCCAGTCCTTATTTGCTGGTCAA
TAAGCAGGGTCCCCAGGAATGGGGTAACTTTCAGCACC
CTCTAACCCACTAGTTATTAGTAGACTAATTAAGTAA
ACTTATCGCAAGTTGAGGAACTCAAGAACAACTAAAA
TTCTGCTTTTACTGGGATTTTGTTTTTTCAAACCAGA
AACCTTTACTTAAGTTGACTACTATTAATGAATTTTGG
TCTCTCTTTTAAGTGCTCTTCTTAAAAAATGTTATCTT
ACTGCTGAGAAGTTCAAGTTTGGGAAGTACAAGGAGGA
ATAGAAACTTAAGAGATTTTCTTTTAGAGCCTCTTCT
GTATTTAGCCCTGTAGGATTTTTTTTTTTTTTTTTTT
TTTGGTGTTGTTGAGCTTCAGTGAGGCTATTCATTCA
CTTATACTGATAATGTCTGAGATACTGTGAATGAAATA
CTATGTATGCTTAAACCTAAGAGGAAATATTTTCCCA
AAATTATTCTTCCCGAAAAGGAGGAGTTGCCTTTTGAT
TGAGTTCTTGCAAATCTCACAACGACTTTATTTTGAA
CAATACTGTTTGGGGATGATGCATTAGTTTGAAACAAC
TTCAGTTGTAGCTGTCATCTGATAAAATTGCTTCACA
GGGAAGGAAATTTAACACGGATCTAGTCATTATTCTTG
TTAGATTGAATGTGTGAATTGTAATTGTAAACAGGCA
TGATAATTATTACTTTAAAAACTAAAAACAGTGAATAG
TTAGTTGTGGAGGTTACTAAAGGATGGTTTTTTTTTA
AATAAAACTTTCAGCATTATGCAAATGGGCATATGGCT
TAGGATAAAACTTCCAGAAGTAGCATCACATTTAAAT
TCTCAAGCAACTTAATAATATGGGGCTCTGAAAAACTG
GTTAAGGTTACTCCAAAAATGGCCCTGGGTCTGACAA
AGATTCTAACTTAAAGATGCTTATGAAGACTTTGAGTA
AAATCATTTCATAAAATAAGTGAGGAAAAACAACTAG
TATTAAATTCATCTTAAATAATGTATGATTTAAAAAAT
ATGTTTAGCTAAAAATGCATAGTCATTTGACAATTTC
ATTTATATCTCAAAAAATTTACTTAACCAAGTTGGTCA
CAAAACTGATGAGACTGGTGGTGGTAGTGAATAAATG
AGGGACCATCCATATTTGAGACACTTTACATTTGTGAT
GTGTTATACTGAATTTTCAGTTTGATTCTATAGACTA
CAAATTTCAAAATTACAATTTCAAGATGTAATAAGTAG
TAATATCTTGAAATAGCTCTAAAGGGAATTTTTCTGT
TTTATTGATTCTTAAAATATATGTGCTGATTTTGATTT
GCATTTGGGTAGATTATACTTTTATGAGTATGGAGGT
TAGGTATTGATTCAAGTTTTCCTTACCTATTTGGTAAG
GATTTCAAAGTCTTTTGTGCTTGGTTTTCCTCATTT
TTAAATATGAAATATATTGATGACCTTTAACAAATTTT
TTTTATCTCAAATTTTAAAGGAGATCTTTTCTAAAAG
AGGCATGATGACTTAATCATTGCATGTAACAGTAAACG
ATAAACCAATGATTCCATACTCTCTAAAGAATAAAAG
TGAGCTTTAGGGCCGGGCATGGTCAGAAATTTGACACC
AACCTGGCCAACATGGCGAAACCCCGTCTCTACTAAA
AATACAAAAATCAGCCGGGCATGGTGGCGGCACCTATA
GTCCCAGCTACTTGGGAGGATGAGACAGGAGAGTCAC
TTGAACCTGGGAGGCGGAGGTTGCAGTGAGCTGAGATCA
CGCCATTGCACTCCAGCCTGAGCAATGAAAGCAAAAC
TCCATCTCAAAAAAAAAAAAGAAAAGAAAGAATAAAA
GTGAGCTTTGGATTGCATATAAATCCTTTAGACATGT
AGTAGACTTGTTTGATACTGTGTTTGAACAAATTACGA
AGTATTTTCATCAAAGAATGTTATTGTTTGATGTTAT
TTTTATTTTTATTGCCCAGCTTCTCTCATATTACGTG
ATTTTCTTCACTTCATGTCACTTTATTGTGCAGGGTC
AGAGTATTATTCCAATGCTTACTGGAGAAGTGATTCCT
GTAATGGAACTGCTTTCATCTATGAAATCACACAGTG
TTCCTGAAGAAATAGATGTAAGTTTAAATGAGAGCAAT
TATACACTTTATGAGTTTTTTGGGGTTATAGTATTAT
TATGTATATTATAATATTCTAATTTTAATAGTAAGGA
CTTTGTCATACATACTATTCACATACAGTATTAGCCA
CTTTAGCAAATAAGCACACACAAAATCCTGGATTTTAT
GGCAAAACAGAGGCATTTTTGATCAGTGATGACAAAA
TTAAATTCATTTTGTTTATTTCATTACTTTTTATAATTC
CTAAAAGTGGGAGGATCCCCAGCTCTTATAGGAGCAAT
TAATATTTAATGTAGTGTCTTTTGAAACAAAACTGTGT
GCCAAAGTAGTAACCATTAATGGAAGTTTACTTGTAG
TCACAAATTAGTTTCCTTAATCATTTGTTGAGGACGT
TTTGAATCACACACTATGAGTGTTAAGAGATACCTTT
AGGAAACTATTCTTGTTGTTTTCTGATTTTGTCATTTA
GGTTAGTCTCCTGATTCTGACAGCTCAGAAGAGGAAG
TTGTTCTTGTAAAAATTGTTTAACCTGCTTGACCAGCT
TTCACATTTGTTTCTTCTGAAGTTTATGGTAGTGCACA
GAGATTGTTTTTGGGGAGTCTTGATTCTGGAAATGA
AGGCAGTGTGTATATTGAATCCAGACTTCCGAAAAC
TTGTATATTAAAAGTGTTATTTCAACACTATGTTACAG
CCAGACTATTTTTATTTTTTGATGCATTTTAGAT
AGCTGATACAGTACTCAATGATGATGATATTGGTGACA
GCTGTCATGAAGGCTTCTTCTCAAGTAAGAATTTTTT
CTTTTCATAAAAGCTGGATGAAGCAGATACCATCTTAT
GCTCACCTATGACAAGTATTGGGACAAAGAAAATAAA
AGACTGTCTACTTAGATTGTTCTAGGGACATTACGTAT
TTGAACTGTTGCTTAAATTTGTGTTATTTTTCACTCA
TTATATTTCTATATATATTTGGTGTTATTCCATTTGCT
ATTTAAAGAAACCGAGTTTCCATCCCAGACAAGAAAT
CATGGCCCCTTGCTTGATTCTGGTTTCTTGTTTTACTT
CTCATTAAAGCTAACAGAATCCTTTCATATTAAGTTG
TACTGTAGATGAACTTAAGTTATTTAGGCGTAGAACAA
AATTATTCATATTTATACTGATCTTTTTCCATCCAGC
AGTGGAGTTTAGTACTTAAGAGTTTGTGCCCTTAAACC
```

```
AGACTCCCTGGATTAATGCTGTGTACCCGTGGGCAAG
GTGCCTGAATTCTCTATACACCTATTTCCTCATCTGTA
AAATGGCAATAATAGTAATAGTACCTAATGTGTAGGG
TTGTTATAAGCATTGAGTAAGATAAATAATATAAAGCA
CTTAGAACAGTGCCTGGAACATAAAAACACTTAATAA
TAGCTCATAGCTAACATTTCCTATTTACATTTCTTCTA
GAAATAGCCAGTATTTGTTGAGTGCCTACATGTTAGT
TCCTTTACTAGTTGCTTTACATGTATTATCTTATATTC
TGTTTTAAAGTTTCTTCACAGTTACAGATTTCATGA
AATTTTACTTTTAATAAAAGAGAAGTAAAAGTATAAAG
TATTCACTTTTATGTTCACAGTCTTTTCCTTTAGGCT
CATGATGGAGTATCAGAGGCATGAGTGTGTTTAACCTA
AGAGCCTTAATGGCTTGAATCAGAAGCACTTTAGTCC
TGTATCTGTTCAGTGTCAGCCTTTCATACATCATTTTA
AATCCCATTTGACTTTAAGTAAGTCACTTAATCTCTC
TACATGTCAATTCTTCAGCTATAAAATGATGGTATTT
CAATAAATAAATACATTAATTAAATGATATTATACTG
ACTAATTGGGCTGTTTTAAGCTCTCAATAAGAAAATTTC
TGTGAAAGGTCTCTAGAAAATGTAGGTTCCTATACAA
ATAAAAGATAACATTGTGCTTATAGCTTCGGTGTTTAT
CATATAAAGCTATTCTGAGTTATTTGAAGAGCTCACC
TACTTTTTTTGTTTTTAGTTTGTTTAAAATTGTTTTATA
GGCAATGTTTTTAATCTGTTTTCTTTAACTTACAGTG
CCATCAGCTCACACTTGCAAACCTGTGGCTGTTCCGTT
GTAGTAGGTAGCAGTGCAGAGAAAGTAAATAAGGTAG
TTTATTTTATAATCTAGCAAATGATTTGACTCTTTAAG
ACTGATGATATATCATGGATTGTCATTTAAATGGTAG
GTTGCAATTAAAATGATCTAGTAGTATAAGGAGGCAAT
GTAATCTCATCAAATTGCTAAGACACCTTGTGGCAAC
AGTGAGTTTGAAATAAACTGAGTAAGAATCATTTATCA
GTTTATTTTGATAGCTCGGAAATACCAGTGTCAGTAG
TGTATAAATGGTTTTGAGAATATATTAAAATCAGATAT
ATAAAAAAAATTACTCTTCTATTTCCCAATGTTATCT
TTAACAAATCTGAAGATAGTCATGTACTTTTGGTAGTA
GTTCCAAAGAAATGTTATTTGTTTATTCATCTTGATT
TCATTGTCTTCGCTTTCCTTCTAAATCTGTCCCTTCTA
GGGAGCTATTGGGATTAAGTGGTCATTGATTATTATA
CTTTATTCAGTAATGTTTCTGACCCTTTCCTTCAGTGC
TACTTGAGTTAATTAAGGATTAATGAACAGTTACATT
TCCAAGCATTAGCTAATAAACTAAAGGATTTTGCACTT
TTCTTCACTGACCATTAGTTAGAAAGAGTTCAGAGAT
AAGTATGTGTATCTTTCAATTTCAGCAAACCTAATTTT
TTAAAAAAAGTTTTACATAGGAAATATGTTGGAAATG
ATACTTTACAAAGATATTCATAATTTTTTTTTGTAATC
AGCTACTTTGTATATTTACATGAGCCTTAATTTATAT
TTCTCATATAACCATTTATGAGAGCTTAGTATACCTGT
GTCATTATATTGCATCTACGAACTAGTGACCTTATTC
CTTCTGTTACCTCAAACAGGTGGCTTTCCATCTGTGAT
CTCCAAAGCCTTAGGTTGCACAGAGTGACTGCCGAGC
TGCTTTATGAAGGGAGAAAGGCTCCATAGTTGGAGTGT
TTTTTTTTTTTTTTAAACATTTTCCCATCCTCCA
TCCTCTTGAGGGAGAATAGCTTACCTTTTATCTTGTTT
TAATTTGAGAAAGAAGTTGCCACCACTCTAGGTTGAA
AACCACTCCTTTAACATAATAACTGTGGATATGGTTTG
AATTTCAAGATAGTTACATGCCTTTTTATTTTTCCTA
ATAGAGCTGTAGGTCAAATATTATTAGAATCAGATTTC
TAAATCCCACCCAATGACCTGCTTATTTTAAATCAAA
TTCAATAATTAATTCTCTTCTTTTTGGAGGATCTGGAC
ATTCTTTGATATTTCTTACAACGAATTTCATGTGTAG
ACCCACTAAACAGAAGCTATAAAAGTTGCATGGTCAAA
TAAGTCTGAGAAAGTCTGCAGATGATATAATTCACCT
GAAGAGTCACAGTATGTAGCCAAATGTTAAAGGTTTG
AGATGCCATACAGTAAATTTACCAAGCATTTTCTAAA
TTTATTTGACCACAGAATCCCTATTTTAAGCAACAACT
GTTACATCCCATGGATTCCAGGTGACTAAAGAATACT
TATTTCTTAGGATATGTTTTATTGATAATAACAATTAA
AATTTCAGATATCTTTCATAAGCAAATCAGTGGTCTT
TTTACTTCATGTTTTAATGCTAAAATATTTTCTTTTAT
AGATAGTCAGAACATTATGCCTTTTTCTGACTCCAGC
AGAGAGAAAATGCTCCAGGTTATGTGAAGCAGAATCAT
CATTTAAATATGAGTCAGGGCTCTTTGTACAAGGCCT
GCTAAAGGTATAGTTTCTAGTTATCACAGTGGAAACCA
CTTTTCTAAAATCATTTTTGAGACTCTTTATAGACAA
ATCTTAAATATTAGCATTTAATGTATCTCATATTGACA
TGCCCAGAGACTGACTTCCTTTACACAGTTCTGCACA
TAGACTATATGTCTTATGGATTTATGTTAGTATCATC
AGTGAAACACCATAGAATACCCTTTGTGTTCCAGGTG
GGTCCCTGTTCCTACATGTCTAGCCTCAGGACTTTTTT
TTTTTTAACACATGCTTAAATCAGGTTGCACATCAAA
AATAAGATCATTCTTTTTAACTAAATAGATTTGAATT
TTATTGAAAAAAATTTTAAACATCTTTAAGAAGCTT
ATAGGATTTAAGCAATTCCTATGTATGTGTACTAAAAT
ATATATATTTCTATATATAATATATATATTAGAAAAAAA
TTGTATTTTTCTTTTATTTGAGTCTACTGTCAAGGAGC
AAAACAGAGAAATGTAAATTAGCAATTATTTATAATA
CTTAAAGGGAAGAAAGTTTGTTCACCTTGTTGAATCTAT
TATTGTTATTTCAATTATAGTCCCAAGACGTGAAGAA
ATAGCTTTCCTAATGGTTATGTGATTGTCTCATAGTGA
CTACTTTCTTGAGGATGTAGCCACGGCAAAATGAAAT
AAAAAAATTTAAAAATTGTTGCAAATACAAGTTATATT
AGGCTTTTGTGCATTTTCAATAATGTGCTGCTATGAA
CTCAGAATGATAGTATTTAAATATAGAAACTAGTTAAA
GGAAACGTAGTTTCTATTTGAGTTATACATATCTGTA
AATTAGAACTTCTCCTGTTAAAGGCATAATAAAGTGCT
TAATACTTTTGTTTCCTCAGCACCCTCTCATTTAATT
ATATAATTTTAGTTCTGAAAGGGACCTATACCAGATGC
CTAGAGGAAATTTCAAAACTATGATCTAATGAAAAAA
TATTTAATAGTTCTCCATGCAAATACAAATCATATAGT
TTTCCAGAAATACCTTTGACATTATACAAAGATGAT
TATCACAGCATTATAATAGTAAAAAAATGGAAATAGCC
TCTTTCTTCTGTTCTGTTCATAGCACAGTGCCTCATA
CGCAGTAGGTTATTATTACATGGTAACTGGCTACCCCA
ACTGATTAGGAAAGAAGTAAATTTGTTTTATAAAAAT
ACATACTCATTGAGGTGCATAGAATAATTAAGAAATTA
AAAGACACTTGTAATTTTGAATCCAGTGAATACCCAC
TGTTAATATTTGGTATATCTCTTTCTAGTCTTTTTTTC
CCTTTTGCATGTATTTTCTTTAAGACTCCCACCCCCA
CTGGATCATCTCTGCATGTTCTAATCTGCTTTTTTCAC
AGCAGATTCTAAGCCTCTTTGAATATCAACACAAACT
TCAACAACTTCATCTATAGATGCCAAATAATAAATTCA
TTTTTATTTACTTAACCACTTCCTTTGGATGCTTAGG
TCATTCTGATGTTTTGCTATTGAAACCAATGCTATACT
GAACACTTCTGTCACTAAAACTTTGCACACACTCATG
AATAGCTTCTTAGGATAAATTTTTAGAGATGGATTTGC
TAAATCAGAGACCATTTTTAAAATTAAAAACAATT
ATTCATATCGTTTGGCATGTAAGACAGTAAATTTTCCT
TTTATTTTGACAGGATTCAACTGGAAGCTTTGTGCTG
CCTTTCCGGCAAGTCATGTATGCTCCATATCCCACCAC
ACACATAGATGTGGATGTCAATACTGTGAAGCAGATG
CCACCCTGTCATGAACATATTTATAATCAGCGTAGATA
CATGAGATCCGAGCTGACAGCCTTCTGGAGAGCCACT
TCAGAAGAAGACATGGCTCAGGATACGATCATCTACAC
TGACGAAAGCTTTACTCCTGATTTGTACGTAATGCTC
TGCCTGCTGGTACTGTAGTCAAGCAATATGAAATTGTG
TCTTTTACGAATAAAAACAAAACAGAAGTTGCATTTA
AAAAGAAAGAAATATTACCAGCAGAATTATGCTTGAAG
AAACATTTAATCAAGCATTTTTTCTTAAATGTTCTT
CTTTTTCCATACAATGTGTTTACCCTAAAATAGGTAA
GATTAACCCTTAAAGTAAATATTTAACTATTTGTTTA
ATAAATATATATTGAGCTCCTAGGCACTGTTCTAGGTA
CCGGGCTTAATAGTGGCCAACCAGACAGCCCCAGCCC
CAGCCCCTACATTGTGTATAGTCTATTATGTAACAGTT
ATTGAATGGACTTATTAACAAACCAAAGAAGTAATT
CTAAGTCTTTTTTTTCTTGACATATGAATATAAAATAC
AGCAAAACTGTTAAAATATATTAATGGAACATTTTTT
TACTTTGCATTTTATTTGTTATTCACTTCTTATTTTT
TTTTAAAAAAAAAAGCCTGAACAGTAAATTCAAAAGG
AAAAGTAATGATAATTAATTGTTGAGCATGGACCCAAC
TTGAAAAAAAAAATGATGATGATAAATCTATAATCCT
AAAACCCTAAGTAAACACTTAAAAGATGTTCTGAAATC
AGGAAAAGAATTATAGTATACTTTTGTGTTTCTCTTT
TATCAGTTGAAAAAGGCACAGTAGCTCATGCCTGTAA
GAACAGAGCTTTGGGAGTGCAAGGCAGGCGGATCACT
TGAGGCCAGGAGTTCCAGACCAGCCTGGGCAACATAGT
GAAACCCCATCTCTACAAAAAATAAAAAAGAATTATT
GGAATGTGTTTCTGTGTGCCTGTAATCCTAGCTATTCC
GAAAGCTGAGGCAGGAGGATCTTTTGAGCCCAGGAGT
TTGAGGTTACAGGGAGTTATGATGTGCCAGTGTACTCC
AGCCTGGGGAACACCGAGACTCTGTCTTACTTTAAAA
AAAAAAAAAAAAGCTTGCAATAATGCCTGGCACAT
AGAAGGTAACAGTAAGTGTTAACTGTAATAACCCAGG
TCTAAGTGTGTAAGGCAATAGAAAAATTGGGGCAAATA
AGCCTGACCTATGCTATCACAGAATCAGTTTGAGCTT
AGGTAACAGACCTGTGGAGCACCAGTAATTACACAGTA
AGTGTTAACCAAAAGCATAGAATAGGAATATCTTGTT
CAAGGGACCCCCAGCCTTATACATCTCAAGGTGCAGAA
AGATGACTTAATATAGGACCCATTTTTTCCTAGTTCT
CCAGAGTTTTTATTGGTTCTTGAGAAAGTAGTAGGGGA
ATGTTTAGAAAATGAATTGGTCAACTGAAATTACA
TGTCAGTAAGTTTTTATATATTGGTAAATTTAGTAGA
CATGTAGAAGTTTTCTAATTAATCTGTGCCTTGAAAC
ATTTTCTTTTTTCCTAAAGTGCTTAGTATTTTTTCCGT
```

-continued

TTTTTGATTGGTTACTTGGGAGCTTTTTTGAGGAAAT
TTAGTGAACTGCAGAATGGGTTTGCAACCATTTGGTAT
TTTTGTTTTGTTTTTTAGAGGATGTATGTGTATTTTA
ACATTTCTTAATCATTTTTAGCCAGCTATGTTTGTTTT
GCTGATTTGACAAACTACAGTTAGACAGCTATTCTCA
TTTTGCTGATCATGACAAAATAATATCCTGAATTTTTA
AATTTTGCATCCAGCTCTAAATTTTCTAAACATAAAA
TTGTCCAAAAAATAGTATTTTCAGCCACTAGATTGTGT
GTTAAGTCTATTGTCACAGAGTCATTTTACTTTTAAG
TATATGTTTTTACATGTTAATTATGTTTGTTATTTTA
ATTTTAACTTTTTAAAATAATTCCAGTCACTGCCAAT
ACATGAAAAATTGGTCACTGGAATTTTTTTTTGACTT
TTATTTTAGGTTCATGTGTACATGTGCAGGTGTGTTA
TACAGGTAAATTGCGTGTCATGAGGGTTTGGTGTACAG
GTGATTTCATTACCCAGGTAATAAGCATAGTACCCAA
TAGGTAGTTTTTTGATCCTCACCCTTCTCCCACCCTCA
AGTAGGCCCTGGTGTTGCTGTTTCCTTCTTTGTGTCC
ATGTATACTCAGTGTTTAGCTCCCACTTAGAAGTGAGA
ACATGCGGTAGTTGGTTTTCTGTTCCTGGATTAGTTC
ACTTAGGATAATGACCTCTAGCTCCATCTGGTTTTTAT
GGCTGCATAGTATTCCATGGTGTATATGTATCACATT
TTCTTTATCCAGTCTACCATTGATAGGCATTTAGGTTG
ATTCCCTGTCTTTGTTATCATGAATAGTGCTGTGATG
AACATACACATGCATGTGTCTTTATGGTAGAAAAATTT
GTATTCCTTTAGGTACATATAGAATAATGGGGTTGCT
AGGGTGAATGGTAGTTCTATTTTCAGTTATTTGAGAAA
TCTTCAAACTGCTTTTCATAATAGCTAAACTAATTTA
CAGTCCCGCCAGCAGTGTATAAGTGTTCCCTTTTCTCC
ACAACCTTGCCAACATCTGTGATTTTTTGACTTTTTA
ATAATAGCCATTCCTAGAGAATTGATTTGCAATTCTCT
ATTAGTGATATTAAGCATTTTTTCATATGCTTTTTAG
CTGTCTGTATATATTCTTCTGAAAAATTTTCATGTCCT
TTGCCCAGTTTGTAGTGGGGTGGGTTGTTTTTTGCTT
GTTAATTAGTTTTAAGTTCCTTCCAGATTCTGCATATC
CCTTTGTTGGATACATGGTTTGCAGATATTTTCTCC
CATTGTGTAGGTTGTCTTTTACTCTGTTGATAGTTTCT
TTTGCCATGCAGGAGCTCGTTAGGTCCCATTTGTGTT
TGTTTTTGTTGCAGTTGCTTTTGGCGTCTTCATCATAA
AATCTGTGCCAGGGCCTATGTCCAGAATGGTATTTCC
TAGGTTGTCTTCCAGGGTTTTTACAATTTTAGATTTTA
CGTTTATGTCTTTAATCCATCTTGAGTTGATTTTTGT
ATATGGCACAAGGAAGGGGTCCAGTTTCACTCCAATTC
CTATGGCTAGCAATTATCCCAGCACCATTTATTGAAT
ACGGAGTCCTTTCCCCATTGCTTGTTTTTTGTCAACTT
TGTTGAAGATCAGATGGTTGTAAGTGTGTGGCTTTAT
TTCTTGGCTCTCTATTCTCCATTGGTCTATGTGTCTGT
TTTTATAACAGTACCCTGCTGTTCAGTTCCTATAGC
CTTTTAGTATAAAATCGGCTAATGTGATGCCTCCAGCT
TTGTTCTTTTTGCTTAGGATTGCTTTGGCTATTTGGG
CTCCTTTTTGGGTCCATATTAATTTTAAAACAGTTTTT
TCTGGTTTTGTGAAGGATATCATTGGTAGTTTATAGG
AATAGCATTGAATCTGTAGATTGCTTTGGGCAGTATGG
CCATTTTAACAATATTAATTCTTCCTATCTATGAATA
TGGAATGTTTTTCCATGTGTTTGTGTCATCTCTTTATA
CCTGATGTATAAAGAAAAGCTGGTATTATTCCTACTC
AATCTGTTCCAAAAAATTGAGGAGGAGGAACTCTTCCC
TAATGAGGCCAGCATCATTCTGATACCAAAACCTGGC
AGAGACACAACAGAAAAAGAAAACTTCAGGCCAATAT
CCTTGATGAATATAGATGCAAAAATCCTCAACAAAAT
ACTAGCAAACCAAATCCAGCAGCACATCAAAAAGCTGA
TCTACTTTGATCAAGTAGGCTTTATCCCTGGGATGCA
AGGTTGGTTCAACATACACAAATCAATAAGTGTGATTC
ATCACATAAACAGAGCTAAAAACAAAAACCAACAAGAT
TATCTCAATAGGTAGAGAAAAAGGTTGTCAATAAAATTT
AACATCCTCCATGTTAAAAACCTTCAGTAGGTCAGGT
GTAGTGACTCACACCTGTAATCCCAGCACTTTGGGAGG
CCAAGGCGGGCATATCTCTTAAGCCCAGGAGTTCAAG
ACGAGCCTAGGCAGCATGGTAGAACCCCATCTCTACA
AAAAAAAAAAAAAAAAAATTAGCTTGGTATGGTGAC
ATGCACCTATAGTCCCAGCTATTCAGGAGGTTGAGGTG
GGAGGATTGTTTGAGCCCGGGAGGCAGAGGTTGGCAG
CGAGCTGAGATCATGCCACCGCACTCCAGCCTGGGCAA
CGGAGTGAGACCCTGTCTCAAAAAAGAAAAATCACAA
ACAATCCTAAACAAACTAGGCATTGAAGGAACATGCCT
CAAAAAAATAAGAACCATCTATGACAGACCCATAGCC
AATATCTTACCAAATGGGCAAAAGCTGGAAGTATTCTC
CTTGAGAACCGTAACAAGACAAGGATGTCCACTCTCA
CCACTCCTTTTCAGCATAGTTCTGGAAGTCCTAGCCAG
AGCAATCAGGAAAGAGAAAGAAAGAAAGACATTCAGA
TAGGAAGAGAAGAAGTCAAACTATTTCTGTTTGCAGGC
AGTATAATTCTGTACCTAGAAAATCTCATAGTCTCTG

-continued

CCCAGAAACTCCTAAATCTGTTAAAAATTTCAGCAAAG
TTTTGGCATTCTCTATACTCCAACACCTTCCAAAGTG
AGAGCAAAATCAAGAACACAGTCCCATTCACAATAGCC
GCAAAACGAATAAAATACCTAGGAATCCAGCTAACCA
GGGAGGTGAAAGATCTCTATGAGAATTACAAAACACTG
CTGAAAGAAATCAGAGATGACACAAACAAATGGAAAT
GTTCTTTTTTAACACCTTGCTTTATCTAATTCACTTAT
GATGAAGATACTCATTCAGTGGAACAGGTATAATAAG
TCCACTCGATTAAATATAAGCCTTATTCTCTTTCCAGA
GCCCAAGAAGGGGCACTATCAGTGCCCAGTCAATAAT
GACGAAATGCTAATATTTTTCCCCTTTACGGTTTCTTT
CTTCTGTAGTGTGGTACACTCGTTTCTTAAGATAAGG
AAACTTGAACTACCTTCCTGTTTGCTTCTACACATACC
CATTCTCTTTTTTGCCACTCTGGTCAGGTATAGGAT
GATCCCTACCACTTTCAGTTAAAACTCCTCCTCTTAC
TAAATGTTCTCTTACCCTCTGGCCTGAGTAGAACCTA
GGGAAAATGGAAGAGAAAAAGATGAAAGGGAGGTGGGG
CCTGGGAAGGGAATAAGTAGTCCTGTTTGTTTGTGTG
TTTGCTTTAGCACCCTGCTATATCCTAGGTGCTGTGTTA
GGCACACATTATTTTAAGTGGCCATTATATTACTACT
ACTCACTCTGGTCGTTGCCAAGGTAGGTAGTACTTTCT
TGGATAGTTTGTTCATGTTACTTACAGATGGTGGGCT
TGTTGAGGCAAACCCAGTGGATAATCATCGGAGTGTGT
TCTCTAATCTCACTCAAATTTTTCTTCACATTTTTTG
GTTTGTTTTGGTTTTTGATGGTAGTGGCTTATTTTGT
TGCTGGTTTGTTTTTGTTTTTTTTTTGAGATGGCAAG
AATTGGTAGTTTTATTTATTAATTGCCTAAGGGTCTCT
ACTTTTTTTAAAAGATGAGAGTAGTAAAATAGATTGA
TAGAGACATACATACCCTTACTGGGGACTGCTTATATT
CTTTAGAGAAAAAATTACATATTAGCCTGACAAACAC
CAGTAAAATGTAAATATATCCTTGAGTAAATAAATGAA
TGTATATTTTGTGTCTCCAAATATATATATCTATATT
CTTACAAATGTGTTTATATGTAATATCAATTTATAAGA
ACTTAAAATGTTGGCTCAAGTGAGGGATTGTGGAAGG
TAGCATTATATGGCCATTTCAACATTTGAACTTTTTC
TTTTTCTTCATTTTCTTCTTTTCTTCAGGAATATTTTT
CAAGATGTCTTACACAGAGACACTCTAGTGAAAGCCTT
CCTGGATCAGGTAAATGTTGAACTTGAGATTGTCAGA
GTGAATGATAGCACATGTTTTCTTTTTTAATATATCCT
ACAATGCCTGTTCTATATATTTATATTCCCCTGGATC
ATGCCCCAGAGTTCTGCTCAGCAATTGCAGTTAAGTTA
GTTACACTACAGTTCTCAGAAGAGTCTGTGAGGGCAT
GTCAAGTGCATCATTACATTGGTTGCCTCTTGTCCTAG
ATTTATGCTTCGGGAATTCAGACCTTTGTTTACAATA
TAATAAATATTATTGCTATCTTTTAAAGATATAATAAT
AAGATATAAAGTTGACCACAACTACTGTTTTTTGAAA
CATAGAATTCCTTGGTTTCATGTATCAAAGTGAAATCT
GACTTAGCTTTTACAGATATAATATACACATATATAT
ATCCTGCAATGCTTGTACTATATATGTAGTACAAGTAT
ATATATATGTTTGTGTGTATATATATATAGTACGA
GCATATATACATATTACCAGCATTGTAGGATATATATA
TGTTTATATATTAAAAAAAAGTTATAAACTTAAAACC
CTATTATGTTATGTAGAGTATATGTTATATATGATATG
TAAAATATATAACATATACTCTATGATAGAGTGTAAT
ATATTTTTTATATATATTTAACATTTATAAAATGATA
GAATTAAGAATTGAGTCCTAATCTGTTTTATTAGGTG
CTTTTTTGTAGTGTCTGGTCTTTCTAAAGTGTCTAAATG
ATTTTTCCTTTTGACTTATTAATGGGGAAGAGCCTGT
ATATTAACAATTTGAAGTTGCAGCATTCCATACGTCAAA
CAACAAACATTTTAATTCAAGCATTAACCTATAACAA
GTAAGTTTTTTTTTTTTTTTGAGAAAGGGAGGTTGTT
TATTTGCCTGAAATGACTCAAAAATATTTTTGAAACA
TAGTGTACTTATTTAAATAACATCTTTATTGTTTCATT
CTTTTAAAAAATATCTACTTAATTACACAGTTGAAGG
AAATCGTAGATTATATGGAACTTATTTCTTAATATATT
ACAGTTGTTATAATAACATTCTGGGGATCAGGCCAG
GAAACTGTGTCATAGATAAAGCTTTGAAATAATGAGAT
CCTTATGTTTTACTAGAAATTTTGGATTGAGATCTATG
AGGTCTGTGACATATTGCGAAGTTCAAGGAAATTCGT
AGGCCTGGAATTTCATGCTTCTCAAGCTGACATAAAA
TCCCTCCCACTCTCCACCTCATCATATGCACACATTCT
ACTCCTACCCACCCACTCCACCCCCCTGCAAAAGTACA
GGTATATGAATGTCTCAAAACCATAGGCTCATCTTCTA
GGAGCTTCAATGTTATTTGAAGATTTGGGCAGAAAAA
ATTAAGTAATACGAAATAACTTATGTATGAGTTTTAAA
AGTGAAGTGAAACTAGTTCTGAAGTAGAATGC
AAAATTTGAATGCATTTTTAAAGATAAATTAGAAACT
TCTAAAAACTGTCAGATTGTCTGGGCCTGGTGGCTTA
TGCCTGTAATCCCAGCACTTTGGGAGTCCGAGGTGGGT
GGATCACAAGGTCAGGAGATCGAGACCATCCTGCCAA
CATGGTGAAACCCCGTCTCTACTAAGTATACAAAAATT

-continued

AGCTGGGCGTGGCAGCGTGTGCCTGTAATCCCAGCTA
CCTGGGAGGCTGAGGCAGGAGAATCGCTTGAACCCAGG
AGGTGTAGGTTGCAGTGAGTCAAGATCGCGCCACTGC
ACTTTAGCCTGGTGACAGAGCTAGACTCCGTCTCAAAA
AAAAAAAAAAATATCAGATTGTTCCTACACCTAGTGC
TTCTATACCACACTCCTGTTAGGGGGCATCAGTGGAAA
TGGTTAAGGAGATGTTTAGTGTGTATTGTCTGCCAAG
CACTGTCAACACTGTCATAGAAACTTCTGTACGAGTAG
AATGTGAGCAAATTATGTGTTGAAATGGTTCCTCTCC
CTGCAGGTCTTTCAGCTGAAACCTGGCTTATCTCTCAG
AAGTACTTTCCTTGCACAGTTTCTACTTGTCCTTCAC
AGAAAAGCCTTGACACTAATAAAATATATAGAAGACGA
TACGTGAGTAAAACTCCTACACGGAAGAAAAACCTTT
GTACATTGTTTTTTGTTTTGTTTCCTTTGTACATTTT
CTATATCATAATTTTTGCGCTTCTTTTTTTTTTTTT
TTTTTTTTTTTCCATTATTTTAGGCAGAAGGGAAAA
AAGCCCTTTAAATCTCTTCGGAACCTGAAGATAGACC
TTGATTTAACAGCAGAGGGCGATCTTAACATAATAATG
GCTCTGGCTGAGAAAATTAAACCAGGCCTACACTCTT
TTATCTTTGGAAGACCTTTCTACACTAGTGTGCAAGAA
CGAGATGTTCTAATGACTTTTTAAATGTGTAACTTAA
TAAGCCTATTCCATCACAATCATGATCGCTGGTAAAGT
AGCTCAGTGGTGTGGGGAAACGTTCCCCTGGATCATA
CTCCAGAATTCTGCTCTCAGCAATTGCAGTTAAGTAAG
TTACACTACAGTTCTCACAAGAGCCTGTGAGGGGATG
TCAGGTGCATCATTACATTGGGTGTCTCTTTTCCTAGA
TTTATGCTTTTGGGATACAGACCTATGTTTACAATAT
AATAAATATTATTGCTATCTTTTAAAGATATAATAATA
GGATGTAAACTTGACCACAACTACTGTTTTTTTGAAA
TACATGATTCATGGTTTACATGTGTCAAGGTGAAATCT
GAGTTGGCTTTTACAGATAGTTGACTTTCTATCTTTT
GGCATTCTTTGGTGTGTAGAATTACTGTAATACTTCTG
CAATCAACTGAAAACTAGAGCCTTTAAATGATTTCAA
TTCCAACAGAAAGAAAGTGAGCTTGAACATAGGATGAGC
TTTAGAAAGAAAATTGATCAAGCAGATGTTTAATTGG
AATTGATTATTAGATCCTACTTTGTGGATTTAGTCCCT
GGGATTCAGTCTGTAGAAATGTCTAATAGTTCTCTAT
AGTCCTTGTTCCTGGTGAACCACAGTTAGGGTGTTTG
TTTATTTTATTGTTCTTGCTATTGTTGATATTCTATG
TAGTTGAGCTCTGTAAAAGGAAATTGTATTTTATGTTT
TAGTAATTGTTGCCAACTTTTTAAATTAATTTTCATT
ATTTTTTGAGCCAAATTGAAATGTGCACCTCCTGTGCCT
TTTTCTCCTTAGAAAATCTAATTACTTGGAACAAGT
TCAGATTTCACTGGTCAGTCATTTTCATCTTGTTTTCT
TCTTGCTAAGTCTTACCATGTACCTGCTTTGGCAATC
ATTGCAACTCTGAGATTATAAAATGCCTTAGAGAATAT
ACTAACTAATAAGATCTTTTTTTAGACAACCACTGAAC
AGTTCCTTGAGTACTTCCTTCTTGCATTTCTGCCTATG
TTTTTGAAGTGTTGCTGTTTGCCTGCAATAGGCTAT
AAGGAATAGCAGGAGAAATTTTACTGAAGTGCTGTTTT
CCTAGGTGCTACTTTGGCAGAGCTAAGTTATCTTTTG
TTTTCTTAATGCGTTTGGACCATTTTGCTGGCTATAAA
ATAACTGATTAATATAATTCTAACACAATGTTGACAT
TGTAGTTACACAAACACAAATAAATATTTTATTTAAA
TTCTGGAAGTAATATAAAAGAAAATATATTTATAA
GAAAGGGATAAAGGTAATAGAGCCCTTCTGCCCCCCAC
CCACCCAAATTTACACAACAAAATGACATGTTCGAATG
TGAAAGGTCATAATAGCTTTCCCATCATGAATCAGAAA
GATGTGGACAGCTTGATGTTTTAGACAACCACTGAAC
TAGATGACTGTTGTACTGTAGCTCAGTCATTTAAAAAA
TATATAAATACTACCTTGTAGTGTCCCATACTGTGTT
TTTTACATGGTAGATTCTTATTTAAGTGCTAACTGGTT
ATTTTCTTTGGCTGGTTTATTGTACTGTTATACAGAA
TGTAAGTTGTACAGTGAATAAGTTATTAAAGCATGTG
TAAACATTGTTATATATCTTTTCTCCTAAATGGAGAA
TTTTGAATAAAATATATTTGAAATTTTGCCTCTTTCAG
TTGTTCATTCAGAAAAAAATACTATGATATTTGAAGA
CTGATCAGCTTCTGTTCAGCTGACAGCATGCTGGATC
TAAACTTTTTTTAAAATTAATTTTGTCTTTTCAAAGA
AAAAATATTTAAGAAGCTTTATAATATAATCTTATGT
TAAAAAAACTTTCTGCTTAACTCTCTGGATTTCATTT
TGATTTTTCAAATTATATATTAATTCAAATGTAAA
ATACTATTTAGATAAATTGTTTTTAAACATTCTTATT
ATTATATAATTAATATAACCTAAACTGAAGTTATTCAT
CCCAGGTATCTAATACATGTATCCAAAGTAAAAATCC
AAGGAACTCGAACACTTTCATCTGCAAAGCTAGGAATA
GGTTTGACATTTTCACTCCAAGAAAAAGTTTTTTTTT
GAAAATAGAATAGTTGGGATGAGAGGGTTTCTTTAAAG
AAGACTAACTGATCACATTACTATGATTCTCAAAGAA
GAAACCAAAACTTCATATAATACTATAAAGTAAATATA
AAATAGTTCCTTCTATAGTATATTTCTATAATGCTAC

-continued

AGTTTAAACAGATCACTCTTATATAATAATACTATTTTGAT
TTTGATGTAGAATTGCACAAATTGATATTTCTCCTAT
GATCTGCAGGGTATAGCTTAAAGTAACAAAAACAGTCA
ACCACCTCCATTTAACACACAGTAACACTATGGGACT
AGTTTTTATTACTTCCATTTTACAAATGAGGAAACTAAA
GCTTAAAGATGTGTAATACACCGCCCAAGGTCACACA
GCTGGTAAAGGTGGATTTCATCCCAGACAGTTACAGTC
ATTGCCATGGGCACAGCTCCTAACTTAGTAACTCCAT
GTAACTGGTACTCAGTGTAGCTGAATTGAAAGGAGAGT
AAGGAAGCAGGTTTTACAGGTGTCTACTTGCACTATTCA
GAGCCCGAGTGTGAATCCCTGCTGTGCTGCTTGGAGAA
GTTACTTAACCTATGCAAGGTTCATTTTGTAAATATT
GGAAATGGAGTGATAATACGTACTTCACCAGAGGATTT
AATGAGACCTTATACGATCCTTAGTTCAGTACCTGAC
TAGTGCTTCATAAATGCTTTTTCATCCAATCTGACAAT
CTCCAGCTTGTAATTGGGGCATTTAGAACATTTAATA
TGATTATTGGCATGGTAGGTTAAAGCTGTCATCTTGCT
GTTTTCTATTTGTTCTTTTTGTTTTCTCCTTACTTTT
GGATTTTTTTATTCTACTATGTCTTTTCTATTGTCTTA
TTAACTATACTCTTTGATTTATTTTAGTGGTTGTTTT
AGGGTTATACCTCTTTCTAATTTACCAGTTTATAACCA
GTTTATATACTACTTGACATATAGCTTAAGAAACTTA
CTGTTGTTGTCTTTTTGCTGTTATGGTCTTAACGTTTT
TATTTCTACAAACATTATAAACTCCACACTTTATTGT
TTTTTTAATTTTACTTATACAGTCAATTATCTTTTAAAG
ATATTTAAATATAAACATTCAAAACACCCCAATTAAA
AGTCAGAGATTGTTAATACCACATGATCTCACTTACAC
ACAGAATTGAAAAACTTGGAACTCATAGAAGCAGAGA
GTAAAAACATGGTTACCAGGTGCTGGGGAGAGGCGGTG
GGCTGGGGAGATGTTGGTCAAAGTTAGACAGGAGGAA
TAAGTTCAAGAGATCTATTGTACAACTTATTCAGTTAG
ATAGGAGGAATAAGCTAAAGATCAAGAGATCTATTGT
ACAATGTGACTATAACCAACAACATATATTGTACACTT
GAAAATTGCTAACAGTATCTTTTAAGTGTTCTCTCTA
CAAATAAATATGTGAGGTAATGTATATATATTAATTAACT
GTAGTCATTTCACAATGTATACTTATTTCAAACATC
ATATTGTATGCTATAAATATATACAACTTTTATTTTTC
AATTTTAGAAATGTCCTTAAAAAATCAGATTTTCAGA
TCAGATAAAAAAGCAAGACCCAACTATATGCTGCAAC
AGGAAACACACCTTAAAAATAAAGGACGAACAAACAG
ATTAAAAGTAAAAGGATGGAGAAAAGATACATCATATT
GGTAATTAGAAGAAAACTGGAGTGACAATATGAAACA
AAATAGATTTCAGAGCAAAGAAATATTACCAGGGGTAAA
AATGATCATTTTATAATGATAAAAGAGTCAGTTCAGC
AAAAGGATATAACAGTCCTAAATGTTTTTTCACCTCAT
AGCTGTGTCAAAATAGATGAAGCAAAAACTGATAGAA
CTGTAAGAAGTAGACAAGTCCACAATTATGTTTGGAGA
TTTTTTTTTTTTTTTTTTTTGTCGCCCAGGCTGGAGT
GCAGTGGCAGGATCTCAGCTCACTGCAAGCTCCGCCTC
CCAGGTTCACGCCATTCTCCTGCTTCAGCCTCCCCAG
TAGCTGGGACTACAGGCGGCCACCACCACGCCTGGCTA
ATTTTTTTGTATTTTTAGTAGAGACGGGGTTTCACCG
TGTTAGCCAGGATGGTCTCGATCTCCTGACCTCGTGAT
CTGCCTGCCTCGGCCTCCCAAAGTGCTGGGATTACAG
GCATGAGCCACTGCACGCCAGCCTGGAGATTTTTAATATC
CTTTCAATGTTTAGTAGAACAAGAATACACAAAATCA
GTAAGGATATAGAAGATTAGAACAAGACTATCAAACAA
TTTGACTTAAATGACATTTGTAGAGCACAGCAGTCCC
CAACAACAATAAATCACAACATTCTTTCCAAGAGTACAT
GAAACATGTACCAAGATAGACCCGTATTTTGAGCCATG
AAACAAATCTTGATAAATTTAAAAGGATTCAAGTCATA
GAAAATATGTTCTCTGACCACAATGGAATTAAATTAT
TAACCAATAACAAATATCTGGGAAACCTCAAAAACTT
GGACACCAGCGCTTTTAAAAGACTAAATAATTTCTAA
ATTACTCTGTGTGGGGGAAAAGAAATGGATTAGAG
AGCAAAAGGGTATCAGAGTGCTGTGGTACGATTTTT
ATGAAGAGTGGAACAGAATCTGCCTTTGGCGTTTCCCC
ACTACAGCCCATTCTTCACATTGAAAGAACACATGATC
CTTCTAAAATTAAATCTAACGATCACTTCTGCTTAATG
GCTCTCCAACACTTACAGAATTAGGTCCAAAATTCTA
GCACAGTTTCTGTTCATCTTTCTAACCTTTCTTCCCAC
AGGTCTAGCTAGTACGTATTTCTTTTATTGCATTTAT
TACACTATTCCTTTGCTTATCTATCTCCCCACCTAGGC
TAAAGAACAAGATTCTTGTCTTTTTCATTTTTGTGTC
TCAGTGCCTAGCATGGTGCCAGGCACACAGCATGCTTC
CAGTAAATGTTAGCTGGGATGATGTAATGAGTATATT
AAATATTAATTTATTTGTTTTTCCCCAAAAAGAATTAT
TTCCTGCAAATCAAGGAAATTGCTTTCTTTATATAAT
CAAAAACTTATTTTCCCAGAAGATTCTTCATTAAAAAT
TAAGCCTATGCACAACCTAGCTCTAAAGTTTCAAAGA
TTTTAGGCAGCAATTTTTCAATCTTTTTGAAGTAATAC

```
ATTTGAATCTTTTCAAATTTCTGTTTCTGCATTTGTG
CCACACCATCTCATCTCTTGCTGAAATGTTTTTGTTAA
ATTAATTGCTTGATAAATTGCTAAGTACTTTTCATCA
GACCAATTAGGACAATAGTAAGTATCCATCTGTGGAGC
GCGGACATTCAAGAAATCTGATCCAGTATTTAGAAAG
TCATTCCTGAGCTGAGTTGGCTCAAACTGGCACCTTCT
GGCATTTGCTTGTGGGTGGGGAATGTGGAATGCTTTG
AAAGCTGAATGAGTTTGTCAAGTTTTAAAATTCCCTTA
TGGCTAAAGGAAAACAACATTCATTGTTTAAAAACAC
CATTGTTTGTTTTTTCTGCTTTTTTGTTCTTTGGAGCC
TGAATCTGCAAAAACACTCACACCCAGCATTTTGCTT
CATGTACCACTCCTAAGATGTTTTTAGAGACTTGAATA
GTGTCTCCGCACTACTTTTTATTGTGATTGTTCAGAA
TGTTCATAACAAATGGTAAAAAGTCAGTTTTAGTGCTC
AAATTGAGTTTTATGGAGAAAGACCATAATTTATGTT
TGTCATTGTAAATTGATAGGAGAATTTTTGGAAGTTTG
CGTCCTAGAACCAGATTTCCAAGGCTCAGATCCTTAT
TTTCTCACTTCCTAGCTGTGTGACCTTAGACAAGGTAT
TAAACCTGTCTGTGCTGCCTCAGTGTCCTCATCTATT
CTTTAAGAGTAAGAATAGAACCTACCCGATAGAGTCAC
TTGAAGATTAAGTGGGTTAGTAAATTCAGAATGCTTG
GAACAGTAACTAGCACAGAATAAGTGTCCAATAAAATT
GGGTTGCAGCTATTATCAGTATTATTCCTGTCATAAT
CATCATCACCATTAAGCAATTAAATGTAGAGTTCCAAA
ATTTGATTATGAAACTACAGTTATACAGCCATGATTC
CCGGTGATACCACGTCAGTAACAAGATTATTTCCTTAG
CTTGAGCCAGTCACTACCTCATTGCATGTGGCAGAGT
GTGTTGCCGTAGGCAAATGTCATTGTAGGGAATGAAAA
AAAAATTGCCTGTGAGCTGCTCTCCAGAGGCCTCATC
CCATTTTCCCATCGTCCACTTTACTCCATCTCCACTGC
CACTATTAGGACCTTATCATTTCTTGTCTAGATTAAT
TCAACAGCTTCTTCCTTCTAGTCTCCATGATTTCACC
CACTAGCCATCCCCTCCCCTTTGCCCAATTTTCTCCA
TTTATGGTAGAGTGATCTTTCTAATAGGAAACTCCTGA
CTTGCCTTAAAAAGCCCTCATTGAGGCCGGACGTGGT
GGCTCATGCCTGTAATCCCAGCACTTTGGGAGGCCGAG
GCAGGTGGATCACGAGGTCAAGAGATTGAGACCATCG
TGACTAACACAGTGAAACCCCATCTGTACTAAAAATAC
AAGAAATTAGCCAGGCGTGGTGGCGGGTGCCTGTAGT
CGCAGCTACTTGGGAGGCTGAGGCAGGAGAATGGCGTG
AACCCGGGAGGCAGAGCTTGCAGTGAGCCGAGATTGC
GCCACTGCACTCCAGCCTGGGCGACAGAGTGAGACTCC
GTCTCAAAAAAAAAAAGCCTCATTGACAACCTTCAA
CCCACAATCCATGGTGAAGCACAGGAGCCTTGGGGATC
TGCCCCCAGCACACCTCTCCACCCTTGTCTCTCACTG
CTCCTGCCTTCATGGAGAGCCCTGATGAACTATTTGTA
GTTTCCCCTGACTCACCTTGCTCATTGCTGGGCCTGTG
TGCGTGTTGCTCCCACTACCTGCAATACGCTTACCCAC
TTCACCTGGGTGAACTTTACTTAGGATTCACCTTAGG
TGGGCATCATGTTCTTCCAGGCCCCTCCTCTAACTTTT
AGTTGAGAGTATTCCAGACTTAAGGCTCCATGGGATA
GGGATCTTGTCTATGCACCAGCTTATTCCCAACTGCCT
GGCACGTAATGCATTTATTAAATATATATTGAATTGA
TTACCCTACTTGGGGCTCTTGTTTGCTTCTACACTTAC
AGTTCTAGCATAGCACTTAACTCATTATCATGCATCA
TTATTATGGGTTTGTTTTGTCTCCCATTAGACTGTGAG
CTCCACAAGGCTGTGTCCTTGTCTTATACATCATTGT
ATTTCCAGCTTCCAACATAGTGCTTGCCATGACACAGG
AAGTCAGTAAGCTCTGAATGAATGAATAGTATCTACA
TACCATTAATCTGAGGTTTAAAGTTTCCCCAAATTCTG
AAGCAAGGGGATTTACGGACTTCCCTGACAATTTTTG
GATGTCATCCCAATGATACCACTAACATTTTAAGGGAC
AGCTTGCATATATACATTTTTCTGGATGGCAGTTTTT
TTTCCCACAGGCTTCATCAGATATTTCTCCATAGCCTT
CCTCAGATTCTCAAAGGGGTCTCTGATTCCCCCAAAA
GATAAGAAACTGTCATAAAAAATTATTTCTAAATATCA
ATTGTTAAATAAATGTTTGCAAAGCAGCCTGATGAA
TCATTTCAGGCCACTTGACCCCAGTAGGTTAGAGAGTT
TGTGCTCTGCAATCTGACTGCTTCCAGCAGTCTCACT
GCTGCTGGACTGTGGCACTTCCAATTGGCAGCAGGGCA
AGTTTCTTCTGGATGAATATTCTGTCATAGGGGTCCC
CCTTCCACACATACCTGTAGGAGCAGTTTGAAACTCAT
ATGCATGGTCTTCCTGGTTCTAGGCACATGAGTCATT
TAAGCTGCTGGAGCCAGGACCAGCTAGTATGCTAGCCC
GGCATTCAGAAAGTTAAATTTGGGGTCAAAACTGAG
AACCTTCTTTGATCCACCTTGGCCAGCATTTTCTCTG
GCTTCCATTAATAGCCTCAACATTTTTTTTTTTCTG
GCCTAGACCCACACAGGCAAGAGACCAGAGCTTCTCTA
AGGAGCTAAGGGAAAGCACATTTTAAAAATAACTTGA
GCAAATGAATTCATCTGGCAAAAGCAACCCCACTACGT
AAAATAAACCTTTTTAGTTTCGCAATAGCAGTTCCTG

AAAATGTAAACAACCTCAGGGTCTACATGCACTGAATC
ATTTGCTGAACAGAAAGTCCCTGGTCCAAATTCTGCA
AGAATAAACACCTTACAAAACTAGGGGTCAATGACCTT
CATATGGGAACAAGGAGGGTGTGGGGGGCAGCAACCC
ACCCTGAGGACAATGAGAAAGTCTTGAGACTTGATATT
CAAAATGCTGGCTTTCTAAACCAAAAACTGGCATGAG
TGGAGGGAGAAGGGGAGGGTGGGCACAGTCTATGCCTC
AGGCTCTTGCTCAGACCCTACCAGGCCCCTGCCTTCC
CTAGGGAAAGCGAGAGTCTACTCACTGTCATGAAGCCA
GAGGAAGGCCCTGCAGGTTTCACTGTGTGTTCTGTTG
ACAAGATGATGGTTCCATTGAAACTGTAATAACATACT
TGGCCAACTAAGCCCATACGATCGTAGTAACTTTGTA
CCCAGTCCTAGCTTTTCAAACATAATGATAATATGTTC
TTTCTAATGTGGCCCATACTGTTCTAATGAACTTATG
CTGAGTTTTTCTGAGTACTAGAATAATATTCGCCATAA
ATAATAGATATAATTATTCTCATTTAATATTTGCGTA
GCTCTTCTTTAAAGCAGAAAGTATTTTCTCATTCCTTA
CTAGAACCTTTCTGTGTGAGGAGCACTGAGCTAGAAC
CCATATCTTAGAATGGTCAGAATTTTGGAGAAATTCAGG
GAAAAGGCACTGGACTCATTTTTAAAGACTAGAAAAT
GCAACCTCCAGAAAAAGATTCAAGAGTTTTTTACTCCC
AGAGATGTAGGAAAGATTGGAGTAAATCTTAATATTA
TATTTCAGGTAAACAAAGGATCACTGTCAAAATAGCAG
CATTTATTGAGTAATGGCTGTGTGCCAGGTACTTTAC
AGTTTCACATTTAACCCTCATAATAACCTTGTAAAGTG
GATATCCCTCAGTACATGATGAGAACACTGAAGCTT
AGGTTAAATGATTGTCCAAATCGGACAATCATTTTCAA
AATCTCCCCCTTTTTTTCTCCTTTCTTATCTGCAAGG
CAGATTGCCCTTTCCCTTTCAGTGAAACTTGTGCATGA
CCACATGACTCTCTTTGGCCAATGAAACATGAACAAG
CAGCGTTTATCACTTTCAGATGGAAGGCTTTGCATGAG
CTTTGCCTCCTTTTCACTCTGCCACAGTGGCCACTAA
CATTCCAGATAGTGGCGCTCTGCAGGCTAGGTCCTATA
GTGGGAGCTAGGTGAGGCCCCCTTTCCCACCCCCA
TCAAGATGTGCATGCTGCATAAGCCATGCATTAATCTT
TGCAGTTTTAAGCCACTAAGTTTTGGAGTTATATTAA
TCATTAATCATGGTTCTCAAGAGAAACAGAGTGGGGA
GTGGTATTCATTATGGGAATTGGCTTACATGATTATG
GAAGCTGAGTAGTCCCCCAGTCTGCTGTTTTTGAGCTG
GAGAACTAGAGGAGCCAGTGGTATAATTCAGCCCAAG
CCTGAAGGCCTGAGAAATGGGATGGGGGAATTGGGAGG
GTGGGTGTGCTAGGGTAGGATAAGTCCTGAAGTTCAA
AGGCCAGCCAGAAGGGTGGATGTTTCAGCACCAGAAGAG
AGAGCAAATTCGCTTTTCTTCTGCCTTTTTGTCCTCT
CTGGGCCCTCAATGGATTGGATGATGCCCTCCCACATT
GGTAAGGGTGGATCTTCTATACTCAGTCTGCTAATTT
CTTCCAGAAACATCTTCACAGACACATCCAGAAATAAT
GTTTTACCAGCTATCTCGGTATCCCTTAGCCTAGTCC
ATATTTAAAAATTAATGATCACAAGCAGTTGTTTGTTT
CCACAGCAAAACCTGGGTGACAGACCAAGTGACCCAG
ATGACTAGAATTTGACCTTCTTTTGTTGCCCACACCAT
ACTCTGAACTAACATGCTGTGCTGCCTTCCAAGTGGA
GAATGATGGCTAAGTATCTTCTACCTAATTTGAGTCAC
AGAAAAAAAAAAAAAAGGTTATTAACTGCAGTGACAA
GAATTGTGATTTCCCCAGGGGCAGATCAAGACTGATAG
ATAAGAGAAGTGAGGAACATCTGGGGAATGTCCATTG
AAAATTTACTCAGAAGAGAAGAATAATTAATATAATAA
TATGATATATTGAATTATAATAAATAATATTTTGATG
TATTTCCTTCCAGACATGTTTAAGTTATAGACTTTGAG
TATATTTTCTCAAAGGGGGTTCTATGTAAGAGACTAT
TTCTTAATATAGTTCCTAGCTTGGAATTGCTCTTGCTG
GTTTAAGCTGAGCTTATTTTATTACAGACTTCACAAC
AATAACGTTTTCCTTCACTAGTCAGTACACAAGATGGT
CTTCATTTTCCAGTTTGGAATCCCACCATTCAGAGCC
TGAGACAAGGCTAGTATGCAGTTAGTTTGTTTGGGAG
GTGATTCCAGGAAGTGGGAATGAGAGATCAGTCAGCC
TGCAACACGAAGGAGGAAAAGTCAATATAAGGATGAAT
TTGGCAATTGGCCGTTTCATGCAACTGGGGCTAAATT
TTGCTTGGCTCTCTAAGAAATGTAAAGAATGCCTCCCG
TAATTGCTCACCTCAAGTATTTATTCATTGGCTCTCA
TGCTCCATTGGTTGTCCATGAGAACTTTAGCCCTCCCT
CGCTGCGACGACCTGCTGCTTTCTCCTAGGCTGA
GCAAGCTCCTGCATCTGTGGAAACCGTCCCGGGGCAGA
TAGTGAAATAATGACTGCTGCGTGCTTGAGATCTGGG
AAAGAGGCCACATCATAAGTGCACTGAAATCAGAGATG
TGTCAAGAGATGTGACACAGGGCATCTGAGGTGTCTA
CTGCACCAGCTATAACTCCCTAAACGCTAATCTCAGTT
CTTACAGAGGGGATGGATGCAAGGGAACAGTCATGAT
TGAGAGCACCGAAGAAGCTCTGTATGAACCTTAGGCAA
GTTTCCTAATCTCCAAAATGAAGGTAATAATACCCAC
CATCCAAGATCTTCGGGAGGAATAGATGAACTAATGTA
```

```
TGTGAAAATGTCCAGCACAGGTCCTAACCCATAGTAG
GTGCTCACCAAATGTTAGTTCCCTGCCCTCCACGTTGT
GTGTATCCGGAGCTGCACTAGATGCTGAGGCAAATGG
TCTCAAATGTACTTTAACACTTAATGACTGAGATTTTT
TCTGAGCTGCCTACAGGTTATTGAACTATATTCATTAT
TAATAATAATATATATGGCCACTTCAGGCAACTGGGGC
TAAATTTTGCTTGGCTCTCTAAGAAATGTAAAGAATG
CCTCCTGTAATTGCTCACCTCAAGTATTTATTCATTGG
CTCTCGTGCTTTATTGGTTGTCCCTGAGGACTTTAGC
CCTCTCTCACTGCAGCACAGACACTGTGCTTTCTCCTA
GTTTCTGTGGCAAGTGACAGGAGCCCACCTCAAACTA
AAGCAAAAGGGACTTCATTGGCTCTTGTAGCTAGGAAT
TCCAGGGTTGGCACTGGCTTTGGGCACTACTGGATGC
AGGAATTCAAACAATGTCTTCAACTCTTTCTTTTGGTG
TTTCTCTCAGCTGTGCTTCTCTTGTCGTTTCTTTTTC
CCATTTTACAGATAAGTTCATCCGTAACTGAGAGAGGT
GAAAAGGGGATGGCTGCAGAGAACTCTGGCTTATATC
ATCCTTGCTTGCTGACCTCAAGGTCCATGTATAAATTC
TCAGAGAAGAAGCCCTCTGGTTGGTGATGCTTGGAAC
ATGCCCTGGAGGGTGGGCCCCTTGAAGTGGAGCTTGCT
GGAACCACATGGGCTGGAGCAAGGCGCTAGGGCCAGA
AGAGAGAGGTAGGCAGGGCTGCTGGCCAGGCACTCTTC
ACCAAGACAAGGCAAGAGGAGGGGCATGATTGAGGCA
GTGATACAGAAAGCAGACAGTAGAGGTCGTGGCAAGTG
TGCCGTTACTTGCTACCTGTGGTTGATGGGAGAGTCA
CACCACATTTAGGAGGAGAGAATCCATTTGCCACTTCT
GACAATGCCACAAGAATCACATATTTCATCCAGAGGT
TGAATTTGGCCCATGCTGAGCTTTAAAATACAGAGCTG
TCTTGGAACAATGGCTCAGTACATTCATTTGGTGTCC
AACAAAGCCTGCCTCTGTTGCCTTCCCTCTCTCTGTGT
GCCCTTCAAGATCTTCATTGTGCTTTGGGGAGAGAAA
GAGAAAATGTCATATCAGGGTAGCTCACCCCATGTGTC
CTGGACTCAGGAAAGAGTATCTTATCACCTTACTCT
TTTGTTATTATAAAAAATAAAGGTGTTAAGTCTTCAAAT
AAAAATAAAGAAGTATAGAAAAAATTTTAAATTAACCT
GTTATGATTCTACCTAGAGAACCATTGTCAACATCTTG
GTATATGTACTTCCAGATACTTTCCTATGAATATATA
CATTGTAGATTTTTTAATATTAAAAGGCTATCATGCTG
CTTTGTATACAGGCTTTCTTTACTGAATATGTAATATA
ATACACAGACAAATATACAAATCCTAAGCCATCAACTC
ATTGAATTTTATTCATTGTTTTTAATACCTGCATTG
TGTTCCATTGTTAGGCTATGTCACAACATATTTAATTA
AGCCCCTATTGATGAATATTAATTTACTCTATTTGCC
AGTTCATTCCAGTCCAACATTTATTGAGTGTCTACTTA
CGGGCCAGGCACTCTTGTATTCATCAAGATCACCACA
TTATCTGTATCAGTTATTTATTGCCACAATAAAACTGC
ATAACAAATCACTCCAAAATGTAGCACCTTAAACTA
CAACTACTTATTATTTCTCAAGAGTCAATGGGTCAGCT
GAGCAGTTCTGCCGATAGGGGTCAAGGTCAACACATT
TCAACTAGACTACTTGTAAAAAAGAATGAGTGTCTGGG
TAGGTGTTCTTCTAAAAATAAAACAAGGAATGAGG
AAATTGCAGGTAGGATAAGAGGGGTGGTTGGCAACCAA
ACCCCACAAAAGGCAGACAAATTTTAAGGAAACATAA
TGCCAGACTCCTATGTCATCATCCAAGTAGATGCAGTG
AAGTATAACCTGGGCGTAGGTAGGAGTGGGGA
GAGCAGAGGAGAAGGAAGGGAGATTGCTTTTCATCACT
TTTGGATTCCCTAATAACAGACATGACTGCCAGTATT
AAAATTTAACAAAGGATATCTGATCATTAATTTTCCTG
TATAAGTCACTGGTGATCTTCAACATCTCTCCCTCCC
TTCCTCCCTTCCTTCCTCCCACCCTCCCTTCCTTCCTT
CTTTCCTCTTTTGCTTTCAACTTCCTTTTCTCGTTTC
CTTTTGCTTTCTTTCTCTTCTCCCTTTTTTCTGTCACT
CTGGGCGTATGTAGTAGTGTAAAAAGGTTGACAGAGA
AATCAAATATAACAGGAGCAGGGCCCTGAGAAAAGCAC
CTGGCATCCTGTAGGCAAACCATTGTTTCTAAAAGAA
GGGACTGAGAGATTGAGGAGCTCAGGACATTGCCAAAT
GAACAAGGCAAGCACATTTATTCAGTACCAAACAAAC
GGAAAACGGCCTTTCCAAATAACTGAACCTATAAAACAG
CCTTTTCACAAGAGTACCGTAATTACTGGCCAACAGC
AACAATGAAAACAACTCCCAAACAAAGAAATATTTCT
GGATTAAAAGCCATGAGATCTGGATTCTAACAAGCTG
TGCTCCTCAAACTACAAGTACAAAATCTGGCTCTAAAC
TAACAAGCTATGAGCCTCAAACTGATGACTGGCATGT
TTGGGTCTCCATCTCCTTCTTGGGGGTTGGGGTCTTAG
AGACCCTTTTCCACGCCCTGATTCTCTTACTAGTGTG
TATGCTTTCCTTTTGACTTCTCATGCTGACCGTCTGAG
CAGGAGTGAGAAGCAATTTCAAAGGAAAACATCGTTT
ATCATCTGCTGAAAGAAACCAAAAAGAACACAGGAAA
CAAAAAGACAAGGAAGGGAATGAAAATGTAATTCAT
TTTATTAAAAGAAGAATTATTCTTCTGGGACACTGGA
TAGAAACCTTAATGAGTTACCTAGCTATCATAAATCC

TCTAACAGAGAAGAGAAGAGAAAGAAACAAAGACGGAA
GAGGGCAGGATAAAAGAAAGAAAAAAGGAAGGGAAAA
ATGAAGGAAGGAAGTTATCTATTCATTTCTACAGAGAC
TCTGCTGAGCAGTAGACAAGAAGACTTGGGAAAAATT
TAACTGAAACTTTTCCAAAAATCTTTTCAGAGGGATTT
TTTCCCTCTGAAAAGCATCATTAGAGGCTGTTCAATA
CCCAAGGCAAGCCTCTTTCATATTACTTACTGTACATG
AAACACTCATGCAATTGAGGCTAGCCAGAGGCCATTT
AGAAATTCAATAATTATTCAACCCAAGGGGCTTTCCAA
ATGGTGAAGTAGCTTCTTAAGAGGAAATTAATATTGA
GCAGTATAGCAAACCTAATTGGAATCTTGAGAAAATAG
TTCTGTGTCGTTAGAACAGCTAGAGGCTAAAGAAGAT
CAGGTTGGATGATACCTTCATTTTTGTCTCTTTCCTTA
ATTATGATGTAAAAGGGAAAAATCTTGTTTATTTTCTA
TGCCAGGAGGGTAGAGGGTGATTTGGAGAGGTTCCAAG
TTTATCAAAATCTACCTTCAGTCTGGCAGTAGAAAAG
TTTACTTCCTTCATTTCTTTCCTATAGACATTCAAAGA
GAGCTAAGGAGATCCAAAAACCTTTTTTCTATATTT
GCAATGCAAGGCAGTTGGGAATTAATGACTGATTTGTT
GGTGAGGGCAGTGGGCATTGATCACAAAAGCAGTAAA
GCTGTGTTTCTCAAAGAGAGAAAGTCTCTTTGAGATCT
TCATTATTTTACTATTTAGAAGAGAAAGGGCGTTAT
ATCACGTTGGAAGCATCCATGAGTCACTAGTCTCTTCT
CTATCTTTCTATGCCTTTCTGTATTAATTACTTTGAA
AGCACAACATTCCAAACCCATTGAGCACACAGTGGTCT
GATTTCTCCACTTGTGAAAGGTGCTAAAGTCTCACTG
TAGGATTAATTTGGGGGTCCAGGCTATGGGCTTGTAGA
TATGACTACCTTAGACTTTGGTTCTCCTGGCAACTAA
CCCTTTTTGGATCGTATCTAAGTTGACCTGTTTCACAG
TGAGAGAACTCCTCTCCATTACTCAGAATACTGAGGC
AGATCACAAGTGTACCACACCTGGCTAATGTTAAGCCA
GACAGAAACATCAGGCTCATCTCTTGAGAAGAAGGGT
CGCTTATTAAGGATACAAACTATTTTTTTTTTTTTTT
TTGAGACGGGTCTTGCTCTGTCTTAGAGTGCAGT
GGTGCAATCATAGCTCACTGCAGCCTCCAACCACATGGG
TATTTTAAATAAGAAAAAAATACCATCTGATAGATA
TGAAGGAGCATTGGGTCACTATAAACAAAACAGATTCT
AAGAGCAGGAAGAAAGAGTACAGTCTCTTTTCAATAA
TTTTTTTTTAAACTTGGGAAAGAACACTCACTCTATTC
CTATAGACCAGAAAGCAGATAATTGTCCATTATGATT
CCACATGACACTATCTTGTTCAGCTGTCACTGAAACAA
CTTTGAACACTGTCATATGTTCTTCCCAGCTCCTGAA
CTCTGACCTTTTTATGCCTTAGTTCACTTTCACAAAA
AGGGATTGATGTAATGTGCATTTCAGAGGAAACGACT
ATAGACATTTAGTGTCATTATAAATGTTGAAGTATG
CTGGCAGAAATTATGCCTTAAGATCATATATGGATTC
TTGTATGGTTTGAAATTGCTTAAAAGATATATATGATC
TCTAAAATGTGTGTATATATATGATGTCTTCTT
ATATATCTATATGTGATATATTTATATATATATATAAATC
TGTGTATATCACATATATAAATTTGCTGTTATTTGAA
TTGCCATTACCTCAGTGCTTAGGGGAAGCCATGCAGCGT
TTGTTTCTTTTCAGTACCCAGAGTTAATTAACATAAG
TTATCACAGAAGCTCCCATAAGCATTGAGACAATTTCT
CTATACCTGTGACTATTTAAGGTTTTGAAAACAAAAC
AGAAGCAGGTAAGAGGAAGGTACGCTTTACTATTGAAG
ATTTATTAGGTACACATTTAGATTTGTGAACTCACAT
TGCTTAGGATGAAAGGGACTCTTGAGGATGTCTGCTGT
TTGTTAGTGAACTGCCTGTAACAATTACAATTAGCAC
ACACATGAGCACAATGAACTGGGTAGTCAGCTCAGCC
AAAATGAATAGAAATAGCCTCTTACCAAATTTACTTT
GAGTAGCCCTTGGACTCTGAGCACTGCTGCCCAGAGCA
ATATGACTGTAGGTCCAAGTTTGTCAATGACTATGCA
AATGTGCTTTCTTCGCTTTTACTCTATTGTCATCTGTC
TATTACAATGTTGCTATGGTGACACCTTTCCAATATC
CCTGTGCTTCTTTGGTATCCTCTAAGGGGAAGCTGTAA
TGAAGTGGCTTGGCAAAGAATCCTCTTGGAATTTTT
TTTTTTTCATATGCTACTGAAAACCAGCATGATTTTCC
TCTTATGGGAAATGTATAAAGTATGAGTTGGAAATGA
TGGAAATTAATCTGTACTGACTTGGGCAAGGAATGTGA
ATGTTATTCATTCTGTTCCAAACTACCTGAAAATATT
CTCTTTCTGTTCCTACTTTCCAGGAGATAACATCTTAA
GGGACACTGAAGCTTGTGCGTGTGTGAGTGAAACACG
TGCTGGGGGCTCTTGAGCTCATGAGGGAGGGGCTACAT
GTCGGTGGGTGATAACTGTATGCTGGAAACAATGAT
AGGTGGTGACCCTGGAGCACTTACCATGTGACAGGTGT
TATGCTAAGCATGTTGTATGCATTCCTTCATTGAATGA
ACAGCTACCTATATTATCCTCATTTTATAAGATGAGGT
AACAGAGCTTCAGAAAGGTTAGACTCAGCTGCTATGG
GTCTGTCTGACTCTGGTGTTCTTCCTCTTAAAAACTGG
GGCACTTTGGAAATAGATTCCTCGGTGATGAACAGA
AATATTGCTTAGCGGCTGTATTTTTGTATCTGGCAGTT
```

-continued
```
TTCCCATATTTGAGTCTTATATTCACAATCGTATCT
TTACATTACACAAAAGTGACACAGAATTAGAGTCATTT
AATCCAGGGTTGATATCATTAAGTCATGACTATTTAT
TAAATGTTTCTTACAATATCTGAGATGATATTGCAAAA
GATGTAAGTGATTTTAGAAGTTCTCACTTCGTAGTTA
GTTGCAGAAACCTCTTTTGGAGGAGGGATGTTTTCTCT
ATATATCCTAATTTCTACTTAATATATTTCCACACCT
CTTTGAAGTGTGTAGTAAGAATGGTAAAATGCAGTACT
TCGTCATTTGGTACAGTTCAATCAATATGCATTAAGA
TGTGATCATATGGTAATAGAAAAATGTGAAAGATCCA
ATTCTTTTTCTCCAGAAGGCAGGAAGCTCATATTTGA
TTTCTGTTACTATAAACTATAAAAACGTTTCAAATGTA
GTTTACCCGTAACCATCACCCTGCAAGGGTGATATTG
CTCCCCGCCAATTTACGGAGGAGAATACTGAGGCTTTA
AGGTTGTAGATAGACCAAGACCACACAAGTAGAGAGT
GGCGGGCTGTGGGTTGAGCTTTAAAATCCAGGTTCATC
CATGACTCCCAGTGTGTTCTAGTAAATCCACTAGAAT
CTGAGTATTTTCCAATGATTTATGCTCCGCTCTGTGTC
AGGCAGTTCATGGTATTTTTCAACAATCAGAAATCC
TGGGGAAGGCAAACTGTTTCCCCCTCTCTAGGTGCCTT
GGAAGTGGCCGTTGTGGACCCAGAGATCATCCTTTCT
GATCTGACACCTTCTTCACTGCCCTGGCCCAGTGTCTT
TTCTGCAAGGCTGGAAGCCCCCTTAGACTGGTCATGT
CCCATCTCTTTCCGGAGGGAAGATGATCCCAAAGACGA
CTTTTCTCTCCACGGTGCTGCCATACCGCAGGCGGCC
GCCAGGGGTCCCCGCTCGGCGTCCCCGCAGAGACAGTCG
AGCCCCGGCCGGCTGCGCGGCGCGCTGGGTGCATGAG
GGGGCTGCTCCGGAGCGACGGCGGCTGCAGCTGGAGCC
AGGCGCTCGCCCGTCCGCCGGTTGGCTCGCCGGGACC
TCGCGCACCGGCGGCAGAGTCCCTTGCGTGGATTGGCA
AGCGACGCCCCACCTGCCCCGAGCTCACCATTTTCTT
TCGCGCTGGCTGCAGCTGACCCGGCGAAGGGAGCCGAC
CGGGCCCTGGGCTGGAGGTAAAACCCCACGGTGAGTA
AGAACCCGCTCCAAGCTAGGGGAGGCGGCGCAGCCCGG
TGGCTGCTCGCTCCCGATCTCGCCCGGCGGGCGGCG
AGGTTTGGGGCGCACCTGGGCGCGGGTGCAAGAAGGTG
CGGGAGGCGGCGGACCGGTCTTCTGCCCGCCGGCCAC
GGGCTTCCGGGGCTGGAGTCCTCTTCAGACCCCTGCCG
GCGCCTGGGTTTCTGGCCGGCTCCTCGTGTGCACTTC
CCGGCAGGAACAAGGGTCGCCCACTTTCCACCCCGGGA
TCTTGATTTGTCCTTGATTTGAAAAGATATAAATCAA
TAAGATCGTCCTTCTTTCGGGGTGCAAGACTCCGAGCC
CATCCCCAGCCGCGGACGCCTGCAGGGTGCGTGTTGG
GCTGTGGGTGGCGGGAAGACAAACTTTTACAAAAGTGC
GCCTGGGCTGGGGGACAACGCTTGGGCGTCCTGATCC
TGAGGGAGGAGTCTCGGCTTGGGGCAGCGTAGGGGAAG
TCCGCACCGTCAGCCAGGTCGCCCCCGGGGCTGACGA
TGCCTCACGGAGGTGGGGAGCGTGTAAAGGCCGTACAA
ATCGCGCTTAACTTTGGGGCCAACAACTGTCAAACAT
CTGGAATCCCAGCCCCTCCCTTTCCCTGAACTGGGGAA
GAAGGTGAAAACCCTTCAAGTTTTCTTTGATTGCCCC
TTCCCACCTTCAGACCCCTGCTGGGAGGGTAAAGCGCC
GACCCCTGGTGCCTGGCAAGTACCAGAGACTCTAAAT
CTCTCGGGATCCCCCCCTCGCGCTCTTTCCTGACCCT
CTCCCCTAACCCTCCCCACAGAGATCTCTCTACGCAG
CCGACTGAGATCGTGGCGAATGGCCTTTTGTTTCTCCG
CGTTTCCCCTATTGTTTGCCTTTCCAACATCTGGCGG
GGCTTGGGGAGAGAAGGAAGCCCCTCTGGTCCCCCTCC
CCGGCCCCACGCCAGCTCCGGCAGGGGATCCCAGCT
GGGAAAGTGGAGGAGCCCGACCCCAGCGAGGCCGCCCC
ACCCCGCCTTGTGGTTAGAGGGCGGAGGGAAAGTTG
TTCCTTCCCCGCCTCCGCTGCTGCCTGTGGCCCAGGGC
GCATTTCTCAGATCTCAGCCCAGGCGCGCCGCAAAGG
CTCAAATCCGAGAAGGTGCTGCTTTCGAGACAGTGGAA
GCGCGTTCCGCCCCAATCCAGAGCGTCCAGTGGTTGG
TTCCAGAGGATTTCAATCTCTAGCCAAAGGCGTTGGGG
CTGGGCCGCTGCTAGGGCAGTGGGAGGGGATCGGGGC
ACCTTTGGTAGGCGGAAAGCTGAGATTCTGGGGTCCAC
AAGTTTCCAAGGGCGGGAGGGCAGGCTAGTCGCCAAA
AAGAGAACGAAGATGCAAATAACGAGGAAGCCTTATGA
CGTTGCCTGGAAATAGTAGTGTGGTGGTTCACTCCGG
AATGAACGTGGAGTTCTGGCTTTGAGTACCGCTCCAAG
TTTAAATCCCAAGTCCCCTTTCTTCATTGTAGAAAAA
GAGGACTCAGACGACGCAACACAGATACGGCTAGAGCA
CAGTTCCTGCTTCCACGTCCCAGAGAACAAGTGGCTT
AGGATGGTCCCGAGTTCCCCTGTGGGTGCGCTTGTGG
GTTGCAGGCGGCCCTGTTTCCCTGCACAAGTCAGATG
CTTACACATTGTGTTCATTCTTAGTGTGGATTATTGAT
TAAAGAACTGGGGCAAAAGCAAAGTAGCTACTCTGAG
AAGTCAGGGTCCCCAGATGGTGCCCAGCGAGTTGTCTT
GCCTCTGAGGGGAGGCTGACTGAGACTGTGCACCTGT
```
-continued
```
TAGAACCTATGCTACCCCATAGCCTTGCAGTTGACTTG
CTGTTGCCAGCTTTTCCTGTGGGATCCCCAATGAGTC
CCTCTTCCAAGGAAGCTCAATTACACTTTTGATTCCTC
CTCAACCCAGGGGAAGAAAGAGGCTTCTGTAGGAACA
TTATGATCTATGTACCCACTCAGACATTGTCAGTGGAT
ACCAGAAGCTTGGCTCTGCACAGCTCTGAGAGTTTTC
CCTTTGCGAACTCAACAGAACTTTTGAGTTTCCATTTA
ACATAAAAGAAGTGAGACTGCTAAGCCAGGAATGCGA
CACATAGAGCACTTTCTCTAGTGATTTCTGGGTATTAT
ATCTCTTTACCTTCCCAACGGTGGAACCAGGAAAAGA
AAAAAAAGCAACATCTTTGAAGTACTGCAAGGCACTTT
ACAAACATTTCATTATGAAATGATCCCCAAGGAAGG
ATTCCTTTGAAATTTAGCAGCAGCAACCCAGAAGCAAC
AAAAAAGACCAAAGTTACTCAAGAAGTACCCAAAGGC
ATCATTAACAAAATAAAAGAGCATTTCTTGTCTTGGCC
TACCCCGCTAAGGAAAACAGGGTAATTATAGTGGAAG
TTAAGCTTG
```

In some embodiments, the human C9ORF72 gene and flanking sequences comprise a sequence that is, e.g., at least 75, 80, 85, 90, 95, 96, 97, 98, or 99% identical to the sequence above. As used herein, the term "percent sequence identity" or "percent identity" or "% identity" is the identity fraction times 100. The "identity fraction" for a sequence optimally aligned with a reference sequence is the number of nucleotide matches in the optimal alignment, divided by the total number of nucleotides in the reference sequence, e.g. the total number of nucleotides in the full length of the entire reference sequence.

In some embodiments, the number of GGGGCC hexanucleotide repeats (e.g., $(GGGGCC)_n$ in SEQ ID NO: 63) is 300-800, 300-700, 400-600, or 500-600. In some embodiments, the number of GGGGCC hexanucleotide repeats (e.g., $(GGGGCC)_n$ in SEQ ID NO: 63) is 500-600. In some embodiments, the number of GGGGCC hexanucleotide repeats (e.g., $(GGGGCC)_n$ in SEQ ID NO: 63) is greater than 300, 400, 500, 600, 700 or 800. In some embodiments, the number of GGGGCC hexanucleotide repeats (e.g., $(GGGGCC)_n$ in SEQ ID NO: 63) is greater than 500. In some embodiments, the transgenic mouse is an FVB, balb-C or C57B/6 strain mouse. In some embodiments, the transgenic mouse is an FVB strain mouse. In some embodiments, the mouse can be used to screen for therapies for the treatment of ALS or FTD, e.g., a therapy described herein or a candidate therapeutic agent.

A transgenic mouse as described herein can be made using any method known in the art or described herein, e.g., Example 4 (see also, e.g., PCT Publication Number WO2001010199 and WO2013022715; and US Publication Number US20110113496 and 20060031954, each of which are incorporated by reference herein). For example, a transgenic mouse described herein may be produced by introducing transgenes (e.g., the human C9ORF72 gene, optionally with flanking sequences) into the germline of the mouse. Embryonal target cells at various developmental stages can be used to introduce transgenes. Different methods are used depending on the stage of development of the embryonal target cell. The specific line(s) of any animal used to practice this disclosure are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). The line(s) may themselves be transgenics, and/or may be knockouts (e.g., obtained from animals which have one or more genes partially or completely suppressed). The transgene construct may be introduced into a single stage embryo. The zygote is the preferred target for micro-injection. The use of zygotes as a target for gene transfer has a major advantage in that in most cases the injected DNA will be incorporated into the host gene before the first cleavage (Brinster et al. (1985) PNAS 82:4438-4442). Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote. Thus, the exogenous genetic material should be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane.

Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter. Any technique which allows for the addition of the exogenous genetic material into nucleic genetic material can be utilized so long as it is not destructive to the cell, nuclear membrane, or other existing cellular or genetic structures. Introduction of the transgene nucleotide sequence into the embryo may be accomplished by any means known in the art such as, for example, microinjection, electroporation, or lipofection. The exogenous genetic material is preferentially inserted into the nucleic genetic material by microinjection. Microinjection of cells and cellular structures is known and is used in the art. In the mouse, the male pronucleus reaches the size of approximately 20 micrometers in diameter which allows reproducible injection of 1-2pl of DNA solution. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1-7 days, depending on the species, and then reimplant them into the surrogate host.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

Aspects of the disclosure also relate to polynucleotides, e.g., a bacterial artificial chromosome (BAC) vector, comprising SEQ ID NO: 63.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Examples

Example 1

Figures 2A, 2B:
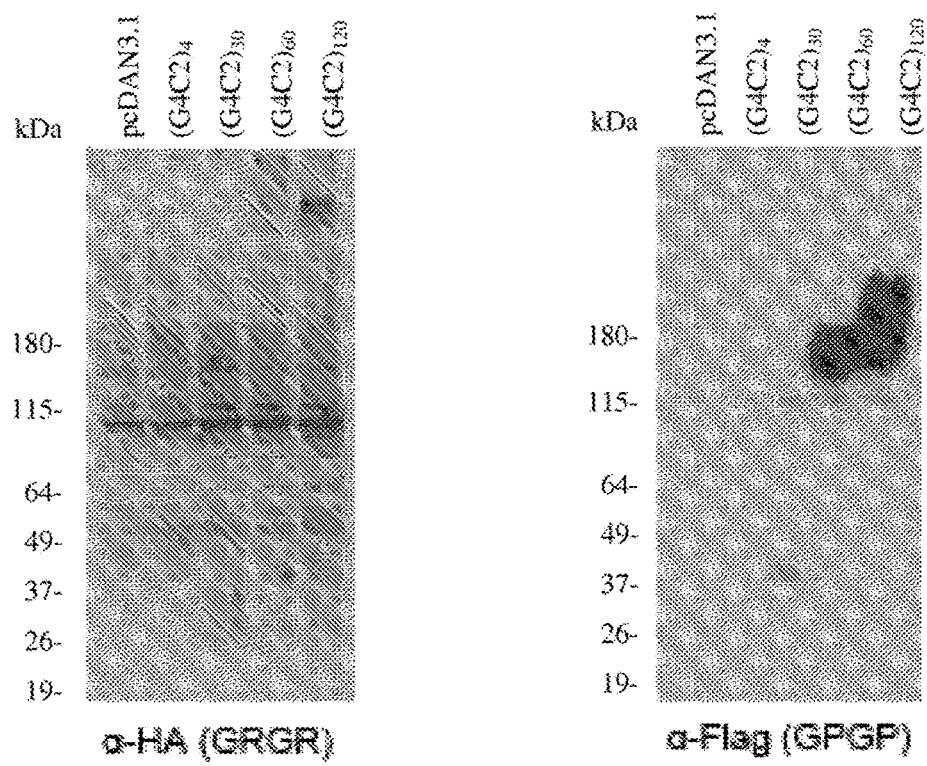
FIG. 2A is a diagram of an expression vector for expressing RAN translation proteins in cells. CMV=cytomegalovirus promoter. 6×Stop=6 stop codons, two in each frame. (GGGGCC)exp=a GGGGCC repeat sequence that extends for 4, 30, 60, or 120 repeats. (GR)HA-(GP)Flag-(GA)Myc=a HA, flag or myc tag that corresponds to the poly-(Gly-Arg), poly-(Gly-Pro), and poly-(Gly-Ala) repeat proteins, respectively. SV40 poly(a)= transcription terminator and poly A signal.
FIG. 2B is a photograph of a western blot depicting that GR and GP RAN translation proteins are expressed in cells transfected with 30, 60 or 120 GGGGCC repeat sequences.
Figure 3:
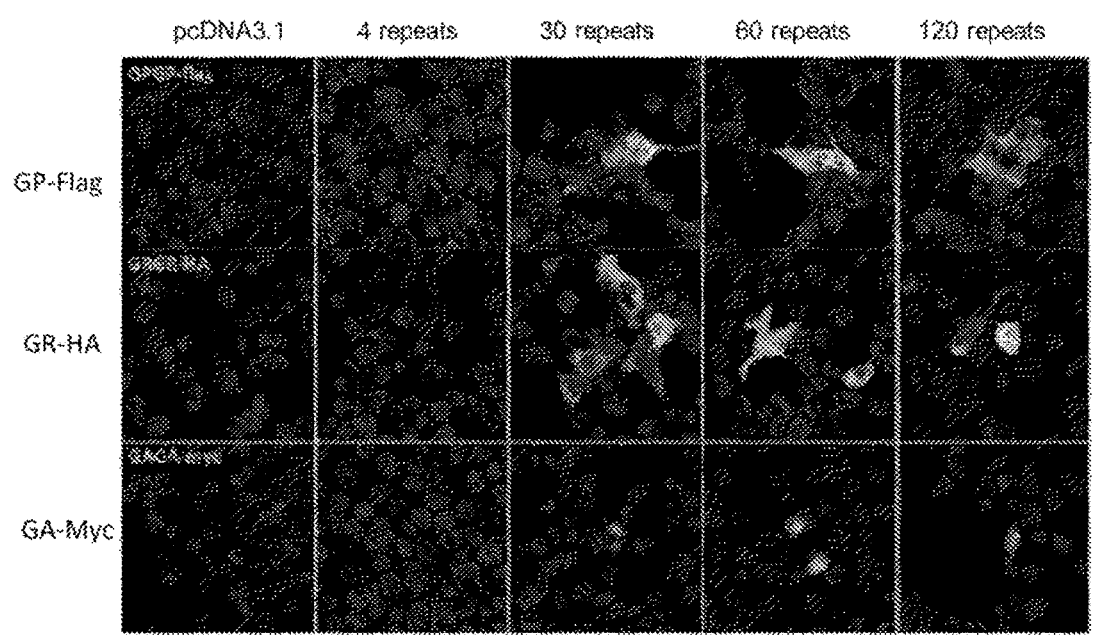
FIG. 3 is a photograph of an immunofluorescence staining of cells expressing GP, GR, or GA RAN proteins in cells transfected with 30, 60 or 120 GGGGCC repeat sequences.

A construct containing a CMV promoter, a (GGGGCC) expansion motif containing either 4, 30, 60, or 120 repeats of GGGGCC, and an HA, FLAG, or MYC tag were transfected into cells (FIG. 2A). It was shown by western blot that poly-(GR) and poly-(GP) proteins were produced in cells transfected with constructs containing 30, 60 or 120 repeats of GGGGCC (FIG. 2B). It was further shown using immunofluorescence of cells that GP-flag, GR-HA, and GA-Myc proteins were expressed in cells transfected with constructs containing 30, 60 or 120 repeats of GGGGCC (FIG. 3). These results show that GGGGCC repeat regions are capable of initiating translation independent of an AUG start codon (repeat-associated non-ATG (RAN) translation), and that poly-(GP), -(GR), and (GA)-repeat proteins are produced.

Figure 4:
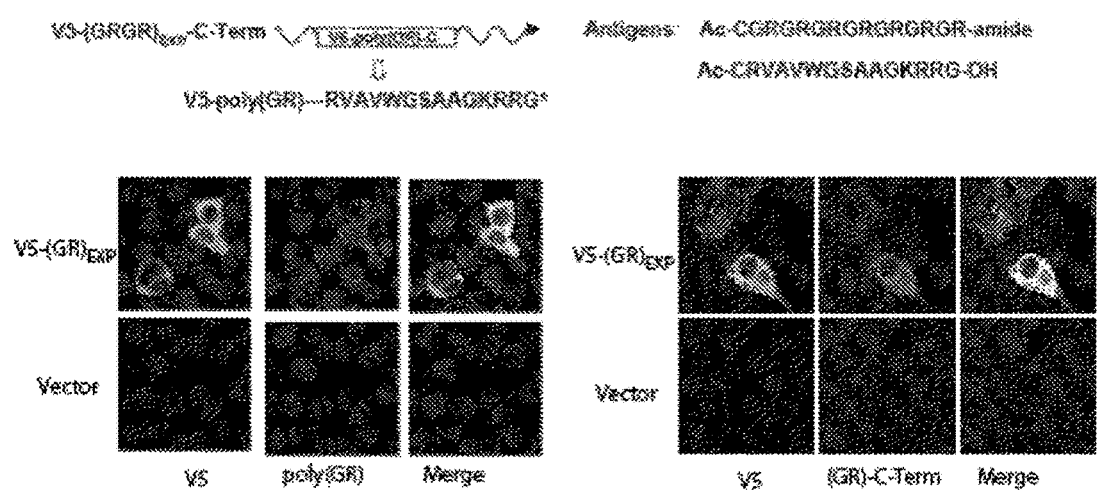
FIG. 4 is a diagram of the poly-(GR) and GR-c-terminus antigens and a series of photographs of immunofluorescence staining showing that the poly-(GR) and (GR)-c-terminal antibodies detect poly-(GR) RAN proteins.

Antibodies to a poly-(GR) sequence or to the C-terminus of the poly-(GR)-repeat protein were generated. Fluorescent staining using these antibodies showed that these antibodies were capable of detecting the poly-(GR) repeat protein (FIG. 4).

Figure 5:
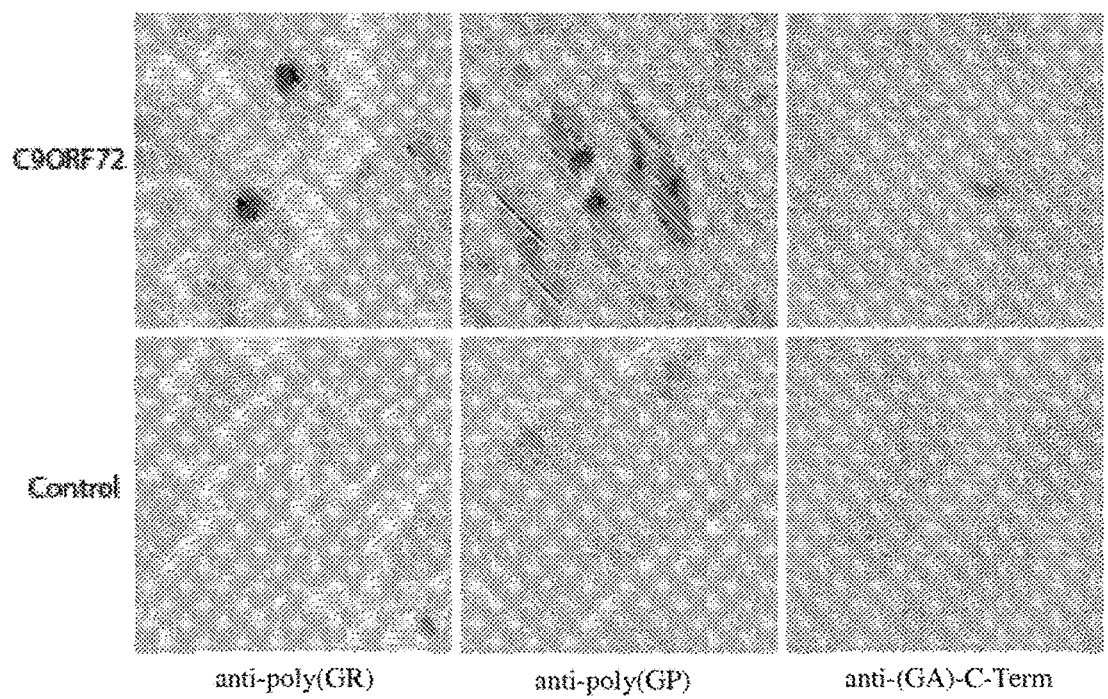
FIG. 5 is a series of photographs of tissue from C9ORF72 ALS patients or control patients showing that poly-(GR), poly-(GP), and poly-(GA) di-amino acid-repeat-containing proteins are expressed by C9ORF72 ALS patients.

Antibodies were further generated to a poly-(GP) sequence and the C-terminus of the poly-(GA)-repeat protein. The anti-poly-(GR), anti-poly-(GP), and anti-poly-(GA)-C-term antibodies were then used to stain sections of brain tissue from patients with C9ORF72 ALS or controls (FIG. 5).

Figure 1:
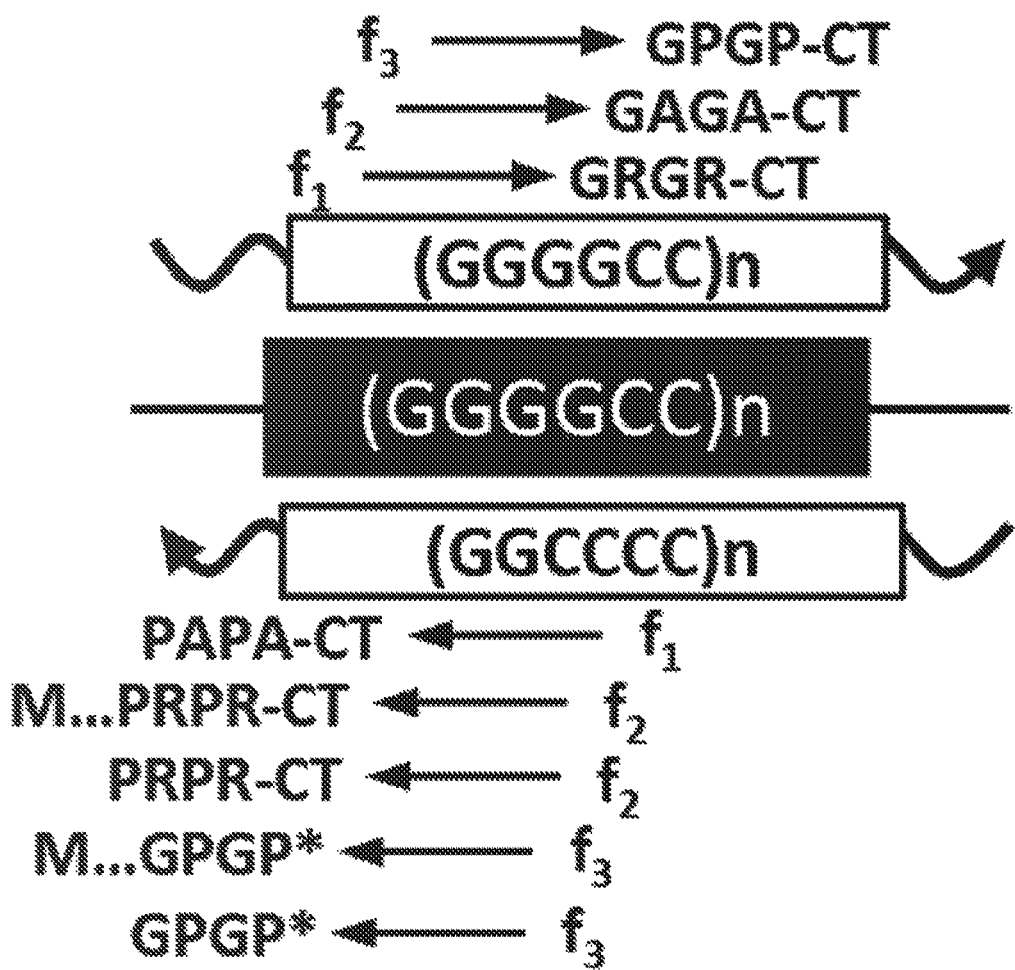
FIG. 1 is a drawing showing that transcripts are produced in the sense and anti-sense direction on the C9ORF72 gene, and that repeat-associated non-ATG (RAN) translation proteins are translated in all three reading-frames from both the sense and anti-sense C9ORF72 transcripts. The drawing also shows that Met . . . poly-(Pro-Arg) and Met . . . poly-(Gly-Pro) proteins are translated through ATG-initiated translation on the anti-sense transcript. CT=predicted to and/or shown to contain a c-terminal domain. *=end of protein (due to stop codon). M=Methionine.
Figure 6:
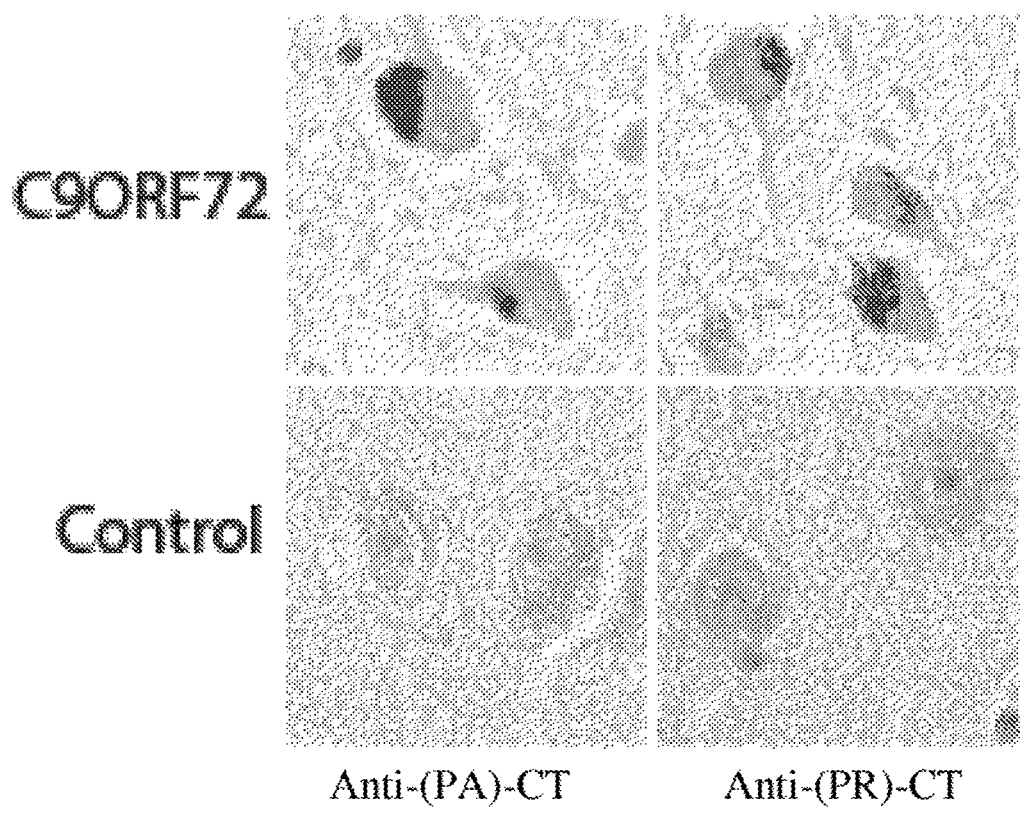
FIG. 6 is a series of photographs of tissue from C9ORF72 ALS patients or control patients showing that poly-(PA) and poly-(PR) di-amino acid-repeat-containing proteins are expressed by C9ORF72 ALS patients.

It was then hypothesized that transcripts of C9ORF72 may be produced in both a sense and anti-sense direction (see FIG. 1). It was further hypothesized that these antisense transcripts may also undergo RAN translation to produce further repeat proteins from the 5'-GGCCCC-3' repeats present in the anti-sense transcript. As shown in FIG. 6, both poly-(PA) and poly-(PR) proteins were detectable in brain tissue samples from patients with C9ORF72 ALS but not in controls. These results indicate that di-amino acid-repeat-containing proteins, such as RAN proteins are produced from both a sense and anti-sense transcript produced from the C9ORF72 locus.

Figure 7A:
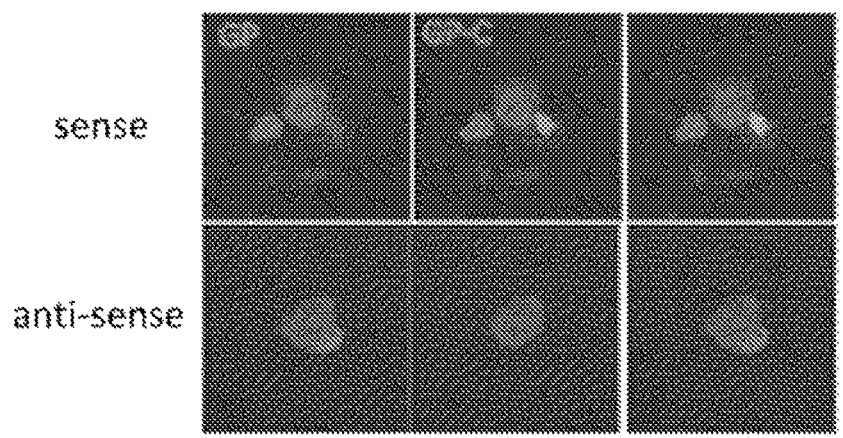
FIG. 7A is a series of photographs of immunofluorescence staining showing antibodies generated to recognize the GP repeat motif (GP) or the unique C-terminal region of the same GP-RAN proteins (GP-C) colocalize in 20% of patient cells. Cells that stain for and GP-C and GP express GP-RAN protein in the sense direction and that cells showing only GP staining express RAN-GP or Met . . . GP from the anti-sense strand.
Figure 7B:
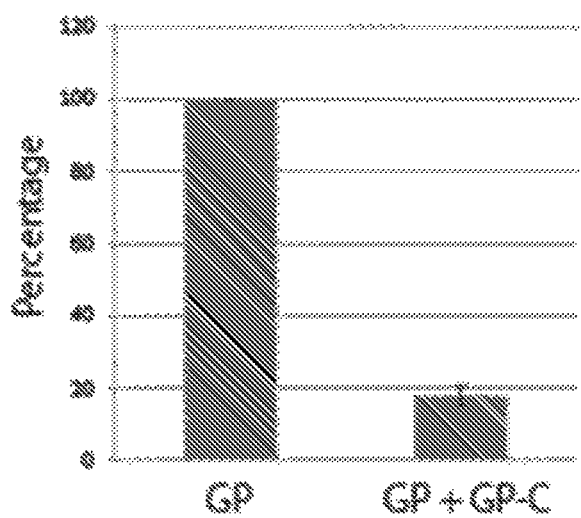
FIG. 7B is a graph depicting the percentage of GP and GP+GP-C in patient cells.

FIG. 7 shows that approximately 20% of aggregates detected with the anti-GP antibody (GP) also co-localize with antibodies directed against the unique C-terminus of the sense GP protein (GP-C). Consistent with the increases levels of antisense transcripts that seen in affected brains, these co-localization data suggest the more ~80 percent of the GP dipeptide aggregates are expressed from C9ORF72 antisense transcripts.

Figure 12:
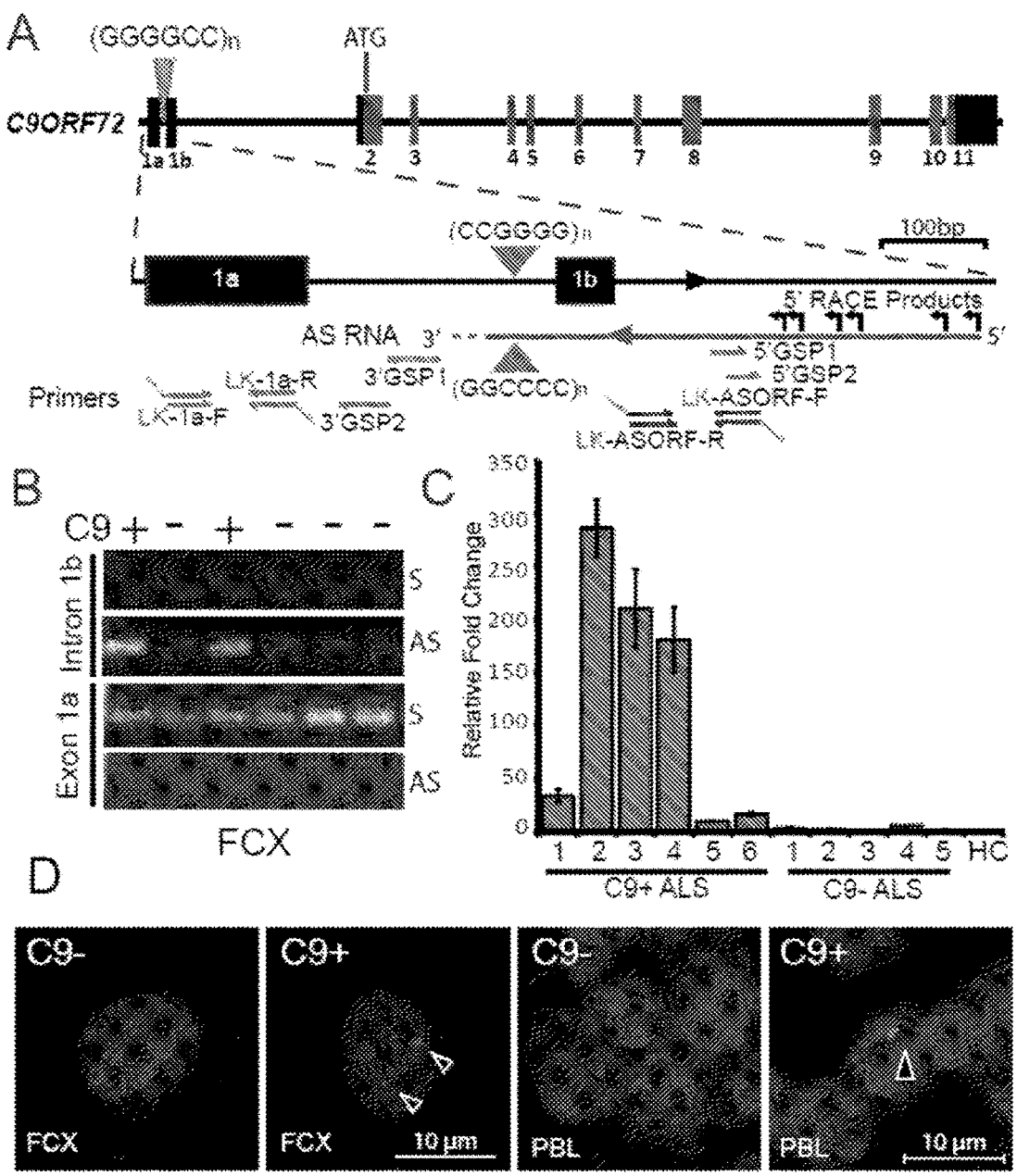
FIG. 12 is a series of schematics, graphs and images showing that G2C4 antisense transcripts are elevated by strand specific RT-PCR and accumulate as RNA foci in C9ORF72 patient tissues. (A) Schematic diagram of C9ORF72 gene and antisense transcripts and relative location of primers for strand-specific RT-PCR and RACE primers. (B) Strand-specific RT-PCR of sense (S) and antisense (AS) transcripts (across intron 1b and exon 1) from frontal cortex of C9(+) and C9(−) ALS patients. (C) strand-specific qRT-PCR showing elevated antisense mRNA in C9(+) compared to C9(−) ALS patients. (D) In situ hybridization with G4C2-Cy3 probe showing G2C4 antisense RNA foci (arrowheads) in C9(+) frontal cortex and peripheral blood leukocytes (PBLs) which are absent in C9(−) cases. Nuclear foci in FCX are indicated by arrow heads. FCX=frontal cortex. PBL=peripheral blood leukocytes.

Additionally, the anti-sense transcript was found to be dramatically elevated in subjects with ALS compared to controls (FIG. 12). The primers for the qPCR assay for detecting the anti-sense transcript levels are shown in the table below.

| | | |
|---|---|---|
| ORF F2 | AGTCGCTAGAGGCGAAAGC (SEQ ID NO: 36) | primer in c9orf72 antisense orf |
| ORF R2 | CGAGTGGGTGAGTGAGGAG (SEQ ID NO: 37) | |
| ORF F2+lk | CGACTGGAGCACGAGGACACT GAAGTCGCTAGAGGCGAAAGC (SEQ ID NO: 38) | |
| ORF R2+lk | CGACTGGAGCACGAGGACACT GACGAGTGGGTGAGTGAGGAG (SEQ ID NO: 39) | for RT 1st strand |
| Linker GA | CGACTGGAGCACGAGGACACT (SEQ ID NO: 40) | for RT-per with ORF F1 and F2 |

Further, di-amino acid repeat-containing proteins were found to be present in the blood (including in the serum and plasma) and in the brain of subjects with ALS (FIGS. 9 and 10) but not in control subjects.

Example 2

Figure 8:
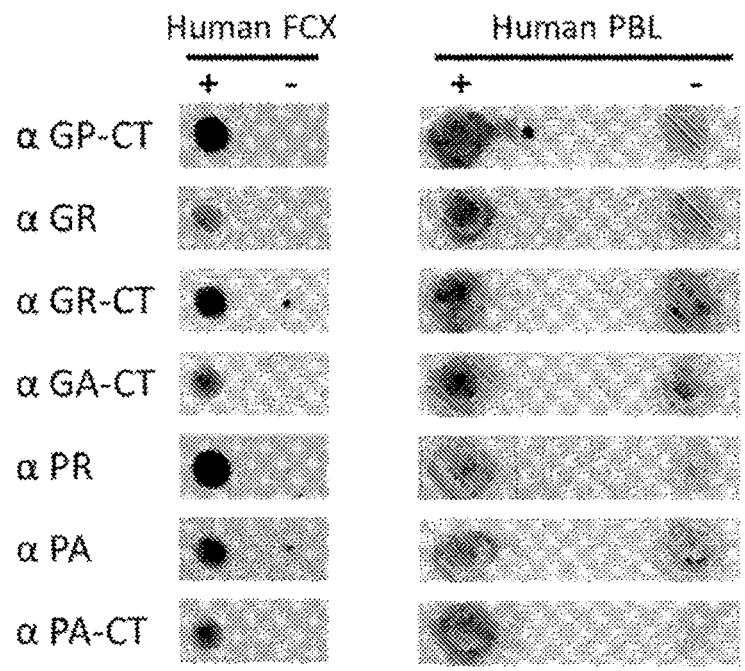
FIG. 8 is a picture of a dot blot showing that di-amino acid repeat-containing proteins are found in the blood (PBL) and the brain (FCX, frontal cortex) of subjects with ALS, but not controls.
Figure 9:
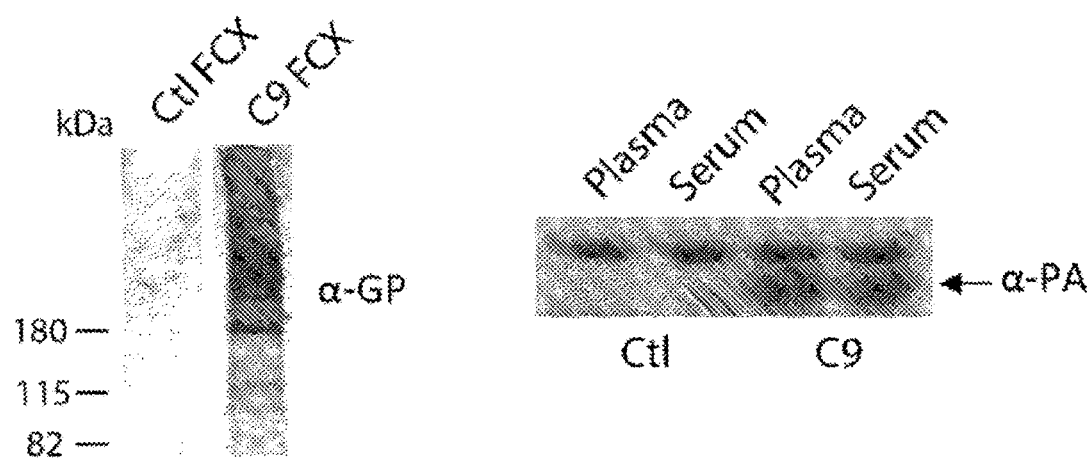
FIG. 9 is a photograph of a western blot showing that GP-repeat proteins are present in the brain (FCX) of subjects with ALS but not controls and that PA-repeat proteins are present in the plasma and serum of subjects with ALS but not controls.

According to some aspects of the disclosure, di-amino acid repeat-containing protein (such as RAN protein) accumulation in blood and cerebral spinal fluid (CSF) substantively contribute to C9ORF72 ALS/FTD and that plasmapheresis and bone marrow transplantation will reverse progression of the disease. According to some aspects of the disclosure, di-amino acid repeat-containing protein accumulation in blood and circulating CSF infiltrates the brain parenchyma and leads to protein accumulation, neuroinflammatory changes, CNS dysfunction and neuronal death. Aspects of the disclosure are based in part on the following. First, blood brain barrier (BBB) impairment is an early feature of disease in ALS patients (4, 5) and higher rates of ALS and other neurological diseases are found in patients who have had traumatic brain injuries (6). In some embodiments, without wishing to be bound by theory, ALS is in part caused by BBB disruptions that allow for the CNS entry of immune cells and other harmful substances that accelerate ALS/FTD. Secondly, as described herein di-amino acid repeat-containing proteins were found to accumulate in ALS patient blood samples (FIGS. 8 and 9).

Although plasmapheresis and bone marrow transplants have been tested as therapeutic strategies for ALS in the past, it is not clear if any of these cases were C9ORF72 positive or if treatment was early enough to have an effect. Accordingly, in some embodiments, ALS treatment (e.g., plasmapheresis or BMT) is initiated when above-normal levels of one or more di-amino acid repeat-containing proteins are detected in the blood of a subject.

The data presented herein on di-amino acid repeat-containing protein accumulation in C9ORF72 ALS patient tissues and blood indicates that reduction of blood (and perhaps also CSF) di-amino acid repeat-containing-protein load may help treat ALS in C9ORF72 ALS patients. According to some aspects of the disclosure, reduction may be achieved, for example, using plasmapheresis or a bone marrow transplant.

Methods

A detailed evaluation is performed on gene carriers from a C9ORF72 family (CNSA-1) and patients in the clinic including a gene-positive patient with early signs of motor neuron disease or fronto-temporal cognitive dysfunction, or both. Di-amino acid repeat-containing protein expression is correlated with repeat length in CNSA family samples and additional samples collected in clinic. Di-amino acid repeat-containing protein expression in blood is determined in longitudinally collected samples and correlated with disease onset and clinical severity. These methods are expected to characterize di-amino acid repeat-containing protein expression in C9ORF72 positive expansion study subjects and to determine if di-amino acid-repeat-containing protein expression occurs throughout life or increases with age and if di-amino acid repeat-containing protein levels quantitatively correlate with disease severity.

Plasmapheresis is tested to determine if lower di-amino acid repeat-containing-protein load in the blood and CSF reverses signs of the disease. Plasmapheresis is performed on five C9ORF72 positive individuals with early signs of the disease. Six plasmaphereses, each with 2-liter exchange with normal human albumin, is performed over two weeks, followed by one plasmapheresis weekly for the next six months. The study may be prolonged, if required. The primary outcome measure is the Appel ALS Rating Scale (AALSRS). Clinical evaluations including neurological examination, speech evaluation, neuropsychological testing, the ALS Functional Rating Scale (ALSFRS), EMG, and needle muscle biopsy for immunohistopathological evaluations of the vastus lateralis muscle are performed to assess disease progression immediately before and after the treatment period. Venipuncture and lumbar puncture are also performed before and after the 6-month (or if applicable, also after the prolonged) treatment period to assess the concentration of serum and CSF levels of RAN translation and ATG-translation products.

Bone marrow transplant in an animal model is tested to determine if BMT prevents di-amino acid repeat-containing-protein accumulation in blood and the brain. In a first cohort of animals, bone marrow from RANT-positive mice are ablated and replaced with wild-type donor marrow to test if protein aggregate load in the brain decreases. In a parallel set of experiments, RANT-negative animals are transplanted with RANT-positive bone marrow to test if CNS protein accumulation occurs in animals that only express the transgene in hematopoietic cells. Both groups of treated animals are compared to wild-type and untreated RANT control animals using a combination of behavioral, functional and neuropathological assessments.

Figure 10:
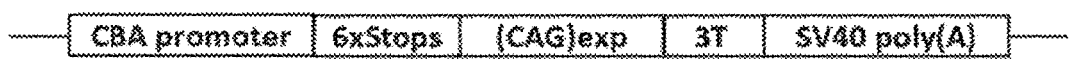
FIG. 10 is a schematic of the RAN translation mouse model construct containing 6× stops, a CAG repeat region, tags for detecting each CAG repeat frame, and a terminator sequence.
Figure 11:
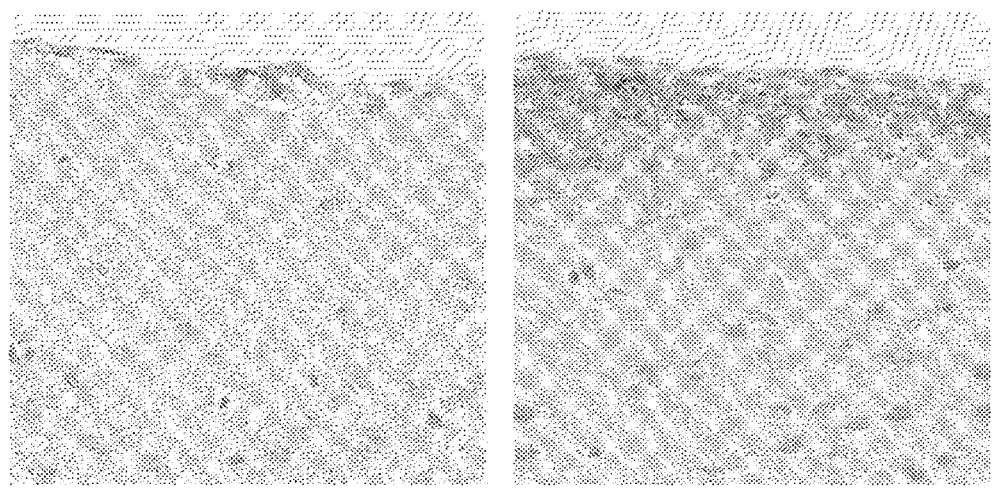
FIG. 11 depicts two photographs showing that poly-Gln proteins accumulated in the brain of RAN translation (RANT) mice containing the construct in FIG. 10, but not in control mice.

A RAN translation mouse model has been generated. Transgenic mice were generated using a construct containing 6 stop codons (two in each reading frame) immediately upstream of a CAG expansion mutation and followed by 3 separate epitope tags in each reading frame (FIG. 10). The CAG repeat generates poly-Gln RAN proteins, which have been previously associated with diseases in humans such as fragile X syndrome. The RANT mouse model produced poly-Gln RAN proteins, which were found to localize at high levels under the pia surface in the brain which is exposed to the cerebral spinal fluid (FIG. 11). This RANT mouse model is used in the studies outlined in Example 2. Accordingly, detection of poly-amino acid repeat containing proteins (e.g., mono- or di-amino acid repeat containing proteins) may be indicative of a risk for a brain disorder associated with the poly-amino acid repeat containing proteins. Accordingly, methods described herein may be used to detect or treat other neurological diseases.

Example 3

Introduction

The chromosome 9p21-linked form of ALS/FTD, the most common cause of familial FTD and ALS identified to date, is caused by an expanded GGGGCC ($G_4C_2$) hexanucleotide repeat in intron 1 of chromosome 9 open reading frame 72 (C9ORF72) (1, 2). The C9ORF72 mutation is found in 40% of familial and 7% of sporadic ALS cases and 21% of familial and 5% of sporadic FTD patients (3). The discovery of the C9ORF72 expansion has generated substantial excitement because it connects ALS and FTD to a large group of disorders caused by microsatellite expansion mutations (4).

Traditionally, microsatellite expansion mutations located in predicted coding- and noncoding regions were thought to cause disease by protein gain-, or loss-, of-function or RNA gain-of-function mechanisms (4). Protein loss-of-function has been proposed to underlie C9ORF72-driven ALS/FTD because the expansion mutation leads to decreased levels of variant 1 transcripts and potential decreases in C9ORF72 protein expression (1, 2). Additionally, because the C9ORF72 $G_4C_2$ expansion mutation is located in an intron, several studies have pursued the hypothesis that C9-linked ALS-FTD results from a toxic RNA gain-of-function mechanism in which $G_4C_2$ expansion RNAs sequester important cellular factors in nuclear RNA foci. Multiple $G_4C_2$ RNA binding proteins have been identified, but so far there is no demonstration that any of these candidates directly bind endogenous expansion transcripts or co-localize with RNA foci observed in patient cells or autopsy tissue (5-8).

In this mechanism, hairpin-forming microsatellite expansion transcripts express proteins in one or more reading frames without an AUG-initiation codon (9). While a variety of names have recently been ascribed to these RAN translated proteins (e.g. homopolymeric, dipeptide, RANT), it is proposed that all proteins expressed across microsatellite expansion mutations in the absence of an ATG-initiation codon be referred to as RAN proteins to prevent confusion as additional expansion mutations that undergo RAN translation are identified.

Here it is shown that C9ORF72 ALS/FTD antisense transcripts containing the GGCCCC ($G_2C_4$) expansion accumulated in patient brains as nuclear, and infrequent cytoplasmic, foci. Additionally, a novel panel of antibodies directed to both the repeat motifs and unique C-terminal regions was developed and both sense and antisense RAN proteins were demonstrated to accumulate in C9ORF72 patient CNS autopsy tissue. The discovery of antisense $G_2C_4$ RNA foci and three novel antisense RAN proteins in C9ORF72 patient brains suggests that bidirectional transcription and RAN translation are fundamental pathologic features of C9ORF72 ALS/FTD.

Results

Antisense RNA Foci in C9ORF72-Expansion Patients

Figure 19D:
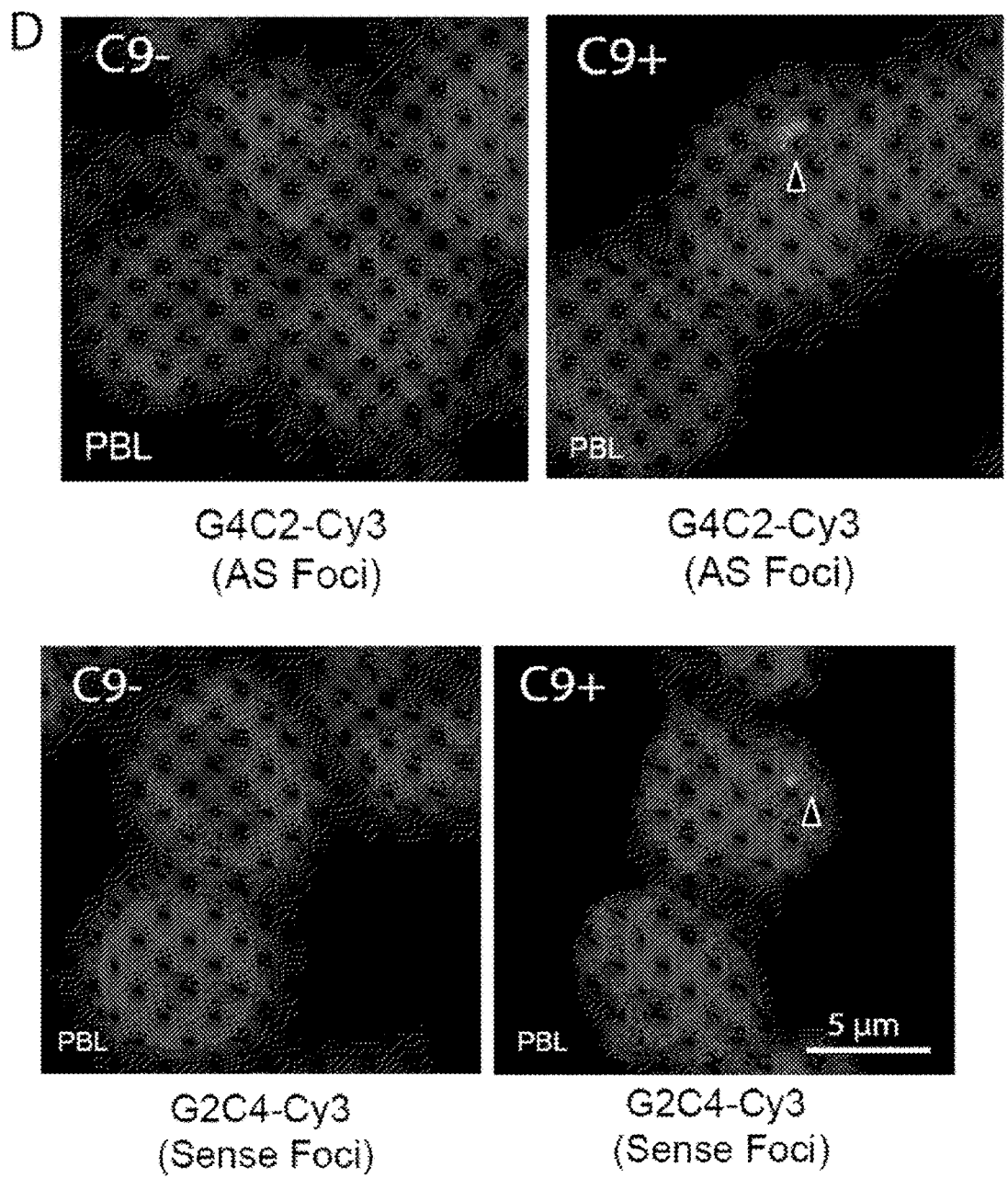

A series of experiments was performed to test the hypotheses that antisense (AS) C9ORF72 expansion transcripts form AS $G_2C_4$ RNA foci and express AS proteins by RAN translation or from short AS open-reading frames (AS-ORFs). First, it was confirmed that C9ORF72 antisense transcripts are expressed using a linkered strand-specific RT-PCR strategy to compare expression of the sense and antisense transcripts in intron 1b, 5' of the antisense $G_2C_4$ expansion, and exon 1a. For the antisense strand in intron 1b, strand-specific RT-PCR was performed using LK-ASORF-R primer for the RT reaction and ASORF-F and the LK for PCR to specifically amplify antisense-cDNAs (FIG. 12A). Similar strategies were used to amplify sense transcripts from the same region of intron 1b and sense and antisense transcripts in exon 1a. Intron 1b antisense transcripts were detected by RT-PCR in frontal cortex from C9(+) ALS/FTD patients but not C9(−) ALS/FTD or normal controls (FIG. 12B) and qRT-PCR shows these transcripts are dramatically increased among six C9(+) ALS/FTD cases (FIG. 12C). In contrast, intron 1b sense transcripts were not detected by RT-PCR (FIG. 12B) in frontal cortex. In blood, both intron 1b sense and antisense transcripts are detectable and the dramatic C9(+) elevation of the intron 1b antisense transcripts was not observed. 5' RACE showed intron 1b AS transcripts begin at varying sites 251-455 basepairs (bp) upstream of the $G_2C_4$ repeat (FIGS. 12A, 19B). In contrast, 3'RACE, using 3'GSP1 or 3'GSP2 primers located 40 and 90 bp 3' of the $G_2C_4$ repeat, did not detect transcripts. These data showed that the 3' end of the AS transcript does not overlap the sense exon 1a region, located 170 bp 3' of the antisense $G_2C_4$ repeat. Consistent with this result, sense but not antisense transcripts are detected by strand specific linkered-RT-PCR using primers overlapping exon 1a (FIG. 12B). To determine if antisense transcripts include the $G_2C_4$ repeat expansion, RNA fluorescence in situ hybridization (FISH) was performed using a Cy3-labelled (G4C2)4 probe to detect putative antisense $G_2C_4$ RNA foci. The results showed nuclear (FIG. 12D) and rare cytoplasmic (FIG. 19C) $G_2C_4$ RNA foci accumulate in C9(+) but not C9(−) ALS frontal cortex. The detection of foci in the cytoplasm showed that antisense expansion transcripts can be found in the same cellular compartment as the protein translation machinery, presumably where RAN translation occurs. Because RNA foci in peripheral tissues may provide biomarkers of the disease, peripheral blood leukocytes (PBLs) were examined and both sense and antisense RNA foci were detected in C9(+) but not C9(−) PBLs (FIG. 12D, FIG. 19D). It was discovered that the RNA-FISH signal from the Cy3-G4C2 probe detecting AS-foci may be competed with excess unlabeled G4C2 oligo, and these foci were resistant to DNase I and sensitive to RNase I digestion (FIG. 19E, F). Taken together, this shows that C9ORF72 antisense transcripts are elevated in the frontal cortex in C9(+) ALS but not C9(−) ALS or normal controls. It was also shown for the first time that antisense transcripts containing the $G_2C_4$ expansion mutation are expressed and accumulate in nuclear and rare cytoplasmic RNA foci in C9(+) frontal cortex. Additionally, it was shown that sense and antisense foci accumulate in blood, providing potential biomarkers of C9ORF72 ALS/FTD in a readily accessible tissue.

RAN Translation of GGCCCC Repeat Expansion In Vitro

To test if the antisense $G_2C_4$ expansions undergo RAN translation, a triply tagged $G_2C4$ minigene was generated, $(G_2C_4)_{EXP}$-3T, lacking an ATG initiation codon, by inserting a 6×STOP codon cassette (two stops in each frame) upstream of $G_2C_4$ expansions of 40 or 70 repeats and three different C-terminal epitope 8 tags to monitor protein expression in all reading frames [e.g., ($G_2C_4$EXP transcripts translated in three frames results in Gly-Pro (GP), Pro-Ala (PA) and Pro-Arg (PR) RAN proteins] (FIG. 13A). Immunoblotting detected two epitope-tagged RAN proteins, PR-Myc and GP-Flag, but not PAHA (FIG. 13B). The (PR)40- and (PR)70-3×Myc proteins migrated at approximately their predicted sizes of 20 and 27 kDa, respectively. In contrast, the (GP)40- and (GP)70-3×Flag proteins migrated substantially higher than their predicted sizes (10-15 kDa) at 50 and 75 kDa, respectively (FIG. 13B). The faint lower molecular weight bands on this blot may result from repeat contractions seen during bacterial culture or differences in translational start site. Immunofloresence (IF) showed antisense RAN proteins are expressed in all three reading frames (FIG. 13C). The detection of PA-HA by IF but not western blotting may be caused by a lower frequency of cells expressing RAN PA-HA from these constructs. Additionally, recombinant GP-Flag and PA-HA proteins had a cytoplasmic localization whereas PR-Myc proteins were distributed in both the nucleus and cytoplasm. These localization differences may result from different properties of the repeat motifs or the C-terminal flanking sequences found in this epitope tagged construct. In an additional series of experiments also it was shown that sense G4C2-expansion constructs containing 30, 60 and 120 repeats express GP-Flag, GR-HA and GA-Myc RAN proteins (FIG. 20). In summary, these data showed that recombinant $G_2C_4$ and $G_4C_2$ expansion transcripts express RAN proteins in all six reading frames.

Dual Immunological Strategy to Detect RAN Proteins

Since amino acid repeats can be found in a range of different proteins, a dual immunological strategy was used and antibodies that recognize the predicted repeat motifs described herein or their corresponding unique C-terminal regions were developed. A schematic diagram showing eight putative C9ORF72 RAN proteins is shown in FIGS. 13D and 21. Predicted proteins include six putative RAN proteins and two putative proteins with additional ATG-initiated N-terminal sequence. Unique C-terminal regions are predicted in five of the six predicted reading frames. To test for the accumulation of these proteins in vivo a series of polyclonal antibodies against the predicted repeat motifs or available corresponding C-terminal regions, were developed (FIGS. 13D, 21). Antibodies to test for putative antisense proteins [rabbit α-PA, α-PA-CT, α-PR, α-PR-CT, α-GP α-GP-CT (sense), and mouse α-GP] were generated and their specificities demonstrated in cells transfected with constructs expressing epitope-tagged recombinant protein by western blot and IF detection (FIGS. 13E, 22). Additional antibodies detecting repeat and C-terminal regions expressed in the sense direction are characterized in FIG. 23.

Antisense $G_2C_4$ RAN Proteins Accumulate in Brain

Several approaches were used to determine if novel antisense (AS) proteins are expressed in C9ORF72 expansion positive autopsy tissue. To overcome the obstacle that aggregated proteins are difficult to isolate from human brain, a sequential protein extraction protocol (23) was used on frozen C9(+) and C9(−) ALS frontal cortex autopsy samples. Antisense PA and PR proteins were detected with α-PA, α-PA-CT, α-PR, α-PR-CT on immuno-dot blots of 1% Triton-X100 insoluble, 2% SDS soluble extracts from a subset of C9(+) but not C9(−) ALS patients (FIG. 14A). Additional immuno-dot blots showing evidence for sense-RAN protein (GP, GR, GA) 10 accumulation in C9(+) ALS/FTD frontal cortex are shown in FIG. 24. α-PA, α-PR and α-GP antibodies also detected high molecular weight smears in 2% SDS insoluble fractions from C9(+) ALS frontal cortex samples after resuspending the pellets in sample buffer containing 8% SDS (23) (FIG. 3B). The differences in migration pattern seen for the recombinant proteins (FIG. 13B), which migrate as one or more bands, and the smears observed in patient tissue extracts (FIG. 14B) reflect differences in the RAN proteins due to much longer repeat tracts in patient samples and their extraction from highly insoluble aggregates. Immunohistochemistry (IHC) was next used to show that protein aggregates were detectable in the perikaryon of hippocampal neurons from C9(+) ALS/FTD autopsy tissue but not in C9(−) ALS patients or control subjects using antibodies against the repeat motifs (α-PA, α-PR, α-GP) as well as antibodies directed to predicted C-terminal sequences beyond the PA and PR repeat tracts (α-PA-CT and α-PR-CT) (FIGS. 14C, 25). Previous studies using antibodies directed against the GP repeat motif, detected aggregates, which were assumed to be expressed from the sense strand (10, 11). It is noted that GP repeat-containing proteins are predicted to be expressed from both sense and antisense transcripts (FIG. 13D) In the sense direction the predicted RAN GP protein contains a unique C-terminal (CT) sequence. In contrast, the antisense GP protein has a stop codon immediately after the repeat. To distinguish sense-GP RAN proteins from antisense-GP proteins, a double label IF experiments was performed on C9(+) human hippocampal autopsy sections using rabbit α-GP-CT to detect the CT region of the sense-GP protein and mouse α-GP to detect both sense and antisense GP expansion proteins. Double labeling showed two types of inclusions: a) putative sense inclusions double labeled with mouse α-GP and rabbit α-GP-CT sense and; b) putative antisense inclusions singly labeled with mouse-α-GP (FIG. 14D). Approximately 18% of inclusions showed the sense pattern with double labeling and 82% 11 of inclusions showed the antisense pattern and were positive for α-GP and negative for α-GP-CTsense (FIGS. 14E,F). These data showed the importance of characterizing protein aggregates with both repeat and C-terminal antibodies. Taken together, these results show that insoluble, aggregate-forming antisense-RAN proteins are expressed from all three antisense reading frames.

$G_2C_4$ Expansions and RAN Proteins are Toxic to Cells

Figure 13:
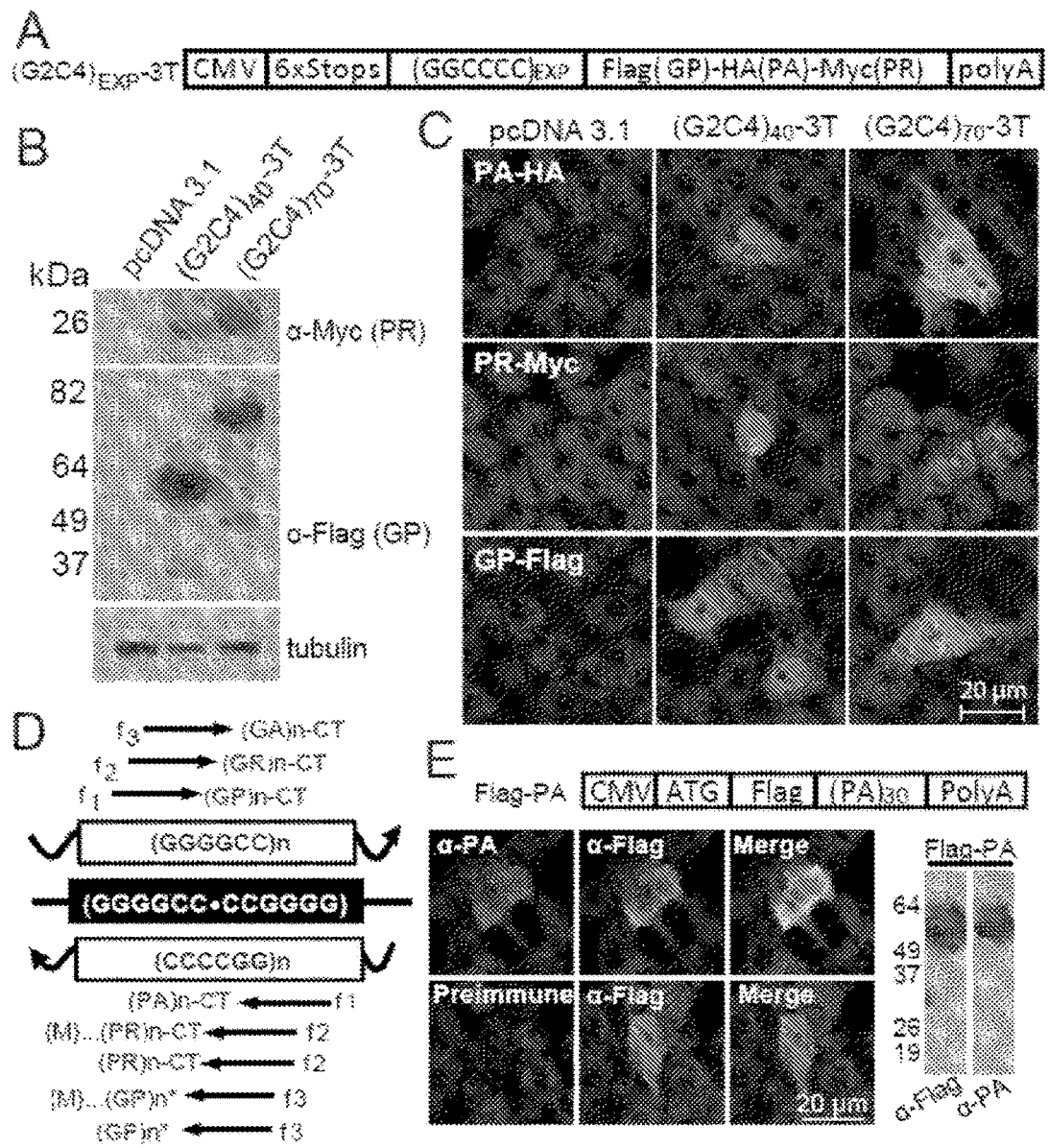
FIG. 13 is a series of schematics, graphs and images showing in vitro evidence for RAN translation of antisense $G_2C_4$ expansion and dual immunological detection strategy. (A-C) Immunoblots (B) and IF staining (C) of HEK293T cells 48 hours post-transfection with the $(G_2C_4)_{EXP}$-3T construct (A). (B) PR and GP expansion proteins detected by western and (C) PA, PR and GP detected by IF in transfected cells. (D) Diagram of putative proteins translated from sense and antisense transcripts. CT=C-terminal, f1-3: reading frame 1-3. (E) Abbreviated example of validation of α-PA rabbit polyclonal antibody. IF staining of HEK293T cells transfected with constructs with 5' Flag epitope tagged PA protein and corresponding immunoblots. See FIGS. 22 and 23 for additional controls and validation of eight additional antibodies generated against repeat motifs and CT regions.
Figure 14A:
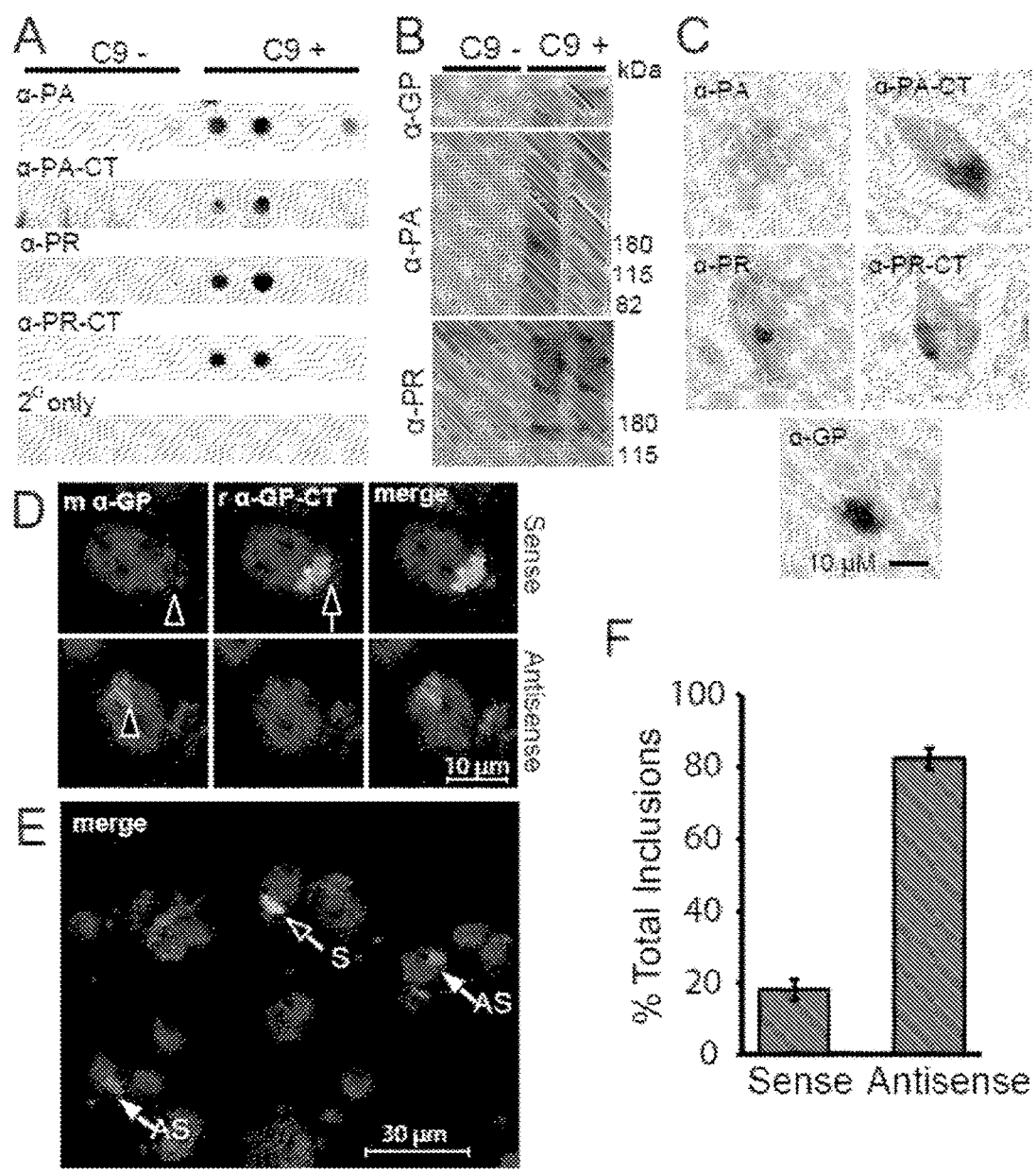
FIGS. 14A and 14B are a series of images and graphs showing in vivo evidence for RAN-translation of the $G_2C_4$ AS repeat and toxicity studies. (A) Dot blot of C9(+) and C9(−) frontal cortex lysates probed with α-PA, α-PA-CT, α-PR, α-PR-CT antibodies. (B) Immunoblots of C9(+) and C9(−) ALS frontal cortex lysates. (C) IHC detection of PA, PR and GP protein aggregates in hippocampal neurons from C9(+) ALS patients detected with α-PA, α-PA-CT, α-PR, α-PRCT and α-GP antibodies. (D) IF staining with mouse α-GP (arrowhead) and rabbit α-GP-CT (arrow) of C9(+) hippocampal tissue with sense inclusions positive for both antibodies (upper panel) and antisense inclusions positive for only GP repeat antibody (lower panel). (E) IF staining of larger region showing sense (S) and antisense (AS) staining. (F) Quantitation of double (sense) and single (antisense) labeled aggregates. (G-J) RAN and PR toxicity studies (G) $G_2C_4$ expansion constructs (+/−ATG-PR-3T)+/−ATG initiation codon in PR frame and 3'epitope tags. (H) Protein blots showing levels of PR and GP in cells transfected with constructs in (G). (I) LDH and (J) MTT assays of transfected HEK293T cells.
Figure 14B:
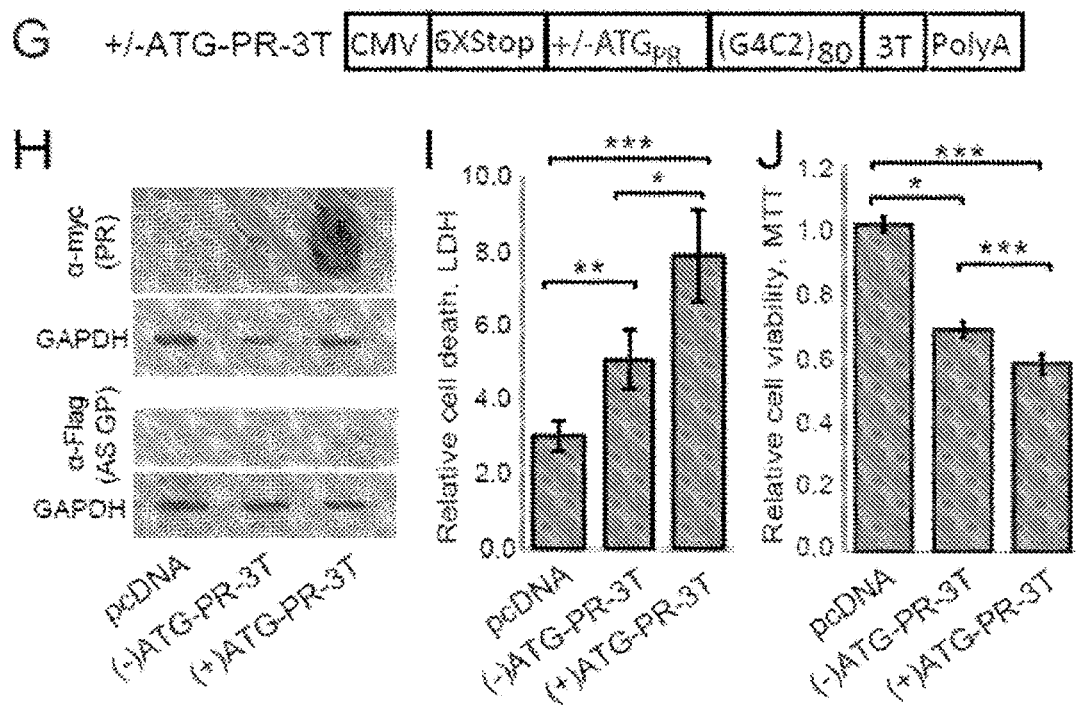
Figure 26A:
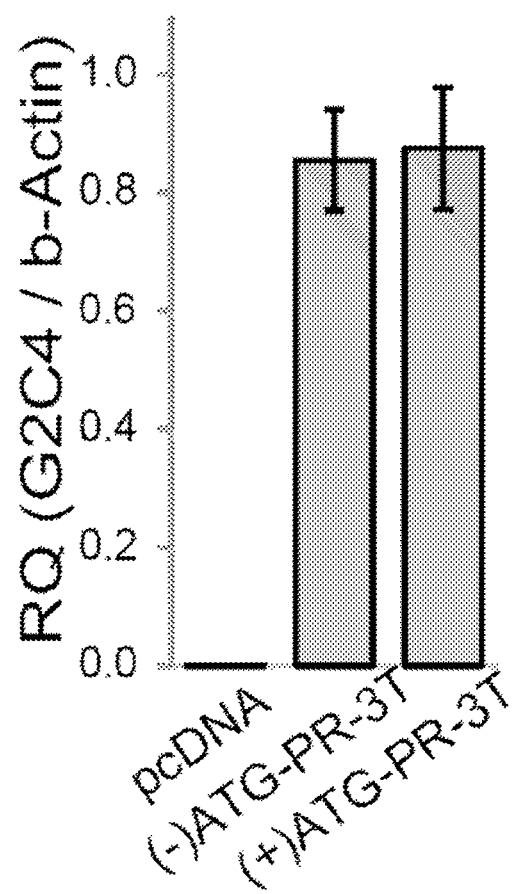
Figure 26D:
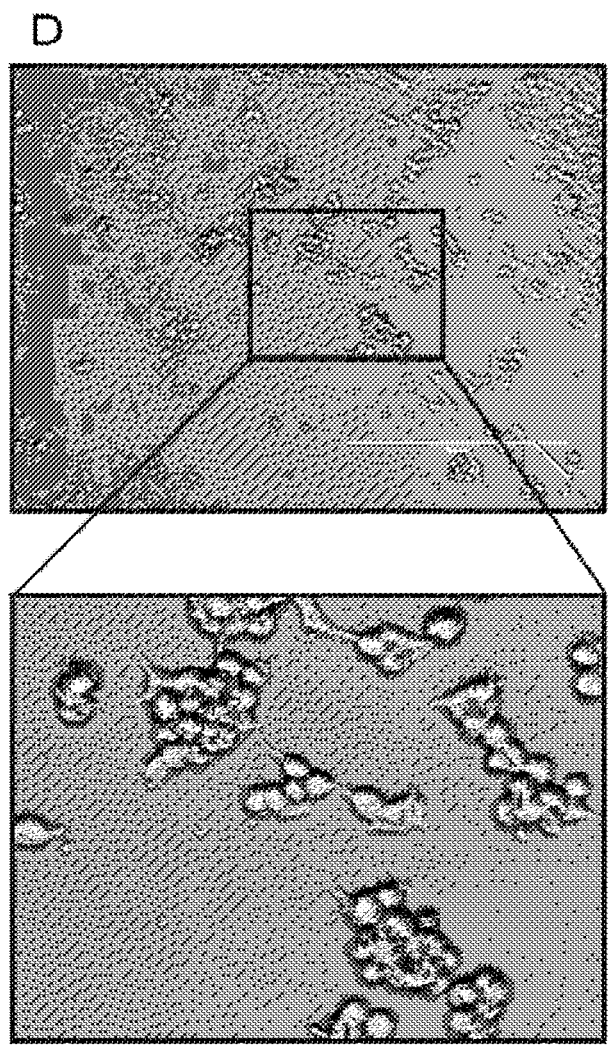

In addition to antisense GP and PR RAN proteins expressed by RAN translation, two of the antisense reading frames have upstream ATG initiation codons that may result in both ATG-initiated GP and PR proteins (M-GPAS and M-PRAS) (FIGS. 13D and 21). It was shown that the presence of an ATG-initiation codon does not prevent RAN translation from also occurring in all three reading frames (9). Therefore antisense GP and PR proteins may be expressed by both AUG-initiated and/or RAN translation. To explore the effects that an ATG-initiation codon has on RAN protein expression for the $G_2C_4$ expansion, an additional minigene construct was generated by placing an ATG initiation codon in front of the $G_2C_4$ repeat (FIG. 14G). The PR frame was selected for analysis because an ATG initiation codon naturally occurs in this reading frame. Western blotting shows that HEK293T cells transfected with (+)ATG-PR-3T express substantially higher levels of PR protein compared to (−)ATG-PR-3T transfected cells (FIG. 14H). In contrast, qRT-PCR and Western blotting showed transcript levels (FIG. 26A) and levels of RAN-translated GP (FIG. 14H) were comparable. Similar to FIG. 13, RAN-translated PA was not detectable by Western blot. The effects of these constructs on cell viability was then tested using complementary assays; lactate dehydrogenase (LDH) detection and methylthiazol tetrazolium (MTT). For the LDH assay, cells transfected with the (−)ATG-PR-3T or (+)ATG-PR-3T construct showed 1.9 and 2.9 fold increases in cell death compared to vector control cells (p=0.008 and 0.001), respectively. Additionally, (+)ATG-PR-3T transfected cells, which express elevated levels of PR protein showed a 1.5 fold increase in cell 12 death compared to cells transfected with the (−)ATG-PR-3T construct (p=0.034). The MTT assay showed similar results. Cells transfected with (−)ATG-PR-3T and +ATG-PR-3T constructs showed dramatic decreases in the number of metabolically active cells, 33% (p<0.00001) and 43% (p<0.00001), respectively compared to untreated cells or empty vector controls (FIG. 14J). Additionally, elevated PR expression in cells transfected with (+)ATG-PR-3T had significantly lower levels of metabolic activity compared to (−)ATG-PR-3T cells (p<0.05). By light microscopy cell detachment and changes in cell morphology were evident in −ATG-PR-3T compared to control cells and these phenotypes worsened in (+)ATG-PR-3T cells which express elevated levels of PR (FIG. 26B-D). Taken together, these data demonstrated that: 1) the $G_2C_4$ expansion mutation is toxic to cells—this toxicity may be caused by effects of the DNA, $G_2C_4$ RNA and/or RAN-translated PR, GP or PA proteins; 2) increased PR protein expressed in cells transfected with the (+)ATG-PR-3T construct increases cell toxicity and death above levels caused by the DNA, $G_2C_4$ RNA and RAN protein effects. Therefore the PR protein was shown to be intrinsically toxic to cells.

All Six RAN Proteins Form Aggregates in the Brain

Figure 15A:
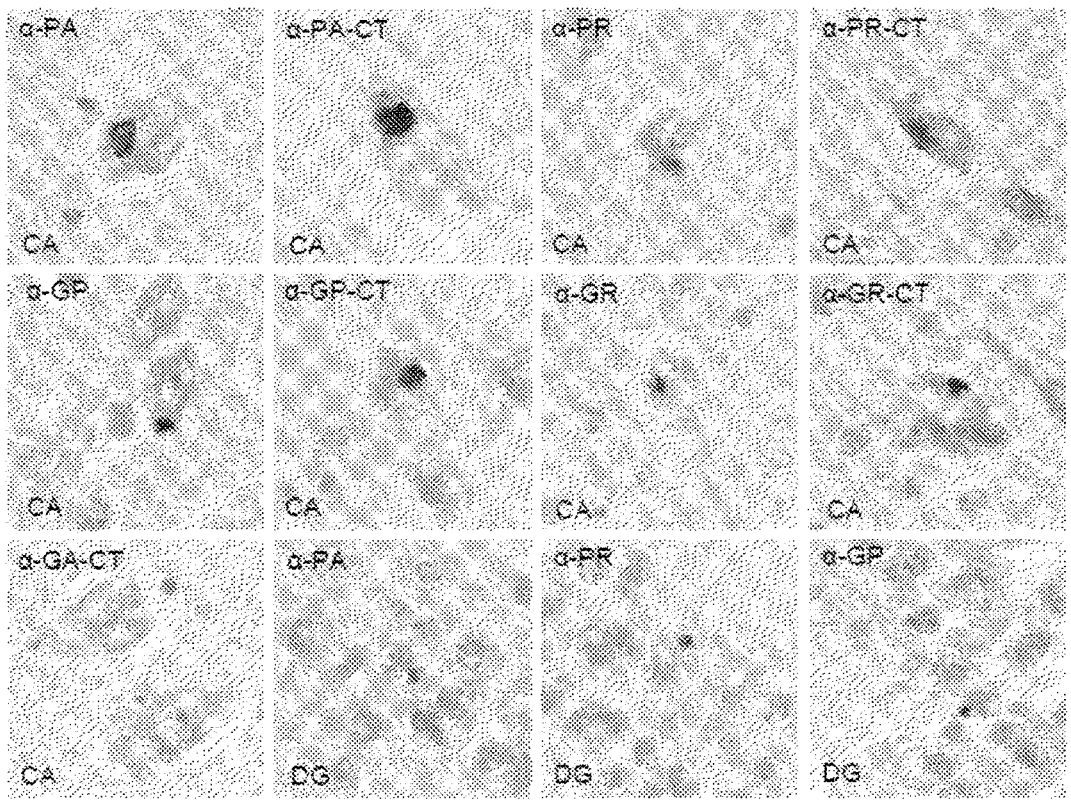
FIGS. 15A and 15B are a series of images showing in vivo evidence for RAN translation in both antisense and sense directions of C9ORF72. Cytoplasmic inclusions detected by IHC using antibodies against sense (α-GR, α-GR-CT, α-GA, α-GP-CT) and antisense (α-PA, α-PA-CT, α-PR, α-PR-CT) and α-GP which recognizes GP proteins made in both the sense and antisense directions. Aggregates were found in neurons of cornu ammonis (CA) and dentate gyrus (DG) regions of the hippocampus and the motor cortex (MC) of C9(+) ALS autopsy tissue.
Figure 15B:
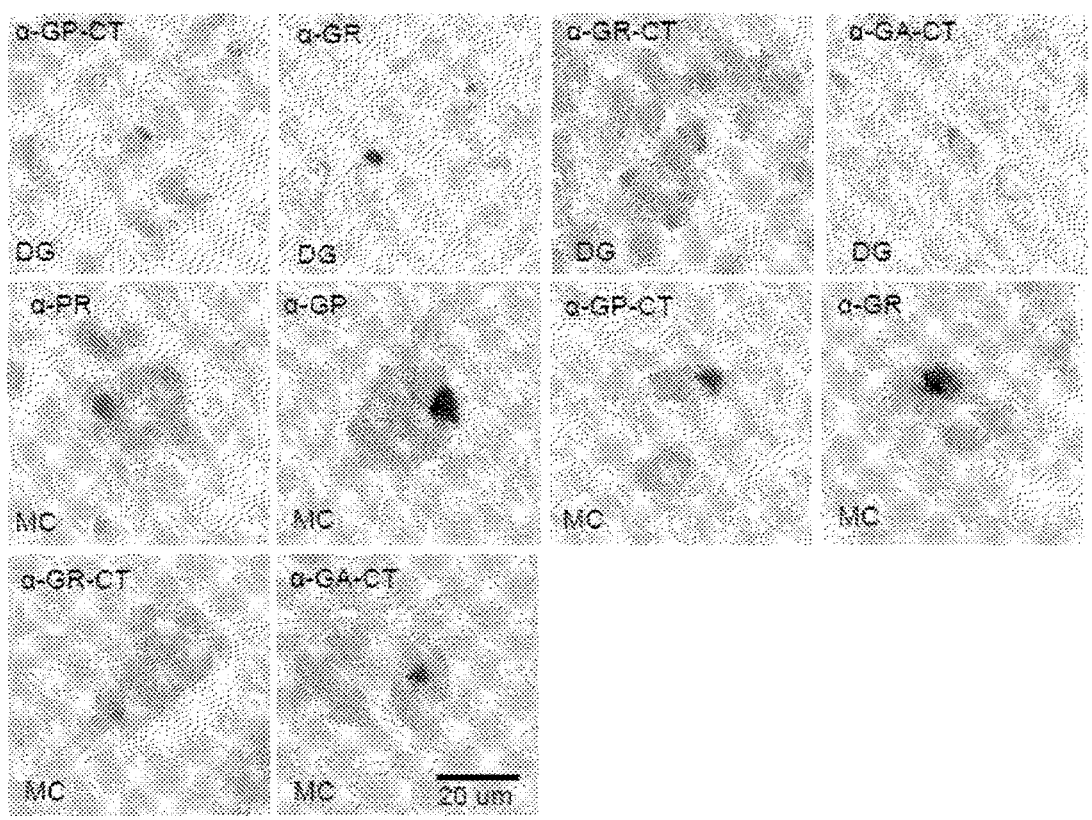

To determine if all six RAN proteins from both sense and antisense RNA strands are expressed in C9(+) ALS patients, IHC staining was performed on sections of paraffin-embedded brain tissues using nine polyclonal antibodies against repeat-expansion and/or C-terminal sequences of these proteins. In C9(+) cases there were abundant globular and irregular-shaped neuronal cytoplasmic inclusions (NCIs) in the hippocampus, the majority of which were in the dentate gyrus and in pyramidal cells in the CA regions. These RAN inclusions were also detected in C9(+) motor cortex (FIG. 15). GP positive inclusions were detected in all examined C9(+) cases but not in C9(−) cases or normal control sections in the hippocampus as well as in the motor cortex using α-GP. In the CA regions of the 13 hippocampus and in the motor cortex, clusters of aggregates were frequently found in C9(+) cases with aggregates in >20% of neurons (FIG. 27). Fewer aggregates were detected with the α-GP-CT sense antibody, consistent with double labeling experiments (FIG. 14D-F) that showed most GP aggregates are translated from C9ORF72 antisense strand. PA inclusions were detected in hippocampus in four out of six C9(+) cases tested and in one out of two motor cortex samples (FIG. 27). In C9(+) cases, the frequency of PA inclusions were significantly lower in the hippocampus and motor cortex compared with GP inclusions, but high-intensity regional staining with extremely large PA inclusions found in >50% of neurons were found in one patient (FIG. 27). PR positive inclusions were also seen in hippocampus in all C9(+) cases examined and in motor cortex in one out of two C9(+) cases tested. Similar to the PA staining, PR inclusions are less frequent but intense regional staining was occasionally observed. In the sense direction, GR positive inclusions were found in the hippocampus and motor cortex in all C9(+) cases examined, but appeared less frequent than the GP aggregates. GA inclusions were only occasionally detected by IHC as small perinuclear inclusions in hippocampus and in motor cortex (FIG. 15, 27). The apparent differences in the frequency of various types of aggregates may result from differences in protein conformation and epitope availability or differences in the affinities of these antibodies, which were designed to different epitopes. Taken together, this data showed that all six RAN proteins form aggregates in the C9(+) autopsy brains.

Inclusions of RAN Proteins in Upper and Lower Motor Neurons

Figure 16A:
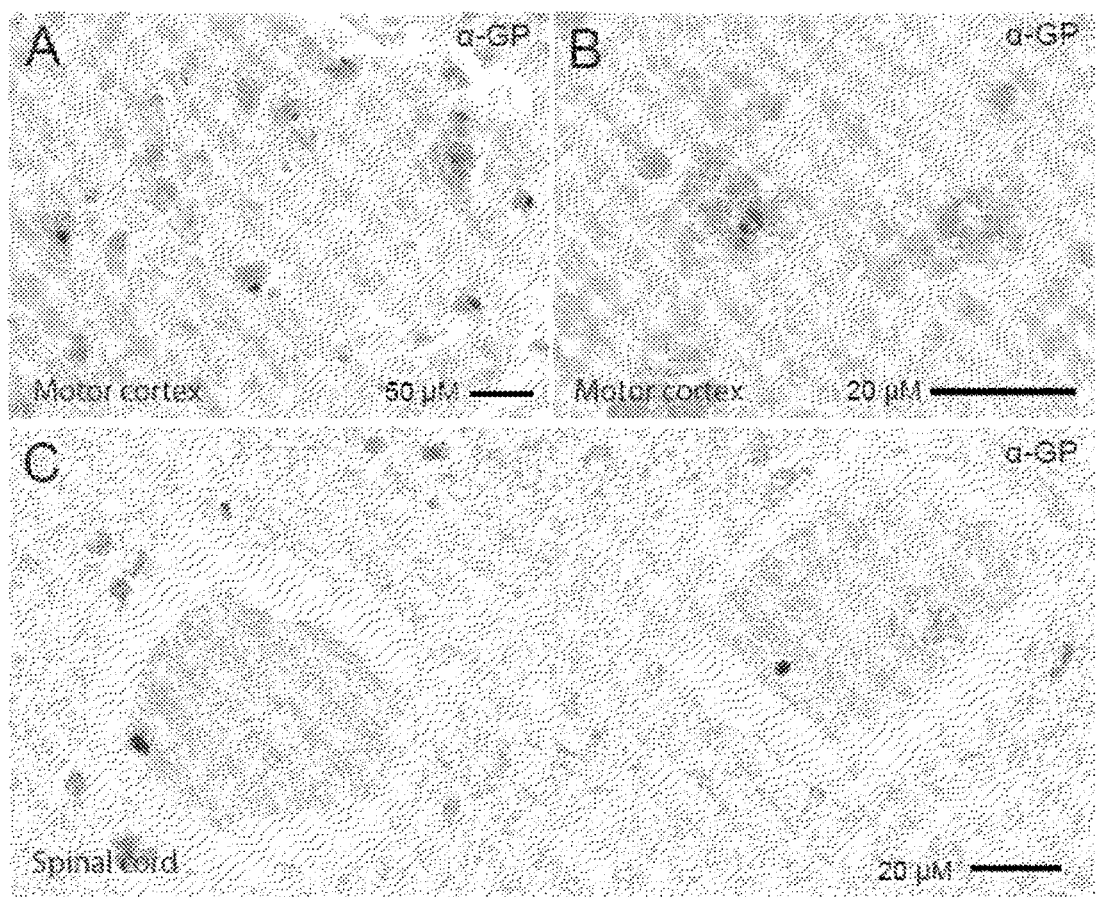
FIGS. 16A and 16B are a series of images of clustered RAN protein aggregates and RAN aggregates in motor neurons. IHC showing cytoplasmic α-GP aggregates in: (A) in layer III of motor cortex. (B) upper motor neuron in layer V of the motor cortex; (C) lower motor neurons in the spinal cord (L-S.C). (D) in cornu ammonis, CA, (E) and dentatus gyrus, DG regions of the hippocampus. (F and G) IHC showing abundant PA and PR cytoplasmic inclusions in the pre-subiculum (PrSub) from one patient.
Figure 16B:
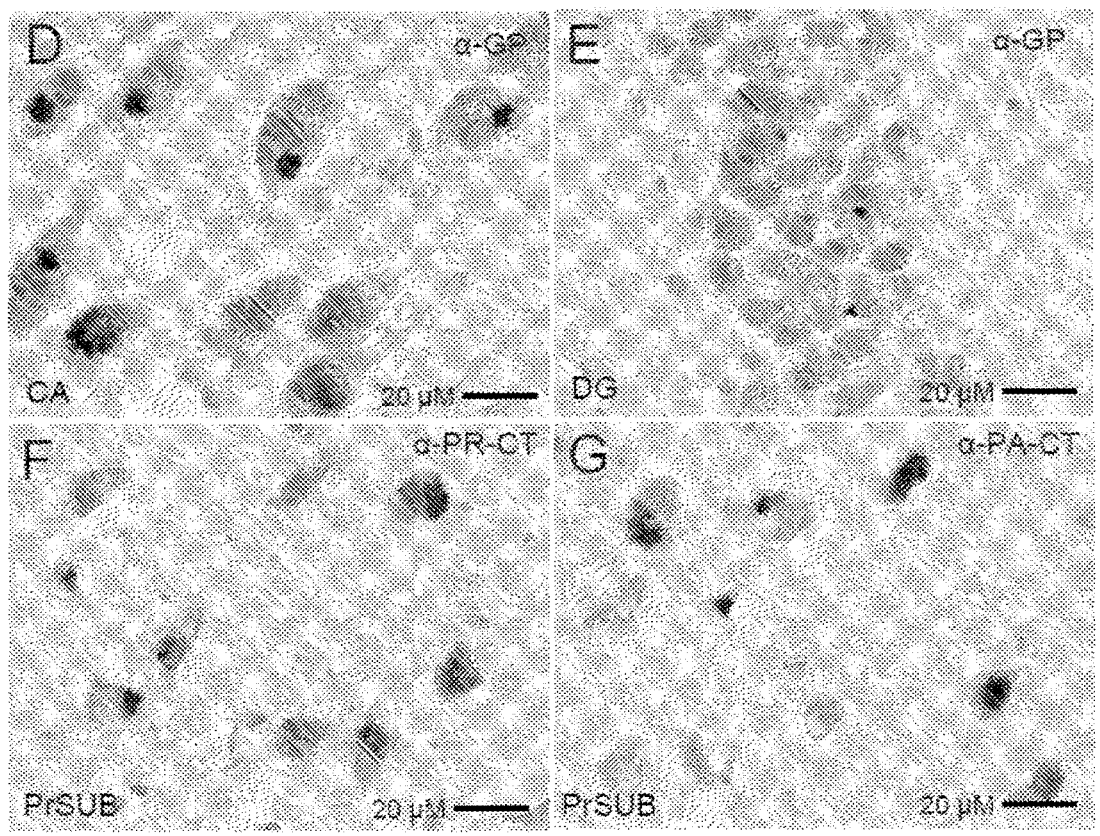

A central feature of ALS is the gradual degeneration and death of upper motor neurons in motor cortex and lower motor neurons in the brain stem and spinal cord. To test if RAN proteins accumulate in upper and lower motor neurons, IHC was performed using all nine antibodies against predicted proteins in both sense and antisense directions. In C9(+) cases, abundant GP-positive neuronal cytoplasmic inclusions were seen in all layers of motor cortex, with frequent GP aggregates in pyramidal neurons of layer III and throughout layer V (FIG. 16A). Although cell death and atrophy made motor-neurons in layer V difficult to identify, GP inclusions in remaining upper motor neurons were found (FIG. 16B). Additionally, PA-, PR-, GR- and GA-positive inclusions were also found in the motor cortex (FIGS. 15, 27). Using a similar series of experiments performed in spinal cord sections, GP aggregates in all three cases examined and aggregates in lower motor neurons in two out of three C9(+) patients were detected, but not in C9(−) ALS cases or normal controls (FIG. 16C). This is the first report of RAN protein accumulation in motor neurons. The discovery of GP-aggregates in both upper and lower motor neurons links C9 RAN-protein accumulation to the neurons selectively vulnerable in ALS.

High Density Clustering of RAN-Protein Aggregates

Figure 17:
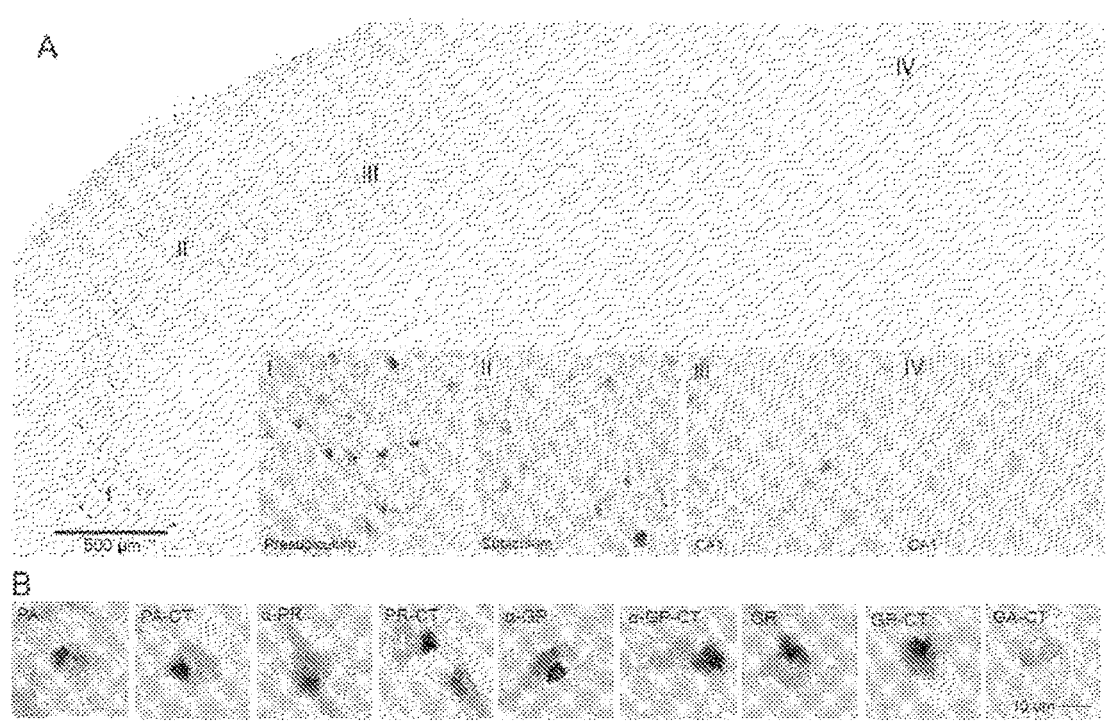
FIG. 17 is a series of images of clustered staining of RAN proteins. (A) Low power image of IHC staining with α-PA-CT shows variations in staining intensity (dark spots are positive) in regions I-IV with insets showing higher-power images. (B) Examples of aggregates from region I show immunoreactivity against all nine antibodies with similar staining for antibodies against repeat and unique C-terminal epitopes.

Both sense and antisense proteins accumulated in neurons of C9ORF72 autopsy brains. In general, two types of aggregation patterns were observed: 1) isolated cytoplasmic aggregates and 2) high-density clustered cytoplasmic aggregates in which ~10 to more than 50% of neurons were positive. Clustered aggregates were most frequently detected for GP and were found in the dentate gyrus (DG) and CA1-4 of the hippocampus (FIG. 16D, E). The clustered GP aggregates in DG were smaller and less frequent than the large cytoplasmic aggregates in CA regions. Additional clustered GP aggregates were frequently found in subiculum and presubiculum of the hippocampus as well as 15 the motor cortex. Immunostaining of serial sections showed that multiple proteins are often found in the same region. For example, intense clustered staining for PA, PR, GP, GA and GR proteins was found in the same region of the presubiculum in serial sections from one C9 (+) patient (see FIGS. 16F,G). Immunostaining for PA showed that some brain regions have abundant aggregates whereas other regions in the same section are relatively spared. For example, FIG. 17A illustrates a gradient of PA inclusions (presubiculm>subiculum>CA1) across hippocampal regions in a single section in one patient. PA inclusions in this patient were numerous (>50% of neurons) in presubiculum (I), moderate in subiculum (II), and rare in CA1 hippocampal regions (III and IV). Consistent with the focal regional staining seen in this section, PA staining was not detected in sections from a separate block of hippocampal tissue taken from the same patient. These data shows that expression of the PA RAN protein is variable from cell to cell or that aggregation of PA in one cell triggers aggregation in neighboring cells as has been proposed in a mouse model of Parkinson's disease (24). Next, serial sections from this C9(+) case were used to show that antibodies directed against both the repeat motifs (α-PA, α-PR, α-GP, α-GR) and corresponding C-terminal regions (α-PA-CT, α-PR-CT, α-GP-CT, α-GR-CT α-GA-CT) detect aggregates in the same densely staining region of the presubiculum (region I) (FIG. 17B). These results showed that both sense and antisense RAN protein aggregates accumulate in this region. The detection of similar aggregates in using antibodies that recognize either the repeat motifs or specific C-terminal regions confirms that these antibodies are recognizing proteins expressed across both the $G_2C_4$ and $G_4C_2$ expansion transcripts and provides new tools to understand the biological impact of RAN translation in C9ORF72 ALS/FTD.

Discussion

There has been much excitement about the discovery that an intronic micro satellite expansion mutation in C9ORF72 causes a common form of both familial and sporadic ALS/FTD (1, 2). The three major pathological mechanisms being considered for this disease include haploinsufficiency (1, 2), RNA gain-of-function (5-8), and RAN translation (9, 11-13). To date, efforts to understand the molecular mechanisms of this disease have focused exclusively on understanding the consequences of the C9ORF72 expansion mutation in the sense direction. The results reported here show that C9ORF72 expansion mutation is also expressed in the antisense direction and show that antisense RNA foci and antisense RAN proteins contribute to C9ORF72 ALS/FTD. We show for the first time: 1) antisense C9ORF72 but not sense transcripts are elevated in C9(+) autopsy tissue; 2) antisense $G_2C_4$ expansion transcripts form RNA foci that accumulate in C9+ brain and blood; 3) RAN translation occurs across antisense $G_2C_4$ expansion constructs in cell culture; 4) that sense and antisense RAN proteins accumulate in C9(+) autopsy brains using a dual immunological approach with both repeat and C-terminal antibodies; 5) RAN protein aggregates accumulate in upper and lower motor neurons linking RAN translation directly to the key pathologic feature of ALS. Since the initial report that $G_4C_2$ RNA foci accumulate in C9ORF72 ALS/FTD patient tissues (1, 2), a leading hypothesis is that $G_4C_2$ sense transcripts sequester and dysregulate RNA binding proteins similar to the sequestration of MBNL proteins in DM1, DM2 and SCA8 (4). Several groups have already reported $G_4C_2$ binding proteins and are testing their potential role in disease (5-8). The discovery that antisense $G_2C_4$ foci also accumulate in patient cells shows that $G_2C_4$ antisense RNAs and binding proteins may play a role. Additionally, the discovery of sense and antisense foci in C9(+) peripheral blood may prove useful as an easily accessible biomarker of C9ORF72 ALS/FTD. Biomarkers that monitor both sense and antisense transcripts may be particularly important as therapies that decrease expression of one strand may increase expression of the other strand. Using a dual immunological approach it was shown that $G_2C_4$ antisense transcripts express novel antisense proteins (PA, PR, GP) by RAN translation and/or from two short ORFs (Met-AS-PR and Met-AS-GP).

Materials and Methods cDNA constructs. CCCGGGGCC(GGGGCC)$_2$GGGGCCC (SEQ ID NO: 64) and CCCGGGGCC(GGGGCC)$_{28}$GGGGCCC (SEQ ID NO: 65) fragments that contain upstream 6×Stop codons were synthesized and cloned into pIDTSmart vector by Integrated DNA Technologies. 6×Stops-(GGGGCC)$_4$-3T and 6×Stops-(GGGGCC)$_{30}$-3T constructs were generated by subcloning NheI/XhoI fragment into pcDNA3.1 vector containing triple epitopes. To expand the size of the GGGGCC repeats, SmaI/XhoI fragment was subcloned into PspOMI blunted with T4 DNA polymerase/XhoI of pcDNA-6×Stops-(GGGGCC)$_{EXP}$-3T. To reverse the orientation of GGGGCC repeats in pcDNA-6×Stop-3T construct, SmaI/ClaI fragment was subcloned into pBluescript SK+ to generate pBluescript-(GGGGCC)$_{EXP}$. The AfeI/XhoI fragment pBluescript-(GGGGCC)$_{EXP}$ was subcloned into pcDNA-6×Stop-3T to make pcDNA-6×Stop-(GGCCCC)$_{EXP}$-3T construct.

RT-PCR.

1) Strand-specific RT-PCR in autopsy tissues: Total RNA was isolated from Frontal cortex autopsy tissues and peripheral blood lymphocytes (PBL) of ALS patients and healthy controls with TRIzol (Invitrogen). To detect transcripts from both strands, cDNA was generated from 0.25 µg of total RNA using the SuperScript III system (Invitrogen) with linkered strandspecific reverse primers and PCR with strand specific forward and linker (LK) primers. The PCR reactions were done as follows: 94° C. for 3 min, then 35 cycles of 94° C. for 45 s, 58° C. for 45 s and 72° C. for 1 min followed by 6 min at 72° C. Bands were cloned and sequence to verify their specificity of the PCR amplification. 2) RT-PCR for toxicity assay in 293T cells: Total RNA from cells was extracted using miRNeasy Mini kit (Qiagen) according to the manufacturer's protocol. Total RNA was reverse transcribed using the Superscript III RT kit (Invitrogen) and random-hexamer primers. The expression of the different G4C2-3×Tag constructs were analyzed by RT-PCR and qPCR using primer set: 3×Tag-Fw and 3×Tag-Rv. β-Actin expression was used as a reference gene amplified with primer set ACTB3 and ACTB4. Primer sequences are listed in FIG. 27.

Real Time RT-PCR.

Two step quantitative PCR was performed on a MyCycler Thermal Cycler system (Bio-Rad) using SYBER Green PCR Master Mix (Bio-Rad) and ASORF strand-specific cDNA and primer sets. Control reactions were performed with human beta-actin primers ACTB3 and ACTB4 using oligo dT synthesized total cDNA as template. Two stage PCR was performed for 40 cycles (95° C. 30 s, 60° C. 30 s) in an optical 96 well plate with each sample cDNA/primer pair done in triplicate. The relative fold changes were generated by first normalizing each experimental Ct value to their beta actin Ct value and then normalized to the healthy control antisense AACt. Primer sequences are listed in FIG. 28.

Rapid Ampliciation of 5' and 3' cDNA Ends (5' and 3' RACE).

Four µg of total RNA from 2 C9(+) ALS patients and 2 C9(−) ALS patients frontal cortex autopsy tissues were used for 5' and 3' RACE (5' RACE systems and 3' RACE; Life Technologies). In 5'RACE, Primer ASORF R was used for gene specific first strand cDNA synthesis and nested reverse primers are 5'GSP1 and 5'GSP2. In 3'RACE, nested forward primers are 3'GSP1 and 3'GSP2. The 3' RACE and 5' RACE products were gel-extracted, cloned with TOPO TA Cloning (Invitrogen) and sequenced. Primer sequences are listed in FIG. 28.

Production of Polyclonal Antibodies.

The polyclonal rabbit antibodies were generated by New England Peptide and the polyclonal mouse antibody was generated by the Interdisciplinary Center for Biotechnology Research (ICBR) at the University of Florida. In sense strand (GGGGCC), antisera were raised against synthetic poly(GP), poly(GR) peptides and C terminal regions of predicted GP, GR, and GA RAN proteins (FIG. 21). In antisense strand (GGCCCC), antisera were raised against synthetic poly(PA), poly(PR) peptides and the C terminal regions of predicted PA and PR RAN proteins. Peptides used to generate antibodies to both antisense and sense proteins and their use for Western blot, immunofluorescence (IF) and immunohistochemistry (IHC) is summarized in Table S3.

Cell Culture and Transfection.

HEK293T cells were cultured in DMEM medium supplemented with 10% fetal bovine serum and incubated at 37° C. in a humid atmosphere containing 5% CO2. DNA transfections were performed using Lipofectamine 2000 Reagent (Invitrogen) according to the manufacturer's instructions.

Human Samples.

Frozen frontal cortex tissue samples for biochemical and histological analysis included samples from six C9(+) ALS, five C9(−) ALS controls and one normal control were used in this research. Additionally, paraffin embedded fixed tissues from C9(+) ALS/FTD and C9(−) ALS/FTD cases as well as a normal control. Peripheral blood lymphocytes (PBL) were isolated from the buffy coat of freshly collected whole blood following brief centrifugation at 2000×g. Red blood cells (RBC) were preferentially lysed and removed using RBC Lysis Buffer (Roche), PBLs centrifuged, washed once with PBS and dried on slides. This study was conducted in compliance with the Declaration of Helsinki. Institutional review boards of the University of Florida and Johns Hopkins University approved the study. Written, informed consent was obtained from participants or relevant parties at the time of enrollment.

Immunofluorescence.

The subcellular distribution of polymeric proteins was assessed in transfected HEK293T cells by immunofluorescence. Cells were plated on 8 well tissue-culture chambers and transfected with plasmids the next day. Forty-eight hours post-transfection, cells were fixed in 4% paraformaldehyde (PFA) in PBS for 30 min and permeabilized in 0.5% triton X-100 in PBS for 15 min on ice. The cells were blocked in 1% normal goat serum in PBS for 30 min. After blocking, the cells were incubated for 1 hour at RT in blocking solution containing the rabbit anti-Myc (Abcam), mouse anti-HA (Covance), mouse anti-Flag (Sigma), rabbit anti-GR and rabbit anti-GR-CT primary antibodies at a dilution of 1:400. The slides were washed three times in PBS and incubated for 1 hour at RT in blocking solution containing Goat anti-rabbit conjugated to Cy3 (Jackson ImmunoResearch, PA) and goat anti-mouse conjugated to Alexa Fluor 488 (Invitrogen) secondary antibodies at a dilution of 1:200. The slides were washed three times in PBS and mounted with mounting medium containing DAPI (Invitrogen).

RNA-FISH.

Slides with cells were fixed in 4% PFA in PBS for 10 min and incubated in prechilled 70% ethanol for 30 min on ice. Following rehydration in 40% formamide in 2×SSC for 10 min, the slides were blocked with hybridization solution (40% formamide, 2×SSC, 10 mg/ml BSA, 100 mg/ml dextran sulfate and 10 mg/ml yeast tRNA) for 10 minutes at 55° C. and then incubated with 200 ng/ml denatured RNA probe in hybridization solution at 55° C. for 2 hours. After hybridization the slides were washed 3 times with 40% formaminde in 2×SSC and briefly washed one time in PBS. Autofluorescence of lipofuscin was quenched by 0.25% of Sudan Black B in 70% ethanol and the slides were mounted with mounting medium containing DAPI (Invitrogen). The specificity of the RNA foci was determined by treating cells prior to FISH detection with either RNAse (100 ug/mL in 2×SSC), DNase (1 U/ul in DNaseI buffer) or Protease K (120 ug/mL in 2 mM CaCl2, 20 mM Tris, pH 7.5). Treated cells were incubated at 37° C. for 30 minutes, washed 3 times with PBS then 3 times with 2×SSC. Subsequent FISH detected was performed as described above. Antisense foci specificity was determined using standard FISH detection to first hybridize slides with 10-fold excess unlabeled (G4C2)4 oligo followed by hybridization with either G4C2-cy3 (antisense probe) or $G_2C_4$-cy3 (sense probe). Subsequent treatment and detection were performed as described above.

Western Blotting.

Transfected cells in each well of a six-well tissue-culture plate were rinsed with PBS and lysed in 300 µL RIPA buffer with protease inhibitor cocktail for 45 min on ice. DNA was sheared by passage through a 21-gauge needle. The cell lysates were centrifuged at 16,000×g for 15 min at 4° C., and the supernatant was collected. The protein concentration of the cell lysate was determined using the protein assay dye reagent (Bio-Rad). Twenty micrograms of protein were separated in a 4-12% NuPAGE Bis-Tris gel (Invitrogen) and transferred to a nitrocellulose membrane (Amersham). The membrane was blocked in 5% dry milk in PBS containing 0.05% Tween-20 (PBS-T) and probed with the n anti-Flag (1:2000), anti-Myc (1:1000), anti-HA (1:1000), or rabbit polyclonal antibodies (1:1000) in blocking solution. After the membrane was incubated with anti-rabbit or anti-mouse HRP-conjugated secondary antibody (Amersham), bands were visualized by the ECL plus Western Blotting Detection System (Amersham). Sequential extraction of patient frontal cortex autopsy tissue was performed as follows: tissue was homogenized in PBS containing 1% Triton-X100, 15 mM MgCl2, 0.2 mg/ml DNase I and protease inhibitor cocktail and centrifuged at 16,000×g for 15 min at 4° C. The supernatant was collected. The pellet was resuspended in 2% SDS and incubated at room temperature for 1 hour, then centrifuged at 16,000×g for 15 min at 4° C. The supernatant was collected and the 2% SDS insoluble pellet was resuspended in 8% SDS, 62.5 mM Tris-HCl pH 6.8, 10% glycerol and 20% 2-Mercaptoethanol for protein blotting (25).

Protein Slot Blot.

1% Triton-X100 soluble fraction and 2% SDS soluble fraction from the sequential extraction was immobilized onto nitrocellulose membranes with Bio-Dot 96-well microfiltration system (Bio-Rad) under vacuum. The membranes were washed in PBS-T and blotted with each rabbit polyclonal antibody (1:2000) using the same protocol as western blotting.

Immunohistochemistry.

Ten-micrometer sections were deparaffinized in xylene and rehydrated through graded alcohol, incubated with 95-100% formic acid for 5 min, and washed with distilled water for 10 min. HIER was performed by steaming sections in citrate buffer, pH 6.0, at 90° C. for 30 min. To block nonspecific immunoglobulin binding, a serum-free block (Biocare Medical) was applied for 30 min. Rabbit polyclonal antibodies were applied at a dilution of from 1:5000 to 1:15,000 in serum-free block (Biocare Medical) and incubated overnight at 4° C. Linking reagent (streptavidin and/or alkaline phosphatase, Covance) was applied for 30 min at room temperature. These sections were incubated in 3% H2O2 for 15 min to bleach endogenous peroxidase activity. Then labeling reagent (HRP, Covance) was applied for 30 min at room temperature. Peroxidase activity was developed with NovaRed substrate (Vector) and sections were counterstained with hematoxylin.

Cell Toxicity Assays.

All the transfection experiments were performed using Lipofectamine 2000 (Invitrogen), according to the manufacturer's instruction and at a 60% cell confluence. 500 ng of each vector was transfected in 35 mm wells. Cell death was determined by measuring Lactate dehydrogenase (LDH) cell release, using CytoTox 96 non-radioactive cytotoxicity assay (Promega) according to the manufacturer's instructions. Absorbance was recorded at 490 nm and total LDH release was measured by lysing the cells with 1% Triton X-100. In each experiment, determinations were performed in quintuplicates for each experimental condition and average data calculated. Statistical significance was determined using the two tailed unpaired Student t test for single comparisons ($p<0.05$) and the analysis of variance (ANOVA) when multiple pairwise conditions were compared.

Cell Viability Assays.

HeK293T cells were transfected in 96 well plates and cell viability was determined 42 hours post-transfection with the 3-(4,5-dimethythiazol-.2-yl)-2,5-diphenyl tetrazolium bromide (MTT) assay. MTT was added to cell culture media at 0.5 mg/mL final concentration and incubated for 45 minutes at 37° C. Cells were then lysed with 100 µL of DMSO upon medium removal and absorbance was measured at 595 nm. In each experiment, determinations were performed in quintuplicates. Statistical significance was determined using Student's t test ($p<0.05$).

Example 4. BAC Transgenic Mouse Model of C9ORF72 ALS to Test the Hypothesis that Both Sense and Antisense Transcripts Contribute to ALS/FTD Rationale:

A mouse model of C9ORF72 ALS/FTD that recapitulates the sense and antisense transcripts is critical for modeling this disease. BAC clones were isolated from a human patient which contain ~800 G4C2 repeats. These BAC clones were used to generate 8 founder lines. These mice are useful, for example, to answer the following questions: Does both RAN protein expression and RNA gain of function contribute to C9ORF72 ALS/FTD? Are sense and antisense mechanisms both important in C9ORF72 pathogenesis?

Approach:

BAC clones containing the full human C9ORF72 gene plus flanking sequences were isolated from a human patient with ~800 GGGGCC repeats and inserted into the pCC1BAC™ plasmid (Epicentre®). The BAC insert chosen for use in the mouse extended from bp 27,625,470 to 27,527,137 of human genome reference sequence on Chromosome 9 (FIG. 29). The coordinates above do not include extra repeats from this patient. It was found that the BAC insert DNA contained about 800 repeats in some clone preps but was very unstable. Pronuclear injections were performed and 8 FVB founder lines were generated—2 independent lines which were confirmed expansion mutations. The BAC repeat size in the mice was ~500 repeats but varied between progeny and may grow or shrink in size as the mouse colony is expanded and additional generations of mice are propagated in the laboratory. BAC expansion mice expressed both sense and antisense versions of the C9ORF72 gene. Sense and anti-sense GGGCC RNA foci were present in mice that had the GGGGCC repeats, but not in control mice (FIGS. 30-31).

At least two expansion and two control lines are selected for detailed characterization. Behavioral characterization includes rotorod analysis, grip strength, balance beam and open field assessments. Molecular characterization of sense and antisense transcripts and RAN proteins are performed by RT-PCR, RACE, immunoblot, immunohistochemistry and immunofluorescence. Immunohistochemistry, immunofluorescence and FISH studies are performed to correlate sites of RNA foci and C9-RAN proteins accumulation with pathological changes. RAN-protein accumulation in the CNS, CSF, muscle, blood and other tissues are examined at various times during development.

Relevance:

Results from these studies will lead to a better understanding of the role that RAN translation plays in C9ORF72 ALS/FTD. Additionally, these studies will help to prioritize individual protein targets by determining which proteins are found most frequently in autopsy tissue and identifying overt differences in the toxicities of individual RAN proteins. Information from cellular and mouse models will also inform future studies on the effectiveness of various treatment strategies.

REFERENCES

1. DeJesus-Hernandez M, et al. (2011) Expanded GGGGCC hexanucleotide repeat in noncoding region of C9ORF72 causes chromosome 9p-linked FTD and ALS. *Neuron* 72(2):245-256.
2. Renton A E, et al. (2011) A hexanucleotide repeat expansion in C9ORF72 is the cause of chromosome 9p21-linked ALS-FTD. *Neuron* 72(2):257-268.
3. Majounie E, et al. (2012) Frequency of the C9orf72 hexanucleotide repeat expansion in patients with amyotrophic lateral sclerosis and frontotemporal dementia: a cross-sectional study. *Lancet Neurol* 11(4):323-330.
4. Nelson D L, Orr H T, & Warren S T (2013) The unstable repeats—three evolving faces of neurological disease. *Neuron* 77(5):825-843.
5. Reddy K, Zamiri B, Stanley S Y, Macgregor R B, Jr., & Pearson C E (2013) The disease-associated r(GGGGCC)n repeat from the C9orf72 gene forms tract length-dependent uni and multimolecular RNA G-quadruplex structures. *J Biol Chem* 288(14):9860-9866.
6. Mori K, et al. (2013) hnRNP A3 binds to GGGGCC repeats and is a constituent of p62-positive/TDP43-negative inclusions in the hippocampus of patients with C9orf72 mutations. *Acta Neuropathol* 125(3):413-423.
7. Xu Z, et al. (2013) Expanded GGGGCC repeat RNA associated with amyotrophic lateral sclerosis and frontotemporal dementia causes neurodegeneration. *Proc Natl Acad Sci USA* 110(19):7778-7783.
8. Almeida S, et al. (2013) Modeling key pathological features of frontotemporal dementia with C9ORF72 repeat expansion in iPSC-derived human neurons. *Acta Neuropathol*.
9. Zu T, et al. (2011) Non-ATG-initiated translation directed by microsatellite expansions. *Proc Natl Acad Sci USA* 108(1):260-265.
10. Ash P E, et al. (2013) Unconventional translation of C9ORF72 GGGGCC expansion generates insoluble polypeptides specific to c9FTD/ALS. *Neuron* 77(4):639-646.
11. Mori K, et al. (2013) The C9orf72 GGGGCC Repeat Is Translated into Aggregating Dipeptide—Repeat Proteins in FTLD/ALS. *Science*.
12. Todd P K, et al. (2013) CGG repeat-associated translation mediates neurodegeneration in fragile X tremor ataxia syndrome. *Neuron* 78(3):440-455.

13. Ash P E A, et al. (2013) Unconventional Translation of C9ORF72 GGGGCC Expansion Generates Insoluble Polypeptides Specific to c9FTD/ALS *Neuron*.
14. Strausberg R L, et al. (2002) Generation and initial analysis of more than 15,000 full-length human and mouse cDNA sequences. *Proc Natl Acad Sci USA* 99(26): 16899-16903.
15. Venter J C, et al. (2001) The sequence of the human genome. *Science* 291(5507):1304-1351.
16. Beausoleil S A, Villen J, Gerber S A, Rush J, & Gygi S P (2006) A probability-based approach for high-throughput protein phosphorylation analysis and site localization. *Nat Biotechnol* 24(10):1285-1292.
17. Sopher B L, et al. (2011) CTCF regulates ataxin-7 expression through promotion of a convergently transcribed, antisense noncoding RNA. *Neuron* 70(6):1071-1084.
18. Chung D W, Rudnicki D D, Yu L, & Margolis R L (2011) A natural antisense transcript at the Huntington's disease repeat locus regulates HTT expression. *Hum Mol Genet* 20(17):3467-3477.
19. Wilburn B, et al. (2011) An antisense CAG repeat transcript at JPH3 locus mediates expanded polyglutamine protein toxicity in Huntington's disease-like 2 mice. *Neuron* 70(3):427-440.
20. Ladd P D, et al. (2007) An antisense transcript spanning the CGG repeat region of FMR1 is upregulated in premutation carriers but silenced in full mutation individuals. *Hum Mol Genet* 16(24):3174-3187.
21. Moseley M L, et al. (2006) Bidirectional expression of CUG and CAG expansion transcripts and intranuclear polyglutamine inclusions in spinocerebellar ataxia type 8. *Nat Genet* 38(7):758-769.
22. Cho D H, et al. (2005) Antisense transcription and heterochromatin at the DM1 CTG repeats are constrained by CTCF. *Mol Cell* 20(3):483-489.
23. Li H, Wyman T, Yu Z X, Li S H, & Li X J (2003) Abnormal association of mutant huntingtin with synaptic vesicles inhibits glutamate release. *Hum Mol Genet* 12(16):2021-2030.
24. Luk K C, et al. (2012) Pathological alpha-synuclein transmission initiates Parkinson-like neurodegeneration in nontransgenic mice. *Science* 338(6109):949-953.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

What is claimed is:

1. A method of producing an antibody, the method comprising administering to a subject a poly-(Pro-Arg) di-amino acid repeat-containing protein.

2. The method of claim 1, wherein the poly-(Pro-Arg) di-amino acid repeat-containing protein comprises the sequence set forth in SEQ ID NO: 19.

3. The method of claim 1, further comprising the step of isolating the antibody from the subject.

* * * * *